United States Patent
Harwig et al.

(10) Patent No.: US 11,352,367 B2
(45) Date of Patent: Jun. 7, 2022

(54) INDENE DERIVATIVES USEFUL IN TREATING PAIN AND INFLAMMATION

(71) Applicant: TARO PHARMACEUTICALS INC., Brampton (CA)

(72) Inventors: Curtis Harwig, Vancouver (CA); Jeremy D. Pettigrew, Vancouver (CA); Jennifer Cross, Vancouver (CA); Jeyaprakashnarayanan Seenisamy, Vancouver (CA); Mahesh Narayan Keregadde, Vancouver (CA); Karthikeyan Iyanar, Vancouver (CA)

(73) Assignee: TARO PHARMACEUTICALS INC., Brampton (CA)

( * ) Notice: Subject to any disclaimer, the term of this patent is extended or adjusted under 35 U.S.C. 154(b) by 0 days.

(21) Appl. No.: 17/045,675

(22) PCT Filed: Apr. 5, 2019

(86) PCT No.: PCT/US2019/026138
§ 371 (c)(1),
(2) Date: Oct. 6, 2020

(87) PCT Pub. No.: WO2019/195777
PCT Pub. Date: Oct. 10, 2019

(65) Prior Publication Data
US 2021/0032264 A1   Feb. 4, 2021

Related U.S. Application Data

(60) Provisional application No. 62/654,191, filed on Apr. 6, 2018.

(51) Int. Cl.
| | | |
|---|---|---|
| *C07D 493/10* | (2006.01) | |
| *C07D 231/54* | (2006.01) | |
| *C07D 401/08* | (2006.01) | |
| *C07D 403/08* | (2006.01) | |
| *C07D 417/08* | (2006.01) | |
| *A61P 29/00* | (2006.01) | |

(52) U.S. Cl.
CPC ............ *C07D 493/10* (2013.01); *A61P 29/00* (2018.01); *C07D 231/54* (2013.01); *C07D 401/08* (2013.01); *C07D 403/08* (2013.01); *C07D 417/08* (2013.01)

(58) Field of Classification Search
CPC .. C07D 493/10; C07D 231/54; C07D 401/08; C07D 403/08; C07D 417/08; A61P 29/00
See application file for complete search history.

(56) References Cited

U.S. PATENT DOCUMENTS 9,765,085 B2 * 9/2017 Mackenzie ............. C07C 35/23

OTHER PUBLICATIONS

Nickel et al., A Phase II Study of the Efficacy and Safety of the Novel Oral SHIP1 Activator AQX-1125 in Subjects with Moderate to Severe Interstitial Cystitis/Bladder Pain Syndrome, The Journal of Urology, Mar. 2016, pp. 747-754, vol. 196, No. 3.

* cited by examiner

*Primary Examiner* — Timothy R Rozof
(74) *Attorney, Agent, or Firm* — Paratus Law Group, PLLC

(57) ABSTRACT

Compounds of formula (I): wherein, $R^1$, $R^2$, $R^3$, $R^{4a}$, $R^{4b}$ and $R^5$ are described herein, or a stereoisomer, enantiomer or tautomer thereof or mixtures thereof, or a pharmaceutically acceptable salt or solvate thereof, are described herein, as well as other compounds. These compounds are useful in treating inflammation and/or pain. Compositions comprising a compound of the invention are also disclosed, as are methods of using the compounds to treat inflammation and/or pain.

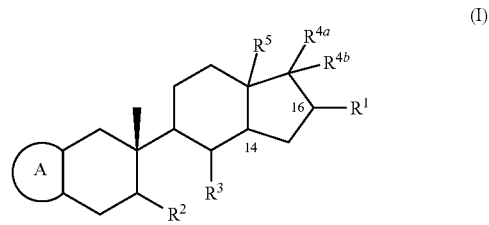

(I)

38 Claims, No Drawings

INDENE DERIVATIVES USEFUL IN TREATING PAIN AND INFLAMMATION

CROSS REFERENCE TO PRIOR APPLICATION

This application is a National Stage Patent Application of PCT International Patent Application No. PCT/US2019/026138 (filed on Apr. 5, 2019) under 35 U.S.C. § 371, which claims priority to U.S. Provisional Patent Application No. 62/654,191 (filed on Apr. 6, 2018), which are all hereby incorporated by reference in their entirety.

FIELD OF THE INVENTION

The present invention is generally directed to indene derivatives which are useful in treating inflammation and/or pain, as well as to compositions and methods related to the same.

BACKGROUND OF THE INVENTION

Tissue injury results in the initiation of a complex cascade of cellular events which result in redness, swelling, heat and pain at the site of insult. This inflammatory response is the normal mechanism by which the body contains and removes pathogens and repairs tissue damage. These classic and acute signs of inflammation are in large part attributable to the influx and accumulation of activated leukocytes and the subsequent release of mediators such as histamine, leukotrienes, substance P, prostaglandins, cytokines, reactive oxygen species and proteases. Activated immune cells and their proinflammatory products can also induce sensitization of peripheral nociceptors, contributing to the development of both acute and chronic inflammatory pain.

Normal inflammation is a tightly controlled, temporary, process, involving many different cell types, and is ultimately followed by a resolution phase featuring the expression of anti-inflammatory mediators and involving cell subsets that coordinate the tissue repair process. Inflammatory disease occurs when this normal cycle of activation/repair goes awry, resulting in a chronic state of immune cell activation and misdirection of the immune response towards host tissue. Inflammatory pain is also a protective response, designed to shield the injured tissue from further damage, but under conditions of uncontrolled inflammation, the multi-faceted interplay between the immune and nervous systems can drive the establishment of chronic pain and create a host of pathologies which are difficult to manage, creating a large personal and economic burden on society.

One of the key signaling pathways involved in the initiation and propagation of immune cell activation is the phosphoinositide-3-kinase (PI3K) pathway. In response to extracellular signals, phosphoinositide 3-kinase (PI3K) becomes activated and phosphorylates phosphatidylinositol-4,5-bisphosphate (PI-4,5-P2) within the plasma membrane to generate phosphatidylinositol-3,4,5-trisphosphate (PIP3). PIP3 then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of PIP3 are normally tightly regulated by PI3K, the inositol 5-phosphatases SHIP1 (SH2 domain-containing inositol phosphatase), SHIP2, and by the inositol 3-phosphatase PTEN.

To date, a number of small molecule SHIP modulators have been disclosed, including sesquiterpene compounds such as pelorol. Other reported SHIP1 modulators include the compounds described in U.S. Pat. Nos. 8,765,994, 7,601,874, 9,000,050, 9,540,353, and 9,765,085 U.S. Published Patent Application No. 2017/0253596.

Pain is another critical component of a body's defense system. In general, pain is a basic bodily sensation induced by a noxious stimulus, received by nerve endings (nociceptive receptors) and characterized by physical discomfort (such as pricking, throbbing, or aching), and typically leads to evasive action (i.e., removing oneself from the source of the stimulus). Pain is typically classified into two main categories: acute and chronic pain.

Acute or nociceptive pain is part of a rapid warning relay instructing the motor neurons of the central nervous system to minimize detected physical harm. It is mediated by nociceptors, which are free nerve endings that terminate just below the skin, in tendons, joints, and in body organs. They serve to detect cutaneous pain, somatic pain and visceral pain. Nociception can be associated with nerve damage caused by trauma, diseases such as diabetes, shingles, irritable bowel syndrome, late stage cancer or the toxic effects of chemotherapy.

Chronic pain is typically classified into two types: inflammatory nociceptive pain and neuropathic pain. Inflammatory nociceptive pain is associated with tissue damage and the resulting inflammatory process.

Neuropathic pain is produced by damage to and/or inflammation of the neurons in the peripheral and central nervous systems and involves sensitization of these systems.

One of the challenges for researchers is that chronic pain may involve a mix of both inflammatory and neuropathic components. In inflammatory nociceptive pain, inflammation may cause damage to the neurons and produce neuropathic pain. Likewise, neuronal injury may cause an inflammatory reaction (neurogenic inflammation) that contributes to inflammatory pain.

While significant strides have been made in the field of anti-inflammatory agents and analgesics, there remains a need for effective small molecule for the treatment of inflammation and/or pain. There is also a need for pharmaceutical compositions containing such compounds, as well as for methods relating to the use thereof to treat diseases, disorders or conditions that would benefit from such treatment. The present invention fulfills these needs, and provides other related advantages.

SUMMARY OF THE INVENTION

The present invention is generally directed to compounds which are useful in treating inflammation and/or pain, pharmaceutical compositions comprising the compounds and methods of using the compounds and the pharmaceutical compositions of the invention for the treatment of inflammation and/or pain.

Accordingly, in one aspect, this invention is directed to compounds of formula (I):

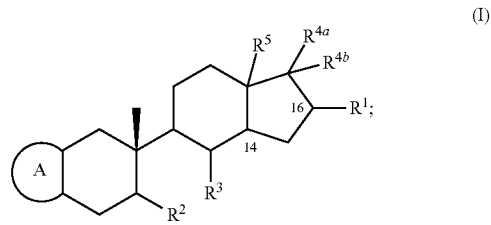

wherein:

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
or $R^{4a}$ is an optionally substituted aryl and $R^{4b}$ is a bond to C16;
or $R^{4a}$ and $R^{4b}$ together form alkylidene, provided that

is a fused 5- or 6-membered N-heteroaryl substituted by substituted aryl, substituted aralkyl, substituted cycloalkyl or substituted heteroaryl;
or $R^{4a}$ is alkyl and $R^{4b}$ is hydrogen, provided that

is a fused 5- or 6-membered N-heteroaryl substituted by substituted aryl, substituted aralkyl, substituted cycloalkyl or substituted heteroaryl;
or $R^{4a}$ and $R^1$ together form an optionally substituted bicyclic heterocyclyl and $R^{4b}$ is hydrogen;
or $R^{4a}$, $R^{4b}$ and $R^1$ together form a fused optionally substituted heteroaryl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl; and
$R^9$ is a direct bond or a straight or branched alkylene chain;
or a stereoisomer, enantiomer or tautomer thereof or mixtures thereof, or a pharmaceutically acceptable salt or solvate thereof.

In another aspect, this invention is directed to compositions comprising a pharmaceutically acceptable excipient, carrier and/or diluent and a compound of formula (I), or a stereoisomer, enantiomer or tautomer thereof or mixtures thereof; or a pharmaceutically acceptable salt or solvate thereof.

In another aspect, this invention is directed to methods for treating inflammation and/or pain in a mammal comprising administering an effective amount of a compound of formula (I), or a stereoisomer, enantiomer or tautomer thereof or mixtures thereof; or a pharmaceutically acceptable salt or solvate thereof, as set forth above, to the mammal in need thereof.

In another aspect, this invention is directed to methods for treating inflammation and/or pain in a mammal comprising administering a composition comprising an effective amount of a compound of formula (I), or a stereoisomer, enantiomer or tautomer thereof or mixtures thereof; or a pharmaceutically acceptable salt or solvate thereof, as set forth above, to the mammal in need thereof.

In another aspect, this invention is directed to methods of preparing compounds of formula (I), or stereoisomers, enantiomers or tautomers thereof or mixtures thereof; or pharmaceutically acceptable salts or solvates thereof.

In another aspect, this invention is directed to the use of the compounds of the invention, as set forth above, or a stereoisomer, enantiomer or tautomer thereof or mixtures thereof, or a pharmaceutically acceptable salt or solvate thereof, or the use of a pharmaceutical composition comprising a pharmaceutically acceptable excipient and a compound of the invention, as set forth above, or a stereoisomer, enantiomer or tautomer thereof or mixtures thereof, or a pharmaceutically acceptable salt or solvate thereof, in the preparation of a medicament for the treatment of inflammation and/or pain.

These aspects and embodiments thereof are described in more detail below. To this end, various references are set forth herein which describe in more detail certain background information, procedures, compounds and/or compositions, and are each hereby incorporated by reference in their entirety.

DETAILED DESCRIPTION OF THE INVENTION

Definitions

As used in the specification and appended claims, unless specified to the contrary, the following terms have the meaning indicated:

"Oxo" refers to =O.
"Cyano" refers to —CN.
"Nitro" refers to —$NO_2$.
"Alkyl" refers to a straight or branched hydrocarbon chain radical consisting solely of carbon and hydrogen atoms, containing no unsaturation, having from one to twelve carbon atoms, preferably one to ten carbon atoms, more preferably one to eight carbon atoms, most preferably one to six carbon atoms and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, 6-methylheptan-2-yl, 5-ethyl-6-methylheptan-2-yl and the like. When specifically stated in the specification, an alkyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20}$)$_2$, —N($R^{20}$)C(O)O$R^{22}$, —N($R^{20}$)C(O)$R^{22}$, —N($R^{20}$)S(O)$_p R^{22}$ (where p is 1 to 2), —S(O)$_p$O$R^{22}$ (where p is 1 to 2), —S(O)$_t R^{22}$ (where t is 0 to 2), and —S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: alkyl, halo, haloalkyl, cyano, nitro, aryl, cycloalkyl, heterocycyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., —CH$_2$—, —CH$_2$—CH$_2$—, —CH$_2$—CH$_2$—CH$_2$—, and the like. The alkylene chain is attached to the rest of the molecule through a single bond and to the radical group through a single bond. The radical group can be attached to any carbon in the alkylene chain. When specifically stated in the specification, an alkylene chain may be optionally substituted by one of the following groups: alkyl, alkenyl, halo, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^2$ is alkyl, haloalkyl, cycloalkyl, cycloalkylalkyl, aryl, aralkyl, heterocyclyl, heterocyclylalkyl, heteroaryl or heteroarylalkyl.

"Alkylidene" refers to a straight or branched hydrocarbon radical group consisting solely of carbon and hydrogen, containing at least one double bond, having from one to seven carbon atoms, and that is attached to the rest of the molecule through a double bond, e.g., methylene, ethylidene, propylidene, and the like. When specifically stated in the specification, an alkylidene radical may be optionally substituted by one of the following groups: alkyl, halo, haloalkyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, cyano, nitro, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_p$R$^{22}$ (where p is 1 to 2), —R$^{21}$—N=C(OR$^{20}$)R$^{20}$, —R$^{21}$—S(O)OR$^{22}$ (where p is 1 to 2), —R$^{21}$—S(O)$_p$R$^{22}$ (where t is 0 to 2), and —R$^{21}$—S(O)$_p$N(R$^{20}$)$_2$ (where p is 1 to 2) where each R$^{20}$ is independently hydrogen, alkyl, alkenyl, alkynyl, haloalkyl, cycloalkyl, cycloalkylalkyl, optionally substituted aryl, aralkyl, heterocyclyl, heterocyclylalkyl, heteroaryl or heteroarylalkyl; each R$^{21}$ is independently a direct bond or a straight or branched alkylene chain; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, halo, haloalkyl, cyano, nitro, oxo, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_p$R$^{22}$ (where p is 1 to 2), —R$^{21}$—N=C(OR$^{20}$)R$^{20}$, —R$^{21}$—S(O)$_p$OR$^{22}$ (where p is 1 to 2), —R$^{21}$—S(O)$_t$R$^{22}$ (where t is 0 to 2), and —R$^{21}$—S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene chain; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —R$_b$R$_g$ where R$_b$ is an alkylene chain as defined above and R$_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro, fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperdinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, 1,1-dioxo-thiomorpholinyl and 1,6-dioxaspiro[4.5]decanyl. When specifically stated in the specification, a heterocyclyl group may be optionally substituted by one or more substituents selected from the group consisting of alkyl, alkenyl, halo, haloalkyl, cyano, oxo, thioxo, nitro, aryl, aralkyl, cycloalkyl, cycloalkylalkyl, optionally substituted heterocyclyl, optionally substituted heterocyclylalkyl, optionally substituted heteroaryl, optionally substituted heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and where the optional substituents on the heterocyclyl, heterocyclylalkyl, heteroaryl and heteroarylalkyl substitutents are selected from alkyl, halo or haloalkyl.

"Heterocyclylalkyl" refers to a radical of the formula $-R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocydic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzo[d]imidazolyl, benzimidazopyrimidinyl, benzo[4,5]imidazo[1,2-a]pyrimidinyl, benzthiazolyl, benzindolyl, benzodioxolyl, benzofuranyl, benzooxazolyl, benzothiazolyl, benzo[d]isoxazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazo[1,2-a]pyridinyl, imidazo[1,2-a]pyrimidinyl, imidazo[1,2-a]pyrazinyl, imidazo[1,5-a]pyrazinyl, imidazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyrdinyl, pyridinonyl, pyrazinyl, pyrimidinyl, pryrimidinonyl, pyridazinyl, pyrido[2,3-d]pyrimidinonyl, pyrazolo[1,5-a]pyrimidinyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e., thienyl). When specifically stated in the specification, a heteroaryl group may be optionally substituted by one or more substituents selected from the group consisting of alkyl, alkenyl, halo, haloalkyl, cyano, oxo, thioxo, nitro, thioxo, optionally substituted aryl, optionally substituted aralkyl, optionally substituted cycloalkyl, cycloalkylalkyl, heterocyclyl, heterocyclylalkyl, optionally substituted heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R_bR_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent. Furthermore, some of the crystalline forms of the compounds of the invention may exist as polymorphs, which are included in the present invention.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of inflammation and/or pain in the mammal, preferably a human. The amount of a compound of the invention which constitutes a "therapeutically effective amount" will vary depending on the compound, the inflammation and/or pain and its severity, the manner of administration, and the age of the mammal to be treated, but can be determined routinely by one of ordinary skill in the art having regard to his own knowledge and to this disclosure.

"Treating" or "treatment" as used herein covers the treatment of inflammation and/or pain in a mammal, preferably a human, having the inflammation and/or pain, and includes:

(a) preventing the inflammation and/or pain from occurring in a mammal, in particular, when such mammal is predisposed to the condition but has not yet been diagnosed as having it;

(b) inhibiting the inflammation and/or pain, i.e., arresting its development;

(c) relieving (or ameliorating) the inflammation and/or pain, i.e., causing regression of the inflammation and/or pain; or (d) relieving (or ameliorating) the symptoms resulting from the inflammation and/or pain, e.g., relieving inflammation and/or pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts or solvates thereof, may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. Compounds of the invention may also possess axial chirality which may result in atropisomers. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure,* 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

Certain carbons are identified by numerals in the formulae of the compounds of the invention. For purposes herein, the carbon at numeral 14 in formula (I) is indicated herein as C14 and the carbon at numeral 16 is indicated herein as C16, and so forth.

These numerals may or may not be the same as the locants in the compound names given herein.

When a substituent is indicated as being substituted, such as —$R^9$—$OR^7$, it is understood that the substituent may be substituted by the indicated substituent at any carbon in the substituent. Thus, for example, when the $R^9$ in the —$R^9$—$OR^7$ substituent is an alkylene chain, the —$OR^7$ group in the —$R^9$—$OR^7$ group can be on any carbon in the $R^9$ alkylene chain.

The chemical naming protocol and structure diagrams used herein are a modified form of the I.U.P.A.C. nomenclature system, using ChemDraw 17.0 software program, wherein the compounds of the invention are named herein as derivatives of a central core structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I) wherein

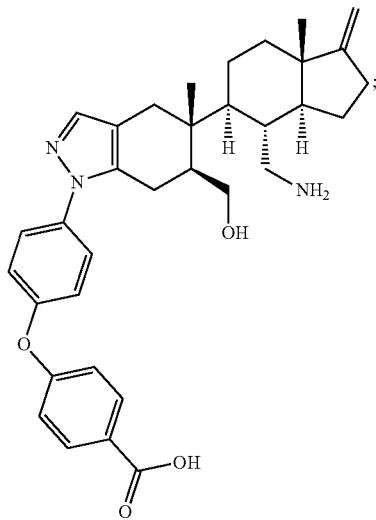 [SMILES: C=C1CC[C@H]2[C@H](CN)[C@@H]([C@@]3(C)Cc4cnn(-c5ccc(Oc6ccc(C(=O)O)cc6)cc5)c4C[C@@H]3CO)CC[C@]12C]

is 1-(4-(4-carboxyphenoxy)phenyl)pyrazolyl, R is hydrogen, $R^2$ is —$CH_2OH$, $R^3$ is —$CH_2$—$NH_2$, $R^{4a}$ and $R^{4b}$ together form methylene and $R^5$ is methyl, i.e., a compound of the following structure:

is named herein as 4-(4-(((5R,6S)-5-(((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenoxy)benzoic acid.

Embodiments of the Invention

Of the various aspects of the invention set forth above in the Summary of the Invention, certain embodiments are preferred.

Of the compounds of formula (I), or a stereoisomer, enantiomer or tautomer thereof or mixtures thereof, or a pharmaceutically acceptable salt or solvate thereof, as described above in the Summary of the Invention, a first embodiment are compounds of formula (I) wherein:

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl; and
$R^9$ is a direct bond or a straight or branched alkylene chain;
or a stereoisomer, enantiomer or tautomer thereof or mixtures thereof, or a pharmaceutically acceptable salt or solvate thereof.

Of this embodiment, an embodiment are compounds of formula (I) wherein:

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is a direct bond;
or a stereoisomer, enantiomer or tautomer thereof or mixtures thereof, or a pharmaceutically acceptable salt or solvate thereof.

One embodiment of this embodiment are compounds of formula (I) wherein:

is a fused 5-membered N-heteroaryl optionally substituted by one or more substitutents selected from alkyl, haloalkyl, —C(O)$OR^7$, —N($R^8)_2$, —C(O)N($R^8)_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is a direct bond;
or a stereoisomer, enantiomer or tautomer thereof or mixtures thereof, or a pharmaceutically acceptable salt or solvate thereof.

Of this embodiment, an embodiment are compounds of formula (I) selected from:
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol;
(1R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol;
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-1,7a-dimethyloctahydro-1H-inden-1-ol;
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol;
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol;
(1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol; and
(1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol.

Another embodiment of this embodiment are compounds of formula (I) wherein:

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$,
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is straight or branched alkylene chain;
or a stereoisomer, enantiomer or tautomer thereof or mixtures thereof, or a pharmaceutically acceptable salt or solvate thereof.

Of this embodiment, an embodiment are compounds of formula (I) wherein:

is a fused 5-membered N-heteroaryl optionally substituted by one or more substitutents selected from alkyl, haloalkyl, —C(O)OR$^7$, —N(R$^8$)$_2$, —C(O)N(R$^8$)$_2$ or optionally substituted aryl;
R$^1$ is hydrogen;
R$^2$ is —R$^6$—OR$^7$;
R$^3$ is —R$^9$—OR$^7$ or —R$^6$—N(R$^8$)$_2$;
R$^{4a}$ is —R$^9$—OR$^7$ and R$^{4b}$ is hydrogen, alkyl or optionally substituted heteroaryl;
R$^5$ is alkyl;
each R$^6$ is a straight or branched alkylene chain;
each R$^7$ is independently selected from hydrogen or alkyl;
each R$^8$ is independently selected from hydrogen or alkyl; and
R$^9$ is a straight or branched alkylene chain;
or a stereoisomer, enantiomer or tautomer thereof or mixtures thereof, or a pharmaceutically acceptable salt or solvate thereof.

Of this embodiment, an embodiment is the compound of formula (I) selected from:
(2S,5R)-5-ethyl-2-((1R,3aS,4S,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-yl)-6-methylheptan-3-ol.

Of the compounds of formula (I), or a stereoisomer, enantiomer or tautomer thereof or mixtures thereof, or a pharmaceutically acceptable salt or solvate thereof, as described above in the Summary of the Invention, a second embodiment are compounds of formula (I) wherein:

(A)

is an optionally substituted fused 5- or 6-membered N-heteroaryl;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ and R$^1$ together form an optionally substituted bicyclic heterocyclyl and R$^{4b}$ is hydrogen;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl; and
each R$^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) wherein:

(A)

is an optionally substituted fused 5- or 6-membered N-heteroaryl;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ and R$^1$ together form an optionally substituted bicyclic heterocyclyl and R$^{4b}$ is hydrogen;
R$^5$ is alkyl;
each R$^6$ is a straight or branched alkylene chain;
each R$^7$ is independently selected from hydrogen or alkyl; and
each R$^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) wherein:

(A)

is a fused 5-membered N-heteroaryl optionally substituted by one or more substitutents selected from alkyl, haloalkyl, —C(O)OR$^7$, —N(R$^8$)$_2$, —C(O)N(R$^8$)$_2$ or optionally substituted aryl;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ and R$^1$ together form an optionally substituted bicyclic heterocyclyl and R$^{4b}$ is hydrogen;
R$^5$ is alkyl;
each R$^6$ is a straight or branched alkylene chain;
each R$^7$ is independently selected from hydrogen or alkyl; and
each R$^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) selected from:
((5R,6S)-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol; and
((5R,6S)-5-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol.

Of the compounds of formula (I), or a stereoisomer, enantiomer or tautomer thereof or mixtures thereof, or a pharmaceutically acceptable salt or solvate thereof, as described above in the Summary of the Invention, a third embodiment are compounds of formula (I) wherein:

(A)

is an optionally substituted fused 5- or 6-membered N-heteroaryl;
R$^1$ is hydrogen;
R$^2$ is —R$^6$—OR$^7$;
R$^3$ is —R$^6$—OR$^7$ or —R$^6$—N(R$^8$)$_2$;
or R$^{4a}$, R$^{4b}$ and R$^1$ together form a fused optionally substituted heteroaryl;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl; and
each R$^8$ is independently selected from hydrogen or alkyl, or a stereoisomer, enantiomer or tautomer thereof or mixtures thereof, or a pharmaceutically acceptable salt or solvate thereof.

Of this embodiment, an embodiment are compounds of formula (I) wherein:

(A)

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$,
or $R^{4a}$, $R^{4b}$ and $R^1$ together form a fused optionally substituted heteroaryl;
$R^5$ is alkyl;
each $R^6$ is a straight or branched alkylene chain;
each $R^7$ is independently selected from hydrogen or alkyl; and
each $R^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) wherein:

(A)

is a fused 5-membered N-heteroaryl optionally substituted by one or more substitutents selected from alkyl, haloalkyl, —C(O)$OR^7$, —N($R^8$)$_2$, —C(O)N($R^8$)$_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
or $R^{4a}$, $R^{4b}$ and $R^1$ together form a fused optionally substituted heteroaryl;
$R^5$ is alkyl;
each $R^6$ is a straight or branched alkylene chain;
each $R^7$ is independently selected from hydrogen or alkyl; and
each $R^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) selected from:
((4aS,5R,6S,8aS)-6-((5R,6S)-6-(hydroxymethyl)-5-methyl-4,5,6,7-tetrahydro-1H-indazol-5-yl)-8a-methyl-1,4,4a,5,6,7,8,8a-octahydroindeno[1,2-c]pyrazol-5-yl)methanol;
((5R,6S)-5-((4aS,5R,6S,8aS)-5-(aminomethyl)-8a-methyl-1,4,4a,5,6,7,8,8a-octahydroindeno[1,2-c]pyrazol-6-yl)-5-methyl-4,5,6,7-tetrahydro-1H-indazol-6-yl)methanol;
((5R,6S)-5-((5aS,6R,7S,9aS)-6-(aminomethyl)-9a-methyl-5a,6,7,8,9,9a-hexahydro-5H-indeno[1,2-b]pyridin-7-yl)-5-methyl-4,5,6,7-tetrahydro-1H-indazol-6-yl)methanol; and
((5aS,6R,7S,9aS)-7-((5R,6S)-6-(hydroxymethyl)-5-methyl-4,5,6,7-tetrahydro-1H-indazol-5-yl)-9a-methyl-5a,6,7,8,9,9a-hexahydro-5H-indeno[1,2-b]pyridin-6-yl)methanol.

Of the compounds of formula (I), or a stereoisomer, enantiomer or tautomer thereof or mixtures thereof, or a pharmaceutically acceptable salt or solvate thereof, as described above in the Summary of the Invention, a fourth embodiment are compounds of formula (I) wherein:

(A)

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is an optionally substituted aryl and $R^{4b}$ is a bond to C16.
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) wherein:

(A)

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is an optionally substituted aryl and $R^{4b}$ is a bond to C16.
$R^5$ is alkyl;
each $R^6$ is a straight or branched alkylene chain;
each $R^7$ is independently selected from hydrogen or alkyl; and
each $R^8$ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) wherein:

(A)

is a fused 5-membered N-heteroaryl optionally substituted by one or more substitutents selected from alkyl, haloalkyl, —C(O)$OR^7$, —N($R^8$)$_2$, —C(O)N($R^8$)$_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is an optionally substituted aryl and $R^{4b}$ is a bond to C16.
$R^5$ is alkyl;
each $R^6$ is a straight or branched alkylene chain;
each $R^7$ is independently selected from hydrogen or alkyl; and each R⁸ is independently selected from hydrogen or alkyl,
or a stereoisomer, enantiomer or tautomer thereof or mixtures thereof, or a pharmaceutically acceptable salt or solvate thereof.

Of this embodiment, an embodiment are compounds of formula (I) selected from:
((5R,6S)-5-((3aS,6S,7R,7aS)-7-(aminomethyl)-3a-methyl-3-phenyl-3a,4,5,6,7,7a-hexahydro-1H-inden-6-yl)-5-methyl-4,5,6,7-tetrahydro-1H-indazol-6-yl)methanol; and
((5R,6S)-5-((3aS,6S,7R,7aS)-7-(hydroxymethyl)-3a-methyl-3-phenyl-3a,4,5,6,7,7a-hexahydro-1H-inden-6-yl)-5-methyl-4,5,6,7-tetrahydro-1H-indazol-6-yl)methanol.

Of the compounds of formula (I), or a stereoisomer, enantiomer or tautomer thereof or mixtures thereof, or a pharmaceutically acceptable salt or solvate thereof, as described above in the Summary of the Invention, a fifth embodiment are compounds of formula (I) wherein:

(A)

is a fused 5- or 6-membered N-heteroaryl substituted by substituted aryl, substituted aralkyl, substituted cycloalkyl or substituted heteroaryl;
R¹ is hydrogen;
R² is —R⁶—OR⁷;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen or alkyl;
or a stereoisomer, enantiomer or tautomer thereof or mixtures thereof, or a pharmaceutically acceptable salt or solvate thereof.

Of this embodiment, an embodiment are compounds of formula (I) wherein:

(A)

is a fused pyrazolyl substituted by substituted aryl, substituted aralkyl, substituted cycloalkyl or substituted heteroaryl;
R¹ is hydrogen;
R² is —R⁶—OR⁷;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen or alkyl.

Of this embodiment, a first embodiment are compounds of formula (I) wherein:

(A)

is a fused pyrazolyl substituted by aryl substituted by one or more substituents selected from halo, —R¹⁰—OR¹¹, —R¹⁰—C(O)R¹¹ or —R¹⁰—C(O)OR¹¹;
R¹ is hydrogen;
R² is —R⁶—OR⁷;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl;
each R⁸ is independently selected from hydrogen or alkyl;
each R¹⁰ is independently a direct bond or a straight or branched alkylene chain; and
each R¹¹ is independently hydrogen, alkyl, cycloalkyl or optionally substituted aryl.

Of this embodiment, an embodiment are compounds of formula (I) selected from:
((5R,6S)-5-((3aS,4R,5S,7aS)-4-(aminomethyl)-7a-methyl-1-methyleneoctahydro-1H-inden-5-yl)-1-(4-fluorophenyl)-5-methyl-4,5,6,7-tetrahydro-1H-indazol-6-yl)methanol;
4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenoxy)benzoic acid;
((5R,6S)-5-((3aS,4R,5S,7aS)-4-(aminomethyl)-7a-methyl-1-methyleneoctahydro-1H-inden-5-yl)-2-(4-methoxyphenyl)-5-methyl-4,5,6,7-tetrahydro-2H-indazol-6-yl)methanol;
((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol;
(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(phenyl)methanone;
((5R,6S)-5-((3aS,4R,5S,7aS)-4-(aminomethyl)-7a-methyl-1-methyleneoctahydro-1H-inden-5-yl)-1-(2-fluorophenyl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-1-(2,4-difluorophenyl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-1-(3,4-difluorophenyl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-1-(3-fluorophenyl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-2-(3,4-difluorophenyl)-5-methyl-4,5,6,7-tetrahydro-2H-indazol-6-yl)methanol;
((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(4-(4-fluorophenoxy)phenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-(4-phenoxyphenyl)-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1-(4-(4-fluorophenoxy)phenyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-(4-phenoxyphenyl)-4,5,6,7-tetrahydro-2H-indazol-6-yl)methanol;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(phenyl)methanone;

((5R,6S)-5-((3aS,4R,5S,7aS)-4-(aminomethyl)-7a-methyl-1-methyleneoctahydro-1H-inden-5-yl)-2-(2-fluorophenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(2,4-difluorophenyl)-5-methyl-4,5,6,7-tetrahydro-2H-indazol-6-yl)methanol;

4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenoxy)benzoic acid;

((5R,6S)-5-((3aS,4R,5S,7aS)-4-(aminomethyl)-7a-methyl-1-methyleneoctahydro-1H-inden-5-yl)-2-(3-fluorophenyl)-5-methyl-4,5,6,7-tetrahydro-2H-indazol-6-yl)methanol;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(4-(pent-4-yn-1-yloxy)phenyl)methanone;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(4-(pent-4-yn-1-yloxy)phenyl)methanone;

4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)benzoic acid; and 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)benzoic acid.

Of this embodiment, a second embodiment are compounds of formula (I) wherein:

is a fused pyrazolyl substituted by aralkyl substituted by one or more substituents selected from halo, —R$^{10}$—OR$^{11}$ or —R$^{10}$—C(O)R$^{11}$;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ and R$^{4b}$ together form alkylidene;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl;
each R$^8$ is independently selected from hydrogen or alkyl;
R$^{10}$ is a direct bond or a straight or branched alkylene chain; and
each R$^{10}$ is independently a direct bond or a straight or branched alkylene chain; and
each R$^{11}$ is independently hydrogen, alkyl, cycloalkyl or optionally substituted aryl.

Of this embodiment, an embodiment are compounds of formula (I) selected from:

((5R,6S)-5-((3aS,4R,5S,7aS)-4-(aminomethyl)-7a-methyl-1-methyleneoctahydro-1H-inden-5-yl)-2-(4-methoxybenzyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(4-fluorobenzyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-(4-methoxybenzyl)-5-methyl-4,5,6,7-tetrahydro-1H-indazol-6-yl)methanol; and ((5R,6S)-5-((3aS,4R,5S,7aS)-4-(aminomethyl)-7a-methyl-1-methyleneoctahydro-1H-inden-5-yl)-1-(4-fluorobenzyl)-5-methyl-4,5,6,7-tetrahydro-1H-indazol-6-yl)methanol.

Of this embodiment, a third embodiment are compounds of formula (I) wherein:

is a fused pyrazolyl substituted by cycloalkyl substituted by one or more substituents selected from halo, —R$^{10}$—OR$^{11}$ or —R$^{10}$—C(O)R$^{11}$;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ and R$^{4b}$ together form alkylidene;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl;
each R$^8$ is independently selected from hydrogen or alkyl;
each R$^{10}$ is independently a direct bond or a straight or branched alkylene chain; and
each R$^{11}$ is independently hydrogen, alkyl, cycloalkyl or optionally substituted aryl.

Of this embodiment, an embodiment are compounds of formula (I) selected from:

((5R,6S)-5-((3aS,4R,5S,7aS)-4-(aminomethyl)-7a-methyl-1-methyleneoctahydro-1H-inden-5-yl)-2-(4,4-difluorocyclohexyl)-5-methyl-4,5,6,7-tetrahydro-2H-indazol-6-yl)methanol; and ((5R,6S)-5-((3aS,4R,5S,7aS)-4-(aminomethyl)-7a-methyl-1-methyleneoctahydro-1H-inden-5-yl)-1-(4,4-difluorocyclohexyl)-5-methyl-4,5,6,7-tetrahydro-1H-indazol-6-yl)methanol.

Of this embodiment, a fourth embodiment are compounds of formula (I) wherein:

is a fused pyrazolyl substituted by heteroaryl substituted by one or more substituents selected from halo, —R$^{10}$—OR$^{11}$ or —R$^{10}$—C(O)R$^{11}$;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ and R$^{4b}$ together form alkylidene;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl;
each R$^8$ is independently selected from hydrogen or alkyl;
each R$^{10}$ is independently a direct bond or a straight or branched alkylene chain; and
each R$^{11}$ is independently hydrogen, alkyl, cycloalkyl or optionally substituted aryl.

Of this embodiment, an embodiment are compounds of formula (I) selected from:
((5R,6S)-5-((3aS,4R,5S,7aS)-4-(aminomethyl)-7a-methyl-1-methyleneoctahydro-1H-inden-5-yl)-1-(5-fluoropyridin-2-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-1-(5-fluoropyrimidin-2-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-2-(5-fluoropyrimidin-2-yl)-5-methyl-4,5,6,7-tetrahydro-2H-indazol-6-yl)methanol; and
((5R,6S)-5-((3aS,4R,5S,7aS)-4-(aminomethyl)-7a-methyl-1-methyleneoctahydro-1H-inden-5-yl)-2-(5-fluoropyridin-2-yl)-5-methyl-4,5,6,7-tetrahydro-2H-indazol-6-yl)methanol.

Of the compounds of formula (I), or a stereoisomer, enantiomer or tautomer thereof or mixtures thereof, or a pharmaceutically acceptable salt or solvate thereof, as described above in the Summary of the Invention, a sixth embodiment are compounds of formula (I) wherein:

is a fused 5- or 6-membered N-heteroaryl substituted by substituted aryl, substituted aralkyl, substituted cycloalkyl or substituted heteroaryl;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ is alkyl and R$^{4b}$ is hydrogen;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl; and
each R$^8$ is independently selected from hydrogen or alkyl;
or a stereoisomer, enantiomer or tautomer thereof or mixtures thereof, or a pharmaceutically acceptable salt or solvate thereof.

Of this embodiment, an embodiment are compounds of formula (I) wherein:

is a fused pyrazolyl substituted by substituted aryl, substituted aralkyl, substituted cycloalkyl or substituted heteroaryl;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ is alkyl and R$^{4b}$ is hydrogen;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl; and
each R$^8$ is independently selected from hydrogen or alkyl.

Of this embodiment, a first embodiment are compounds of formula (I) wherein:

is a fused pyrazolyl substituted by aryl substituted by one or more substituents selected from halo, —R$^{10}$—OR$^{11}$ or —R$^{10}$—C(O)R$^{11}$;
R$^1$ is hydrogen;
R$^2$ is —R$^6$—OR$^7$;
R$^3$ is —R$^6$—OR$^7$ or —R$^6$—N(R$^8$)$_2$;
R$^{4a}$ is alkyl and R$^{4b}$ is hydrogen;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl;
each R$^8$ is independently selected from hydrogen or alkyl;
each R$^{10}$ independently is a direct bond or a straight or branched alkylene chain; and
each R$^{11}$ is independently hydrogen, alkyl, cycloalkyl, optionally substituted aryl, or optionally substituted heteroaryl.

Of this embodiment, an embodiment are compounds of formula (I) selected from:
(4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-1H-indazol-1-yl)phenyl)(phenyl)methanone;
(4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-2H-indazol-2-yl)phenyl)(phenyl)methanone;
((5R,6S)-5-((1S,3aS,4S,5S,7aR)-4-(aminomethyl)-1,7a-dimethyloctahydro-1H-inden-5-yl)-1-(4-fluorophenyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-1-(4-methoxyphenyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-2-(4-fluorophenyl)-5-methyl-4,5,6,7-tetrahydro-2H-indazol-6-yl)methanol;

((5R,6S)-5-((1S,3aS,4S,5S,7aR)-4-(aminomethyl)-1,7a-dimethyloctahydro-1H-inden-5-yl)-2-(4-methoxyphenyl)-5-methyl-4,5,6,7-tetrahydro-2H-indazol-8-yl)methanol;

((5R,6S)-5-((1S,3aS,4S,5S,7aR)-4-(aminomethyl)-1,7a-dimethyloctahydro-1H-inden-5-yl)-2-(4-(4-fluorophenoxy)phenyl)-5-methyl-4,5,6,7-tetrahydro-2H-indazol-6-yl)methanol;

((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol hydrochloride;

((5R,6S)-5-((1S,3aS,4S,5S,7aR)-4-(aminomethyl)-1,7a-dimethyloctahydro-1H-inden-5-yl)-5-methyl-2-(4-(pyridin-2-yloxy)phenyl)-4,5,6,7-tetrahydro-2H-indazol-6-yl)methanol;

((5R,6S)-5-((1S,3aS,4S,5S,7aR)-4-(aminomethyl)-1,7a-dimethyloctahydro-1H-inden-5-yl)-5-methyl-1-(4-(pyridin-2-yloxy)phenyl)-4,5,6,7-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-5-methyl-2-(4-(pyridin-4-yloxy)phenyl)-4,5,6,7-tetrahydro-2H-indazol-6-yl)methanol;

((5R,6S)-5-((1S,3aS,4S,5S,7aR)-4-(aminomethyl)-1,7a-dimethyloctahydro-1H-inden-5-yl)-5-methyl-1-(4-(pyridin-4-yloxy)phenyl)-4,5,6,7-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-5-methyl-1-(4-(pyridin-5-yloxy)phenyl)-4,5,6,7-tetrahydro-1H-indazol-6-yl)methanol; and ((5R,6S)-5-((1S,3aS,4S,5S,7aR)-4-(aminomethyl)-1,7a-dimethyloctahydro-1H-inden-5-yl)-5-methyl-2-(4-(pyrimidin-5-yloxy)phenyl)-4,5,6,7-tetrahydro-2H-indazol-6-yl)methanol.

Of this embodiment, a second embodiment are compounds of formula (I) wherein:

(A)

is a fused pyrazolyl substituted by aralkyl substituted by one or more substituents selected from halo, —$R^{10}$—$OR^{11}$ or —$R^{10}$—C(O)$R^{11}$;
$R^1$ is hydrogen;
$R^2$ is —$R^6$—$OR^7$;
$R^3$ is —$R^6$—$OR^7$ or —$R^6$—N($R^8$)$_2$;
$R^{4a}$ is alkyl and $R^{4b}$ is hydrogen;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl;
each $R^{10}$ is independently a direct bond or a straight or branched alkylene chain; and
each $R^{11}$ is independently hydrogen, alkyl, cycloalkyl or optionally substituted aryl.

Of this embodiment, an embodiment are compounds of formula (I) selected from:

((5R,6S)-5-((1S,3aS,4S,5S,7aR)-4-(aminomethyl)-1,7a-dimethyloctahydro-1H-inden-5-yl)-2-(4-methoxybenzyl)-5-methyl-4,5,6,7-tetrahydro-2H-indazol-6-yl)methanol; and ((5R,6S)-5-((1S,3aS,4S,5S,7aR)-4-(aminomethyl)-1,7a-dimethyloctahydro-1H-inden-5-yl)-1-(4-methoxybenzyl)-5-methyl-4,5,6,7-tetrahydro-1H-indazol-6-yl)methanol.

It is understood that any embodiment of the compounds of the invention, as set forth above, and any specific substituent set forth herein for a particular R group in the compounds of the invention, as set forth above, may be independently combined with other embodiments and/or substituents of compounds of the invention to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention.

Another embodiment of the invention are methods for treating inflammation in the presence or absence of pain in a mammal in need thereof is where the inflammation is an autoimmune disease, disorder or condition, an inflammatory disease, disorder or condition, or a neoplastic or cell proliferative disease, disorder or condition.

Another embodiment of the methods for treating inflammation in the presence or absence of pain in a mammal in need thereof is where the inflammation is an autoimmune disease, disorder or condition selected from idiopathic pulmonary fibrosis, an inflammatory bowel disease, rheumatoid arthritis, osteoarthritis, Still's Disease, Sjögren's Syndrome, systemic lupus erythematosus, multiple sclerosis, psoriasis and systemic sclerosis.

Another embodiment of the methods for treating inflammation in the presence or absence of pain in a mammal in need thereof is where the inflammation is an inflammatory bowel disease selected from Crohn's Disease and ulcerative colitis.

Another embodiment of the methods for treating inflammation in the presence or absence of pain in a mammal in need thereof is where the inflammation is an inflammatory disease, disorder or condition selected from acute respiratory distress syndrome, allergic rhinitis, Alzheimer's Disease, asthma, an ocular inflammatory disease, atopic dermatitis, bladder pain syndrome/interstitial cystitis, chronic prostatitis/chronic pelvic pain syndrome (CP/CPPS), chronic obstructive pulmonary disease (COPD) including emphysematous, bronchitic, and alpa 1 anti-trypsin deficiency related COPD; dermal contact hypersensitivy, eczema, eosiniphilic gastrointestinal disorder, fibromyalgia, gout, hepatic fibrosis, irritable bowel syndrome, ischemic reperfusion disease, kidney fibrosis, pancreatitis, Parkisons Disease, post operative inflammation, a seronegative spondyloarthropathy, and vasculitis.

Another embodiment of the methods for treating inflammation in the presence or absence of pain in a mammal in need thereof is where the inflammation is an ocular inflammatory disease selected from allergic conjunctivitis, dry eye, and uveitis.

Another embodiment of the methods for treating inflammation in the presence or absence of pain in a mammal in need thereof is where the inflammation is a seronegative spondyloarthropathy selected from anklyosing spondylitis, psoriatic arthritis, and Reiter's Syndrome.

Another embodiment of the methods for treating inflammation in the presence or absence of pain in a mammal in need thereof is where the inflammation is vasculitis selected from Wegener's Granulomatosis, polyarteritis nodosa, leucocytoclastic vasculitis, Churg-Strauss Syndrome, cryoglobulinemic vasculitis, and giant cell arteritis.

Another embodiment of the methods for treating inflammation in the presence or absence of pain in a mammal in need thereof is where the inflammation is a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

Another embodiment of the methods for treating pain in a mammal in need thereof is where the pain is acute pain, chronic pain, inflammatory pain, nociceptive pain, inflammatory nociceptive pain, neuropathic pain and any combinations thereof.

Another embodiment of the methods for treating pain in a mammal in need thereof is where the pain is in the absence or presence of inflammation.

Another embodiment of the invention is a method of using the compounds of the invention as standards or controls in in vitro or in vivo assays in determining the efficacy of test compounds in treating inflammation and/or pain.

In another embodiment of the invention, the compounds of the invention are isotopically-labeled by having one or more atoms therein replaced by an atom having a different atomic mass or mass number. Such isotopically-labeled (i.e., radiolabelled) compounds of the invention are considered to be within the scope of this invention. Examples of isotopes that can be incorporated into the compounds of the invention include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These isotopically-labeled compounds would be useful to help determine or measure the effectiveness of the compounds, by characterizing, for example, the site or mode of action for the modulation, or binding affinity to pharmacologically important site of action for the modulation. Certain isotopically-labeled compounds of the invention, for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the Synthetic Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

In other embodiments, preferred stereochemistry of the compounds of formula (I) is shown below:

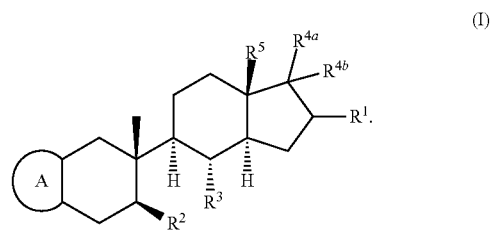

Specific embodiments of the compounds of the invention are described in more detail below in the Preparation of the Compounds of the Invention.

Utility and Testing of the Compounds of the Invention

Compounds and compositions of the invention are useful in treating inflammation and/or pain. In particular, the compounds and compositions of the invention may be used to treat inflammation in the absence of pain, inflammation in the presence of pain or pain in the absence of inflammation, preferably pain in the absence of visible inflammation.

Without being bound to any theory, and for the sole purpose of this invention, the term "inflammation" is intended to include, but not limited to, an autoimmune disease, disorder or condition, an inflammatory disease, disorder or condition, or a neoplastic or cell proliferative disease, disorder or condition; idiopathic pulmonary fibrosis, an inflammatory bowel disease, rheumatoid arthritis, osteoarthritis, Still's Disease, Sjögren's Syndrome, systemic lupus erythematosus, multiple sclerosis, psoriasis and systemic sclerosis; Crohn's Disease or ulcerative colitis; acute respiratory distress syndrome, allergic rhinitis, Alzheimer's Disease, asthma, an ocular inflammatory disease, atopic dermatitis, bladder pain syndrome/interstitial cystitis, chronic prostatitis/chronic pelvic pain syndrome (CP/CPPS), chronic obstructive pulmonary disease (COPD) including emphysematous, bronchitic, and alpa 1 antitrypsin deficiency related COPD; dermal contact hypersensitivity, eczema, eosiniphilic gastrointestinal disorder, fibromyalgia, gout, hepatic fibrosis, irritable bowel syndrome, ischemic reperfusion disease, kidney fibrosis, pancreatitis, Parkinson's Disease, postoperative inflammation, a seronegative spondyloarthropathy or vasculitis; allergic conjunctivitis, dry eye or uveitis; ankylosing spondylitis, psoriatic arthritis or Reiter's Syndrome; vasculitis selected from Wegener's Granulomatosis, polyarteritis nodosa, leucocytoclastic vasculitis, Churg-Strauss Syndrome, cryoglobulinemic vasculitis or giant cell arteritis; a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

For the sole purpose of this invention, the term "pain" is intended to include acute pain, chronic pain, inflammatory pain, nociceptive pain, inflammatory nociceptive pain, neuropathic pain and any combinations thereof. The types of pain intended to be treated by the compounds of the invention include, but are not limited to, pain associated with any of the above disclosed inflammatory diseases, disorders and conditions, burn pain, chronic bone pain, low back pain, neck pain, abdominal pain, somatic pain, visceral pain, myofascial pain, dental pain, cancer pain, chemotherapy pain, temporomandibular joint pain, trauma pain, surgical pain, post-surgical pain, labor pain, bladder pain, musculoskeletal pain, peripherally mediated pain, centrally mediated pain, headache pain, migraine pain, phantom limb pain, peripheral nerve injury pain, post-herpetic pain, non-cardiac chest pain, irritable bowel syndrome pain, fibromyalgia and combinations thereof.

The effectiveness of the compounds of the invention in treating inflammation and/or pain may be determined by any number of known in vitro and in vivo assays, including the assays set forth below in Biological Examples 1-15.

For example, the compounds of the invention may be tested in the following in vitro assays:
A. Rat or human dorsal root ganglion excitability assay (see, e.g., Young, G. T., et al., *Mol. Ther.* 22, 1530-43 (2014), and Tams, D., et al., *Nature Methods* 14 (2017)):
   This assay measures the effect of electrical field stimulation on the excitability of rat or human dorsal root ganglionic cells. Compounds which demonstrate the ability to decrease the excitability response of a cell when tested in this assay may be useful in treating neuropathic pain.
B. T-cell proliferation and cytokine release assay:
   This assay measures the inflammatory response.
C. Metabolism (microsomal stability) (see, e.g., Chiba, M, et al., *AAPS J.* 2009 11(2) 262):
   This assay measures a compound's stability against microsomal metabolism, which is a primary metabolic pathway: Compounds tested in this assay which are relatively more stable than others may be more effective in treating inflammation or pain.

Furthermore, the general value of the compounds of the of the invention in treating inflammation and pain may be established in industry standard animal models for demonstrating the efficacy of compounds in treating inflammation and pain. Examples of these animal models are as follows:
A. Mouse LPS challenge (see, e.g., Kabir, K. et al., *Shock*, 2002, 17(4), 300-3): This is a well-known animal model for inflammation.
B. Mouse formalin pain (see, e.g., Le Bars, D. et al., *Pharmacol. Rev.* 2001, 53(4), 597-652): This is a well-known model of inflammatory and neuropathic pain.
C. Rat TNBS Colitis (see, e.g., Antoniou, E., et al., *Ann Med Surg* (Lond), 2016, 11, 9-15):
   This is a model for inflammatory colitis and measures inflammatory response.
D. Rat CYP Cystitis (see, e.g., Golubeva, A. V., et al., *Physiol. Rev.*, 2014, 2(3), e00260 and Keay, S., et al., BMC Urol, 2012, 12, 17):
   This is a cyclophosphamide-induced cystitis model which measures the effect on visceral/abdominal/pelvic pain. This is directly supportive of use of the compounds for treating nociceptive pain.
E. Rat Ketamine cystitis (see, e.g., Jang, M.-Y., et al., *Urological Science*, 28(3), 123-7, 2017):
   This is a urogenital (upper and lower) model for pain.
F. Rat Chronic Prostatitis/Chronic Pelvic Pain (see, e.g., Radhakrishnan, R. and Nallu, R. S., 2009, *Inflammopharmacology*, 17:23-28):
   This is a model for assessing a compounds ability to treat prostatitis and prostate inflammatory pain.
G. Rat MIA-induced osteoarthritis (see, e.g., Guingamp, C., et al., *Arthritis and Rheumatism*, 40(9), 1997, 1670-9):
   This is a model for chronic nociceptive joint pain, which has both an inflammatory component and a nociceptive component.
H. Rat Carrageenan-induced hyperalgesia and paw edema (see, e.g., Morris, C. J., *Methods Mol. Biol.*, 2003, 225, 115-21): This is an inflammatory response model. It measures both inflammatory and pain responses.
I. Rat Complete Freund's Adjuvant model of inflammatory pain (see, e.g., Fehrenbacher, J. C., et al., *Curr. Protoc. Pharmacol.*, 2012 March, Chapter 5, Unit 5.4):
   This is well-known model for inflammatory pain, particularly in the joints.
J. Rat Spinal nerve ligation model of neuropathic pain (see, e.g., Chung, J. M., et al., *Methods in Molecular Medicine*, 2004, 99, 35-45):
   This is a model for neuropathic pain.
K. Mouse Bleomycin Lung Fibrosis Model (see, e.g., Moore, B. B., et al., *Am J Respir Cell Mol Biol*, 2013, 49(2), 167-79):
   This is an inflammatory response model.

Pharmaceutical Compositions of the Invention and Administration

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat inflammation and/or pain, and preferably with acceptable toxicity to the patient. Typically, the pharmaceutical compositions of the present invention may include a compound in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences* (Mack Pub. Co., N.J. current edition).

In another embodiment, the present invention provides a method for treating inflammation and/or pain generally and, more specifically, to treating the diseases, disorders and conditions as discussed above. Such methods include administering of a compound of the present invention to a mammal, preferably a human, in an amount sufficient to treat the inflammation and/or pain. In this context, "treat" includes prophylactic administration. Such methods include systemic administration of a compound of the invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

Preparation of the Compounds of the Invention

The General Reaction Schemes below illustrate methods to make intermediates and compounds of the present invention, i.e., compounds of formula (I), as set forth above in the Summary of the Invention.

The compounds of the present invention may be prepared by known organic synthesis techniques, including the methods described in more detail in the Synthetic Examples. In general, the compounds of formula (I) may be made by the following General Reaction Schemes, wherein all substituents are as defined above in the Summary of the Invention unless indicated otherwise. Although not generally depicted in the following schemes, one skilled in the art will understand that appropriate protecting group strategies may be useful in preparing compounds of formula (I). Protecting group methodology is well known to those skilled in the art (see, for example, Greene, T. W. and Wuts, P.G.M. Greene's *Protective Groups in Organic Synthesis* (latest edition). In particular, suitable protecting groups for an oxygen atom ("oxygen protecting groups") include, but are not limited to, acetyl, trialkylsilyl or diarylalkylsilyl (e.g., t-butydimethylsilyl, t-butyldiphenylsilyl or trimethylsilyl), tetrahydropyranyl, benzyl, and the like. Suitable protecting groups for a nitrogen atom ("nitrogen protecting groups") include, but are not limited to, benzhydryl (diphenylmethyl), t-butoxycarbonyl, benzyloxycarbonyl, trifluoroacetate, and the like.

It is also understood that one skilled in the art would be able to make the compounds of the invention by similar methods, by methods known to one skilled in the art, or by methods similar to the methods disclosed in U.S. Pat. Nos. 6,635,629, 7,601,874, and 9,765,085 and U.S. Published Patent Application No. 2017/0253596. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein. Certain starting materials, or their salts thereof, may be prepared according to the methods disclosed in U.S. Pat. Nos. 6,635,629, 7,601,874 and 9,765,085 and U.S. Published Patent Application No. 2017/0253596, the relevant disclosures therein are incorporated in reference herein, or by methods known to one skilled in the art.

It is also understood that in the following description, combinations of substituents and/or variables of the depicted formulae are permissible only if such contributions result in stable compounds.

It will also be appreciated by those skilled in the art, although protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

When a compound of the invention is depicted in the General Reaction Schemes below without stereochemistry, it is understood that one skilled in the art would readily recognize that such compounds could also be prepared in an optically pure form by utilizing methods known to one skilled in the art, such as the use of stereoselective reagents, chiral starting materials and phase transfer catalysts.

Abbreviations

The following abbreviations may be used herein in the following General Reaction Schemes and in the Synthetic Examples. If an abbreviation is not included below, it is understood to have its accepted meaning in the field to which it pertains:

Ac for acetyl;
$Ac_2O$ for acetic anhydride;
ACN for acetonitrile
AcOH for acetic acid;
BALF for Bronchoalveolar lavage fluid;
t-BuOH for tert-butanol;
t-BuOOH or TBHP for tert-butyl hydroperoxide;
CFA for Complete Freund's Adjuvant;
CP/CPPS for chronic prostatitis/chronic pelvic pain syndrome;
CSA for camphor sulfonic acid;
DCM for dichloromethane;
DMAP for 4-dimethylaminopyridine;
DMF for N,N-dimethylformamide;
DMP for Dess-Martin periodinane:
DMS for dimethyl sulphide;
DMSO for dimethyl sulfoxide;
DRG for Dorsal root ganglion;
EFS for Electrical field stimulation;
ELISA for enzyme-linked immunosorbent assay;
ELSD for Evaporative Light Scattering Detection;
Eq for equivalents;
EtOAc for ethyl acetate;
EtOH for ethanol;
Fluo 8-AM for Bis(acetoxymethyl) 2,2'-((4-(6-(acetoxymethoxy)-3-oxo-3H-xanthen-9-yl)-2-(2-(bis(2-acetoxymethoxy)-2-oxoethyl)amino)phenoxy)ethoxy)phenyl)azanediyl)diacetate;
h for hours;
$HCO_2Et$ for ethyl formate;
IP for intraperitoneal;
$LiAlH_4$ or LAH for lithium aluminum hydride;
LiHMDS for lithium bis(trimethylsilyl)amide;
LPS for Lipopolysaccharide;
m or min for minutes;
MeLi for methyllithium;
MeOH for methanol;
MIA for monosodium iodoacetate;
$Mn(OAc)_3$ for manganese (III) acetate;
MRM for multiple reaction monitoring;
MS for Mass spectrometry;
Ms for mesyl;
MsCl for mesyl chloride;

NADPH for the reduced form of nicotinamide adenine dinucleotide phosphate;
NaOMe for sodium methoxide;
NMO for N-methylmorpholine N-oxide;
NMR for nuclear magnetic resonance;
Pet ether for petroleum ether,
PPh$_3$ for triphenylphosphine;
PhN(Tf)$_2$ for N-phenyl-bis(trifluoromethanesulfonimide);
PhB(OH)$_2$ for phenyl boronic acid;
Pd(PPh$_3$)$_4$ for tetrakis(triphenylphosphine)palladium(0);
POCl$_3$ for phosphoryl chloride;
RB for round-bottom;
RT for room temperature;
s for second;
TBAF for tetrabutylammonium fluoride;
TBDPS for tert-butyldiphenylsilyl;
TBHP for tert-butyl hydroperoxide:
TBS or TBDMS for tert-butyldimethylsilyl;
TBSCl or TBDMSCl for tert-butyldimethylsilyl chloride;
TEA for triethylamine;
TFA for trifluoroacetic acid;
THF for tetrahydrofuran;
TLC for thin layer chromatography;
TNBS for 2,4,6-trinitrobenzenesulfonic acid;
TPAP for tetrapropylammonium perruthenate;
t$_R$ for retention time;
TTX for tetrodotoxin;
UHPLC for ultra high-pressure liquid chromatography; and
UV for ultraviolet.

The following General Methods and Procedures were used to prepare, seperate or characterize individual compounds of the invention. It will be appreciated that in the following general methods, reagent levels and relative amounts or reagents/intermediates can be changed to suit particular compounds to be synthesized, up or down by up to 50% without significant change in expected results.

1. General LC/MS Analytical Methods

| Method # | Column Details | A | B | Flow rate (ml/min) | | T1 | T2 | T3 | T4 | T5 |
|---|---|---|---|---|---|---|---|---|---|---|
| Ia | A | 0.1% TFA in water | 0.1% TFA in ACN | 1.5 | Time | 0 | 2.5 | 4.5 | 4.6 | 6 |
|   |   |   |   |   | % B | 10 | 95 | 95 | 10 | 10 |
| Ib | B |   | ACN | 2 | Time | 0 | 8 | 8.1 | 8.5 | 10 |
|   |   |   |   |   | % B | 5 | 100 | 100 | 5 | 5 |
| Ic | B | 0.1% TFA in water:ACN (95:5) | 0.1% TFA in ACN | 1.5 | Time | 0 | 2.5 | 4 | 4.5 | 6 |
|   |   |   |   |   | % B | 5 | 95 | 95 | 5 | 5 |
| Id | C | 0.1% formic in water:ACN (95:5) | ACN | 1.5 | Time | 0 | 2.5 | 4 | 4.5 | 6 |
|   |   |   |   |   | % B | 5 | 95 | 95 | 5 | 5 |
| Ie | B | 10 mM NH$_4$HCO$_3$ in water | ACN | 2 | Time | 0 | 4 | 5 | 5.5 | 6.5 |
|   |   |   |   |   | % B | 10 | 95 | 95 | 10 | 10 |
| 1f | A | 0.1% formic acid in water | ACN | 1.5 | Time | 0 | 3 | 5 | 5.5 | 6 |
|   |   |   |   |   | % B | 50 | 95 | 95 | 50 | 50 |
| 1g | B | 10 mM NH$_4$HCO$_3$ in water | ACN | 1 | Time | 0 | 8 | 8.1 | 8.5 | 10 |
|   |   |   |   |   | % B | 5 | 100 | 100 | 5 | 5 |
| 1h | B | 10 mM NH$_4$HCO$_3$ in water | ACN | 1.2 | Time | 0 | 2.5 | 5.0 | 5.5 | 7 |
|   |   |   |   |   | % B | 50 | 95 | 95 | 50 | 50 |
| 1i | D | ACN | 0.1% formic acid in water | 1.5 | Time | 0 | 2.5 | 4.5 | 4.6 | 6 |
|   |   |   |   |   | % B | 10 | 95 | 95 | 10 | 10 |
| 1j | E | 10 mM NH$_4$HCO$_3$ in water | ACN | 1.2 | Time | 0 | 2.5 | 5.0 | 5.5 | 7 |
|   |   |   |   |   | % B | 50 | 95 | 95 | 50 | 50 |
| 1k | E | 10 mM NH$_4$HCO$_3$ in water | ACN | 1.2 | Time | 0 | 3.5 | 4.5 | 5.0 | 6.0 |
|   |   |   |   |   | % B | 10 | 95 | 95 | 10 | 10 |
| 1l | B | 0.1% formic in water:ACN (95:5) | 0.1% TFA in ACN | 1.8 | Time | 0 | 2.5 | 7.0 | 7.1 | 8 |
|   |   |   |   |   | % B | 80 | 98 | 98 | 80 | 80 |

Column details:
A: Atlantis dC18 (50 × 4.6 mm, 5 μm),
B: XBridge C8 (50 × 4.6 mm, 3.5 μm),
C: Zorbax XDB C18 (50 × 4.6 mm, 3.5 μm),
D: Zorbax C18 (50 × 4.6 mm, 5 μm),
E: Zorbax Extend C18 (50 × 4.6 mm, 5 μm), 2. General HPLC Analytical Methods

| Method # | Column Details | A | B | Flow rate (ml/min) | | T1 | T2 | T3 | T4 | T5 |
|---|---|---|---|---|---|---|---|---|---|---|
| 2a | B | 0.1% TFA in water | 0.1% TFA in ACN | 2 | Time % B | 0 5 | 8 100 | 8.1 100 | 8.5 5 | 10 5 |
| 2b | F | 10 mM NH$_4$HCO$_3$ in water | ACN | 1 | Time % B | 0 10 | 15 100 | 20 100 | 26 10 | 30 10 |
| 2c | A | 0.1% TFA in water | 0.1% TFA in ACN | 1.5 | Time % B | 0 5 | 8 100 | 8.1 100 | 8.5 5 | 10 5 |
| 2d | G | 0.1% TFA in water | ACN | 1 | Time % B | 0 10 | 15 100 | 20 100 | 26 10 | 30 10 |
| 2e | B | 10 mM NH$_4$HCO$_3$ in water | ACN | 1 | Time % B | 0 5 | 8 100 | 8.1 100 | 8.5 5 | 10 5 |

Column details:
A: Atlantis dC18 (50 × 4.6 mm, 5 µm),
B: XBridge C8 (50 × 4.6 mm, 3.5 µm),
C: Zorbax XDB C18 (50 × 4.6 mm, 3.5 µm),
F: Phenomenex Gemini C18 (150 × 4.6 mm, 3.0 µm),
G: Atlantis dC18 (250 × 4.6 mm, 5 µm)

3. General Preparative HPLC Methods

| Method # | Column Details | A | B | Flow rate (ml/min) |
|---|---|---|---|---|
| 3a | H | 0.1% TFA in water | 0.1% TFA in ACN | 15 |
| 3b | H | 0.1% formic acid in water:ACN (95:5) | ACN | 15 |
| 3c | I | 10 mM NH$_4$OAc in water | ACN | 22 |
| 3d | I | Water | ACN | 22 |
| 3e | H | 0.1% TFA in water | ACN | 15 |

Column details: H: Sunfire C18 (19 × 150 mm, 5 µm), I: YMC-triart C18 (30 × 250 mm, 5 µm)

General Procedure A

Acetylation with Ac$_2$O

To a stirred solution of the alcohol (1 equivalent) in pyridine at 0° C. were added DMAP (0.05 equivalent) and Ac$_2$O (1 equivalent) and the resultant solution was stirred at ambient temperature. In a standard workup, the mixture was concentrated under reduced pressure, diluted with EtOAc and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure B

TBS Protection of Alcohols

To a stirred solution of the alcohol (1 equivalent) in DMF at ambient temperature was added imidazole (2 equivalents) followed by TBSCl (1 equivalent) at 0° C. The resulting mixture was stirred at ambient temperature. In a standard workup, the mixture was concentrated under reduced pressure, diluted with CH$_2$Cl$_2$ and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure C

Allylic Oxidation with TBHP/Cat

1. Option using Copper(I)Iodide
To a stirred solution of the alkene (1 equivalent) in CH$_2$Cl$_2$:ACN (1:1) at 0° C. were added (TBHP in decane (5 equivalents) and copper(I)iodide (0.1 equivalent) and the resultant mixture was stirred at ambient temperature for 12 hours. In a standard workup, the mixture was concentrated under reduced pressure, diluted with EtOAc and washed consecutively with water and brine. The combined organic extracts were dried (Na$_2$SO$_4$ or MgSO$_4$), filtered and concentrated under reduced pressure. The crude material was purified by flash column chromatography on silica gel.

2. Option Using Manganese(III)Acetate Dihydrate:
To a stirred solution of the alkene (1 equivalent) in CH$_2$Cl$_2$:ACN:EtOAc (1:1:1) at room temperature were added TBHP in decane (5.2 equivalents) and 4 Å molecular sieves, the resultant mixture was stirred at room temperature for 0.5 hours. At this point, was added Mn(OAc)$_3$.2H$_2$O (0.1 equivalent) and stirring was continued overnight at ambient temperature. In a standard workup, the mixture was filtered through a bed of CELITE® and the filtrate was concentrated under reduced pressure. The crude material was purified by flash column chromatography on silica gel.

3. Option Using Selenium Dioxide:
To a stirred solution of the alkene (1 equivalent) in CH$_2$Cl$_2$ at 0° C. were added TBHP in decane (5 equivalents) and SeO$_2$ (0.5 equivalent) and the resultant mixture was stirred at ambient temperature for 12 hours. In a standard workup, the mixture was diluted with CH$_2$Cl$_2$ and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure D

Hydroboration Sequence

To a stirred solution of the ketone (1 equivalent) in THF at 0° C. was added Borane in THF (1 M, 2.23 equivalents).

The resulting mixture was stirred at same temperature for 12 hours. The mixture was quenched with dropwise addition of purified chilled water and stirred for 15 minutes. To the resulting mixture was added sodium perborate tetrahydrate at ambient temperature and stirred for 3 hours. In a standard workup, the mixture was diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure E

Ketal/Acetal Deprotection with AcOH

The Ketal/Acetal protected moiety (1 equivalent) was dissolved in 80% aqueous AcOH. The resulting mixture was heated to 65° C. and stirred for 1 hour. In a standard workup, the mixture was concentrated under reduced pressure and diluted with saturated aqueous $NaHCO_3$. The aqueous was extracted with $CH_2Cl_2$. The combined organic extracts were washed with brine, dried ($Na_2SO_4$ or $MgSO_4$), filtered and concentrated under reduced pressure. The crude material was purified by flash column chromatography on silica gel.

General Procedure F $NaIO_4$ Diol Cleavage

To a stirred solution of the alcohol (1 equivalent) in THF and water (2:1) at ambient temperature was added $NaIO_4$ (2 equivalents). The resulting mixture was stirred at room temperature for 1 hour. In a standard workup, the mixture was diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure G $NaBH_4$ Reduction of Carbonyls

To a stirred solution of the carbonyl compound (1 equivalent) in MeOH at room temperature was added $NaBH_4$ (2 equivalents). The resulting mixture was stirred at ambient temperature 4 hours. In a standard workup, the mixture was concentrated under reduced pressure and diluted with EtOAc and washed consecutively with saturated aqueous $NaHCO_3$ and brine. The combined organic extracts were dried ($Na_2SO_4$ or $MgSO_4$), filtered and concentrated under reduced pressure. The crude material was purified by flash column chromatography on silica gel.

General Procedure H

Acetonide Formation with 2,2-Dimethoxypropane

To a stirred solution of the diol (1 equivalent) in 2,2-dimethoxypropane at 0° C. was added camphorsulphonic acid (0.1 equivalent). The resulting mixture was stirred at ambient temperature 2-4 hours. In a standard workup, the mixture was concentrated under reduced pressure and diluted with EtOAc and washed consecutively with saturated aqueous $NaHCO_3$ and brine. The combined organic extracts were dried ($Na_2SO_4$ or $MgSO_4$), filtered and concentrated under reduced pressure. The crude material was purified by flash column chromatography on silica gel.

General Procedure I

Mesylate Formation

To a stirred solution of the alcohol (1 equivalent) in pyridine at 0° C. was added MsCl (2 equivalents). The resulting mixture was stirred at ambient temperature for 1 hour. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure J

Azide Introduction

To a stirred solution of the mesylate (1 equivalent) in DMF at ambient temperature was added $NaN_3$ (3 equivalents). The resulting mixture was stirred at 80° C. for 8 hours. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure K $K_2CO_3$ Deprotection of Esters/TFA Amides

To the stirred solution of the ester/TFA-protected amide (1 equivalent) in MeOH at ambient temperature was added $K_2CO_3$ (2 equivalents) and few drops of water. The resulting mixture was heated to reflux for 2 hours. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure L

TPAP/NMO Oxidation

To a stirred solution of the alcohol (1 equivalent) in $CH_2Cl_2$ at 0° C. were added $NMO-H_2O$ (2 equivalents), 4 Å molecular sieves and TPAP (0.1 equivalents). The resulting mixture was stirred at ambient temperature for 2 hours. In a standard workup, the mixture was diluted with $CH_2Cl_2$ and filtered through a bed of CELITE® and the filtrate was concentrated under reduced pressure. The crude material was purified by flash column chromatography on silica gel.

General Procedure M

Dess-Martin Periodinane Oxidation

To a stirred solution of the alcohol (1 equivalent) in $CH_2Cl_2$ at 0° C. was added Dess-Martin periodinane (2 equivalents). The resulting mixture was stirred at ambient temperature for 2 hours. In a standard workup, the mixture was diluted with $CH_2Cl_2$ and washed consecutively with saturated aqueous $NaHCO_3$ and brine. The combined organic extracts were dried ($Na_2SO_4$ or $MgSO_4$), filtered and concentrated under reduced pressure. The crude material was purified by flash column chromatography on silica gel.

General Procedure N

Knoevenagel Condensation

To a stirred solution of the sodium hydride (60% dispersion in mineral oil) (4 equivalents) in THF at 0° C. was added the ketone in THF (1 equivalent) dropwise. The resulting mixture was stirred at same temperature for 2 hours. To the resulting mixture was added ethyl formate (6 equivalents) at 0° C. and stirred at ambient temperature for 8 hours. In a standard workup, the mixture was quenched with a saturated aqueous solution of $NH_4Cl$ and the aqueous layer extracted with EtOAc. The combined organic extracts were washed with brine, dried ($Na_2SO_4$ or $MgSO_4$), filtered and concentrated under reduced pressure. The crude material was purified by flash column chromatography on silica gel.

Alternative conditions for the Knoevenagel condensation include the following: To a stirred solution of the ketone in toluene at 0° C. were added sodium methoxide solution (25% wt. in MeOH, 1.5-3 equivalents) and ethyl formate (5-6 equivalents) dropwise and the resultant solution stirred at ambient temperature for 16 hours. In a standard workup, the mixture was concentrated under reduced pressure and diluted with chilled water. The aqueous layer was extracted with EtOAc, washed with brine and the organic layer dried ($Na_2SO_4$ or $MgSO_4$), filtered, concentrated and purified by silica gel chromatography, if required.

General Procedure O

Hydrazine Condensation to Form Pyrazoles

To a stirred solution of the ketone (1 equivalent) in EtOH at ambient temperature was added hydrazine hydrate (2 equivalents) dropwise. The resulting mixture was heated to 70° C. and stirred for 2 hours. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure P

TBS Deprotection with TBAF

The TBS silyl ether (1 equivalent) was dissolved in THF and TBAF (1 M in THF, 2 equivalents) was added at ambient temperature. The mixture was heated to 65° C. and stirred for 2 hours. In a standard workup, the mixture was diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure Q

Azide Reduction with $PPh_3$

To a stirred solution of the azide (1 equivalent) in THF and water (9:1) at ambient temperature was added $PPh_3$ (2 equivalents). The mixture was heated to 60° C. and stirred for 4 hours. In a standard workup, the mixture was diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure R

Azide Reduction with Lithium Aluminum Hydride

To a stirred solution of the azide (1 equivalent) in THF at 0° C. was added LAH (1 M in THF, 2 equivalents) dropwise. The mixture was stirred at room temperature for 4 hours. In a standard workup, the mixture was quenched with saturated solution of $Na_2SO_4$ and filtered through a bed of CELITE®, the aqueous was extracted with EtOAc. The combined organic extracts were washed with brine, dried ($Na_2SO_4$ or $MgSO_4$), filtered and concentrated under reduced pressure. The crude material was purified by flash column chromatography on silica gel.

General Procedure S

Pd-Catalyzed Hydrogenation of Double Bonds

To a stirred solution of the alkene (1 equivalent) in EtOAc at room temperature was added 10% Pd/C (~5-10% of alkene weight) under a nitrogen atmosphere. The mixture was stirred at room temperature for 2-4 hours under 1 hydrogen atmosphere using a balloon. In a standard workup, the mixture was filtered through a bed of CELITE® and filtrate was concentrated under reduced pressure. The crude material was purified by flash column chromatography on silica gel.

General Procedure T

HCl Salt Formation

To a stirred solution of amine (1 equivalent) in MeOH at 0° C. was added HCl solution (2 M) in diethyl ether (5 volumes) and the resultant solution was stirred at 0° C. for 1 hour. The mixture was concentrated under reduced pressure. Diethyl ether was added, the solution was stirred for 10 minutes and filtered. The resulting compound was allowed to dry for approx. 1 hour.

General Reaction Schemes

The following General Reaction Schemes illustrate methods to make compounds of formula (I), or stereoisomers, enantiomers or tautomers thereof or mixtures thereof, or pharmaceutically acceptable salts or solvates thereof, as set forth above in the Summary of the Invention.

General Reaction Scheme 1

Compounds of formula (I-1) are compounds of formula (I), as described above in the Summary of the Invention, and may be prepared according the following General Reaction Scheme 1 wherein $R^5$ is as described above in the Summary of the Invention, $R^{4a}$ and $R^1$ together form an optionally substituted bicyclic heterocyclyl, $R^{4b}$ is hydrogen, $Pg^1$ is an oxygen protecting group, such as tert-butydimethylsilyl or tert-butyldiphenylsilyl and X is halo, preferably chloro:

GENERAL REACTION SCHEME 1
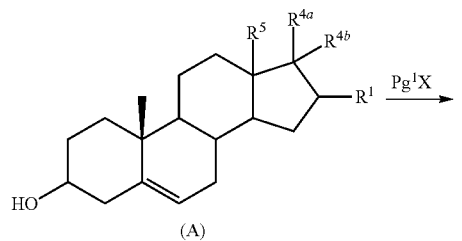
(A)
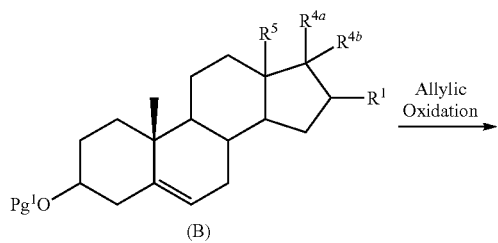
(B)
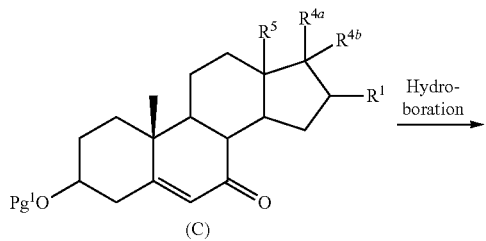
(C)
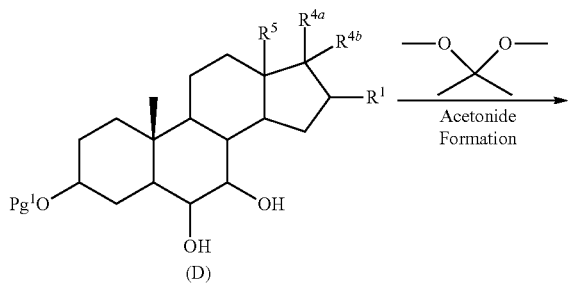
(D)
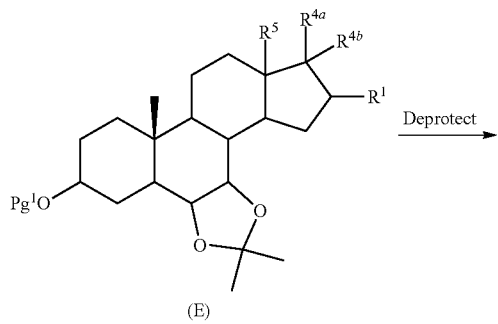
(E)
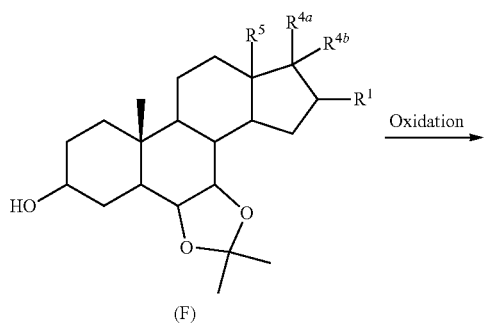
(F)
-continued
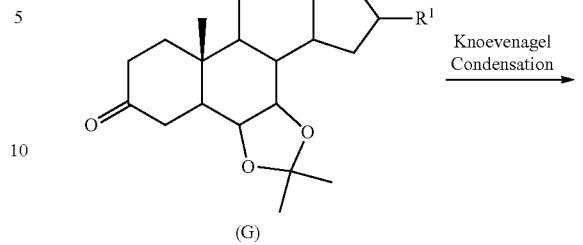
(G)
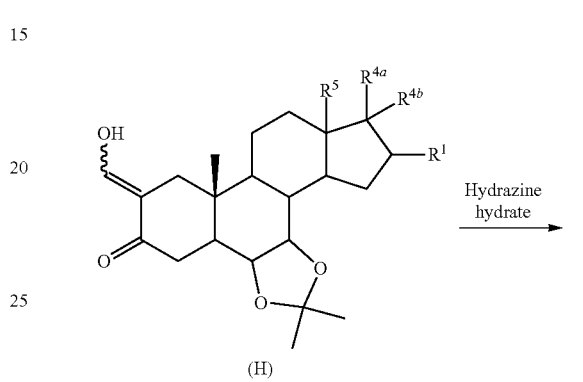
(H)
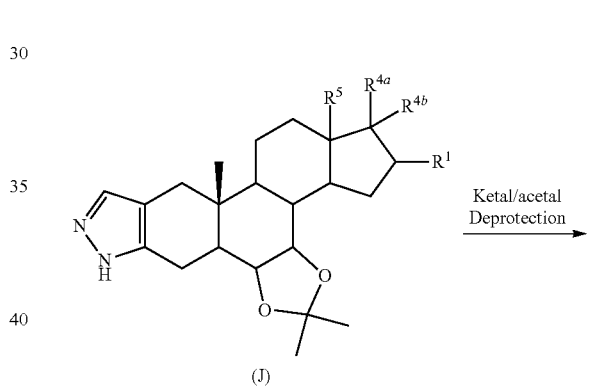
(J)
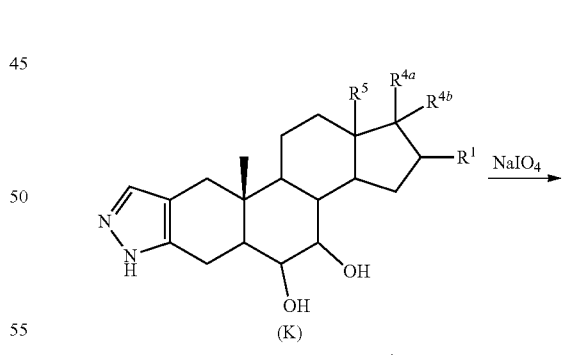
(K)
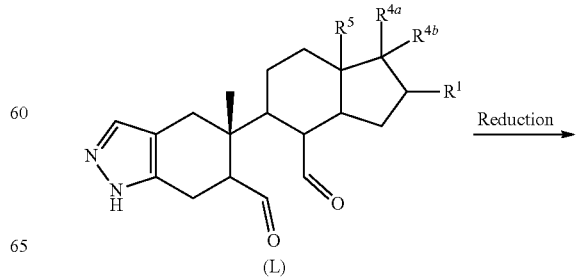
(L)

-continued

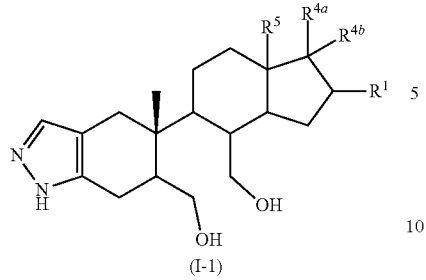

(I-1)

Compounds of formula (A) are commercially available, such as diosgenin, or may be prepared accordingly to methods known to one skilled in the art.

In general, compounds of formula (I-1) are prepared by first treating a compound of formula (A) under appropriate under appropriate General Procedure B conditions to yield a compound of formula (B), which is then treated under appropriate General Procedure C conditions to yield a compound of formula (C), which is then treated under appropriate General Procedure D conditions to yield a compound of formula (D), when is then treated with 2,2-dimethoxypropane under appropriate General Procedure H conditions to yield a compound of formula (E), which is then treated under appropriate General Procedure P conditions to yield a compound of formula (F), which is then oxidized under appropriate General Procedure M conditions to yield a compound of formula (G), which is then treated under appropriate General Procedure N conditions to yield a compound of formula (H), when is then treated with hydrazine hydrate under appropriate General Procedure O conditions to yield a compound of formula (J), when is then treated under appropriate General Procedure E conditions to yield a compound of formula (K), when is then treated under appropriate General Procedure F conditions to yield a compound of formula (L), which is then treated under appropriate General Procedure G conditions to yield a compound of formula (I-1).

An embodiment of General Reaction Scheme 1 is described in more detail below in Synthetic Example 1.

General Reaction Scheme 2

Compounds of formula (I-2) are compounds of formula (I), as described above in the Summary of the Invention, and may be prepared according the following General Reaction Scheme 2 wherein $R^5$ is as described above in the Summary of the Invention, $R^{4a}$ and $R^1$ together form an optionally substituted bicyclic heterocyclyl and $R^{4b}$ is hydrogen:

GENERAL REACTION SCHEME 2

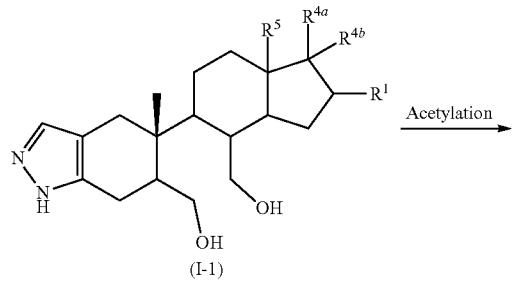

(I-1)

-continued

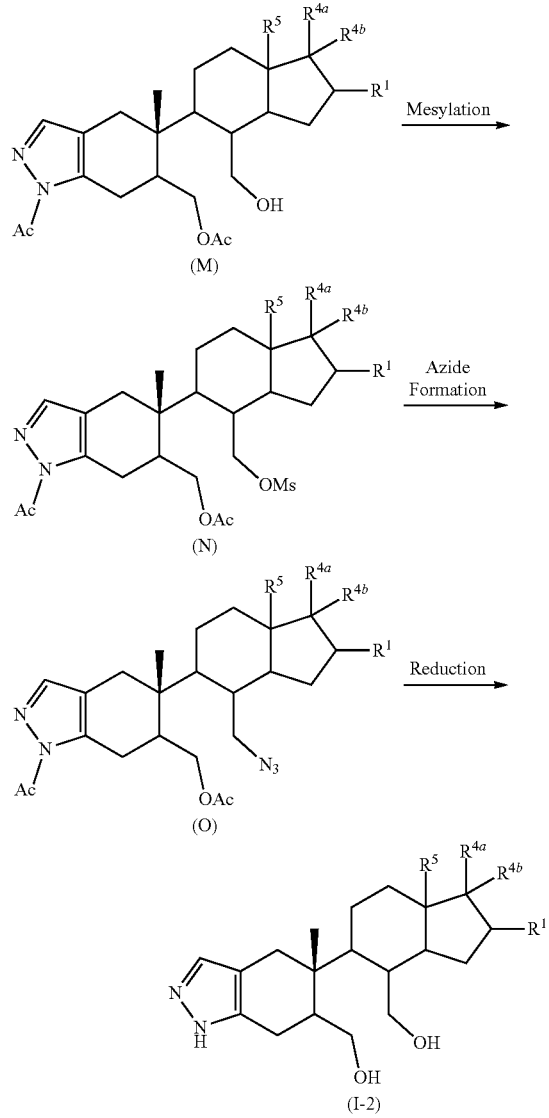

Compounds of formula (I-1) are prepared herein in Reaction Scheme 1 and in Synthetic Example 1.

In general, compounds of formula (I-2) are prepared by first treating a compound of formula (I-1) under the appropriate General Procedure A conditions to yield a compound of formula (M), which is then treated under the appropriate General Procedure I conditions to yield a compound of formula (N), which is then treated under the appropriate General Procedure J conditions to yield a compound of formula (O), when is then treated under the appropriate General Procedure R conditions to yield the compound of formula (I-2).

An embodiment of General Reaction Scheme 2 is described in more detail below in Synthetic Example 2.

General Reaction Scheme 3

Compounds of formula (I-3) are compounds of formula (I), as described above in the Summary of the Invention, and may be prepared according the following General Reaction Scheme 3 wherein $R^1$ is hydrogen, $R^5$ is methyl, $R^{4b}$ is hydrogen, alkyl or optionally substituted heteroaryl, $Pg^1$ is an oxygen protecting group, such as tert-butydimethylsilyl or tert-butyldiphenysilyl and X is halo, preferably chloro:

GENERAL REACTION SCHEME 3

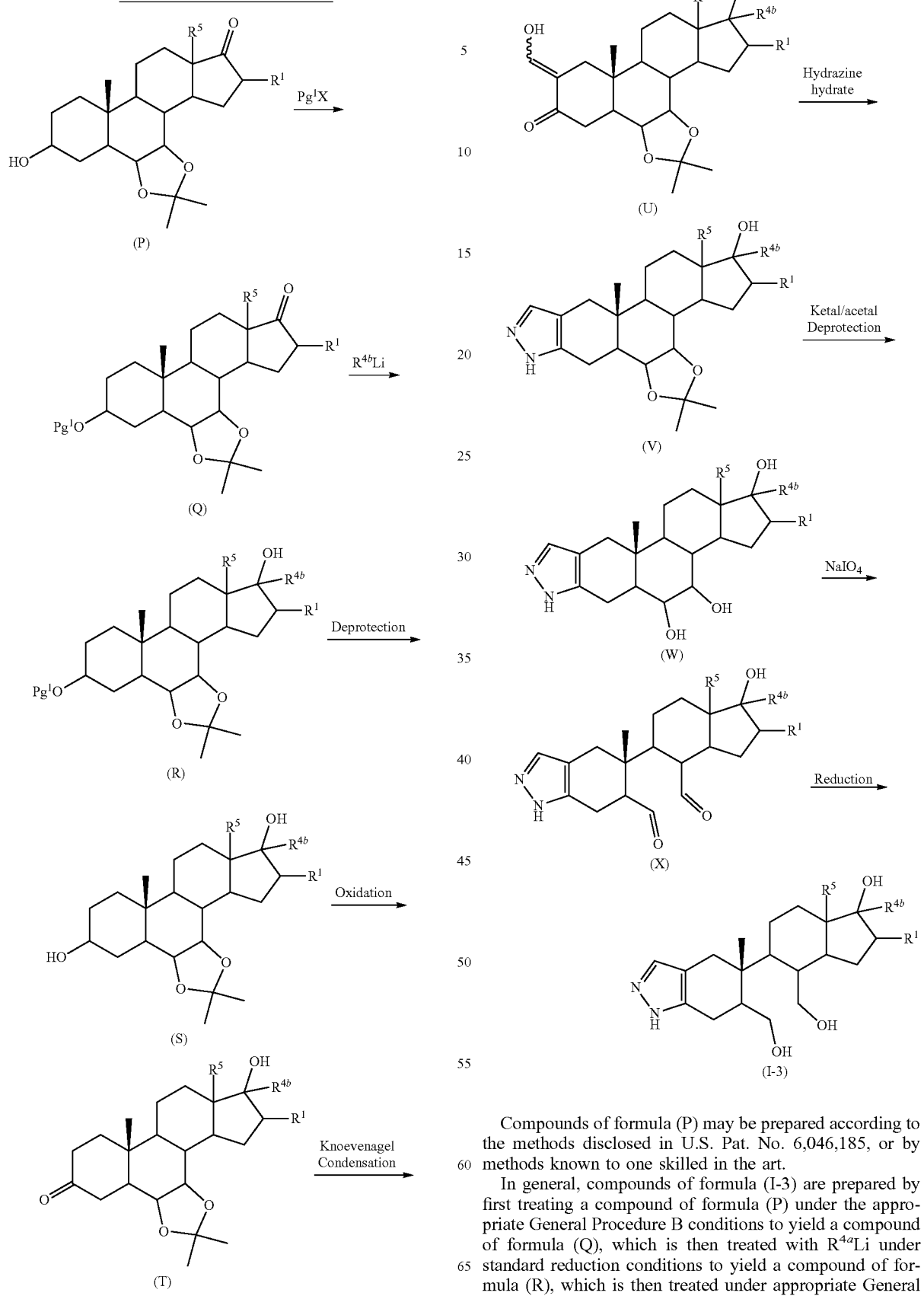

Compounds of formula (P) may be prepared according to the methods disclosed in U.S. Pat. No. 6,046,185, or by methods known to one skilled in the art.

In general, compounds of formula (I-3) are prepared by first treating a compound of formula (P) under the appropriate General Procedure B conditions to yield a compound of formula (Q), which is then treated with $R^{4a}Li$ under standard reduction conditions to yield a compound of formula (R), which is then treated under appropriate General Procedure P conditions to yield a compound of formula (S), which is then treated under appropriate General Procedure M conditions to yield a compound of formula (T), which is then treated under appropriate General Procedure N conditions to yield a compound of formula (U), which is then treated under appropriate General Procedure O conditions to yield a compound of formula (V), which is then treated under appropriate General Procedure E conditions to yield a compound of formula (W), which is then treated under appropriate General Procedure F conditions to yield a compound of formula (X), which is then treated under appropriate General Procedure G conditions to yield a compound of formula (I-3).

An embodiment of General Reaction Scheme 3 is described in more detail below in Synthetic Example 3 and Synthetic Example 8.

Alternatively, when $R^{4b}$ is an optionally substituted heteroaryl, the compound of formula (S) can be treated under appropriate General Procedure L conditions to form a compound of formula (T), when is the treated as described above to form a compound of formula (I-3).

An embodiment of this alternate reaction scheme is described in more detail below in Synthetic Example 4.

General Reaction Scheme 4

Compounds of formula (I-4) are compounds of formula (I), as described above in the Summary of the Invention, and may be prepared according the following General Reaction Scheme 4 wherein $R^1$ is hydrogen, $R^5$ is as described above in the Summary of the Invention, $R^{4a}$ is optionally substituted aryl, and $Pg^1$ is an oxygen protecting group, such as tert-butydimethylsilyl or tert-butyldiphenylsilyl:

GENERAL REACTION SCHEME 4

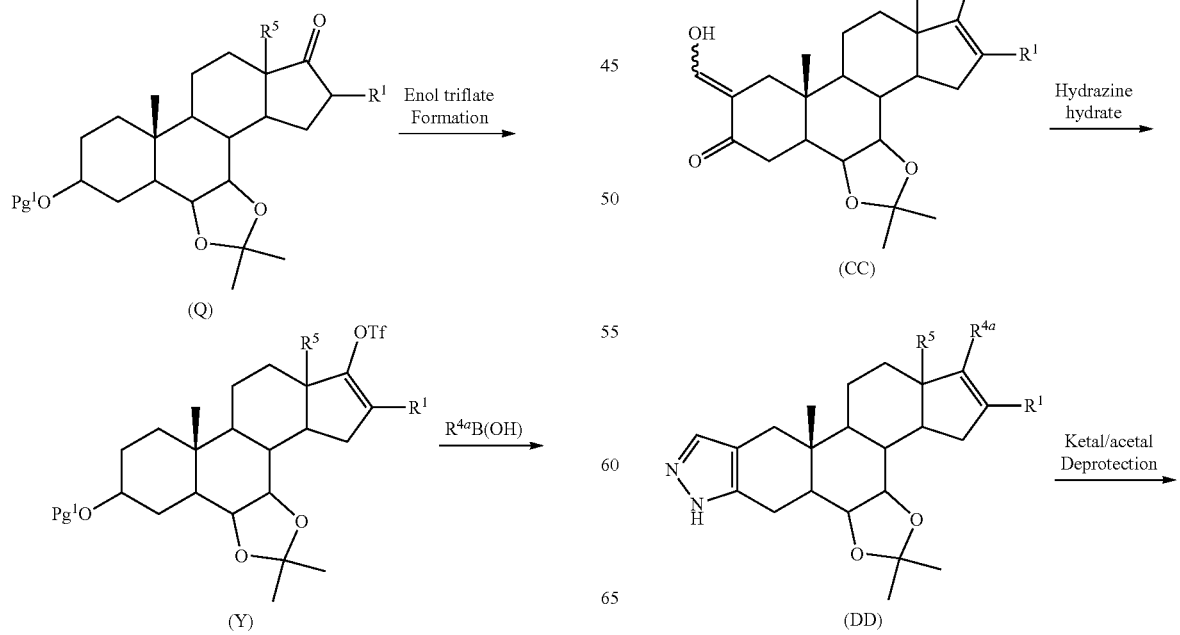

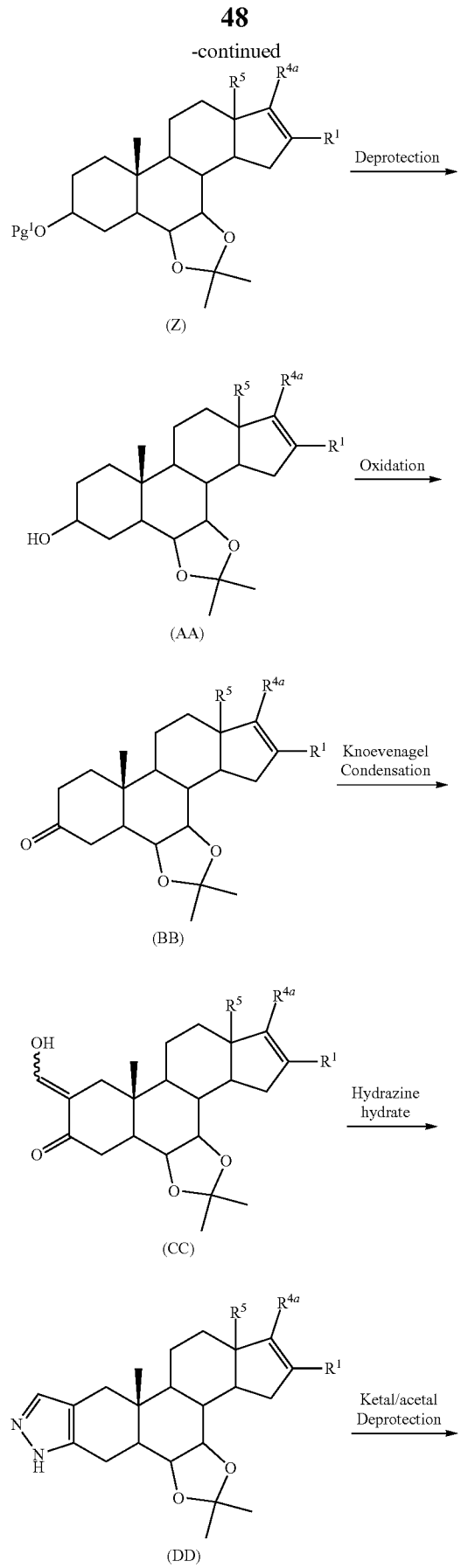

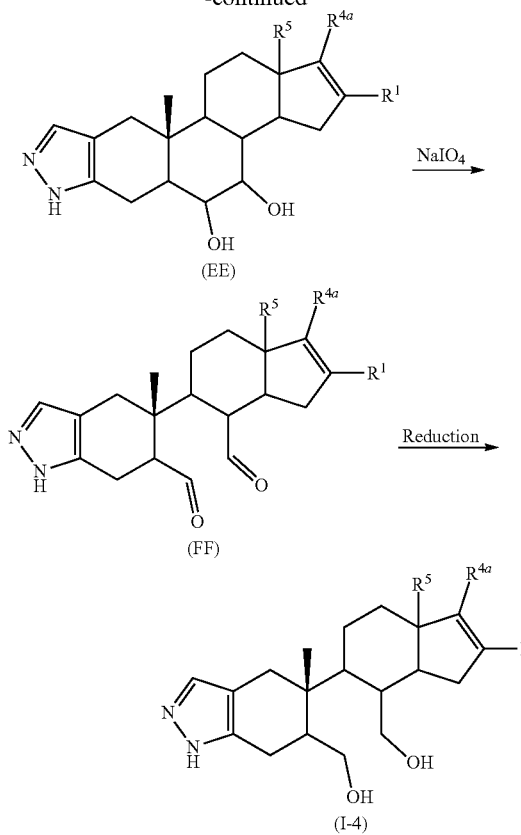

Compounds of formula (Q) may be prepared according to the methods disclosed herein or by methods known to one skilled in the art.

In general, compounds of formula (I-4) are prepared by first treating a compound of formula (Q) under appropriate enol triflate formation conditions to yield the compound of formula (Y), which is then treated with $R^{4a}B(OH)$ under the appropriate cross coupling conditions to yield a compound of formula (Z), which is then treated under the appropriate General Procedure P conditions to yield a compound of formula (AA), which is then treated under the appropriate General Procedure L conditions to yield a compound of formula (BB), which is then treated under the appropriate General Procedure N conditions to yield a compound of formula (CC), which is then treated under the appropriate General Procedure O conditions to yield a compound of formula (DD), which is then treated under the appropriate General Procedure E conditions to yield a compound of formula (EE), which is then treated under the appropriate General Procedure F conditions to yield a compound of formula (FF), which is then treated under the appropriate General Procedure G conditions to yield a compound of formula (I-4).

An embodiment of General Reaction Scheme 4 is described in more detail below in Synthetic Example 5.

General Reaction Scheme 5

Compounds of formula (I-5) are compounds of formula (I), as described above in the Summary of the Invention, and may be prepared according the following General Reaction Scheme 5 wherein $R^1$ is hydrogen, $R^5$ is as described above in the Summary of the Invention, $R^{4a}$ is optionally substituted aryl, $Pg^1$ is an oxygen protecting group, such as tert-butydimethylsilyl or tert-butyldiphenylsilyl and X is halo, preferably chloro:

GENERAL REACTION SCHEME 5

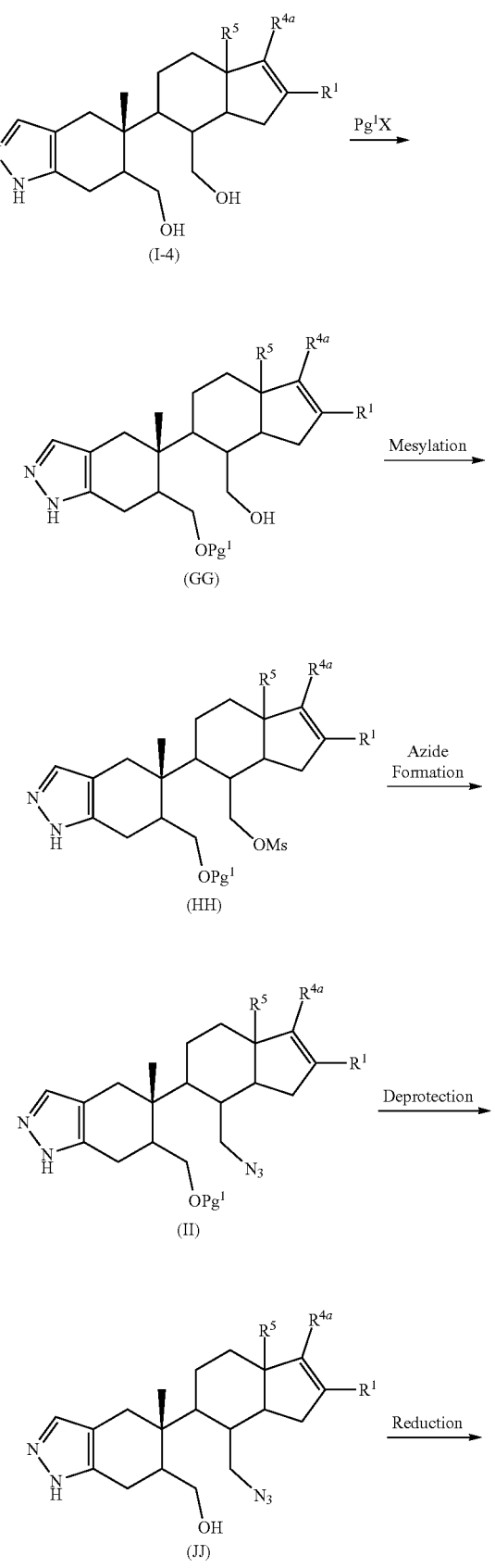

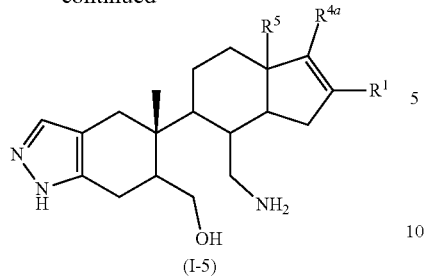

(I-5)

Compounds of formula (I-4) may be prepared according to the methods disclosed herein or by methods known to one skilled in the art.

In general, compounds of formula (I-5) are prepared by first treating a compound of formula (I-4) under the appropriate General Procedure B conditions to yield a compound of formula (GG), which is then treated under the appropriate General Procedure I conditions to yield a compound of formula (HH), which is then treated under the appropriate General Procedure J conditions to yield a compound of formula (II), which is then treated under the appropriate General Procedure P conditions to yield a compound of formula (JJ), which is then treated under the appropriate General Procedure Q conditions to yield a compound of formula (I-5).

An embodiment of General Reaction Scheme 5 is described in more detail below in Synthetic Example 6.

General Reaction Scheme 6

Compounds of formula (I-6) are compounds of formula (I), as described above in the Summary of the Invention, and may be prepared according the following General Reaction Scheme 6 wherein $R^1$ is hydrogen, $R^5$ is as described above in the Summary of the Invention $Pg^1$ is an oxygen protecting group, such as tert-butydimethylsilyl or tert-butyldiphenysilyl and X is halo, preferably chloro:

GENERAL REACTION SCHEME 6

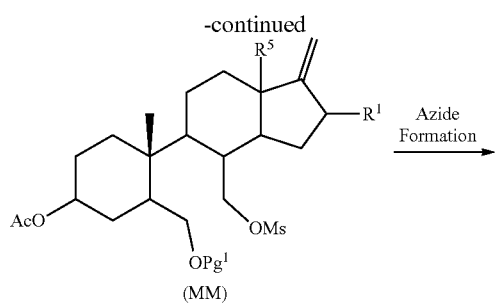

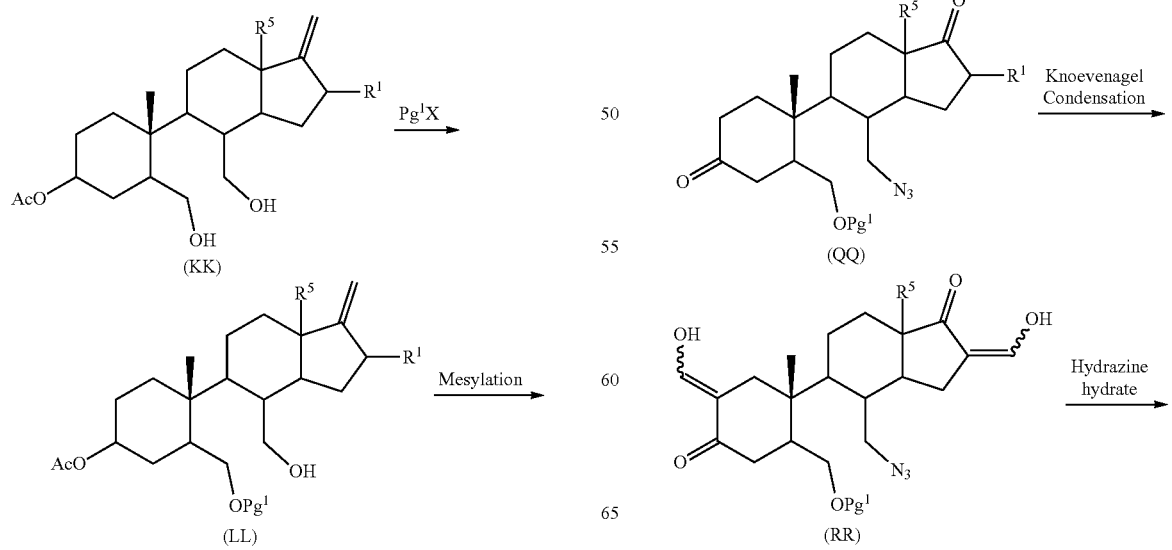

-continued

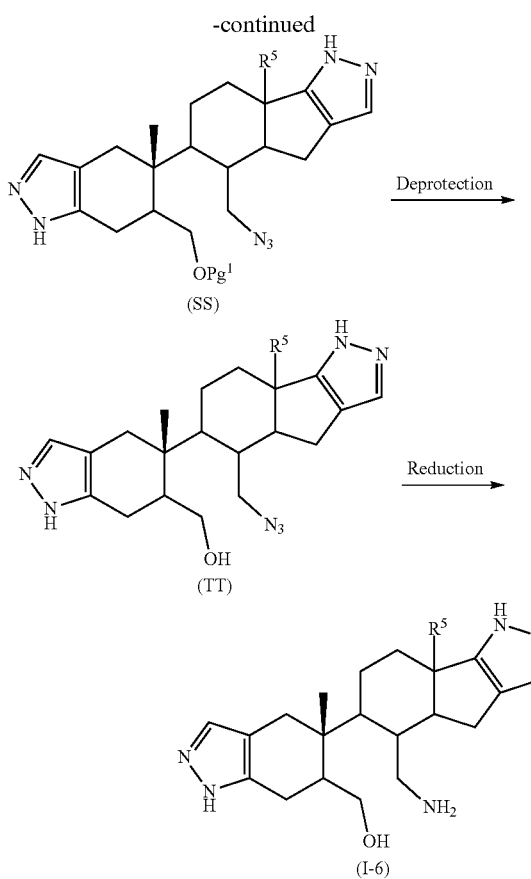

Compounds of formula (KK) may be prepared according to the methods disclosed in U.S. Pat. No. 7,601,874 or by methods known to one skilled in the art.

In general, compounds of formula (I-6) are prepared by first treating a compound of formula (KK) under appropriate General Procedure B conditions to yield a compound of formula (LL), which is then treated under appropriate General Procedure I conditions to yield a compound of formula (MM), which is then treated under appropriate General Procedure J conditions to yield a compound of formula (NN), which is then treated under appropriate General Procedure K conditions to yield a compound of formula (OO), which is then treated under appropriate General Procedure L conditions to yield a compound of formula (PP), which is then treated under appropriate ozonolysis conditions to yield a compound of formula (QQ), which is then treated under appropriate General Procedure N conditions to yield a compound of formula (RR), which is then treated under appropriate General Procedure O conditions to yield a compound of formula (SS), which is then treated under appropriate General Procedure P conditions to yield a compound of formula (TT), which is then treated under appropriate General Procedure R conditions to yield a compound of formula (I-6).

An embodiment of General Reaction Scheme 6 is described in more detail below in Synthetic Example 7.

General Reaction Scheme 7

Compounds of formula (I-7) are compounds of formula (I), as described above in the Summary of the Invention, and may be prepared according the following General Reaction Scheme 7 wherein $R^1$ and $R^5$ are as defined above in the Summary of the Invention, $Pg^1$ is an oxygen protecting group, such as tert-butydimethylsilyl or tert-butyldiphenylsilyl, and X is halo, preferably chloro:

GENERAL REACTION SCHEME 7

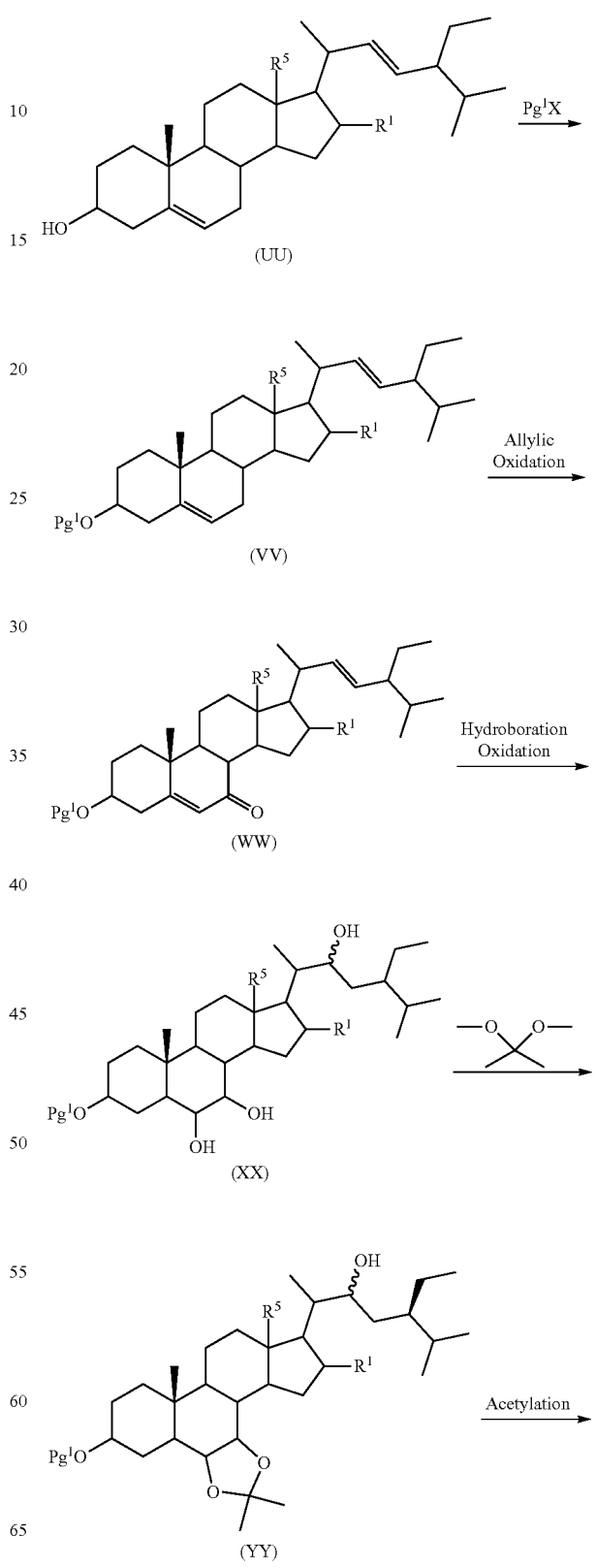

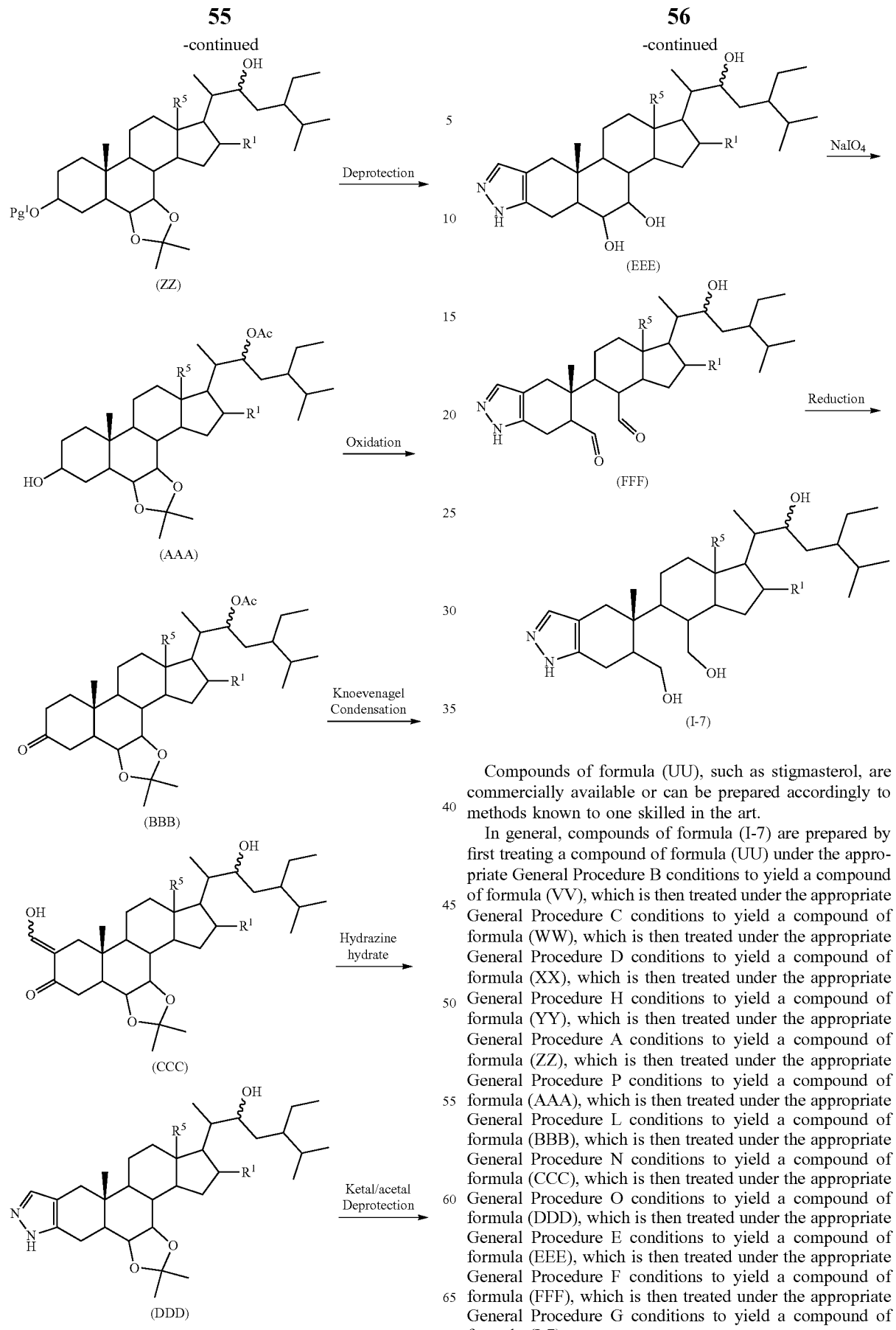

Compounds of formula (UU), such as stigmasterol, are commercially available or can be prepared accordingly to methods known to one skilled in the art.

In general, compounds of formula (I-7) are prepared by first treating a compound of formula (UU) under the appropriate General Procedure B conditions to yield a compound of formula (VV), which is then treated under the appropriate General Procedure C conditions to yield a compound of formula (WW), which is then treated under the appropriate General Procedure D conditions to yield a compound of formula (XX), which is then treated under the appropriate General Procedure H conditions to yield a compound of formula (YY), which is then treated under the appropriate General Procedure A conditions to yield a compound of formula (ZZ), which is then treated under the appropriate General Procedure P conditions to yield a compound of formula (AAA), which is then treated under the appropriate General Procedure L conditions to yield a compound of formula (BBB), which is then treated under the appropriate General Procedure N conditions to yield a compound of formula (CCC), which is then treated under the appropriate General Procedure O conditions to yield a compound of formula (DDD), which is then treated under the appropriate General Procedure E conditions to yield a compound of formula (EEE), which is then treated under the appropriate General Procedure F conditions to yield a compound of formula (FFF), which is then treated under the appropriate General Procedure G conditions to yield a compound of formula (I-7).

An embodiment of General Reaction Scheme 7 is described in more detail below in Synthetic Example 9.

General Reaction Scheme 8

Compounds of formula (I-8) are compounds of formula (I), as described above in the Summary of the Invention, and may be prepared according the following General Reaction Scheme 8 wherein $R^1$ and $R^5$ are as defined above in the Summary of the Invention:

GENERAL REACTION SCHEME 8

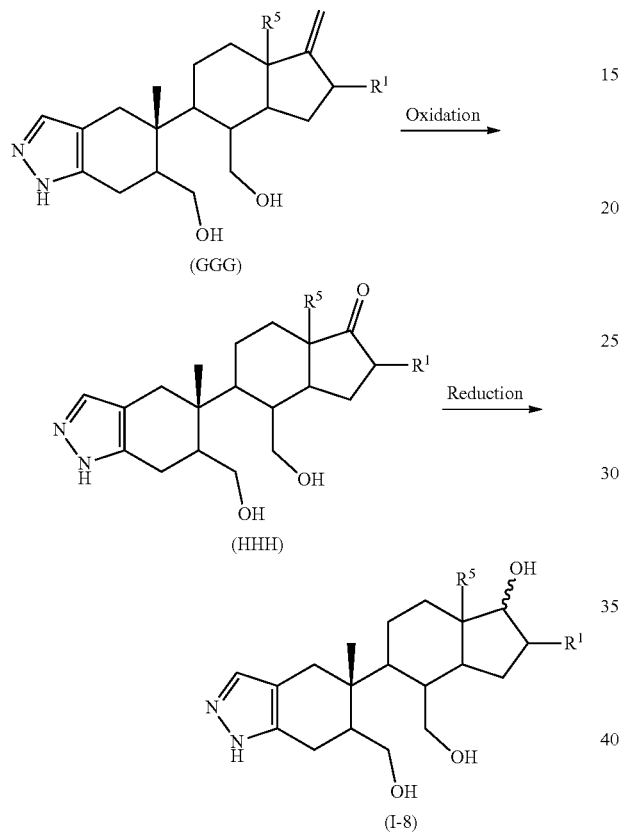

Compounds of formula (GGG) may be prepared according to the methods disclosed in U.S. Pat. No. 9,765,085 or by methods known to one skilled in the art.

In general, compounds of formula (I-8) are prepared by first treating a compound of formula (GGG) under standard osmium tetroxide-catalyzed periodate oxidation conditions to yield a compound of formula (HHH), which is then treated under appropriate General Procedure G conditions to yield a compound of formula (I-8), which is a mixture of enantiomers which can be isolated by standard resolution techniques.

An embodiment of General Reaction Scheme 8 is described in more detail below in Synthetic Example 10.

General Reaction Scheme 9

Compounds of formula (I-9) are compounds of formula (I), as described above in the Summary of the Invention, and may be prepared according the following General Reaction Scheme 9 wherein $R^5$ is as described above in the Summary of the Invention, each $Pg^1$ is an oxygen protecting group, such as tert-butydimethylsilyl or tert-butyldiphenylsilyl and X is halo, preferably chloro:

GENERAL REACTION SCHEME 9

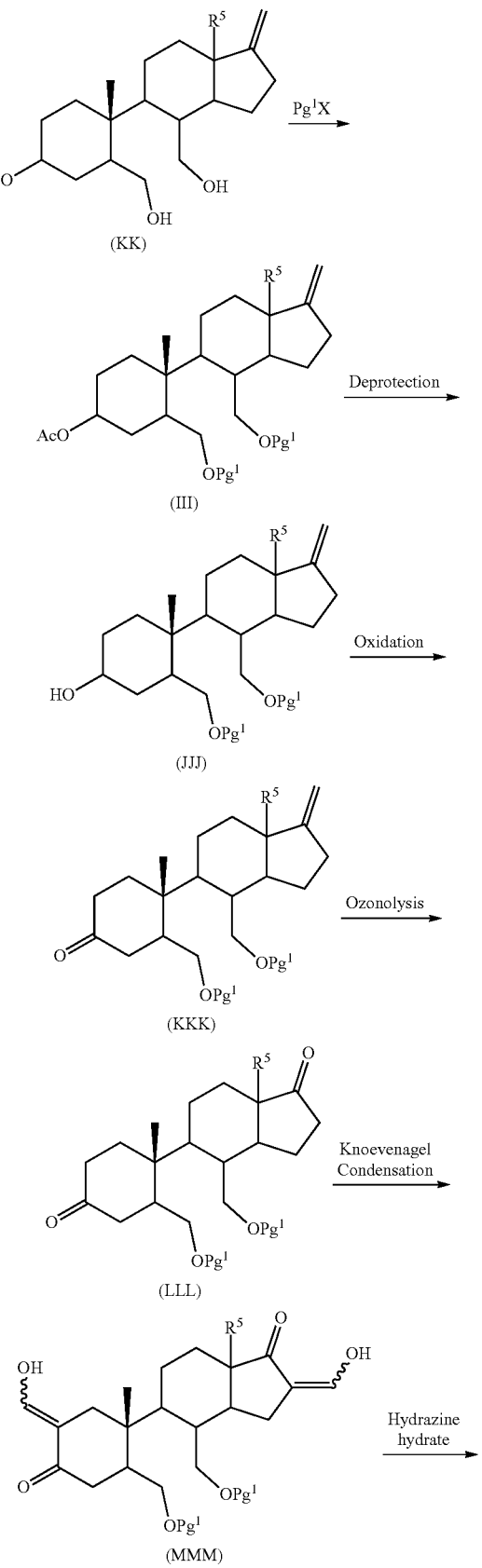

-continued

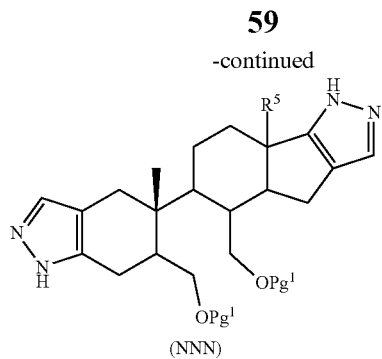

(NNN)

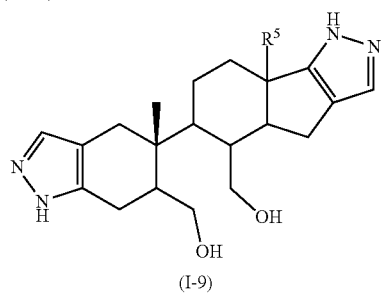

(I-9)

Compounds of formula (KK) may be prepared according to the methods disclosed herein or by methods known to one skilled in the art.

In general, compounds of formula (I-9) are prepared by first treating a compound of formula (KK) under appropriate General Procedure B conditions to yield a compound of formula (III), which is then treated under appropriate General Procedure K conditions to yield a compound of formula (JJJ), which is then treated under appropriate General Procedure L conditions to yield a compound of formula (KKK), which is then treated under appropriate ozonolysis conditions to yield a compound of formula (LLL), which is then treated under appropriate General Procedure N conditions to yield a compound of formula (MMM), which is then treated under appropriate General Procedure O conditions to yield a compound of formula (NNN), which is then treated under appropriate General Procedure P conditions to yield a compound of formula (I-9).

An embodiment of General Reaction Scheme 9 is described in more detail below in Synthetic Example 11.

General Reaction Scheme 10

Compounds of formula (I-10a) and formula (I-10b) are compounds of formula (I), as described above in the Summary of the Invention, and may be prepared according the following General Reaction Scheme 10 wherein $R^1$ and $R^6$ is as described above in the Summary of the Invention, $Pg^1$ is an oxygen protecting group, such as tert-butydimethylsilyl or tert-butyldiphenylsilyl, and $R^{12}$ is a substituted aryl, a substituted aralkyl, a substituted cycloalkyl or a substituted heteroaryl, each substituted by one or more substituents selected from halo, $-R^{10}-OR^{11}$ or $-R^{10}-C(O)R^{11}$ where $R^{10}$ is a direct bond or a straight or branched alkylene chain; and $R^{11}$ is hydrogen, alkyl, cycloalkyl or optionally substituted aryl:

GENERAL REACTION SCHEME 10

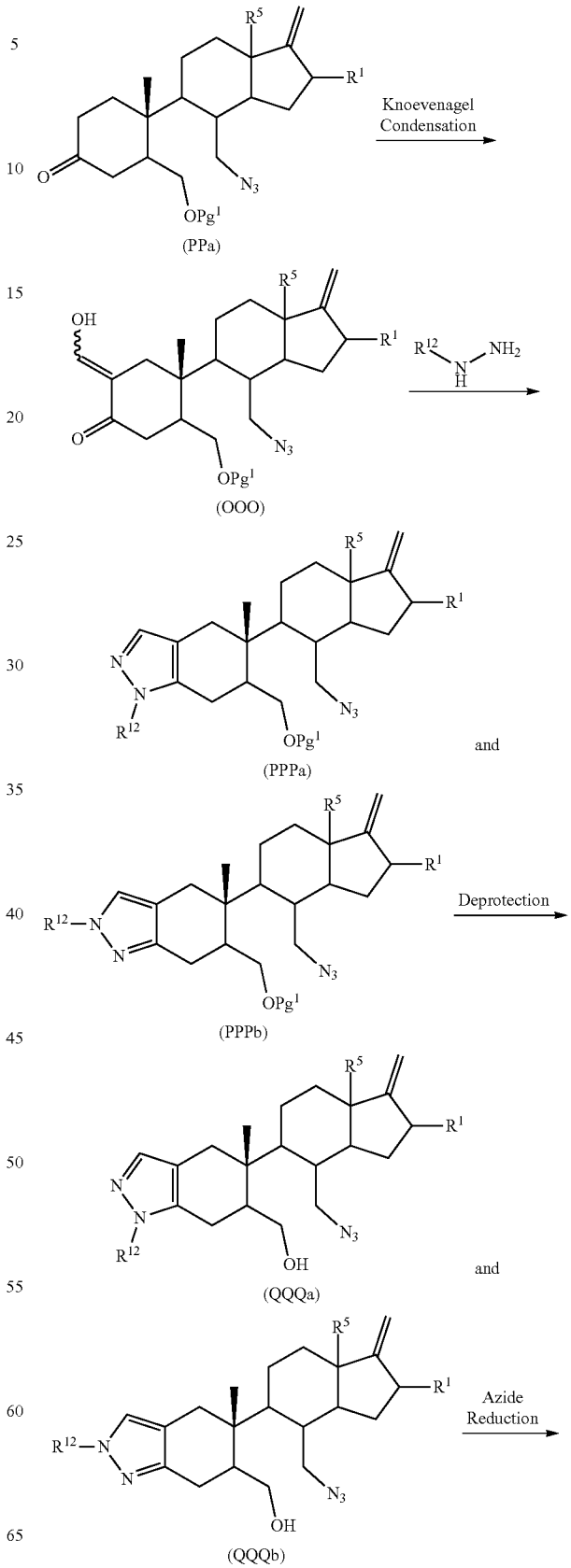

-continued

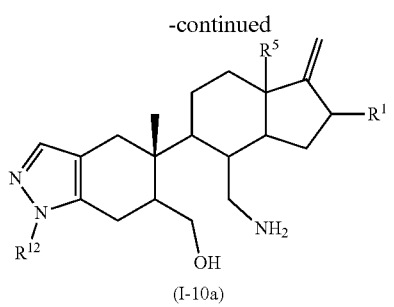

(I-10a)

and

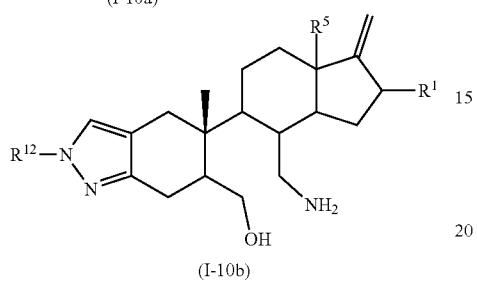

(I-10b)

Compounds of formula (PPa) may be prepared according to the methods disclosed herein or by methods known to one skilled in the art.

In general, compounds of formula (1-10a) and (I-10b) are prepared by first treating a compound of formula (PP) under appropriate General Procedure N conditions to yield a compounds of formula (OOO), which is then treated with the appropriately substituted hydrazine under General Procedure O conditions to yield a mixture of a compound of formula (PPPa) and a compound of formula (PPPb), which is then treated under appropriate General Procedure P conditions to yield a mixture of a compound of formula (QQQa) and a compound of formula (QQQb), which is then treated under the appropriate General Procedure Q conditions to yield a mixture of a compound of formula (I-10a) and a compound of formula (I-10b).

Alternatively, a compound of formula (PPPa) or a compound of formula (PPPb) may be isolated from the mixture of the compound of formula (PPPa) and the compound of formula (PPPb) under standard isolation methods known to one skilled in the art, and then treated under appropriate General Procedure P conditions to yield a compound of formula (QQQa) or a compound of formula (QQQb). The resulting compound of formula (QQQa) or the compound of formula (QQQb) may then be treated under appropriate General Procedure Q conditions to yield a compound of formula (I-10a) or a compound of formula (I-10b).

Alternatively, a compound of formula (QQQa) or a compound of formula (QQQb) may be isolated from the mixture of the compound of formula (QQQa) and the compound of formula (QQQb) under standard isolation methods known to one skilled in the art, and then treated under appropriate General Procedure Q conditions to yield a compound of formula (I-10a) or a compound of formula (I-10b).

Alternatively, a compound of formula (I-10a) or a compound of formula (I-10b) may be isolated from the mixture of the compound of formula (I-10a) and the compound of formula (I-10b) under standard isolation techniques known to one skilled in the art.

Embodiments of General Reaction Scheme 10 and the above alternate isolation processes are described in more detail below in Synthetic Example 12 and in Examples 12.1 to 12.14.

General Reaction Scheme 11

Compounds of formula (I-11a) and (I-11b) are compounds of formula (I), as described above in the Summary of the Invention, and may be prepared according the following General Reaction Scheme 11 wherein $R^1$ is hydrogen, $R^5$ is as described above in the Summary of the Invention, and $Pg^1$ is an oxygen protecting group, such as tert-butydimethylsilyl or tert-butyldiphenylsilyl:

GENERAL REACTION SCHEME 11

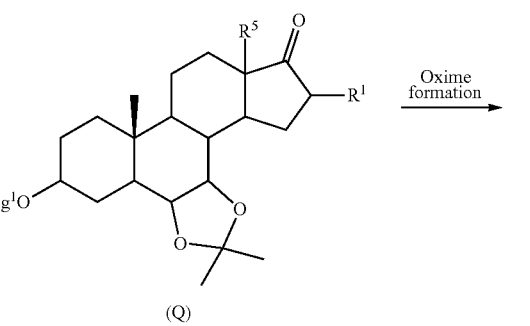

(Q)

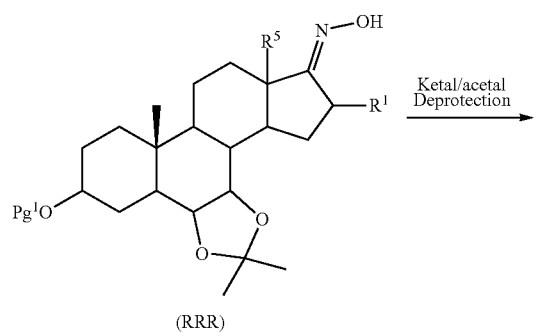

(RRR)

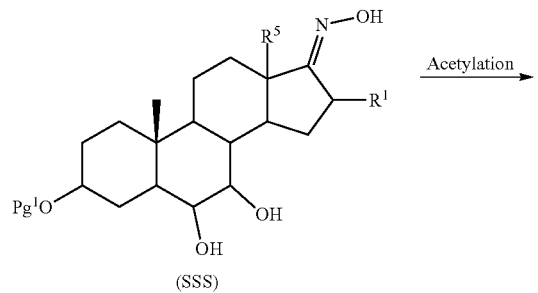

(SSS)

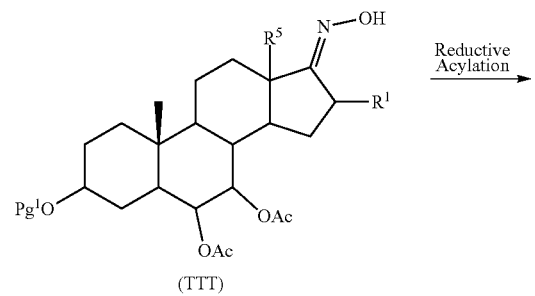

(TTT)

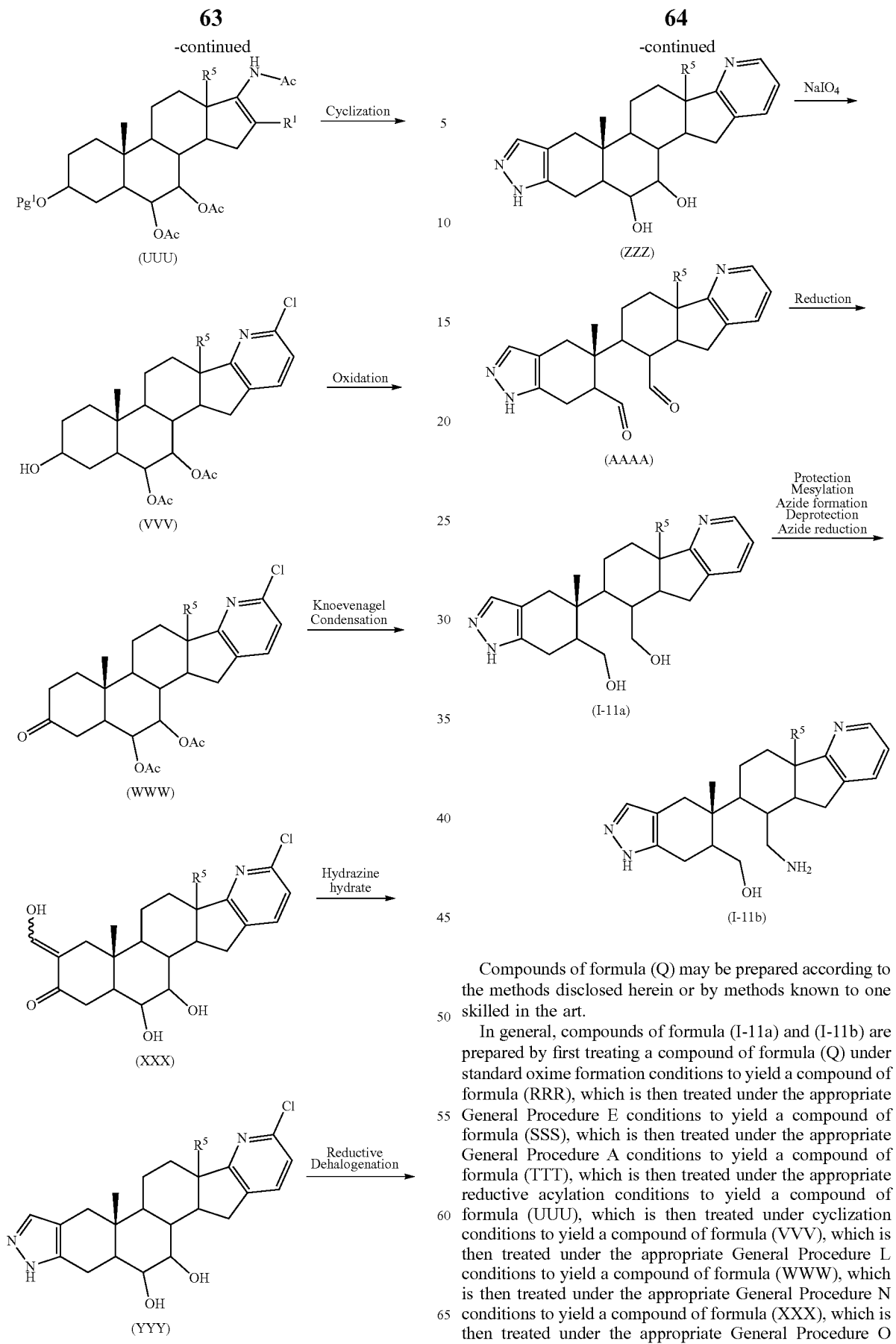

Compounds of formula (Q) may be prepared according to the methods disclosed herein or by methods known to one skilled in the art.

In general, compounds of formula (I-11a) and (I-11b) are prepared by first treating a compound of formula (Q) under standard oxime formation conditions to yield a compound of formula (RRR), which is then treated under the appropriate General Procedure E conditions to yield a compound of formula (SSS), which is then treated under the appropriate General Procedure A conditions to yield a compound of formula (TTT), which is then treated under the appropriate reductive acylation conditions to yield a compound of formula (UUU), which is then treated under cyclization conditions to yield a compound of formula (VVV), which is then treated under the appropriate General Procedure L conditions to yield a compound of formula (WWW), which is then treated under the appropriate General Procedure N conditions to yield a compound of formula (XXX), which is then treated under the appropriate General Procedure O conditions to yield a compound of formula (YYY), which is then treated under standard reductive dehalogenation conditions to yield a compound of formula (ZZZ), which is then treated under the appropriate General Procedure F conditions to yield a compound of formula (AAAA), which is then treated under the appropriate General Procedure G conditions to yield a compound of formula (I-11a), which is then first treated under appropriate General Procedure B conditions, then treated under appropriate General Procedure I conditions, then treated under appropriate General Procedure J conditions, then treated under appropriate General Procedure P conditions and then treated under standard Pd catalyzed reduction conditions to yield a compound of formula (I-11b).

An embodiment of General Reaction Scheme 11 is described in more detail below in Synthetic Example 13.

General Reaction Scheme 12

Compounds of formula (I-12a) and (I-12b) are compounds of formula (I), as described above in the Summary of the Invention, and may be prepared according the following General Reaction Scheme 12 wherein $R^5$ is as described above in the Summary of the Invention, $Pg^1$ is an oxygen protecting group, such as tert-butydimethylsilyl or tert-butyldiphenylsilyl, X is halo, preferably chloro, and $R^{12}$ is a substituted aryl, a substituted aralkyl, a substituted cycloalkyl or a substituted heteroaryl, each substituted by one or more substituents selected from halo, $-R^{10}-OR^{11}$ or $-R^{10}-C(O)R^{11}$ where $R^{10}$ is a direct bond or a straight or branched alkylene chain; and $R^{11}$ is hydrogen, alkyl, cycloalkyl or optionally substituted aryl:

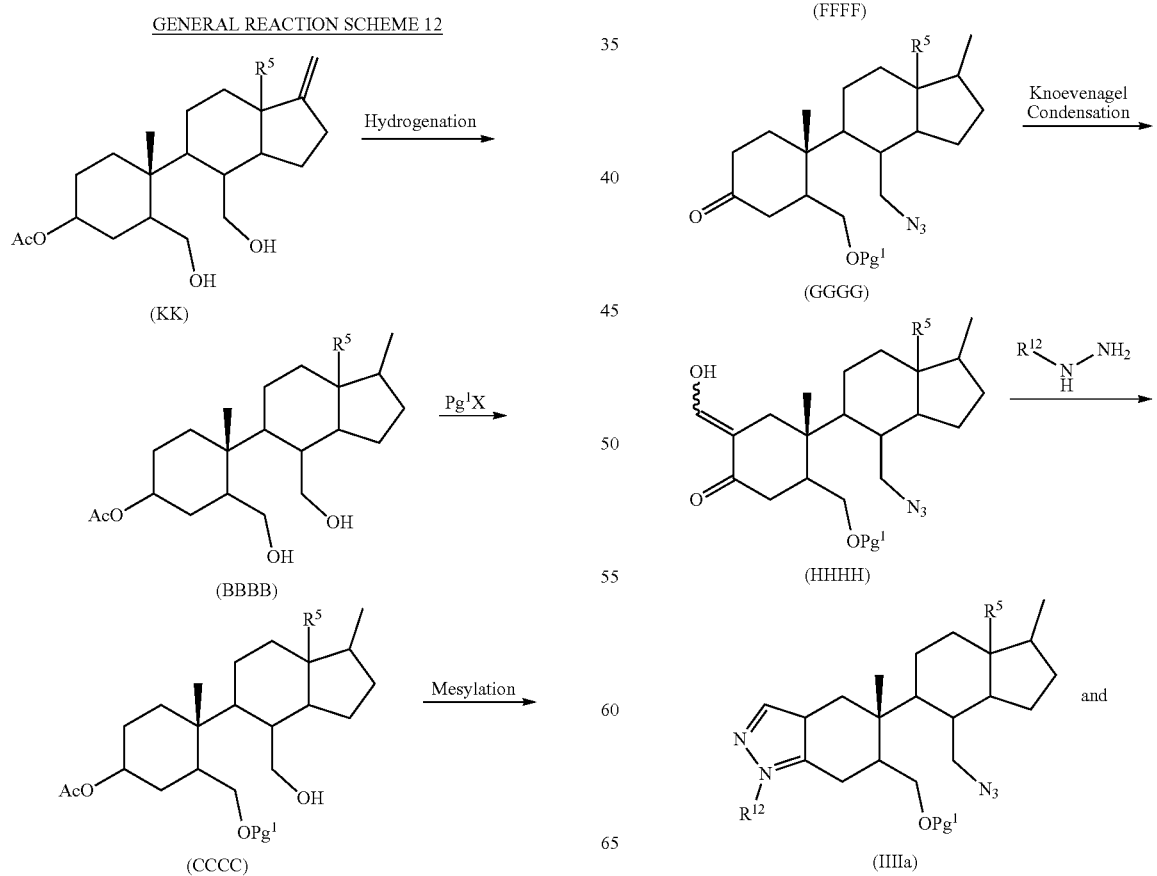

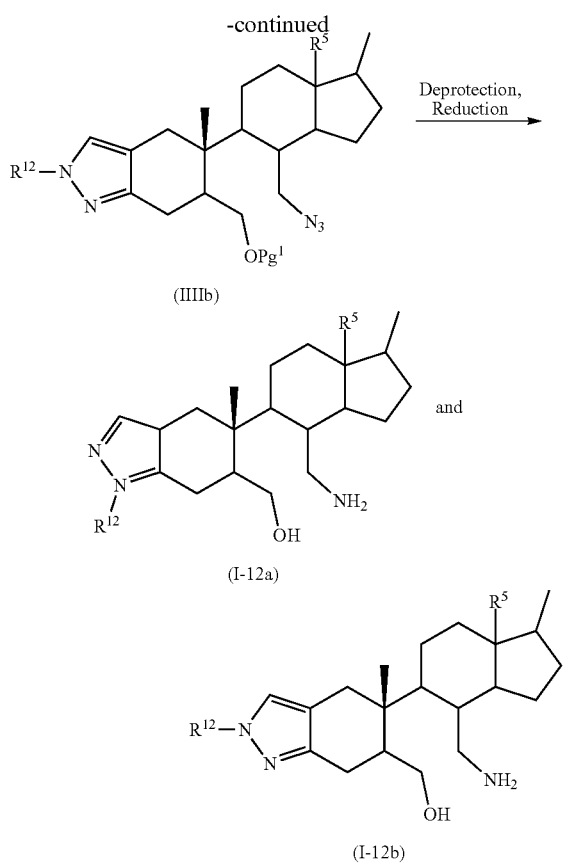

(IIIb)

(I-12a)

(I-12b)

Compounds of formula (KK) may be prepared according to the methods disclosed herein or by methods known to one skilled in the art.

In general, compounds of formula (I-12a) and formula (I-12b) are prepared by first treating a compound of formula (KK) under standard Pd catalyzed hydrogenation conditions to yield a compound of formula (BBBB), which is then treated under appropriate General Procedure B conditions to yield a compound of formula (CCCC), which is then treated under appropriate General Procedure I conditions to yield a compound of formula (DDDD), which is then treated under appropriate General Procedure J conditions to yield a compound of formula (EEEE), which is then treated under appropriate General Procedure K conditions to yield a compound of formula (FFFF), which is then treated under appropriate General Procedure L conditions to yield a compound of formula (GGGG), which is then treated under appropriate General Procedure N conditions to yield a compound of formula (HHHH), which is then treated under appropriate General Procedure O conditions to yield a mixture of a compound of formula (IIIa) and a compound of formula (IIIb), which is then treated under appropriate General Procedure P conditions, followed by treatment under appropriate General Procedure R conditions to yield a mixture of a compound of formula (I-12a) and a compound of formula (I-12b).

Alternatively, a compound of formula (IIIa) or a compound of formula (IIIb) may be isolated from the mixture of the compound of formula (IIIa) and the compound of formula (IIIb) under standard isolation methods known to one skilled in the art, and then treated under appropriate General Procedure Q conditions to yield a compound of formula (I-12a) or a compound of formula (I-12b).

Alternatively, a compound of formula (I-12a) or a compound of formula (I-12b) may be isolated from the mixture of the compound of formula (I-12a) and the compound of formula (I-12b) under standard isolation techniques known to one skilled in the art.

Embodiments of General Reaction Scheme 12 are described in more detail below in Synthetic Examples 14-14.3.

All of the compounds described herein as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

Representative compounds of the invention which were prepared by the methods disclosed herein include (but are not limited to) the compounds listed below in Table 1. The compound (Cpd) numbers in this table correspond to the compound numbers in Synthetic Examples 1-14.3 below.

TABLE 1

| Cpd No. | Compound Name |
|---|---|
| Ia-1 | ((5R,6S)-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol |
| Ia-2 | ((5R,6S)-5-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol |
| Ia-3 | (1S,3aS,4R,5S,7aS)-4-(hydroxymethyl)-5-((5R,6S)-6-(hydroxymethyl)-5-methyl-4,5,6,7-tetrahydro-1H-indazol-5-yl)-1,7a-dimethyloctahydro-1H-inden-1-ol |
| Ia-4 | (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol |
| Ia-5 | ((5R,6S)-5-((3aS,6S,7R,7aS)-7-(hydroxymethyl)-3a-methyl-3-phenyl-3a,4,5,6,7,7a-hexahydro-1H-inden-6-yl)-5-methyl-4,5,6,7-tetrahydro-1H-indazol-6-yl)methanol |
| Ia-6 | ((5R,6S)-5-((3aS,6S,7R,7aS)-7-(aminomethyl)-3a-methyl-3-phenyl-3a,4,5,6,7,7a-hexahydro-1H-inden-6-yl)-5-methyl-4,5,6,7-tetrahydro-1H-indazol-6-yl)methanol |
| Ia-7 | ((5R,6S)-5-((4aS,5R,6S,8aS)-5-(aminomethyl)-8a-methyl-1,4,4a,5,6,7,8,8a-octahydroindeno[1,2-c]pyrazol-6-yl)-5-methyl-4,5,6,7-tetrahydro-1H-indazol-6-yl)methanol |
| Ia-8 | (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol |
| Ia-9 | (2S,5R)-5-ethyl-2-((1R,3aS,4S,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-yl)-6-methylheptan-3-ol |
| Ia-10a | (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol |
| Ia-10b | (1R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol |
| Ia-11 | ((4aS,5R,6S,8aS)-6-((5R,6S)-6-(hydroxymethyl)-5-methyl-4,5,6,7-tetrahydro-1H-indazol-5-yl)-8a-methyl-1,4,4a,5,6,7,8,8a-octahydroindeno[1,2-c]pyrazol-5-yl)methanol |
| Ia-12 | ((5R,6S)-5-((3aS,4R,5S,7aS)-4-(aminomethyl)-7a-methyl-1-methyleneoctahydro-1H-inden-5-yl)-1-(4-fluorophenyl)-5-methyl-4,5,6,7-tetrahydro-1H-Indazol-6-yl)methanol |
| Ia-13 | ((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol |

TABLE 1-continued

| Cpd No. | Compound Name |
|---|---|
| Ia-14 | ((5R,6S)-5-((3aS,4R,5S,7aS)-4-(aminomethyl)-7a-methyl-1-methyleneoctahydro-1H-inden-5-yl)-1-(4-methoxyphenyl)-5-methyl-4,5,6,7-tetrahydro-1H-Indazol-6-yl)methanol |
| Ia-15 | ((5R,6S)-5-((3aS,4R,5S,7aS)-4-(aminomethyl)-7a-methyl-1-methyleneoctahydro-1H-inden-5-yl)-2-(4-methoxyphenyl)-5-methyl-4,5,6,7-tetrahydro-2H-indazol-6-yl)methanol |
| Ia-16 | ((5R,6S)-5-((3aS,4R,5S,7aS)-4-(aminomethyl)-7a-methyl-1-methyleneoctahydro-1H-inden-5-yl)-1-(4-methoxybenzyl)-5-methyl-4,5,6,7-tetrahydro-1H-indazol-6-yl)methanol |
| Ia-17 | ((5R,6S)-5-((3aS,4R,5S,7aS)-4-(aminomethyl)-7a-methyl-1-methyleneoctahydro-1H-inden-5-yl)-2-(4-methoxybenzyl)-5-methyl-4,5,6,7-tetrahydro-2H-indazol-6-yl)methanol |
| Ia-18 | ((5R,6S)-5-((3aS,4R,5S,7aS)-4-(aminomethyl)-7a-methyl-1-methyleneoctahydro-1H-inden-5-yl)-1-(4-fluorobenzyl)-5-methyl-4,5,6,7-tetrahydro-1H-indazol-6-yl)methanol |
| Ia-19 | ((5R,6S)-5-((3aS,4R,5S,7aS)-4-(aminomethyl)-7a-methyl-1-methyleneoctahydro-1H-inden-5-yl)-2-(4-fluorobenzyl)-5-methyl-4,5,6,7-tetrahydro-2H-indazol-6-yl)methanol |
| Ia-20 | (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(phenyl)methanone |
| Ia-21 | (4-((5R,6S)-5-((3aS,4R,5S,7aS)-4-(aminomethyl)-1-methyleneoctahydro-1H-inden-5-yl)-6-(hydroxymethyl)-5-methyl-4,5,6,7-tetrahydro-2H-indazol-2-yl)phenyl)(phenyl)methanone |
| Ia-22 | ((5R,6S)-5-((3aS,4R,5S,7a,S)-4-(aminomethyl)-7a-methyl-1-methyleneoctahydro-1H-inden-5-yl)-1-(3,4-difluorophenyl)-5-methyl-4,5,6,7-tetrahydro-1H-indazol-6-yl)methanol |
| Ia-23 | ((5R,6S)-5-((3aS,4R,5S,7aS)-4-(aminomethyl)-7a-methyl-1-methyleneoctahydro-1H-inden-5-yl)-2-(3,4-difluorophenyl)-5-methyl-4,5,6,7-tetrahydro-2H-indazol-6-yl)methanol |
| Ia-24 | ((5R,6S)-5-((3aS,4R,5S,7aS)-4-(aminomethyl)-7a-methyl-1-methyleneoctahydro-1H-inden-5-yl)-1-(4-(4-fluorophenoxy)phenyl)-5-methyl-4,5,6,7-tetrahydro-1H-indazol-6-yl)methanol |
| Ia-25 | ((5R,6S)-5-((3aS,4R,5S,7aS)-4-(aminomethyl)-7a-methyl-1-methyleneoctahydro-1H-inden-5-yl)-2-(4-(4-fluorophenoxy)phenyl)-5-methyl-4,5,6,7-tetrahydro-2H-indazol-6-yl)methanol |
| Ia-26 | ((5R,6S)-5-((3aS,4R,5S,7aS)-4-(aminomethyl)-7a-methyl-1-methyleneoctahydro-1H-inden-5-yl)-1-(5-fluoropyrimidin-2-yl)-5-methyl-4,5,6,7-tetrahydro-1H-indazol-6-yl)methanol |
| Ia-27 | ((5R,6S)-5-((3aS,4R,5S,7aS)-4-(aminomethyl)-7a-methyl-1-methyleneoctahydro-1H-inden-5-yl)-2-(5-fluoropyrimidin-2-yl)-5-methyl-4,5,6,7-tetrahydro-2H-indazol-6-yl)methanol |
| Ia-28 | ((5R,6S)-5-((3aS,4R,5S,7aS)-4-(aminomethyl)-7a-methyl-1-methyleneoctahydro-1H-inden-5-yl)-5-methyl-1-(4-phenoxyphenyl)-4,5,6,7-tetrahydro-1H-indazol-6-yl)methanol |
| Ia-29 | ((5R,6S)-5-((3aS,4R,5S,7aS)-4-(aminomethyl)-7a-methyl-1-methyleneoctahydro-1H-inden-5-yl)-5-methyl-2-(4-phenoxyphenyl)-4,5,6,7-tetrahydro-2H-indazol-6-yl)methanol |
| Ia-30 | ((5R,6S)-5-((3aS,4R,5S,7aS)-4-(aminomethyl)-7a-methyl-1-methyleneoctahydro-1H-inden-5-yl)-1-(5-fluoropyridin-2-yl)-5-methyl-4,5,6,7-tetrahydro-1H-indazol-6-yl)methanol |
| Ia-31 | ((5R,6S)-5-((3aS,4R,5S,7aS)-4-(aminomethyl)-7a-methyl-1-methyleneoctahydro-1H-inden-5-yl)-2-(5-fluoropyridin-2-yl)-5-methyl-4,5,6,7-tetrahydro-2H-indazol-6-yl)methanol |
| Ia-32 | ((5R,6S)-5-((3aS,4R,5S,7aS)-4-(aminomethyl)-7a-methyl-1-methyleneoctahydro-1H-inden-5-yl)-1-(2-fluorophenyl)-5-methyl-4,5,6,7-tetrahydro-1H-indazol-6-yl)methanol |
| Ia-33 | ((5R,6S)-5-((3aS,4R,5S,7aS)-4-(aminomethyl)-7a-methyl-1-methyleneoctahydro-1H-inden-5-yl)-2-(2-fluorophenyl)-5-methyl-4,5,6,7-tetrahydro-2H-indazol-6-yl)methanol |
| Ia-34 | ((5R,6S)-5-((3aS,4R,5S,7aS)-4-(aminomethyl)-7a-methyl-1-methyleneoctahydro-1H-inden-5-yl)-1-(2,4-difluorophenyl)-5-methyl-4,5,6,7-tetrahydro-1H-indazol-6-yl)methanol |
| Ia-35 | ((5R,6S)-5-((3aS,4R,5S,7aS)-4-(aminomethyl)-7a-methyl-1-methyleneoctahydro-1H-inden-5-yl)-2-(2,4-difluorophenyl)-5-methyl-4,5,6,7-tetrahydro-2H-indazol-6-yl)methanol |
| Ia-36 | 4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenoxy)benzoic acid |
| Ia-37 | 4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenoxy)benzoic acid |
| Ia-38 | ((5R,6S)-5-((3aS,4R,5S,7aS)-4-(aminomethyl)-7a-methyl-1-methyleneoctahydro-1H-inden-5-yl)-1-(4,4-difluorocyclohexyl)-5-methyl-4,5,6,7-tetrahydro-1H-indazol-6-yl)methanol |
| Ia-39 | ((5R,6S)-5-((3aS,4R,5S,7aS)-4-(aminomethyl)-7a-methyl-1-methyleneoctahydro-1H-inden-5-yl)-2-(4,4-difluorocyclohexyl)-5-methyl-4,5,6,7-tetrahydro-2H-indazol-6-yl)methanol |
| Ia-40 | ((5R,6S)-5-((3aS,4R,5S,7aS)-4-(aminomethyl)-7a-methyl-1-methyleneoctahydro-1H-inden-5-yl)-1-(3-fluorophenyl)-5-methyl-4,5,6,7-tetrahydro-1H-indazol-6-yl)methanol |
| Ia-41 | ((5R,6S)-5-((3aS,4R,5S,7aS)-4-(aminomethyl)-7a-methyl-1-methyleneoctahydro-1H-inden-5-yl)-2-(3-fluorophenyl)-5-methyl-4,5,6,7-tetrahydro-2H-indazol-6-yl)methanol |
| Ia-42 | (1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol |
| Ia-43 | ((5aS,6R,7S,9aS)-7-((5R,6S)-6-(hydroxymethyl)-5-methyl-4,5,6,7-tetrahydro-1H-indazol-5-yl)-9a-methyl-5a,6,7,8,9,9a-hexahydro-5H-indeno[1,2-b]pyridin-6-yl)methanol |
| Ia-44 | ((5R,6S)-5-((5aS,6R,7S,9aS)-6-(aminomethyl)-9a-methyl-5a,6,7,8,9,9a-hexahydro-5H-indeno[1,2-b]pyridin-7-yl)-5-methyl-4,5,6,7-tetrahydro-1H-indazol-6-yl)methanol |
| Ia-45 | (4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-1H-indazol-1-yl)phenyl)(phenyl)methanone |
| Ia-46 | (4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-2H-indazol-2-yl)phenyl)(phenyl)methanone |
| Ia-47 | ((5R,6S)-5-((1S,3aS,4S,5S,7aR)-4-(aminomethyl)-1,7a-dimethyloctahydro-1H-inden-5-yl)-1-(4-fluorophenyl)-5-methyl-4,5,6,7-tetrahydro-1H-indazol-6-yl)methanol |
| Ia-48 | ((5R,6S)-5-((1S,3aS,4S,5S,7aR)-4-(aminomethyl)-1,7a-dimethyloctahydro-1H-inden-5-yl)-2-(4-fluorophenyl)-5-methyl-4,5,6,7-tetrahydro-2H-indazol-6-yl)methanol |
| Ia-49 | ((5R,6S)-5-((1S,3aS,4S,5S,7aR)-4-(aminomethyl)-1,7a-dimethyloctahydro-1H-inden-5-yl)-1-(4-methoxyphenyl)-5-methyl-4,5,6,7-tetrahydro-1H-indazol-6-yl)methanol |
| Ia-50 | ((5R,6S)-5-((1S,3aS,4S,5S,7aR)-4-(aminomethyl)-1,7a-dimethyloctahydro-1H-inden-5-yl)-2-(4-methoxyphenyl)-5-methyl-4,5,6,7-tetrahydro-2H-indazol-6-yl)methanol |
| Ia-51 | ((5R,6S)-5-((1S,3aS,4S,5S,7aR)-4-(aminomethyl)-1,7a-dimethyloctahydro-1H-inden-5-yl)-1-(4-methoxybenzyl)-5-methyl-4,5,6,7-tetrahydro-1H-indazol-6-yl)methanol |
| Ia-52 | ((5R,6S)-5-((1S,3aS,4S,5S,7aR)-4-(aminomethyl)-1,7a-dimethyloctahydro-1H-inden-5-yl)-2-(4-methoxybenzyl)-5-methyl-4,5,6,7-tetrahydro-2H-indazol-6-yl)methanol |
| Ia-53 | (1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol |
| Ia-54 | ((5R,6S)-5-((1S,3aS,4S,5S,7aR)-4-(aminomethyl)-1,7a-dimethyloctahydro-1H-inden-5-yl)-2-(4-(4-fluorophenoxy)phenyl)-5-methyl-4,5,6,7-tetrahydro-2H-indazol-6-yl)methanol |
| Ia-55 | ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol |
| Ia-55 · HCl | ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol hydrochloride |
| Ia-56 | ((5R,6S)-5-((1S,3aS,4S,5S,7aR)-4-(aminomethyl)-1,7a-dimethyloctahydro-1H-inden-5-yl)-5-methyl-2-(4-(pyridin-2-yloxy)phenyl)-4,5,6,7-tetrahydro-2H-indazol-6-yl)methanol |
| Ia-57 | ((5R,6S)-5-((1S,3aS,4S,5S,7aR)-4-(aminomethyl)-1,7a-dimethyloctahydro-1H-inden-5-yl)-5-methyl-1-(4-(pyridin-2-yloxy)phenyl)-4,5,6,7-tetrahydro-1H-indazol-6-yl)methanol |

TABLE 1-continued

| Cpd No. | Compound Name |
|---|---|
| Ia-58 | ((5R,6S)-5-((1S,3aS,4S,5S,7aR)-4-(aminomethyl)-1,7a-dimethyloctahydro-1H-inden-5-yl)-5-methyl-2-(4-(pyridin-4-yloxy)phenyl)-4,5,6,7-tetrahydro-2H-indazol-6-yl)methanol |
| Ia-59 | ((5R,6S)-5-((1S,3aS,4S,5S,7aR)-4-(aminomethyl)-1,7a-dimethyloctahydro-1H-inden-5-yl)-5-methyl-1-(4-(pyridin-4-yloxy)phenyl)-4,5,6,7-tetrahydro-1H-indazol-6-yl)methanol |
| Ia-60 | ((5R,6S)-5-((1S,3aS,4S,5S,7aR)-4-(aminomethyl)-1,7a-dimethyloctahydro-1H-inden-5-yl)-5-methyl-1-(4-(pyrimidin-5-yloxy)phenyl)-4,5,6,7-tetrahydro-1H-indazol-6-yl)methanol |
| Ia-61 | ((5R,6S)-5-((1S,3aS,4S,5S,7aR)-4-(aminomethyl)-1,7a-dimethyloctahydro-1H-inden-5-yl)-5-methyl-2-(4-(pyrimidin-5-yloxy)phenyl)-4,5,6,7-tetrahydro-2H-indazol-6-yl)methanol |
| Ia-62 | (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(4-(pent-4-yn-1-yloxy)phenyl)methanone |
| Ia-63 | (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(4-(pent-4-yn-1-yloxy)phenyl)methanone |
| Ia-64 | 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)benzoic acid |
| Ia-65 | 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)benzoic acid |

The following Synthetic Examples, which are directed to the synthesis of the compounds of the invention; and the following Biological Examples, which are directed to representative biological assays for the compounds of the invention, are provided as a guide to assist in the practice of the invention, and are not intended as a limitation on the scope of the invention.

Synthetic Example 1

Synthesis of ((5R,6S)-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol (Compound Ia-1)

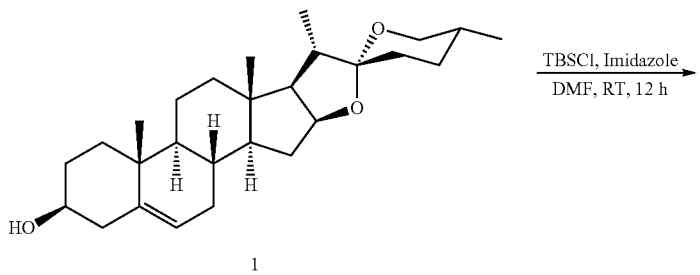

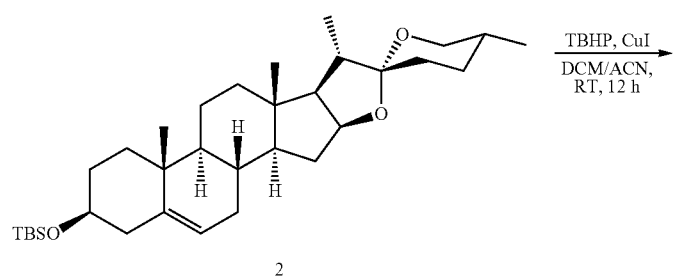

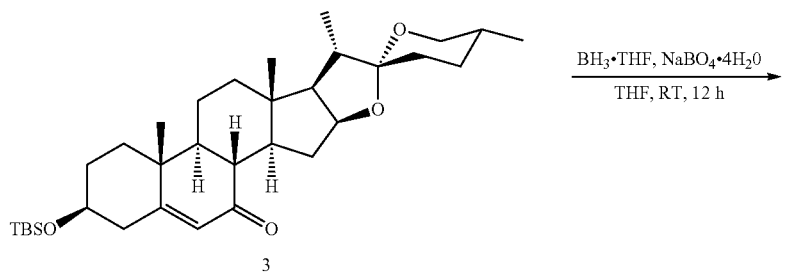

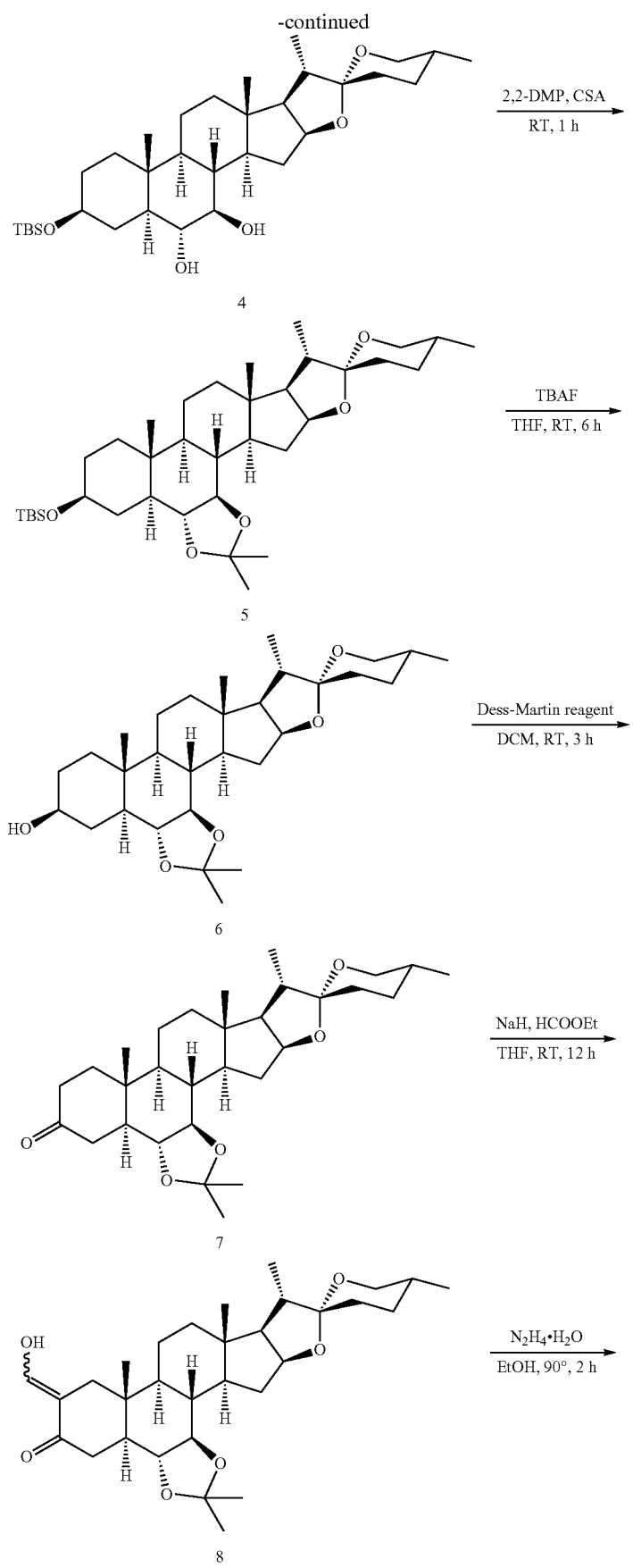

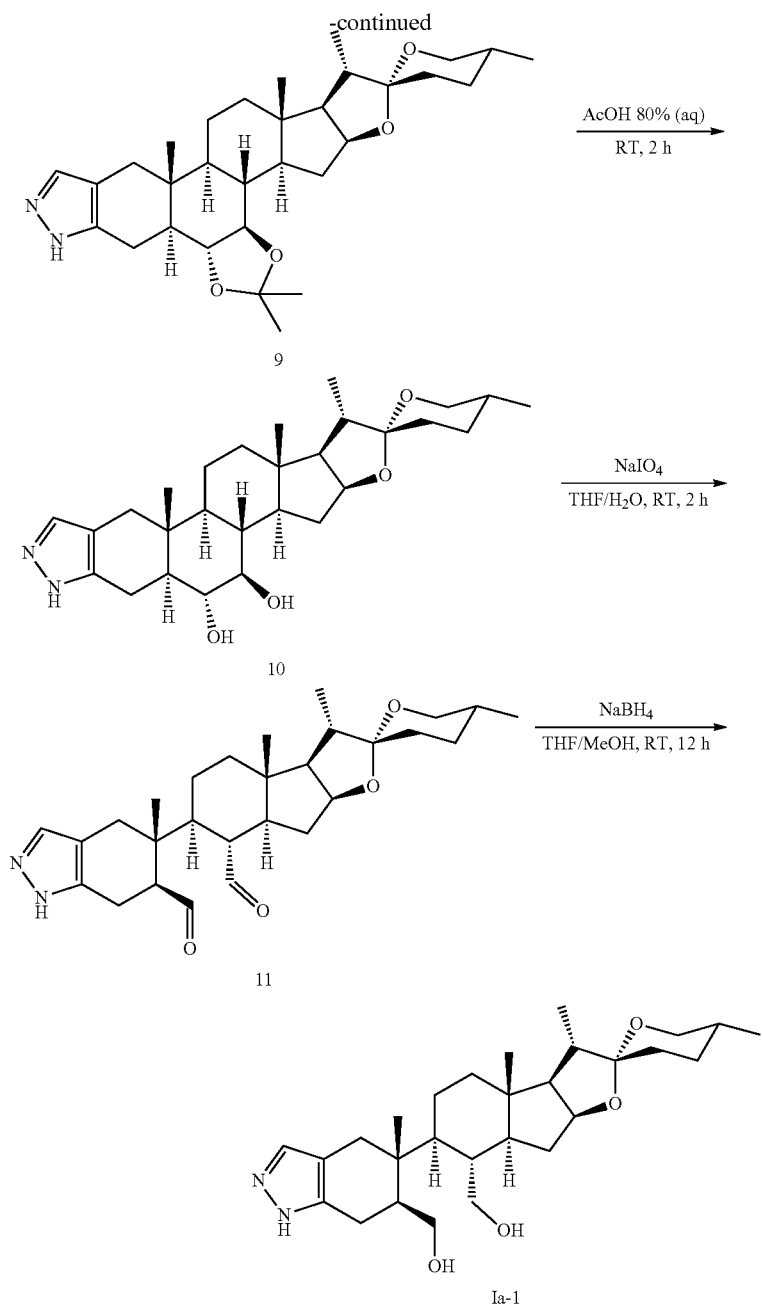

A. Using General Procedure B with diosgenin (Compound 1, 25 g, 60.34 mmol, 1 eq), imidazole (8.2 g, 120.58 mmol, 2 eq), TBSCl (9.08 g, 60.34 mmol, 1 eq) and DMF (200 mL) gave the desired silyl ether tert-butyldimethyl ((((4S,5'R,6aR,6bS,8aS,8bR,9S,10R,11aS,12aS,12bS)-5',6a,8a,9-tetramethyl-1,3,3',4,4',5,5',6,6a,6b,6',7,8,8a,8b,9,11a,12,12a,12b-icosahydrospiro[naphtho[2',1':4,5]indeno[2,1-b]furan-10,2'-pyran]-4-yl)oxy)silane (Compound 2, 21 g, yield: 66%) as an off-white solid after purification by flash column chromatography (230-400 mesh silica gel, eluted with 0-15% pet ether/ethyl acetate).

B. Using General Procedure C with Compound 2 (21 g, 39.74 mmol, 1 eq), TBHP (5-6 M in decane, 36.1 mL, 198.7 mmol, 5 eq), copper(I) iodide (0.75 g, 3.97 mmol, 0.1 eq), acetonitrile (100 mL) and dichloromethane (100 mL) gave the desired enone (4S,5'R,6aR,6bS,8aS,8bR,9S,10R,11aS,12aS,12bS)-4-((tert-butyldimethylsilyl)oxy)-5',6a,8a,9-tetramethyl-3',4,4',5,5',6,6a,6b,6',7,8,8a,8b,9,11a,12,12a,12b-octadecahydrospiro[naphtho[2',1':4,5]indeno[2,1-b]furan-10,2'-pyran]-1(3H)-one (Compound 3, 11.3 g, 53%) as an off-white solid after purification by flash column chromatography (230-400 mesh silica gel, eluted with 0-60% pet ether/ethyl acetate).

C. Using General Procedure D with Compound 3 (11.3 g, 20.83 mmol, 1 eq), 1 M borane in THF solution (41.6 ml, 41.67 mmol, 2 eq), sodium perborate tetrahydrate (9.6 g, 62.51 mmol, 3 eq) and THF (110 mL) gave the desired diol 1R,2R,2aS,4S,5'R,6aR,6bS,8aS,8bR,9S,10R,11aS,12aS,12bR)-4-((tert-butyldimethylsilyl)oxy)-5',6a,8a,9-tetramethyldocosahydrospiro[naphtho[2',1':4,5]indeno[2,1-b]

furan-10,2'-pyran]-1,2-diol (Compound 4, 9 g, 76%) as a white solid after purification by flash column chromatography (230-400 mesh silica gel, eluted with 0-5% dichloromethane/methanol).

D. Using General Procedure H with Compound 4 (9 g, 16 mmol, 1 eq), camphorsulfonic acid (74 mg, 0.32 mmol, 0.02 eq) and 2,2-dimethoxypropane (68.3 g, 656.23 mmol) gave the desired acetonide tert-butyl(((3aR,3bS,5S,5'R,7aR,7bS,9aS,9bR,10S,11R,12aS,13aS,13bR,13cR)-2,2,5',7a,9a,10-hexamethyldocosahydrospiro[furo[3",2":3',4']cyclopenta[1',2':1,2]phenanthro[9,10-d][1,3]dioxole-11,2'-pyran]-5-yl)oxy)dimethylsilane (Compound 5, 9 g) as a pale brown liquid which was used as is in the next step without any further purification.

E. Using General Procedure P with Compound 5 (9 g, 14.9 mmol, 1 eq), TBAF solution (1M in THF, 30 mL, 29.9 mmol, 2 eq) and tetrahydrofuran (90 mL) gave the desired alcohol (3aR,3bS,5S,5'R,7aR,7bS,9aS,9bR,10S,11R,12aS,13aS,13bR,13cR)-2,2,5',7a,9a,10-hexamethyldocosahydrospiro[furo[3",2":3',4']cyclopenta[1',2':1,2]phenanthro[9,10-d][1,3]dioxole-11,2'-pyran]-5-ol (Compound 6, 5 g, 69% over 2 steps) as a white solid after purification by flash column chromatography (230-400 mesh silica gel, eluted with 0-30% pet ether/ethyl acetate).

F. Using General Procedure M with Compound 6 (5 g, 10.23 mmol, 1 eq), Dess-Martin periodinane (6.5 g, 15.35 mmol, 1.5 eq) and dichloromethane (50 mL) gave the desired ketone (3aR,3bS,5'R,7aR,7bS,9aS,9bR,10S,11R,12aS,13aS,13bR,13cR)-2,2,5',7a,9a,10-hexamethylicosahydrospiro[furo[3",2":3',4']cyclopenta[1',2':1,2]phenanthro[9,10-d][1,3]dioxole-11,2'-pyran]-5(3aH)-one (Compound 7, 2.3 g, 46%) as a white solid after purification by flash column chromatography (230-400 mesh silica gel, eluted with 0-10% pet ether/ethyl acetate).

G. Using General Procedure N with Compound 7 (2.3 g, 4.73 mmol), ethyl formate (2.3 mL, 28.39 mmol, 6 eq) and THF (8 mL) gave the desired ketone (3aR,3bS,5'R,7aR,7bS,9aS,9bR,10S,11R,12aS,13aS,13bR,13cR)-6-(hydroxymethylene)-2,2,5',7a,9a,10-hexamethylicosahydrospiro[furo[3",2":3',4']cyclopenta[1',2':1,2]phenanthro[9,10-d][1,3]dioxole-11,2'-pyran]-5(3aH)-one (Compound 8, 2.5 g) as a pale brown solid which was used as is for the next step without any further purification.

H. Using General Procedure O with Compound 8 (2.5 g, 4.86 mmol), hydrazine hydrate (0.36 g, 7.29 mmol) and ethanol (25 mL) gave the desired pyrazole (2R,3a'R,3b'S,5R,8a'R,8b'S,10a'R,10b'R,11'S,13a'S,14a'S,14b'R,14c'R)-2',2',5,8a',10a',11'-hexamethyl-3,3a',3b',4,5,5',6,8',8a',8b',9',10',10a',10b',11',13a',14',14a',14b',14c'-icosahydro-4'H-spiro[pyran-2,12'-[1,3]dioxolo[4',5':3,4]furo[3",2":3',4']cyclopenta[1',2':5,6]naphtho[1,2-f]indazole] (Compound 9, 2.3 g, 88%, over 2 steps) as a white solid after purification by flash column chromatography (230-400 mesh silica gel, eluted with 0-70% pet ether/ethyl acetate).

I. Using General Procedure E with Compound 9 (2.3 g, 4.50 mmol, 1 eq) and acetic acid 80% aqueous solution (15 mL) gave the desired diol (1S,2R,3aS,4aS,4bR,5R,5'R,6R,6aS,11aR,11bS,13aS,13bR)-1,5',11a,13a-tetramethyl-3a,3',4,4a,4b,4',5,5',6,6a,6',7,8,11,11a,11b,12,13,13a,13b-icosahydro-1H-spiro[furo[3",2":3',4']cyclopenta[1',2':5,6]naphtho[1,2-f]indazole-2,2'-pyran]-5,6-diol (Compound 10, 1.4 g, yield: 66%) as an off-white solid after purification by flash column chromatography (230-400 mesh silica gel, eluted with 0-3% dichloromethane/methanol).

J. Using General Procedure F with Compound 10 (1.4 g, 2.97 mmol, 1 eq), sodium metaperiodate (1.27 g, 2.95 mmol, 2 eq), THF (20 mL) and water (10 mL) gave the desired dialdehyde ((R,6S)-5-((2R,3S,3aR,3bS,5'R,6S,7R,7aS,8aS)-7-formyl-3,3b,5'-trimethyltetradecahydrospiro[indeno[2,1-b]furan-2,2'-pyran]-6-yl)-5-methyl-4,5,6,7-tetrahydro-1H-indazole-6-carbaldehyde (Compound 11, 1.2 g, 85%) as a pale yellow foam after purification by flash column chromatography (230-400 mesh silica gel, eluted with 0-1% dichloromethane/methanol).

K. Using General Procedure G with Compound 11 (1.2 g, 2.56 mmol, 1 eq), sodium borohydride (0.195 g, 5.12 mmol, 2 eq), THF (15 mL) and methanol (5 mL) gave the desired diol ((5R,6S)-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol (Compound Ia-1, 1.3 g, 41%) as a pale yellow solid after purification by flash column chromatography (230-400 mesh silica gel, eluted with 0-10% dichloromethane/methanol).

LCMS: (Method 1b) MS m/z: 473.5 (M+1), $t_R$: 4.04 min, Purity: 95.02% (max), 90.75% (220 nm).

HPLC: (Method 2a) $t_R$: 4.00 min, Purity: 93.75% (max), 90.25% (220 nm).

$^1$H-NMR (400 MHz, DMSO-$d_6$): δ δ 12.18 (bs, 1H), 7.19 (bs, 1H), 4.49-4.44 (m, 1H), 4.26-4.23 (m, 2H), 3.81-3.79 (m, 1H), 3.71-3.68 (m, 1H), 3.43-3.36 (m, 2H), 3.24-3.21 (m, 1H), 3.19-3.01 (m, 2H), 3.00-2.95 (m, 1H), 2.09-2.07 (m, 2H), 1.86-1.75 (m, 2H), 1.66-1.51 (m, 10H), 1.36-1.33 (m, 3H), 1.11-1.08 (m, 2H), 0.96-0.89 (m, 6H), 0.75-0.74 (m, 6H).

Synthetic Example 2

Synthesis of ((5R,6S)-5-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol (Compound Ia-2)

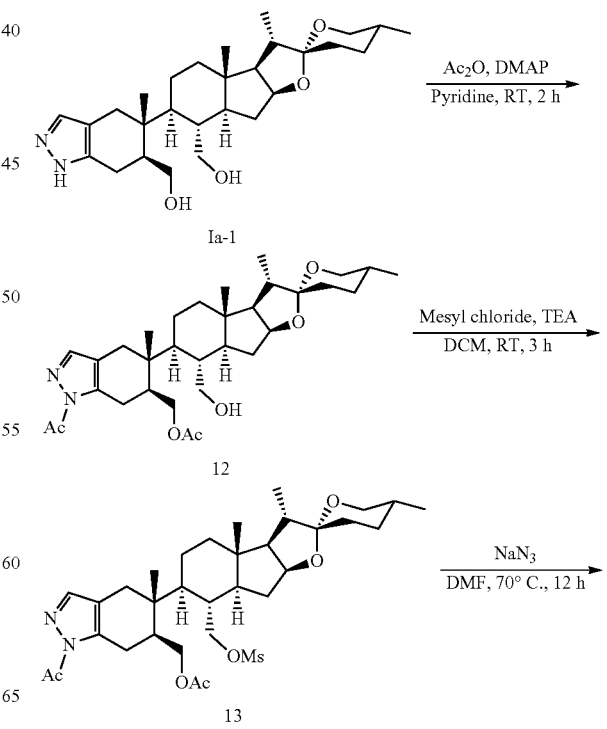

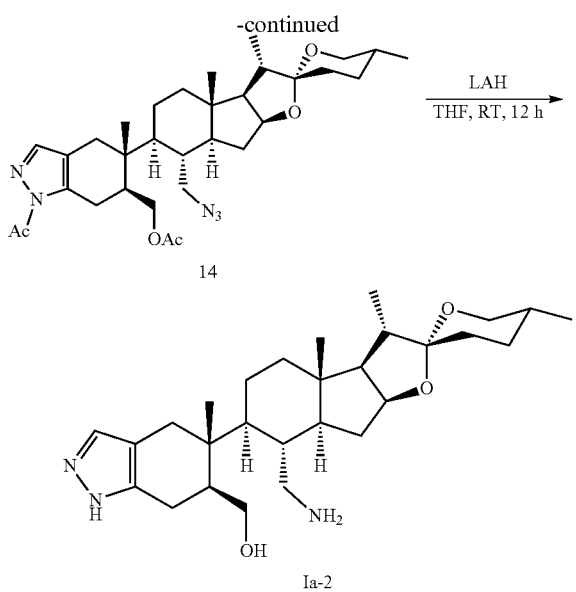

LCMS: (Method 1b) 472.5 (M+1), $t_R$: 3.317 min, 99.56% (Max), 92.46% (220 nm).

HPLC: (Method 2a) $t_R$: 3.146 min, 95.98% (ELSD), 94.86% (220 nm).

$^1$H-NMR (400 MHz, DMSO-$d_6$): δ δ12.24 (bs, 1H), 7.62-7.60 (m, 3H), 7.41-7.25 (m, 1H), 4.50-4.47 (m, 1H), 4.29-4.27 (m, 1H), 3.70-3.68 (m, 1H), 3.45-3.43 (m, 1H), 3.25-3.15 (m, 3H), 2.97-2.92 (m, 2H), 2.33-2.26 (m, 2H), 2.13-2.11 (m, 1H), 1.97-1.82 (m, 3H), 1.71-1.49 (m, 8H), 1.40-1.23 (m, 4H), 1.09-1.06 (m, 1H), 0.92-0.90 (m, 6H), 0.81-0.70 (m, 6H).

Synthetic Example 3

Synthesis of (1S,3aS,4R,5S,7aS)-4-(hydroxymethyl)-5-((5R,6S)-6-(hydroxymethyl)-5-methyl-4,5,6,7-tetrahydro-1H-indazol-5-yl)-1,7a-dimethyloctahydro-1H-inden-1-ol (Compound Ia-3)

A. Using General Procedure A with ((5R,6S)-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol (Compound Ia-1, from Example 1, 0.4 g, 0.846 mmol, 1 eq), Ac$_2$O (0.18 g, 1.77 mmol, 2.1 eq) and pyridine (10 mL) gave the desired diacetate ((5R,6S)-1-acetyl-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methyl acetate (Compound 12, 0.250 g, 47%) as a white foam after purification by flash column chromatography (230-400 mesh silica gel, eluted with 0-4% dichloromethane/methanol).

B. Using General Procedure I with Compound 12 (0.250 g, 0.449 mmol, 1 eq), triethylamine (0.13 mL, 0.0.675 mmol, 1.5 eq), MsCl (0.038 mL, 0.5 mmol, 1.1 eq) and dichloromethane (12 mL) gave the desired mesylate ((5R,6S)-1-acetyl-5-methyl-5-((2R,3S,3aR,3bS,5'R,6S,7R,7aS,8aS)-3,3b,5'-trimethyl-7-(((methylsulfonyl)oxy)methyl)tetradecahydrospiro[indeno[2,1-b]furan-2,2'-pyran]-6-yl)-4,5,6,7-tetrahydro-1H-indazol-6-yl)methyl acetate (Compound 13, 0.25 g) as an colorless gum which was used as is for the next step without any further purification.

C. Using General Procedure J with Compound 13 (0.25 g, 0.394 mmol, 1 eq), sodium azide (0.256 g, 3.94 mmol, 10 eq) and DMF (5 mL) gave the desired azide ((5R,6S)-1-acetyl-5-((2R,3S,3aR,3bS,5'R,6S,7R,7aS,8aS)-7-(azidomethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methyl acetate (Compound 14, 0.190 g, yield: 80%) as an off-white solid after purification by flash column chromatography (230-400 mesh silica gel, eluted with 0-30% pet ether/ethyl acetate).

D. Using General Procedure R with Compound 14 (0.19 g, 0.337 mmol, 1 eq), LAH solution (1 M in THF solution, 1.3 mL, 1.34 mmol, 3 eq) and THF (10 mL) gave the desired amine ((5R,6S)-5-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol (Compound Ia-2, 36 mg, 23%) as an white solid after purification by preparative HPLC (method 3a).

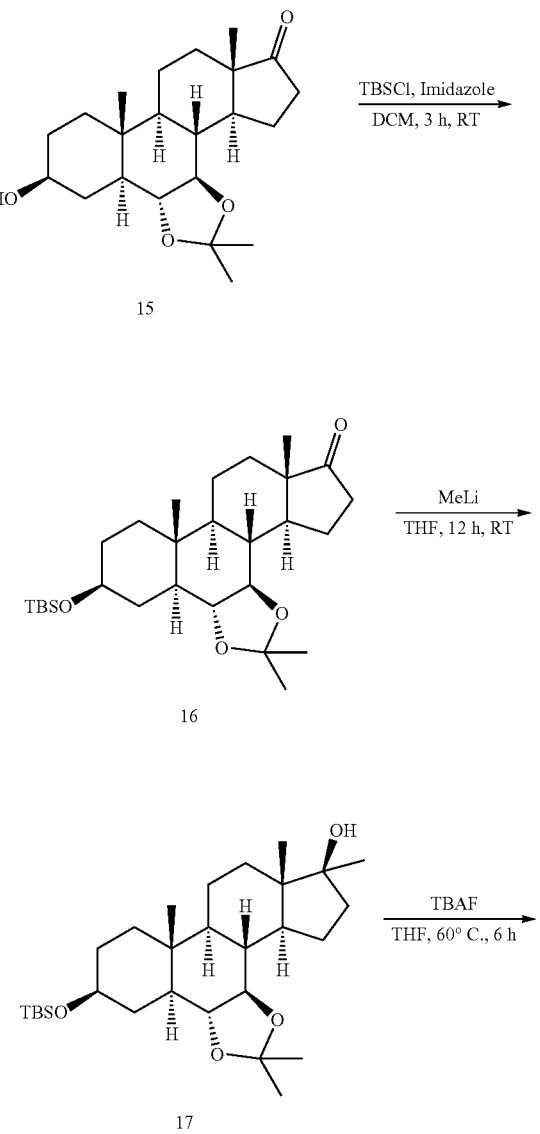

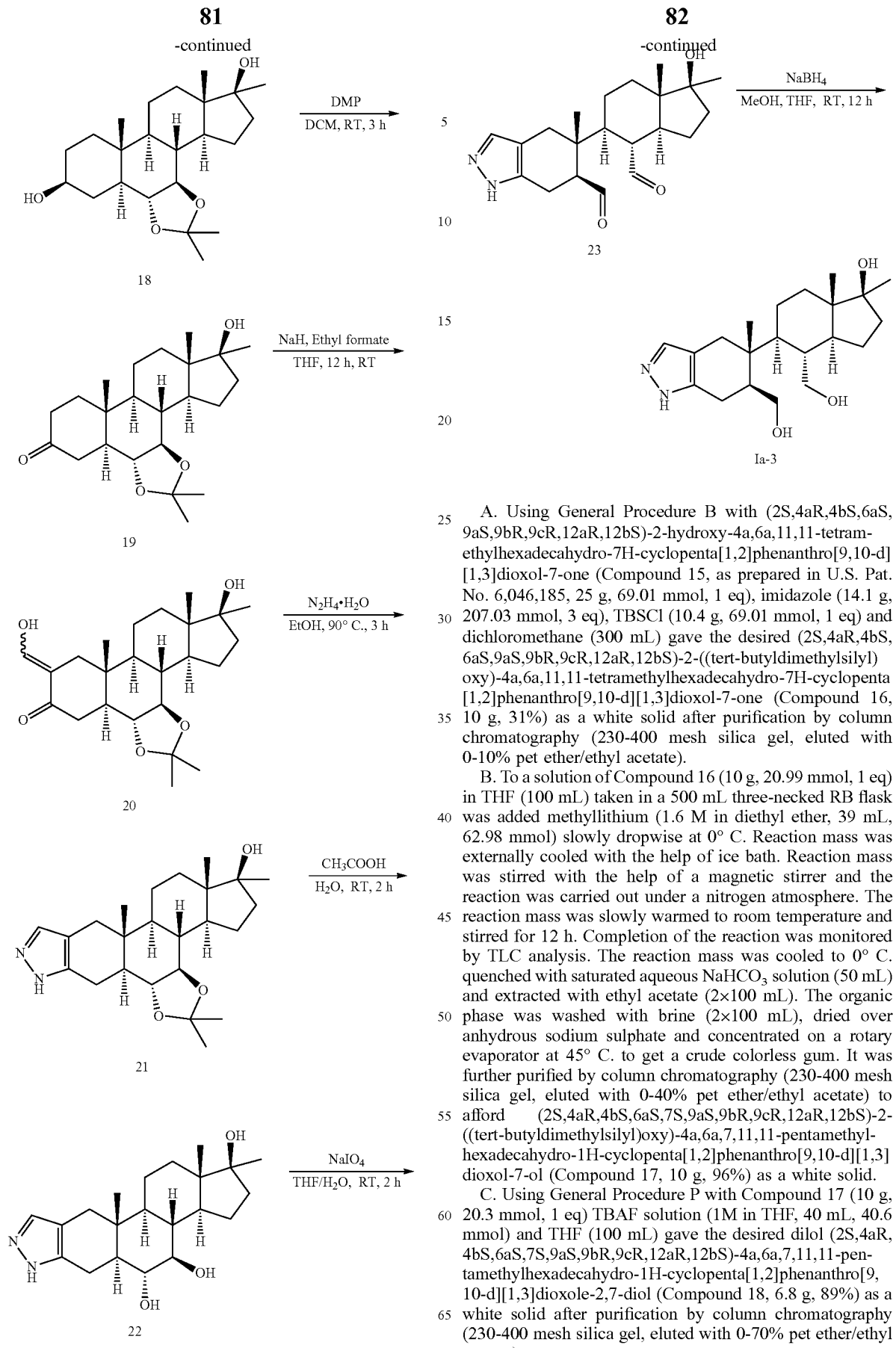

A. Using General Procedure B with (2S,4aR,4bS,6aS, 9aS,9bR,9cR,12aR,12bS)-2-hydroxy-4a,6a,11,11-tetramethylhexadecahydro-7H-cyclopenta[1,2]phenanthro[9,10-d][1,3]dioxol-7-one (Compound 15, as prepared in U.S. Pat. No. 6,046,185, 25 g, 69.01 mmol, 1 eq), imidazole (14.1 g, 207.03 mmol, 3 eq), TBSCl (10.4 g, 69.01 mmol, 1 eq) and dichloromethane (300 mL) gave the desired (2S,4aR,4bS, 6aS,9aS,9bR,9cR,12aR,12bS)-2-((tert-butyldimethylsilyl)oxy)-4a,6a,11,11-tetramethylhexadecahydro-7H-cyclopenta[1,2]phenanthro[9,10-d][1,3]dioxol-7-one (Compound 16, 10 g, 31%) as a white solid after purification by column chromatography (230-400 mesh silica gel, eluted with 0-10% pet ether/ethyl acetate).

B. To a solution of Compound 16 (10 g, 20.99 mmol, 1 eq) in THF (100 mL) taken in a 500 mL three-necked RB flask was added methyllithium (1.6 M in diethyl ether, 39 mL, 62.98 mmol) slowly dropwise at 0° C. Reaction mass was externally cooled with the help of ice bath. Reaction mass was stirred with the help of a magnetic stirrer and the reaction was carried out under a nitrogen atmosphere. The reaction mass was slowly warmed to room temperature and stirred for 12 h. Completion of the reaction was monitored by TLC analysis. The reaction mass was cooled to 0° C. quenched with saturated aqueous NaHCO$_3$ solution (50 mL) and extracted with ethyl acetate (2×100 mL). The organic phase was washed with brine (2×100 mL), dried over anhydrous sodium sulphate and concentrated on a rotary evaporator at 45° C. to get a crude colorless gum. It was further purified by column chromatography (230-400 mesh silica gel, eluted with 0-40% pet ether/ethyl acetate) to afford (2S,4aR,4bS,6aS,7S,9aS,9bR,9cR,12aR,12bS)-2-((tert-butyldimethylsilyl)oxy)-4a,6a,7,11,11-pentamethylhexadecahydro-1H-cyclopenta[1,2]phenanthro[9,10-d][1,3]dioxol-7-ol (Compound 17, 10 g, 96%) as a white solid.

C. Using General Procedure P with Compound 17 (10 g, 20.3 mmol, 1 eq) TBAF solution (1M in THF, 40 mL, 40.6 mmol) and THF (100 mL) gave the desired dilol (2S,4aR, 4bS,6aS,7S,9aS,9bR,9cR,12aR,12bS)-4a,6a,7,11,11-pentamethylhexadecahydro-1H-cyclopenta[1,2]phenanthro[9,10-d][1,3]dioxole-2,7-diol (Compound 18, 6.8 g, 89%) as a white solid after purification by column chromatography (230-400 mesh silica gel, eluted with 0-70% pet ether/ethyl acetate).

D. Using General Procedure M with Compound 18 (6.8 g, 17.9 mmol, 1 eq), Dess-Martin periodinane (11.45 g, 26.9 mmol, 1.5 eq) and dichloromethane (70 mL) gave the desired ketone (4aR,4bS,6aS,7S,9aS,9bR,9cR,12aR,12bS)-7-hydroxy-4a,6a,7,11,11-pentamethylhexadecahydro-2H-cyclopenta[1,2]phenanthro[9,10-d][1,3]dioxol-2-one (Compound 19, 4 g, 59%) as a white solid after purification by column chromatography (230-400 mesh silica gel, eluted with 0-10% pet ether/ethyl acetate).

E. Using General Procedure N with Compound 19 (4 g, 10.63 mmol, 1 eq), sodium hydride (60% in paraffin oil, 1.5 g, 42.52 mmol, 4 eq), tetrahydrofuran (40 mL), and ethyl formate (5.2 mL, 63.78 mmol, 6 eq) gave the desired enone (4aR,4bS,6aS,7S,9aS,9bR,9cR,12aR,12bS)-7-hydroxy-3-(hydroxymethylene)-4a,6a,7,11,11-pentamethylhexadecahydro-2H-cyclopenta[1,2]phenanthro[9,10-d][1,3]dioxol-2-one (Compound 20, 4 g, 93%) as a yellow solid after purification by column chromatography (230-400 mesh silica gel, eluted with 0-15% pet ether/ethyl acetate).

F. Using General Procedure O with Compound 20 (4 g, 9.89 mmol, 1 eq), hydrazine hydrate (0.74 g, 14.84 mmol) and ethanol (40 mL) gave the desired pyrazole (1S,3aS,3bR,3cR,6aR,6bS,11aR,11bS,13aS)-1,5,5,11a,13a-pentamethyl-1,2,3,3a,3b,3c,6a,6b,7,8,11,11a,11b,12,13,13a-hexadecahydrocyclopenta[5,6][1,3]dioxolo[4',5':3,4]naphtho[1,2-]indazol-1-ol (Compound 21, 3.7 g, 94%) as a pale yellow solid after purification by column chromatography (230-400 mesh silica gel, eluted with 0-60% pet ether/ethyl acetate).

G. Using General Procedure E with Compound 21 (3.7 g, 9.24 mmol, 1 eq) and acetic acid (80% aqueous, 20 mL) gave the desired triol (1S,3aS,3bR,4R,5R,5aS,10aR,10bS,12aS)-1,10a,12a-trimethyl-1,2,3,3a,3b,4,5,5a,6,7,10,10a,10b,11,12,12a-hexadecahydrocyclopenta[5,6]naphtho[1,2-f]indazole-1,4,5-triol (Compound 22, 3.2 g) as a crude brown solid which was used for the next step without further purification.

H. Using General Procedure F with Compound 22 (3.2 g, 8.88 mmol, 1 eq), sodium metaperiodate (3.8 g, 17.76 mmol, 2 eq), THF (32 mL) and water (16 mL) gave the desired dialdehyde (5R,6S)-5-((1S,3aS,4R,5S,7aS)-4-formyl-1-hydroxy-1,7a-dimethyloctahydro-1H-inden-5-yl)-5-methyl-4,5,6,7-tetrahydro-1H-indazole-6-carbaldehyde (Compound 23, 3 g, 93% over 2 steps) as a white solid after purification by column chromatography (230-400 mesh silica gel, eluted with 0-1% dichloromethane/methanol).

I. Using General Procedure G with Compound 23 (3 g, 8.37 mmol, 1 eq), sodium borohydride (0.795 g, 20.9 mmol, 2.5 eq), THF (20 mL) and methanol (10 mL) gave the desired triol (1S,3aS,4R,5S,7aS)-4-(hydroxymethyl)-5-((5R,6S)-6-(hydroxymethyl)-5-methyl-4,5,6,7-tetrahydro-1H-indazol-5-yl)-1,7a-dimethyloctahydro-1H-inden-1-ol (Compound Ia-3, 1.3 g, 43%) as a pale yellow solid after purification by column chromatography (230-400 mesh silica gel, eluted with 0-20% dichloromethane/methanol).

LCMS: (Method 1b) MS m/z: 363.3 (M+1), $t_R$: 1.96 min, Purity: 95.36% (max), 92.04% (220 nm).

HPLC: (Method 2a) $t_R$: 1.973 min, Purity: 94.29% (max), 91.75% (220 nm).

$^1$H-NMR (400 MHz, DMSO-d$_6$): δ 12.20 (bs, 1H), 7.24-7.17 (m, 1H), 4.42-4.41 (m, 1H), 4.29-4.10 (m, 2H), 4.08-4.04 (m, 1H), 3.75-3.69 (m, 2H), 3.44-3.40 (m, 1H), 3.18-3.05 (m, 2H), 3.04-2.95 (m, 1H), 2.15-2.07 (m, 2H), 1.80-1.52 (m, 4H), 1.51-1.33 (m, 6H), 1.22-1.17 (m, 2H), 1.15-1.13 (s, 3H), 1.00-0.93 (s, 3H), 0.75-0.72 (s, 3H).

Synthetic Example 4

Synthesis of (1S,3aS,4R,5S7aS)-4-(hydroxymethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol (Compound Ia-4)

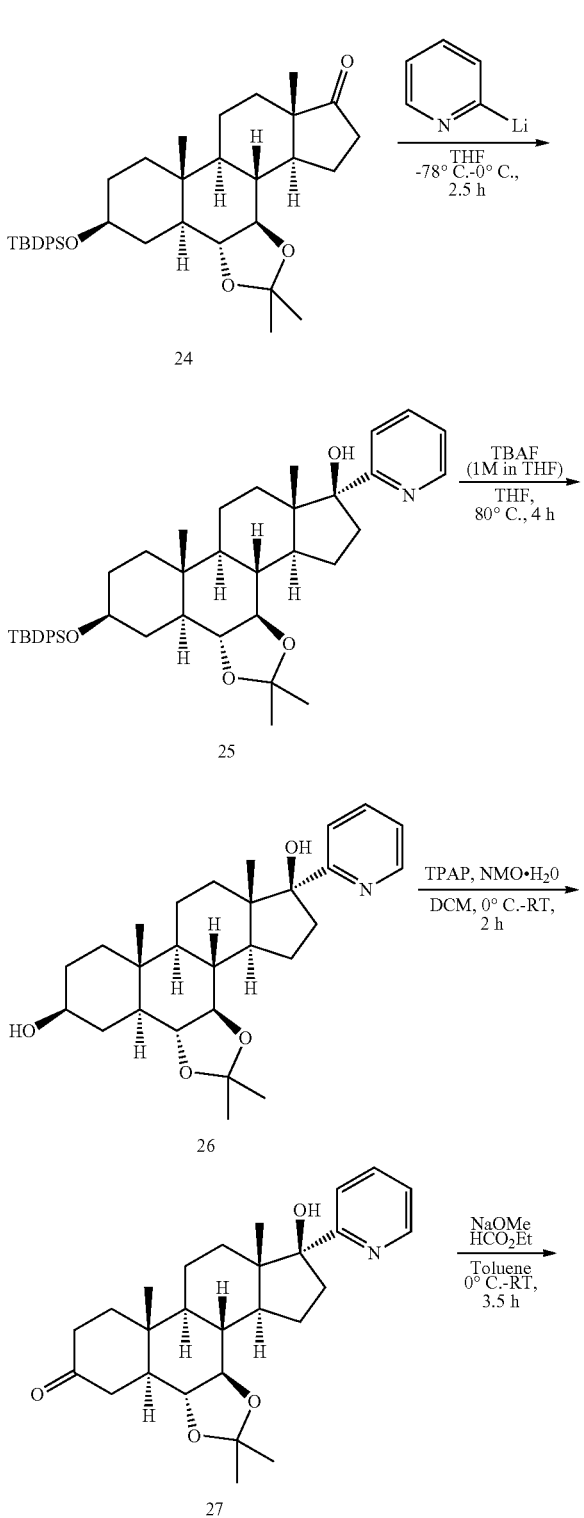

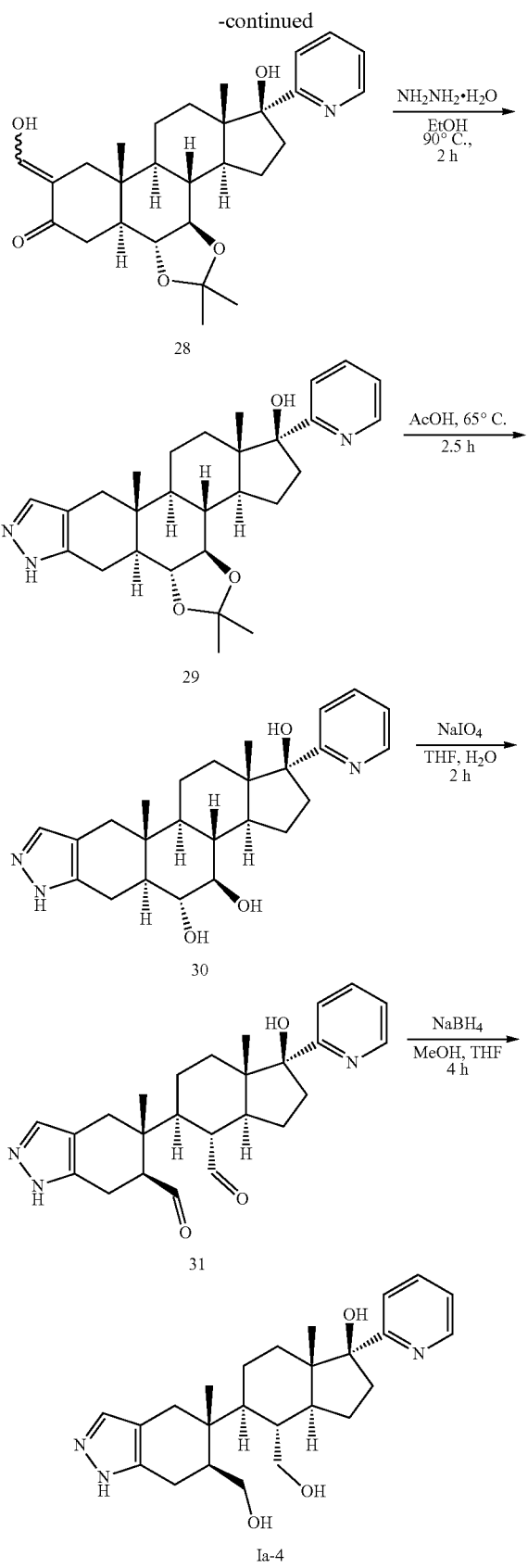

was added a solution of 2-bromopyridine (9.2 g, 58.24 mmol) in THF (30 mL) dropwise. The mixture was stirred at −78° C. for 20 minutes, then a solution of (2S,4aR,4bS,6aS,9aS,9bR,9cR,12aR,12bS)-2-((tert-butyldiphenylsilyl)oxy)-4a,6a,11,11-tetramethylhexadecahydro-7H-cyclopenta[1,2]phenanthro[9,10-d][1,3]dioxol-7-one (Compound 24, as prepared in U.S. Pat. No. 9,765,085, 10 g, 16.64 mmol) in THF (50 mL) was added. The resultant solution was stirred at 0° C. for 2.5 hours. The mixture was diluted with ice cold water (1×50 mL) and the aqueous was extracted with EtOAc (2×50 mL) and washed with brine (1×50 mL). The organic layer was dried over $Na_2SO_4$, filtered and concentrated. The residue was purified by column chromatography on silica gel (230-400 mesh, 0-30% pet ether/ethyl acetate) to afford (2S,4aR,4bS,6aS,7S,9aS,9bR,9cR,12aR,12bS)-2-((tert-butyldiphenylsilyl)oxy)-4a,6a,11,11-tetramethyl-7-(pyridin-2-yl)hexadecahydro-1H-cyclopenta[1,2]phenanthro[9,10-d][1,3]dioxol-7-ol (Compound 25, 8.5 g, 75%) as a yellow foam.

B. Using General Procedure P with Compound 25 (8.5 g, 12.50 mmol), TBAF solution (1 M in THF, 25.0 mL, 25.0 mmol), and tetrahydrofuran (80 mL) gave the desired alcohol (2S,4aR,4bS,6aS,7S,9aS,9bR,9cR,12aR,12bS)-4a,6a,11,11-tetramethyl-7-(pyridin-2-yl)hexadecahydro-1H-cyclopenta[1,2]phenanthro[9,10-d][1,3]dioxole-2,7-diol (Compound 26, 4.0 g, 72%) as an off-white solid after purification by column chromatography (230-400 mesh silica gel, eluted with 0-60% pet ether/ethyl acetate).

C. Using General Procedure L with Compound 26 (4.0 g, 9.06 mmol), NMO (2.12 g, 18.12 mmol), 4 Å molecular sieves (4.0 g) and TPAP (0.75 g, 2.13 mmol) in $CH_2Cl_2$ (40 mL) gave the desired ketone (4aR,4bS,6aS,7S,9aS,9bR,9cR,12aR,12bS)-7-hydroxy-4a,6a,11,11-tetramethyl-7-(pyridin-2-yl)hexadecahydro-2H-cyclopenta[1,2]phenanthro[9,10-d][1,3]dioxol-2-one (Compound 27, 3.5 g, 88%) as an off-white solid after purification by column chromatography (230-400 mesh silica gel, eluted with 15-20% pet ether/ethyl acetate).

D. To a stirred solution of Compound 27 (3.5 g, 7.96 mmol) in toluene (30 mL) at 0° C. were added sodium methoxide solution (25% wt. in MeOH, 3.4 mL, 12.46 mmol) and ethyl formate (3.21 mL, 39.81 mmol) dropwise. The resultant solution was stirred at room temperature for 3.5 hours. The mixture was evaporated under reduced pressure and the residue was diluted with ice cold water (1×30 mL). The aqueous was extracted with EtOAc (2×30 mL) and washed with brine (1×10 mL). The organic layer was dried over $Na_2SO_4$, filtered and concentrated. The residue was purified by column chromatography on silica gel (230-400 mesh, 10-20% pet ether/ethyl acetate) to afford (4aR,4bS,6aS,7S,9aS,9bR,9cR,12aR,12bS)-7-hydroxy-3-(hydroxymethylene)-4a,6a,11,11-tetramethyl-7-(pyridin-2-yl)hexadecahydro-2H-cyclopenta[1,2]phenanthro[9,10-d][1,3]dioxol-2-one (Compound 28, 3.0 g, 81%) as a brown gummy solid.

E. Using General Procedure O with Compound 28 (3.0 g, 6.42 mmol) and hydrazine hydrate (0.63 mL, 12.83 mmol) in EtOH (30 mL) gave the desired pyrazole (1S,3aS,3bR,3cR,6aR,6bS,11aR,11bS,13aS)-5,5,11a,13a-tetramethyl-1-(pyridin-2-yl)-1,2,3,3a,3b,3c,6a,6b,7,8,11,11a,11b,12,13,13a-hexadecahydrocyclopenta[5,6][1,3]dioxolo[4',5':3,4]naphtho[1,2-f]indazol-1-ol (Compound 29, 2.5 g, 84%) as an off-white solid after purification by column chromatography (230-400 mesh silica gel, eluted with 60-80% pet ether/ethyl acetate).

F. Using General Procedure E with Compound 29 (2.5 g, 5.39 mmol) in 80% AcOH (25 mL) gave the desired A. To a stirred solution of n-butyllithium (1.6 M in Hexane, 31.20 mL, 49.92 mmol) in THF (20 mL) at −78° C.

trialcohol (1S,3aS,3bR,4R,5R,5aS,10aR,10bS,12aS)-10a,12a-dimethyl-1-(pyridin-2-yl)-1,2,3,3a,3b,4,5,5a,6,7,10,10a,10b,11,12,12a-hexadecahydrocyclopenta[5,6]naphtho[1,2-f]indazole-1,4,5-triol (Compound 30, 2.0 g, 88%) as an off-white solid after purification by column chromatography (230-400 mesh silica gel, eluted with 10-15% methanol/dichloromethane).

LCMS: (Method 1e) MS m/z: 424.1 (M+1), $t_R$: 2.185 min, Purity: 92.18% (UV).

HPLC: (Method 2e) $t_R$: 5.464 min, Purity: 91.32% (UV).

$^1$H-NMR (400 MHz, CD$_3$OD): δ 8.54-8.53 (m, 1H), 7.81-7.77 (m, 1H), 7.57-7.55 (m, 1H), 7.29-7.26 (m, 1H), 7.23 (s, 1H), 3.29-3.06 (m, 3H), 2.55-2.25 (m, 4H), 2.09-1.95 (m, 3H), 1.70-1.40 (m, 6H), 1.10 (s, 3H), 0.80 (s, 3H), 0.70-0.64 (m, 1H), 0.19-0.12 (m, 1H).

G. Using General Procedure F with Compound 30 (2.5 g, 5.90 mmol) and sodium metaperiodate (2.52 g, 11.80 mmol) in THF:water (4:1, 25 mL) gave the desired dialdehyde (5R,6S)-5-((1S,3aS,4R,5S,7aS)-4-formyl-1-hydroxy-7a-methyl-1-(pyridin-2-yl)octahydro-1H-inden-5-yl)-5-methyl-4,5,6,7-tetrahydro-1H-indazole-6-carbaldehyde (Compound 31, 1.8 g, 72%) as a white solid after purification by column chromatography (230-400 mesh silica gel, eluted with 0-5% methanol/dichloromethane).

H. Using General Procedure G with Compound 31 (1.8 g, 4.27 mmol) and sodium borohydride (0.32 g, 8.46 mmol) in THF:MeOH (1:1, 20 mL) gave the desired trialcohol (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol (Compound Ia-4, 0.85 g, 47%) as a white solid after purification by column chromatography (Neutral alumina, eluted with 0-5% methanol/dichloromethane).

LCMS: (Method 1e) MS m/z: 426.2 (M+1), $t_R$: 2.098 min, Purity: 94.81% (UV).

HPLC: (Method 2e) $t_R$: 4.563 min, Purity: 99.09% (UV).

$^1$H-NMR (400 MHz, CD$_3$OD): δ 8.51 (d, J=4.8 Hz, 1H), 7.80-7.76 (m, 1H), 7.56 (d, J=8.0 Hz, 1H), 7.29-7.23 (m, 2H), 4.02-3.99 (m, 1H), 3.79-3.62 (m, 2H), 3.28-3.23 (m, 1H), 3.12-3.06 (m, 1H), 2.63-2.41 (m, 3H), 2.14-2.05 (m, 4H), 1.91-1.88 (m, 1H), 1.70-1.59 (m, 2H), 1.49-1.31 (m, 4H), 1.09 (s, 3H), 1.04 (s, 3H), 0.02 (bs, 1H).

Synthetic Example 5

Synthesis of ((5R,6S)-5-((3aS,6S,7R,7aS)-7-(hydroxymethyl)-3a-methyl-3-phenyl-3a,4,5,6,7,7a-hexahydro-1H-inden-&-yl)-5-methyl-4,5,6,7-tetrahydro-1H-indazol-6-yl)methanol (Compound Ia-5)

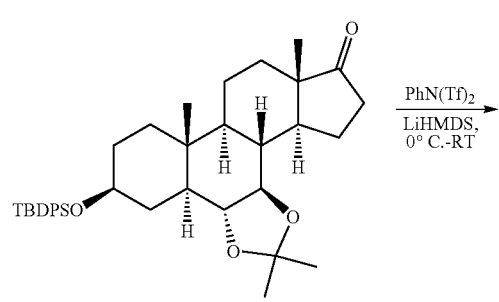

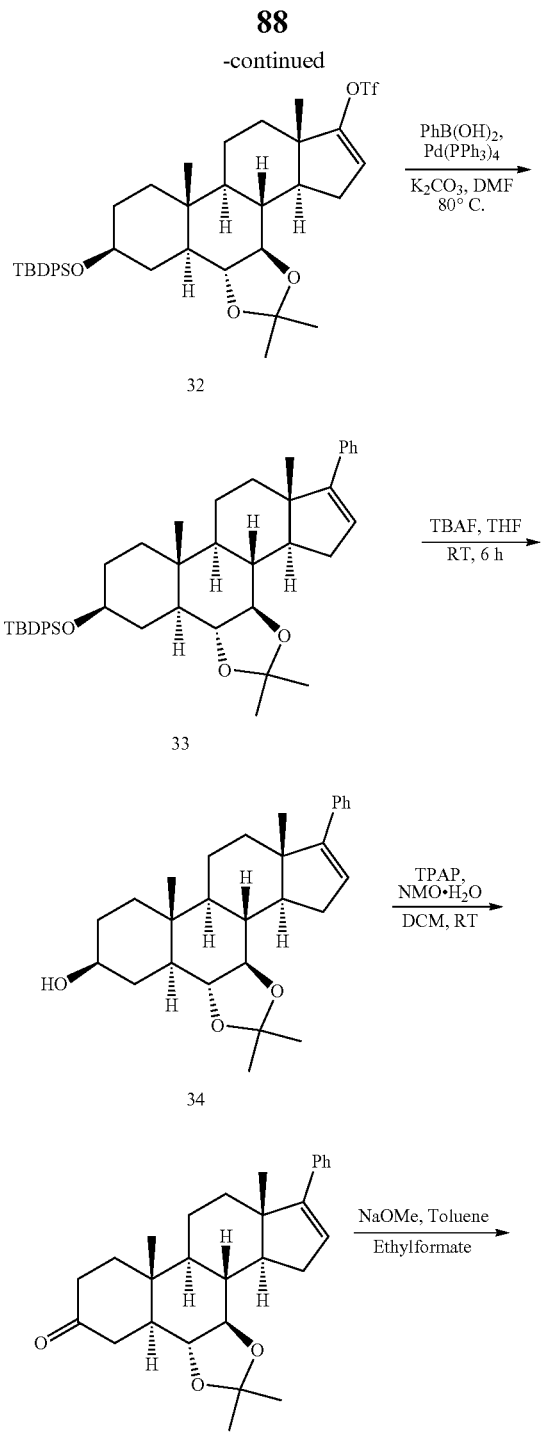

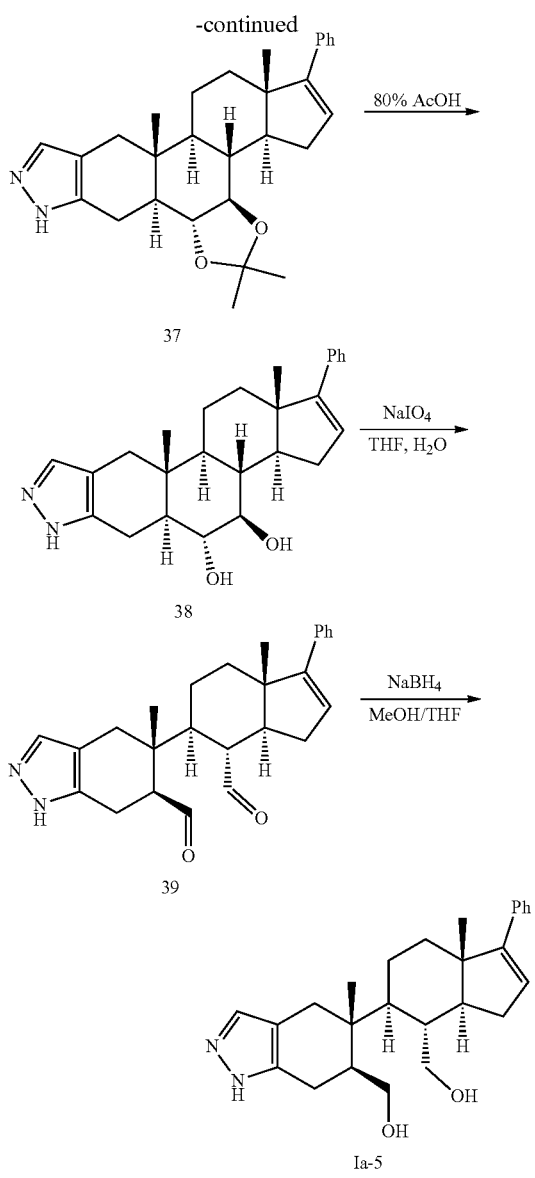

A. To a stirred solution of Compound 24 (from Example 4, 5.0 g, 8.32 mmol) in THF (50 mL) at 0° C. were added N-phenyl-bis(tifluoromethanesulfonimide) (5.95 g, 16.64 mmol) and lithium bis(trimethylsilyl)amide (1 M in THF, 24.96 mL, 24.96 mmol) dropwise. The resultant solution was stirred at room temperature for 2.5 hours. The mixture was diluted with ice cold water (1×50 mL) and the aqueous was extracted with EtOAc (2×50 mL) and washed with brine (1×50 mL). The organic layer was dried over Na$_2$SO$_4$, filtered and concentrated. The residue was purified by column chromatography on silica gel (230-400 mesh, 0-5% pet ether/ethyl acetate) to afford (2S,4aR,4bS,6aS,9aS,9bR,9cR,12aR,12bS)-2-((tert-butyldiphenylsilyl)oxy)-4a,6a,11,11-tetramethyl-2,3,4,4a,4b,5,6,6a,9,9a,9b,9c,12a,12b-tetradecahydro-1H-cyclopenta[1,2]phenanthro[9,10-d][1,3]dioxol-7-yl trifluoromethanesulfonate (Compound 32, 5.1 g, 84%) as an off-white solid.

B. To a stirred solution of Compound 32 (5.1 g, 6.96 mmol) in DMF (50 mL) were added phenyl boronic acid (1.02 g, 8.35 mmol) and potassium carbonate (1.92 g, 13.92 mmol) at room temperature. The reaction mixture was degassed with nitrogen for 20 minutes. To the solution was added tetrakis(triphenylphosphine)palladium(0) (0.80 g, 0.70 mmol) and the reaction was heated to 80° C. and stirred for 3 hours. The reaction mixture was filtered through the bed of CELITE® and the filtrate was evaporated under reduced pressure. The residue was diluted with EtOAc (2×50 mL) then washed consecutively with water (1×10 mL) and brine (1×10 mL). The organic layer was dried over Na$_2$SO$_4$, filtered and concentrated. The crude material was purified by column chromatography on silica gel (230-400 mesh, 0-10% pet ether/ethyl acetate) to afford tert-butyldiphenyl(((2S,4aR,4bS,6aS,9aS,9bR,9cR,12aR,12bS)-4a,6a,11,11-tetramethyl-7-phenyl-2,3,4,4a,4b,5,6,6a,9,9a,9b,9c,12a,12b-tetradecahydro-1H-cyclopenta[1,2]phenanthro[9,10-d][1,3]dioxol-2-yl)oxy)silane (Compound 33, 3.1 g, 67%) as an off-white solid.

C. Following the General Procedure P with Compound 33 (3.0 g, 4.54 mmol) and TBAF (1 M in THF, 9.08 mL, 9.08 mmol) in THF (30 mL), gave the desired alcohol (2S,4aR,4bS,6aS,9aS,9bR,9cR,12aR,12bS)-4a,6a,11,11-tetramethyl-7-phenyl-2,3,4,4a,4b,5,6,6a,9,9a,9b,9c,12a,12b-tetradecahydro-1H-cyclopenta[1,2]phenanthro[9,10-d][1,3]dioxol-2-ol (Compound 34, 1.6 g, 84%) as a white solid after purification by column chromatography (230-400 mesh silica gel, eluted with 0-50% pet ether/ethyl acetate).

D. Using General Procedure L with Compound 34 (1.6 g, 3.79 mmol), NMO hydrate (0.89 g, 6.58 mmol), 4 Å molecular sieves (1.6 g) and TPAP (0.13 g, 0.38 mmol) in CH$_2$Cl$_2$ (15 mL), gave the desired ketone (4aR,4bS,6aS,9aS,9bR,9cR,12aR,12bS)-4a,6a,11,11-tetramethyl-7-phenyl-1,3,4,4a,4b,5,6,6a,9,9a,9b,9c,12a,12b-tetradecahydro-2H-cyclopenta[1,2]phenanthro[9,10-d][1,3]dioxol-2-one (Compound 35, 1.5 g, 94%) as a white solid after purification by column chromatography (230-400 mesh silica gel, eluted with 0-20% pet ether/ethyl acetate).

E. To a stirred solution of Compound 35 (1.5 g, 3.57 mmol) in toluene (15 mL) at 0° C. were added sodium methoxide solution (25% wt. in MeOH, 1.54 mL, 5.64 mmol) and ethyl formate (1.44 mL, 17.85 mmol) dropwise. The resultant solution was stirred at room temperature for 3.5 hours. The mixture was evaporated under reduced pressure and the residue was diluted with ice cold water (1×15 mL). The aqueous was extracted with EtOAc (2×15 mL) and washed with brine (1×15 mL). The organic layer was dried over Na$_2$SO$_4$, filtered and concentrated to give the desired ketone (4aR,4bS,6aS,9aS,9bR,9cR,12aR,12bS)-3-(hydroxymethylene)-4a,6a,11,11-tetramethyl-7-phenyl-1,3,4,4a,4b,5,6,6a,9,9a,9b,9c,12a,12b-tetradecahydro-2H-cyclopenta[1,2]phenanthro[9,10-d][1,3]dioxol-2-one (Compound 36, 1.5 g, 94%) as a brown gummy solid which was taken for next step without purification.

F. Using General Procedure O with Compound 36 (1.5 g, 3.34 mmol) and hydrazine hydrate (0.33 mL, 6.69 mmol) in EtOH (15 mL) gave the desired pyrazole (3aS,3bR,3cR,6aR,6bS,11aR,11bS,13aS)-5,5,11a,13a-tetramethyl-1-phenyl-3,3a,3b,3c,6a,6b,7,8,11,11a,11b,12,13,13a-tetradecahydrocyclopenta[5,6][1,3]dioxolo[4',5':3,4]naphtho[1,2-t]indazole (Compound 37, 1.3 g, 88%) as an off-white solid after purification by column chromatography (230-400 mesh silica gel, eluted with 40-50% pet ether/ethyl acetate).

G. Using General Procedure E with Compound 37 (1.3 g, 2.92 mmol) in 80% AcOH (10 mL) gave the desired dialcohol (3aS,3bR,4R,5R,5aS,10aR,10bS,12aS)-10a,12a-dimethyl-1-phenyl-3,3a,3b,4,5,5a,6,7,10,10a,10b,11,12,12a-tetradecahydrocyclopenta[5,6]naphtho[1,2-f]indazole-4,5-diol (Compound 38, 0.8 g, 68%) as an off-white solid after purification by column chromatography (230-400 mesh silica gel, eluted with 0-5% methanol/dichloromethane).

LCMS: (Method 1d) MS m/z: 405.2 (M+1), $t_R$: 2.106 min, Purity: 93.14% (UV).

HPLC: (Method 2b) $t_R$: 11.323 min, Purity: 94.81% (UV).

$^1$H-NMR (400 MHz, CD$_3$OD): δ 7.39-7.36 (m, 2H), 7.31-7.27 (m, 3H), 7.24-7.22 (m, 1H), 5.94-5.93 (m, 1H), 3.19-3.13 (m, 2H), 2.67-2.63 (m, 1H), 2.53-2.31 (m, 3H), 2.20-2.05 (m, 2H), 1.86-1.58 (m, 5H), 1.57-1.31 (m, 2H), 1.16-1.11 (m, 4H), 0.88 (s, 3H).

H. Using General Procedure F with (3aS,3bR,4R,5R,5aS,10aR,10bS,12aS)-10a,12a-dimethyl-1-phenyl-3,3a,3b,4,5,5a,6,7,10,10a,10b,11,12,12a-tetradecahydrocyclopenta[5,6]naphtho[1,2-f]indazole-4,5-diol (Compound 38, 0.75 g, 1.85 mmol) and sodium metaperiodate (0.79 g, 3.71 mmol) in THF:water (4:1) (10 mL) gave the desired dialdehyde (5R,6S)-5-((3aS,6S,7R,7aS)-7-formyl-3a-methyl-3-phenyl-3a,4,5,6,7,7a-hexahydro-1H-inden-6-yl)-5-methyl-4,5,6,7-tetrahydro-1H-indazole-6-carbaldehyde (Compound 39, 0.78 g) as a white solid which was taken for next step without purification.

I. Using General Procedure G with (5R,6S)-5-((3aS,6S,7R,7aS)-7-formyl-3a-methyl-3-phenyl-3a,4,5,6,7,7a-hexahydro-1H-inden-6-yl)-5-methyl-4,5,6,7-tetrahydro-1H-indazole-6-carbaldehyde (Compound 39, 0.78 g, 1.94 mmol) and sodium borohydride (0.15 g, 3.97 mmol) in THF/MeOH (1:1) (10 mL) gave the desired dialcohol ((5R,6S)-5-((3aS,6S,7R,7aS)-7-(hydroxymethyl)-3a-methyl-3-phenyl-3a,4,5,6,7,7a-hexahydro-1H-inden-6-yl)-5-methyl-4,5,6,7-tetrahydro-1H-indazol-6-yl)methanol (Compound Ia-5, 0.70 g, 89%) as a white solid after purification by column chromatography (Neutral alumina, eluted with 0-5% methanol/dichloromethane).

LCMS: (Method 1d) MS m/z: 407.2 (M+1), $t_R$: 1.961 min, Purity: 91.23% (UV).

HPLC: (Method 2b) $t_R$: 10.912 min, Purity: 95.73% (UV).

$^1$H-NMR (400 MHz, CD$_3$OD): δ 7.38-7.36 (m, 2H), 7.30-7.24 (m, 3H), 7.22-7.18 (m, 1H), 5.93-5.92 (m, 1H), 4.12-4.09 (m, 1H), 3.99-3.96 (m, 1H), 3.79-3.76 (m, 1H), 3.21-3.17 (m, 1H), 2.75-2.28 (m, 5H), 2.18-1.80 (m, 7H), 1.65-1.31 (m, 2H), 1.14 (s, 3H), 1.10 (s, 3H).

Synthetic Example 6

Synthesis of ((5R,6S)-5-((3aS,6S,7R,7aS)-7-(aminomethyl)-3a-methyl-3-phenyl-3a,4,5,6,7,7a-hexahydro-1H-inden-&-yl)-5-methyl-4,5,6,7-tetrahydro-1H-indazol-6-yl)methanol (Compound Ia-6)

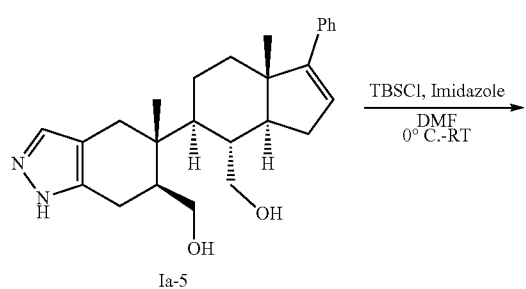

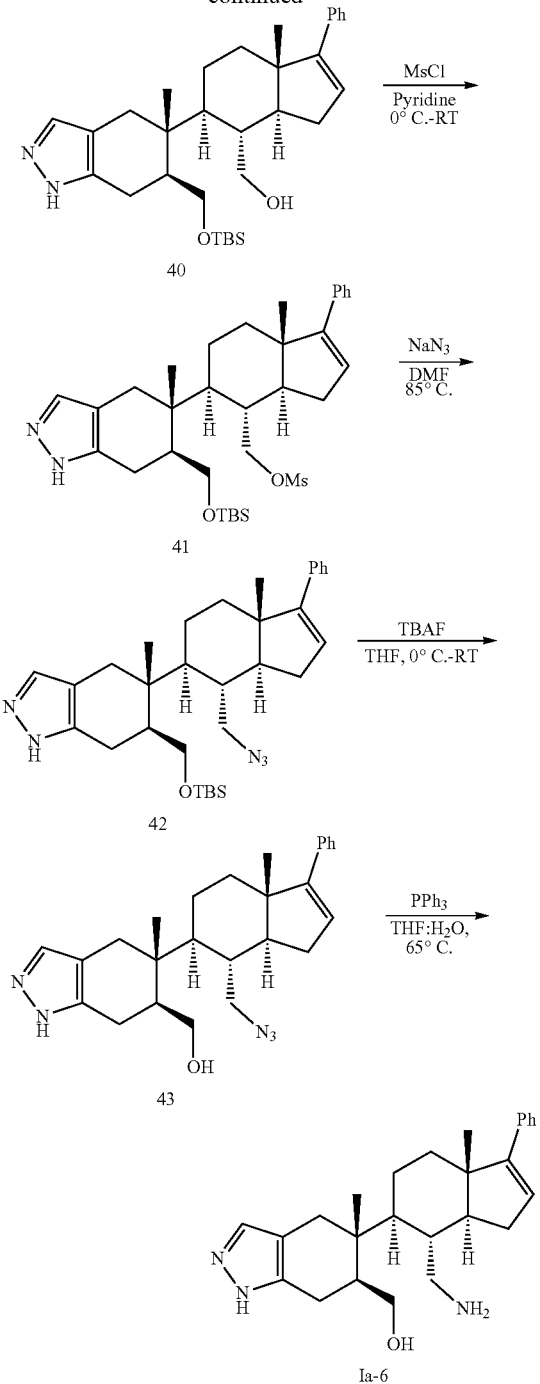

A. Using General Procedure B with Compound Ia-5 (from Example 5, 0.70 g, 1.72 mmol), imidazole (0.35 g, 5.17 mmol) and TBSCl (0.39 g, 2.58 mmol) in DCM (10 mL), followed by purification by column chromatography on silica gel (230-400 mesh, 70-80% pet ether/ethyl acetate) to afford ((3aS,6,7R,7aS)-6-((5R,6S)-6-(((tert-butyldimethylsilyl)oxy)methyl)-5-methyl-4,5,6,7-tetrahydro-1H-indazol-5-yl)-3a-methyl-3-phenyl-3a,4,5,6,7,7a-hexahydro-1H-inden-7-yl) methanol (Compound 40, 0.45 g, 50%) as a white solid.

B. Using General Procedure I with Compound 40 (0.45 g, 0.86 mmol) and MsCl (0.13 mL, 1.68 mmol) in pyridine (5 mL) gave the desired mesylate ((3aS,6S,7R,7aS)-6-((5R, 6S)-6-(((tert-butyldimethylsilyl)oxy)methyl)-5-methyl-4,5, 6,7-tetrahydro-1H-indazol-5-yl)-3a-methyl-3-phenyl-3a,4, 5,6,7,7a-hexahydro-1H-inden-7-yl)methyl methanesulfonate (Compound 41, 0.45 g, 87%) as a yellow gummy solid which was taken for next step without purification.

C. Using General Procedure J with Compound 41 (0.45 g, 0.75 mmol) and sodium azide (0.10 g, 1.54 mmol) in DMF (5 mL), gave the desired azide (5R,6S)-5-((3aS,6S,7R,7aS)-7-(azidomethyl)-3a-methyl-3-phenyl-3a,4,5,6,7,7a-hexahydro-1H-inden-6-yl)-6-(((tert-butyldimethylsilyl)oxy) methyl)-5-methyl-4,5,6,7-tetrahydro-1H-indazole (Compound 42, 0.25 g, 61% over 2 steps) as a white solid after purification by column chromatography (230-400 mesh silica gel, eluted with 0-15% pet ether/ethyl acetate).

D. Using General Procedure P with Compound 42 (0.25 g, 0.46 mmol), TBAF solution (1 M in THF, 0.92 mL, 0.92 mmol), and THF (5 mL) gave the desired alcohol ((5R,6S)-5-((3aS,6S,7R,7aS)-7-(azidomethyl)-3a-methyl-3-phenyl-3a,4,5,6,7,7a-hexahydro-1H-inden-6-yl)-5-methyl-4,5,6,7-tetrahydro-1H-indazol-6-yl)methanol (Compound 43, 0.16 g, 81%) as an off-white solid after purification by column chromatography (230-400 mesh silica gel, eluted with 0-30% pet ether/ethyl acetate).

E. Using General Procedure Q with Compound 43 (0.16 g, 0.37 mmol), triphenylphosphine (0.19 g, 0.72 mmol), water (0.5 mL) and THF (4.5 mL) gave the desired amine ((5R,6S)-5-((3aS,6S,7R,7aS)-7-(aminomethyl)-3a-methyl-3-phenyl-3a,4,5,6,7,7a-hexahydro-1H-inden-6-yl)-5-methyl-4,5,6,7-tetrahydro-1H-indazol-1-yl)methanol (Compound Ia-6, 35 mg, 23%) as a white solid after purification by flash column chromatography (neutral alumina, eluted with 0-10% dichloromethane/methanol).

LCMS: (Method 1e) MS m/z: 406.2 (M+1), $t_R$: 1.990 min, Purity: 79.34% (UV).

HPLC: (Method 2b) $t_R$: 8.992 min, Purity: 84.96% (UV).

$^1$H-NMR (400 MHz, CD$_3$OD): δ 7.37-7.18 (m, 6H), 5.93 (s, 1H), 3.96 (d, J=8.4 Hz, 1H), 3.50-3.31 (m, 1H), 3.19-3.09 (m, 1H), 2.99-2.95 (m, 1H), 2.74-2.35 (m, 4H), 2.19-1.89 (m, 7H), 1.73-1.29 (m, 3H), 1.11-1.06 (m, 6H).

Synthetic Example 6.1

Synthesis of (1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol (Compound Ia-42)

Following the procedure as described in Synthetic Example 6 and making non-critical variations using Compound Ia-8 (from Example 8) to replace Compound Ia-5, the title compound (1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol (Compound Ia-42) was obtained.

LCMS: (Method 1c) MS m/z: 431.1 (M+1), $t_R$: 1.408 min, Purity: 99.84% (ELSD).

Synthetic Example 6.2

Synthesis of (1S,3aS,4R,5S,7aS)-4-(aminomethyl)-5-((R,6S)-6-(hydroxymethyl)-5-methyl-4,5,6,7-tetrahydro-1H-indazol-5-yl)-7a-methyl-1-(pyridin-2-yl) octahydro-1H-inden-1-ol (Compound Ia-53)

Following the procedure as described in Synthetic Example 6 and making non-critical variations a) using Compound Ia-4 (from Example 4) to replace Compound Ia-5 and b) using LiAlH in THF in place of triphenyl phospine in water/THF to reduce the azide to amine, the title compound (1S,3aS,4R,5S,7aS)-4-(aminomethyl)-5-((5R, 6S)-6-(hydroxymethyl)-5-methyl-4,5,6,7-tetrahydro-1H-indazol-5-yl)-7a-methyl-1-(pyridin-2-yl)octahydro-1H-inden-1-ol (Compound Ia-53) was obtained.

LCMS: (Method 1h) MS m/z: 425 (M+1), $t_R$: 1.74 min, Purity: 88.6% (UV).

Synthetic Example 7

Synthesis ((5R,6S)-5-((4aS,5R,6S,8aS)-5-(aminomethyl)-8a-methyl-14,4a,5,6,7,8,8a-octahydroindeno [1,2-c]pyrazol-6-yl)-5-methyl-4,5,6,7-tetrahydro-1H-indazol-6-yl)methanol (Compound Ia-7)

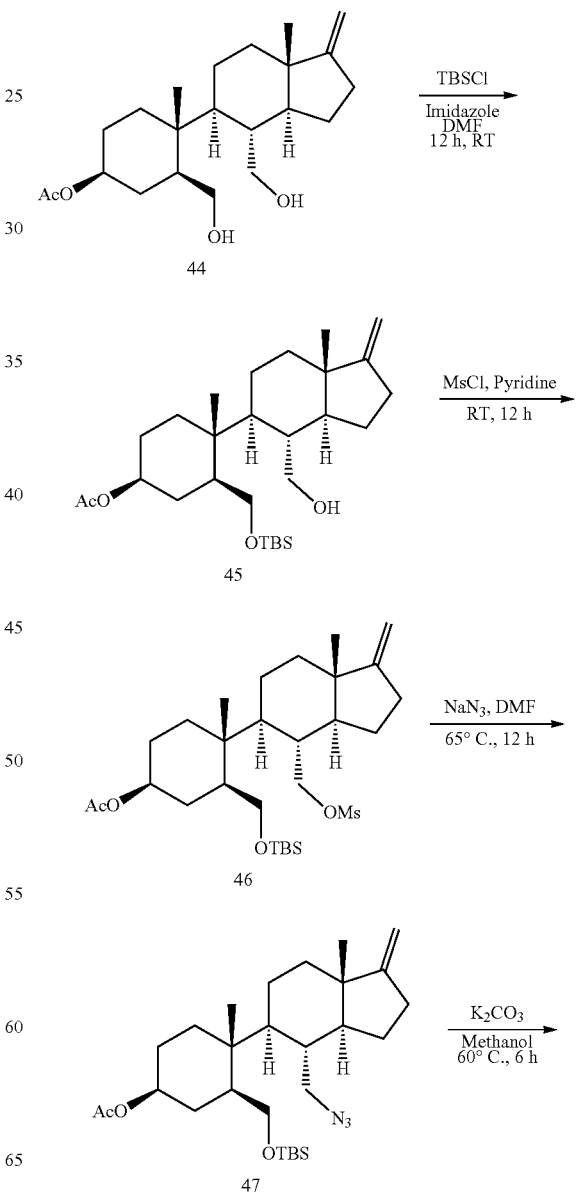

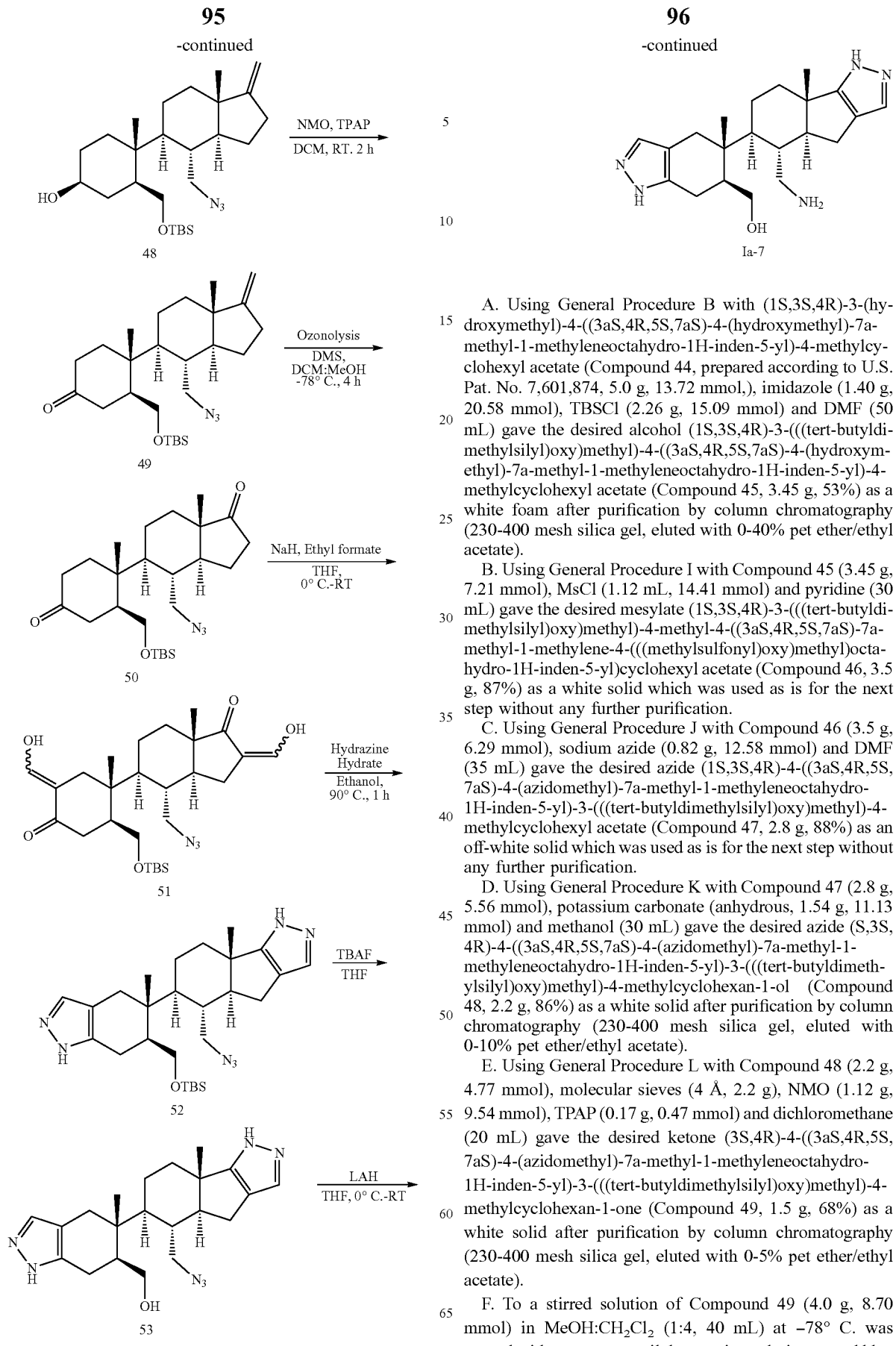

A. Using General Procedure B with (1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl acetate (Compound 44, prepared according to U.S. Pat. No. 7,601,874, 5.0 g, 13.72 mmol,), imidazole (1.40 g, 20.58 mmol), TBSCl (2.26 g, 15.09 mmol) and DMF (50 mL) gave the desired alcohol (1S,3S,4R)-3-(((tert-butyldimethylsilyl)oxy)methyl)-4-((3aS,4R,5S,7aS)-4-(hydroxymethyl)-7a-methyl-1-methyleneoctahydro-1H-inden-5-yl)-4-methylcyclohexyl acetate (Compound 45, 3.45 g, 53%) as a white foam after purification by column chromatography (230-400 mesh silica gel, eluted with 0-40% pet ether/ethyl acetate).

B. Using General Procedure I with Compound 45 (3.45 g, 7.21 mmol), MsCl (1.12 mL, 14.41 mmol) and pyridine (30 mL) gave the desired mesylate (1S,3S,4R)-3-(((tert-butyldimethylsilyl)oxy)methyl)-4-methyl-4-((3aS,4R,5S,7aS)-7a-methyl-1-methylene-4-(((methylsulfonyl)oxy)methyl)octahydro-1H-inden-5-yl)cyclohexyl acetate (Compound 46, 3.5 g, 87%) as a white solid which was used as is for the next step without any further purification.

C. Using General Procedure J with Compound 46 (3.5 g, 6.29 mmol), sodium azide (0.82 g, 12.58 mmol) and DMF (35 mL) gave the desired azide (1S,3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexyl acetate (Compound 47, 2.8 g, 88%) as an off-white solid which was used as is for the next step without any further purification.

D. Using General Procedure K with Compound 47 (2.8 g, 5.56 mmol), potassium carbonate (anhydrous, 1.54 g, 11.13 mmol) and methanol (30 mL) gave the desired azide (S,3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexan-1-ol (Compound 48, 2.2 g, 86%) as a white solid after purification by column chromatography (230-400 mesh silica gel, eluted with 0-10% pet ether/ethyl acetate).

E. Using General Procedure L with Compound 48 (2.2 g, 4.77 mmol), molecular sieves (4 Å, 2.2 g), NMO (1.12 g, 9.54 mmol), TPAP (0.17 g, 0.47 mmol) and dichloromethane (20 mL) gave the desired ketone (3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexan-1-one (Compound 49, 1.5 g, 68%) as a white solid after purification by column chromatography (230-400 mesh silica gel, eluted with 0-5% pet ether/ethyl acetate).

F. To a stirred solution of Compound 49 (4.0 g, 8.70 mmol) in MeOH:CH$_2$Cl$_2$ (1:4, 40 mL) at −78° C. was purged with ozone gas until the reaction solution turned blue in colour. The reaction mixture quenched with dimethyl sulphide (1.08 g, 17.40 mmol) and stirred at room temperature for 4 hours. The reaction mixture was concentrated under reduced pressure. The residue was purified by column chromatography on silica gel (230-400 mesh, 0-10% pet ether/ethyl acetate) to afford (3aS,4R,5S,7aS)-4-(azidomethyl)-5-((1R,2S)-2-(((tert-butyldimethylsilyl)oxy)methyl)-1-methyl-4-oxocyclohexyl)-7a-methyloctahydro-1H-inden-1-one (Compound 50, 2.5 g, 62%) as a yellow solid.

G. Following the General Procedure N with Compound 50 (1.5 g, 3.25 mmol), NaH (60% in paraffin oil, 1.30 g, 32.48 mmol), ethyl formate (3.93 mL, 48.73 mmol) and THF (15 mL) gave the desired ketone (3aS,4R,5S,7aS)-4-(azidomethyl)-5-((1R,2S)-2-(((tert-butyldimethylsilyl)oxy)methyl)-5-(hydroxymethylene)-1-methyl-4-oxocyclohexyl)-2-(hydroxymethylene)-7a-methyloctahydro-1H-inden-1-one (Compound 51, 0.7 g, 42%) as a white solid following purification by column chromatography on silica gel (230-400 mesh, 0-10% pet ether/ethyl acetate).

H. Using General Procedure O with Compound 51 (0.7 g, 1.35 mmol) and hydrazine hydrate (0.33 mL, 6.76 mmol) in EtOH (10 mL) gave the desired pyrazole (4aS,5R,6S,8aS)-5-(azidomethyl)-6-((5R,6S)-6-(((tert-butyldimethylsilyl)oxy)methyl)-5-methyl-4,5,6,7-tetrahydro-1H-indazol-5-yl)-8a-methyl-1,4,4a,5,6,7,8,8a-octahydroindeno[1,2-c]pyrazole (Compound 52, 0.5 g, 73%) as an off-white solid after purification by column chromatography (230-400 mesh silica gel, eluted with 60-80% pet ether/ethyl acetate).

I. Following the General Procedure P with Compound 52 (0.5 g, 0.98 mmol) and TBAF (1 M in THF, 1.96 mL, 1.96 mmol) in THF (5 mL) gave the desired alcohol ((5R,6S)-5-((4aS,5R,6S,8aS)-5-(azidomethyl)-8a-methyl-1,4,4a,5,6,7,8,8a-octahydroindeno[1,2-c]pyrazol-6-yl)-5-methyl-4,5,6,7-tetrahydro-1H-indazol-6-yl)methanol (Compound 53, 0.37 g, 96%) as a yellow foam which was used in the next step without purification.

J. Using General Procedure R with Compound 53 (0.37 g, 0.94 mmol) and LAH (2 M in THF, 0.94 mL, 1.87 mmol) in THF (5 mL), gave the desired alcohol ((5R,6S)-5-((4aS,5R,6S,8aS)-5-(aminomethyl)-8a-methyl-1,4,4a,5,6,7,8,8a-octahydroindeno[1,2-c]pyrazol-6-yl)-5-methyl-4,5,6,7-tetrahydro-1H-indazol-6-yl)methanol (Compound Ia-7, 0.10 g, 29%) as an off-white solid after purification by column chromatography (Neutral alumina, eluted with 0-15% dichloromethane/methanol).

LCMS: (Method 1b) MS m/z: 370.2 (M+1), $t_R$: 1.317 min, Purity: 98.72% (UV).

HPLC: (Method 2a) $t_R$: 1.410 min, Purity: 98.29% (UV).

$^1$H-NMR (400 MHz, CD$_3$OD): δ 7.33-7.24 (m, 2H), 4.00 (dd, J=2.4, 10.8 Hz, 1H), 3.44-3.39 (m, 1H), 3.33-3.27 (m, 1H), 3.18-3.12 (m, 1H), 2.94-2.90 (m, 1H), 2.77-2.53 (m, 3H), 2.44-2.28 (m, 3H), 2.20-2.06 (m, 3H), 1.96-1.81 (m, 1H), 1.78-1.63 (m, 3H), 1.12 (s, 3H), 1.06 (s, 3H).

Synthetic Example 8

Synthesis (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol (Compound Ia-8)

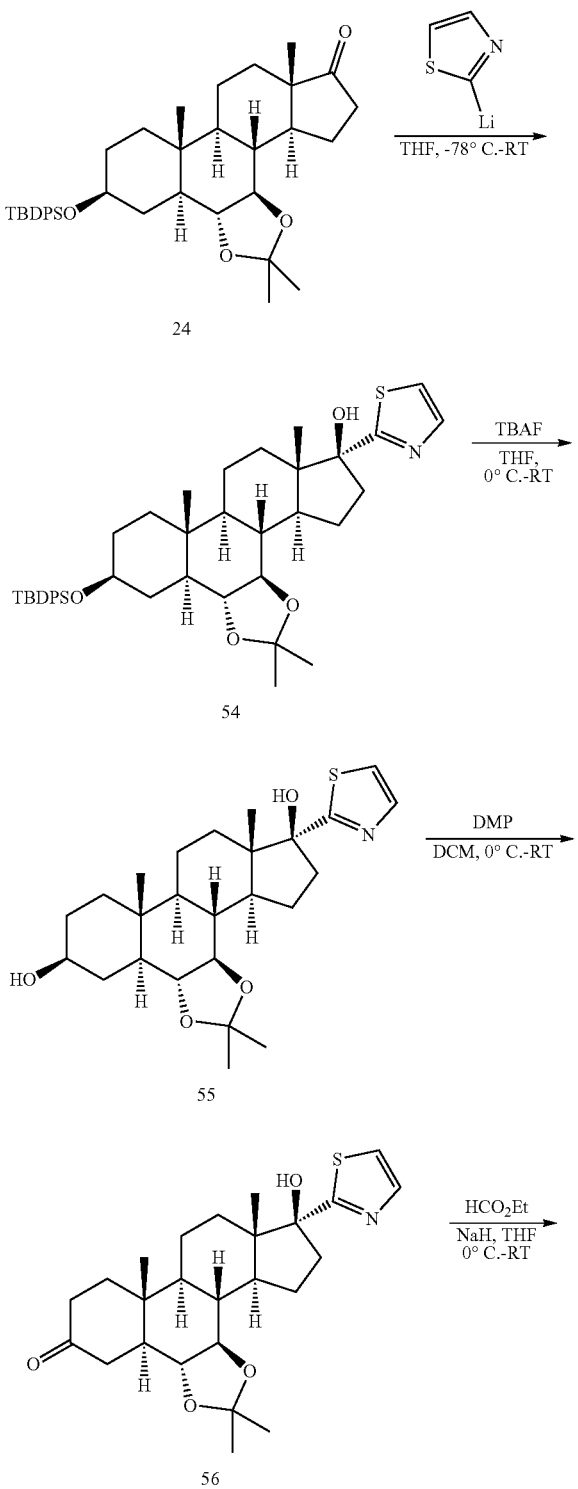

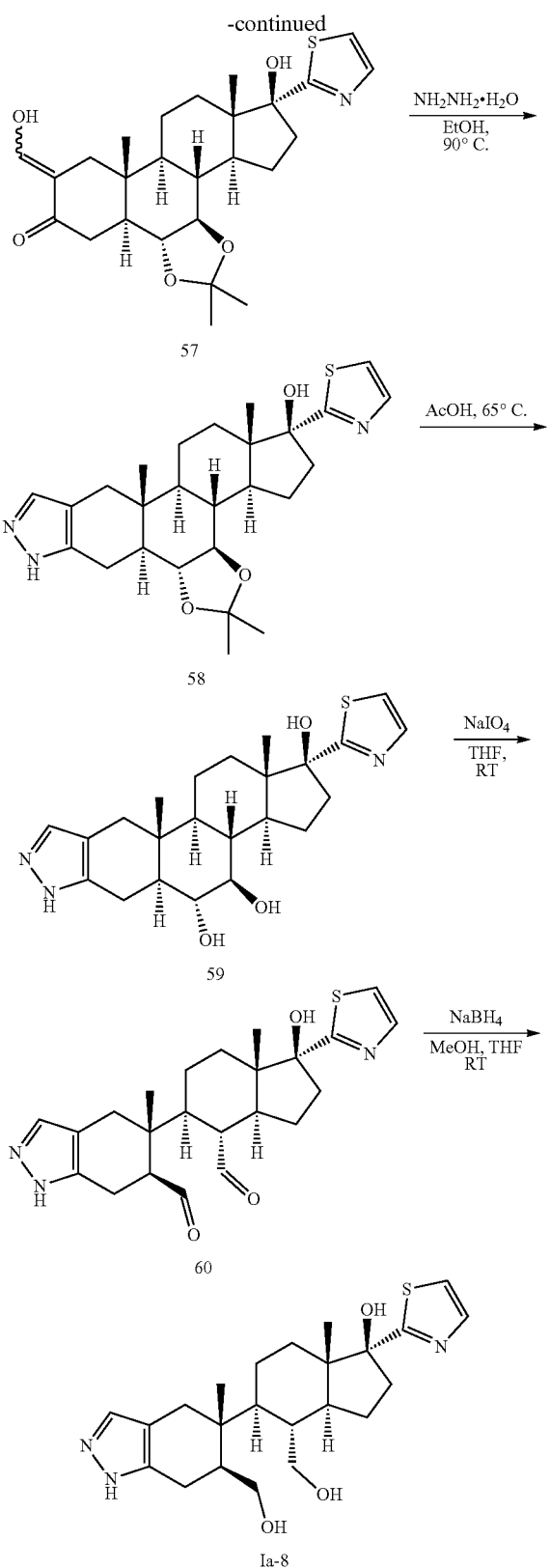

for 20 minutes, then a solution of Compound 24 (from Example 4, 4 g, 6.66 mmol) in THF (20 mL) was added. The resultant solution was stirred at room temperature for 6 hours. The mixture was diluted with ice cold water (1×50 mL) and the aqueous was extracted with EtOAc (2×50 mL) and washed with brine (1×50 mL). The organic layer was dried over $Na_2SO_4$, filtered and concentrated. The residue was purified by column chromatography on silica gel (230-400 mesh, 0-30% pet ether/ethyl acetate) to afford (2S,4aR, 4bS,6aS,7S,9aS,9bR,9cR,12aR,12bS)-2-((tert-butyldiphenylsilyl)oxy)-4a,6a,11,11-tetramethyl-7-(thiazol-2-yl)hexadecahydro-1H-cyclopenta[1,2]phenanthro[9,10-d][1,3]dioxol-7-ol (Compound 54, 3.8 g, 83%) as a white foam.

B. Using General Procedure P with Compound 54 (3.8 g, 5.54 mmol), TBAF solution (1 M in THF, 11.07 mL, 11.07 mmol), and THF (35 mL) gave the desired alcohol (2S,4aR, 4bS,6aS,7S,9aS,9bR,9cR,12aR,12bS)-4a,6a,11,11-tetramethyl-7-(thiazol-2-yl)hexadecahydro-1H-cyclopenta[1,2]phenanthro[9,10-d][1,3]dioxole-2,7-diol (Compound 55, 3.16 g) as a yellow gummy solid which was used in the next step without purification.

C. Following the General Procedure M with Compound 55 (3.16 g, 7.06 mmol) and Dess-Martin periodane (5.99 g, 14.12 mmol) in DCM (30 mL) gave the desired ketone (4aR,4bS,6aS,7S,9aS,9bR,9cR,12aR,12bS)-7-hydroxy-4a, 6a,11,11-tetramethyl-7-(thiazol-2-yl)hexadecahydro-2H-cyclopenta[1,2]phenanthro[9,10-d][1,3]dioxol-2-one (Compound 56, 2.23 g, 71%) as a white solid after purification by column chromatography on silica gel (230-400 mesh, 20-30% pet ether/ethyl acetate).

D. Using General Procedure N with Compound 56 (2.23 g, 5.00 mmol), NaH (60% in paraffin oil, 0.80 g, 20.02 mmol), ethyl formate (2.43 mL, 30.03 mmol) and THF (20 mL) gave the desired ketone (4aR,4bS,6aS,7S,9aS,9bR,9cR, 12aR,12bS)-7-hydroxy-3-(hydroxymethylene)-4a,6a,11,11-tetramethyl-7-(thiazol-2-yl)hexadecahydro-2H-cyclopenta[1,2]phenanthro[9,10-d][1,3]dioxol-2-one (Compound 57, 2.28 g, 96%) as a white solid after purification by column chromatography on silica gel (230-400 mesh, 20-30% pet ether/ethyl acetate).

E. Using General Procedure O with Compound 57 (2.28 g, 4.81 mmol) and hydrazine hydrate (0.94 mL, 19.26 mmol) in EtOH (20 mL) gave the desired pyrazole (1S,3aS,3bR, 3cR,6aR,6bS,11aR,11bS,13aS)-5,5,11a,13a-tetramethyl-1-(thiazol-2-yl)-1,2,3,3a,3b,3c,6a,6b,7,8,11,11a,11b,12,13, 13a-hexadecahydrocyclopenta[5,6][1,3]dioxolo[4',5':3,4]naphtho[1,2-]indazol-1-ol (Compound 58, 2.16 g, 96%) as an off-white solid after purification by column chromatography (230-400 mesh silica gel, eluted with 50-60% pet ether/ethyl acetate).

F. Using General Procedure E with Compound 58 (2.16 g, 4.60 mmol) in 80% AcOH (20 mL) gave the desired trialcohol (1S,3aS,3bR,4R,5R,5aS,10aR,10bS,12aS)-10a, 12a-dimethyl-1-(thiazol-2-yl)-1,2,3,3a,3b,4,5,5a,6,7,10,10a, 10b,11,12,12a-hexadecahydrocyclopenta[5,6]naphtho[1,2-f]indazole-1,4,5-triol (Compound 59, 1.3 g, 66%) as an off-white solid after purification by column chromatography (230-400 mesh silica gel, eluted with 0-10% dichloromethane/methanol).

LCMS: (Method 1d) MS m/z: 430.2 (M+1), $t_R$: 1.242 min, Purity: 95.91% (UV).

HPLC: (Method 2b) $t_R$: 6.987 min, Purity: 95.07% (UV).

$^1$H-NMR (400 MHz, $CD_3OD$): δ 7.72 (d, J=3.2 Hz, 1H), 7.47 (d, J=3.2 Hz, 1H), 7.24 (s, 1H), 3.29-3.09 (m, 3H), 2.58-2.26 (m, 4H), 2.13-1.91 (m, 5H), 1.67-1.43 (m, 5H), 1.06 (s, 3H), 0.77 (s, 3H), 0.40-0.39 (m, 1H).

A. To a stirred solution of n-butyllithium (1.6 M in Hexane, 4.99 mL, 7.99 mmol) in THF (10 mL) at −78° C. was added a solution of 1,3-thiazole (0.68 g, 7.99 mmol) in THF (10 mL) dropwise. The mixture was stirred at −78° C.

G. Using General Procedure F with Compound 59 (1.30 g, 3.03 mmol) and sodium metaperiodate (1.29 g, 6.05 mmol) in THF:water (4:1, 10 mL) gave the desired dialdehyde (5R,6S)-5-((1S,3aS,4R,5S,7aS)-4-formyl-1-hydroxy-7a-methyl-1-(thiazol-2-yl)octahydro-1H-inden-5-yl)-5-methyl-4,5,6,7-tetrahydro-1H-indazole-6-carbaldehyde (Compound 60, 1.2 g, 93%) as a white solid after purification by column chromatography (230-400 mesh silica gel, eluted with 0-5% dichloromethane/methanol).

H. Using General Procedure G with Compound 60 (1.20 g, 2.81 mmol) and sodium borohydride (0.21 g, 5.61 mmol) in THF:MeOH (1:1, 20 mL) gave the desired trialcohol (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol (Compound Ia-8, 0.5 g, 41%) as a white solid after purification by column chromatography (Neutral alumina, eluted with 10-15% dichloromethane/methanol).

LCMS: (Method 1d) MS m/z: 432.2 (M+1), $t_R$: 1.268 min, Purity: 99.98% (ELSD).

HPLC: (Method 2a) $t_R$: 2.264 min, Purity: 97.10% (UV).

$^1$H-NMR (400 MHz, CD$_3$OD): δ 7.73 (d, J=3.2 Hz, 1H), 7.48 (d, J=3.2 Hz, 1H), 7.25 (s, 1H), 4.09-4.01 (m, 1H), 3.98-3.72 (m, 2H), 3.30-3.27 (m, 1H), 3.15-3.09 (M, 1H), 2.65-2.43 (m, 3H), 2.27-2.03 (m, 5H), 1.68-1.40 (m, 6H), 1.06 (2×s, 6H), 0.26-0.21 (m, 1H).

Synthetic Example 9

Synthesis of (2S,5R)-5-ethyl-2-((1R,3aS,4S,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-yl)-6-methylheptan-3-ol (Compound Ia-9)

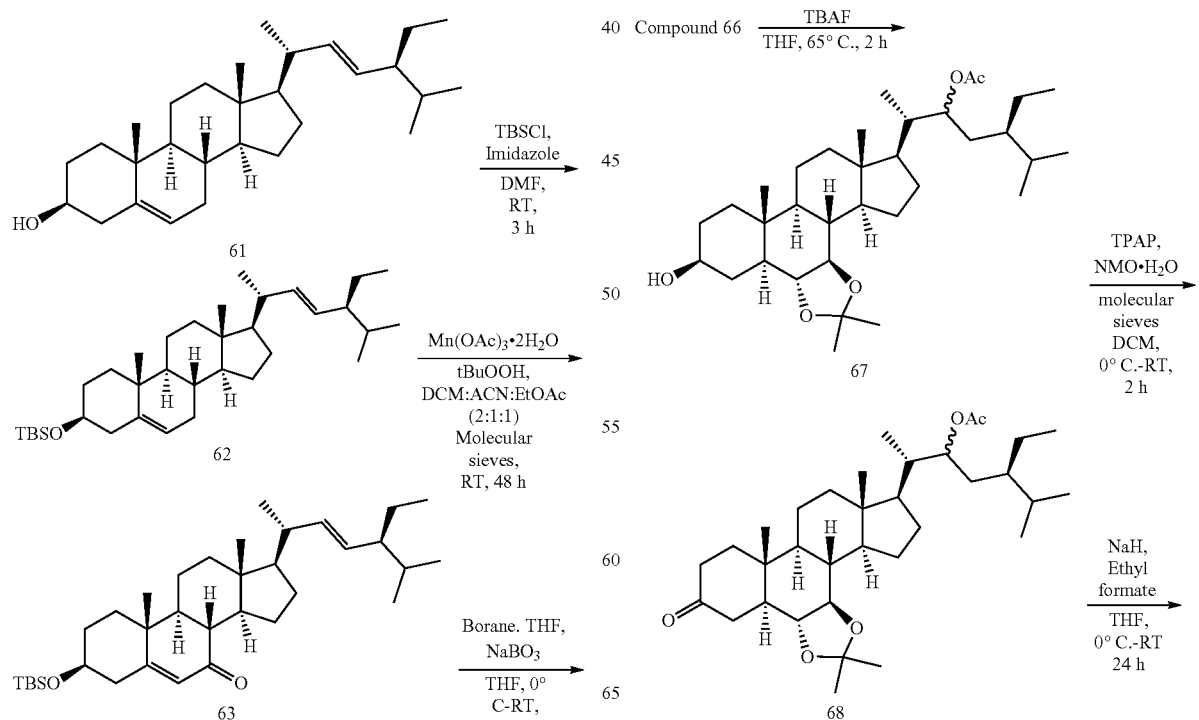

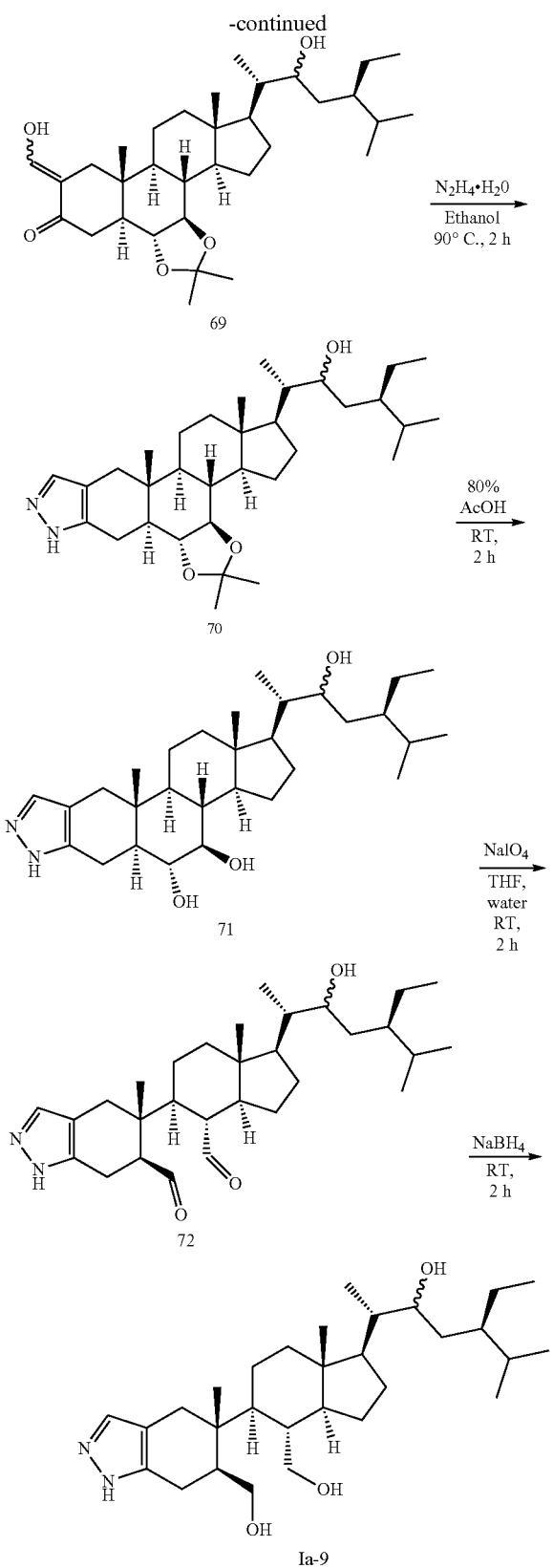

mL) followed by purification by column chromatography on silica gel (230-400 mesh, 0-5% pet ether/ethyl acetate) afforded tert-butyl(((3S,8S,9S,10R,13R,14S,7R)-17-((2R,5S,E)-5-ethyl-6-methylhept-3-en-2-yl)-10,13-dimethyl-2,3,4,7,8,9,10,11,12,13,14,15,16,17-tetradecahydro-1H-cyclopenta[a]phenanthren-3-yl)oxy)dimethylsilane (Compound 62, 38.0 g, 99%) as a colourless gummy solid.

B. Using General Procedure C with Compound 62 (38.0 g, 72.11 mmol), TBHP (5 M in decane, 75.0 mL, 374.97 mmol), 4 Å molecular sieves (38.0 g) and manganese (III) acetate dihydrate (1.93 g, 7.21 mmol) in $CH_2Cl_2$:ACN:EtOAc (2:1:1, 380 mL), gave the desired ketone (3S,8S,9S,1R,13R,14S,17R)-3-((tert-butyldimethylsilyl)oxy)-17-((2R,5S,E)-5-ethyl-6-methylhept-3-en-2-yl)-10,13-dimethyl-1,2,3,4,8,9,10,11,12,13,14,15,16,17-tetradecahydro-7H-cyclopenta[a]phenanthren-7-one (Compound 63, 22.5 g, 58%) as an off-white solid after purification by column chromatography on silica gel (230-400 mesh, 0-5% pet ether/ethyl acetate).

C. Using General Procedure D with Compound 63 (22.5 g, 41.59 mmol), Borane in THF (1 M, 92.75 mL, 92.75 mmol) and sodium perborate tetrahydrate (19.20 g, 124.78 mmol) in THF (200 mL) gave the desired dialcohol (3S,5S,6R,7R,8S,9S,10R,13R,14S,17R)-3-((tert-butydimethylsilyl)oxy)-17-((2S,5R)-5-ethyl-3-hydroxy-6-methylheptan-2-yl)-10,13-dimethylhexadecahydro-1H-cyclopenta[a]phenanthrene-6,7-diol (Compound 64, 24.0 g) as a white solid which was used in the next step without purification.

D. Using General Procedure H with Compound 64 (24.0 g, 41.45 mmol) and camphorsulfonic acid (0.96 g, 4.15 mmol) in 2,2-dimethoxypropane (203 mL, 1658.06 mmol) followed by purification by column chromatography on silica gel (230-400 mesh, 10-15% pet ether/ethyl acetate) afforded (2S,5R)-2-((2S,4aR,4bS,6aR,7R,9aS,9bS,9cR,12aR,12bS)-2-((tert-butyldimethylsilyl)oxy)-4a,6a,11,11-tetramethylhexadecahydro-1H-cyclopenta[1,2]phenanthro[9,10-d][1,3]dioxol-7-yl)-5-ethyl-6-methylheptan-3-ol (Compound 65, 12.0 g, 47%) as a white solid.

E. Using General Procedure A with Compound 65 (12.0 g, 19.38 mmol), DMAP (0.24 g, 1.94 mmol) and $Ac_2O$ (5.42 mL, 57.34 mmol) in pyidine (100 mL) gave the desired ester (2S,5R)-2-((2S,4aR,4bS,6aR,7R,9aS,9bS,9cR,12aR,12bS)-2-((tert-butyldimethylsilyl)oxy)-4a,6a,11,11-tetramethylhexadecahydro-1H-cyclopenta[1,2]phenanthro[9,10-d][1,3]dioxol-7-yl)-5-ethyl-6-methylheptan-3-yl acetate (Compound 66, 11.0 g, 86%) as a yellow gummy solid which was used in the next step without purification.

F. Following the General Procedure P with Compound 66 (11.0 g, 16.64 mmol) and TBAF (1 M in THF, 33.28 mL, 33.28 mmol) in THF (100 mL), gave the desired alcohol (2S,5R)-5-ethyl-2-((2S,4aR,4bS,6aR,7R,9aS,9bS,9cR,12aR,12bS)-2-hydroxy-4a,6a,11,11-tetramethylhexadecahydro-1H-cyclopenta[1,2]phenanthro[9,10-d][1,3]dioxol-7-yl)-6-methylheptan-3-yl acetate as a white solid (Compound 67, 5.0 g, 55%) after purification by column chromatography on silica gel (230-400 mesh, 40-45% pet ether/ethyl acetate).

A. Using General Procedure B with stigmasterol (Compound 61, 30.0 g, 72.75 mmol), imidazole (12.37 g, 181.73 mmol) and TBSCl (16.43 g, 109.04 mmol) in DMF (300

G. Using General Procedure L with Compound 67 (5.0 g, 9.14 mmolNMO hydrate (2.14 g, 18.29 mmol), 4 Å molecular sieves (5.0 g) and TPAP (0.32 g, 0.914 mmol) in CH₂Cl₂ (50 mL) gave the desired ketone (2S,5R)-5-ethyl-6-methyl-2-((4aR,4bS,6aR,7R,9aS,9bS,9cR,12aR,12bS)-4a,6a,11,11-tetramethyl-2-oxohexadecahydro-1H-cyclopenta[1,2]phenanthro[9,10-d][1,3]dioxol-7-yl)heptan-3-yl acetate (Compound 68, 3.8 g, 76%) as an off-white solid after purification by column chromatography on silica gel (230-400 mesh, 5-10% pet ether/ethyl acetate).

H. Using General Procedure N with Compound 68 (3.8 g, 6.97 mmol), sodium hydride (60% in paraffin oil, 1.39 g, 34.87 mmol) and ethyl formate (3.94 mL, 48.82 mmol) in THF (40 mL) gave the desired ketone (4aR,4bS,6aR,7R,9aS,9bS,9cR,12aR,12bS)-7-((2S,5R)-5-ethyl-3-hydroxy-6-methylheptan-2-yl)-3-(hydroxymethylene)-4a,6a,11,11-tetramethylhexadecahydro-2H-cyclopenta[1,2]phenanthro[9,10-d][1,3]dioxol-2-one (Compound 69, 3.0 g, 81%) as a brown gummy solid which was used in the next step without purification.

I. Using General Procedure O with Compound 69 (3.0 g, 5.65 mmol) and hydrazine hydrate (0.55 mL, 11.30 mmol) in EtOH (30 mL) gave the desired pyrazole (2S,5R)-5-ethyl-6-methyl-2-((1R,3aS,3bS,3cR,6aR,6bS,11aR,11bS,13aR)-5,5,11a,13a-tetramethyl-1,2,3,3a,3b,3c,6a,6b,7,8,11,11a,11b,12,13,13a-hexadecahydrocyclopenta[5,6][1,3]dioxolo[4',5':3,4]naphtho[1,2-n]indazol-1-yl)heptan-3-ol (Compound 70, 1.1 g, 37%) as an off-white solid after purification by column chromatography on silica gel (230-400 mesh, 40-50% pet ether/ethyl acetate).

J. Using General Procedure E with Compound 70 (1.1 g, 2.09 mmol) in 80% AcOH (10 mL) gave the desired dialcohol (1R,3aS,3bS,4R,5R,5aS,10aR,10bS,12aR)-1-((2S,5R)-5-ethyl-3-hydroxy-6-methylheptan-2-yl)-10a,12a-dimethyl-1,2,3,3a,3b,4,5,5a,6,7,10,10a,10b,11,12,12a-hexadecahydrocyclopenta[5,6]naphtho[1,2-f]indazole-4,5-diol (Compound 71, 0.9 g, 89%) as an off-white solid after purification by column chromatography on silica gel (230-400 mesh, 10-15% methanol/dichloromethane).

K. Using General Procedure F with Compound 71 (0.9 g, 1.85 mmol) and sodium metaperiodate (0.79 g, 3.70 mmol) in THF:water (4:1, 10 mL) gave the desired dialdehyde (5R,6S)-5-((1R,3aS,4S,5S,7aR)-1-((2S,5R)-5-ethyl-3-hydroxy-6-methylheptan-2-yl)-4-formyl-7a-methyloctahydro-1H-inden-5-yl)-5-methyl-4,5,6,7-tetrahydro-1H-indazole-6-carbaldehyde (Compound 72, 0.72 g, 80%) as a white solid after purification by column chromatography on silica gel (230-400 mesh, 0-5% methanol/dichloromethane).

L. Using General Procedure G with Compound 72 (0.72 g, 1.49 mmol) and sodium borohydride (0.11 g, 2.91 mmol) in THF:MeOH (1:1.10 mL) gave the desired trialcohol (2S,5R)-5-ethyl-2-((1R,3aS,4S,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-yl)-6-methylheptan-3-ol (Compound Ia-9, 53 mg, 7%) as a white solid after purification by preparative HPLC (3a).

LCMS: (Method 1d) MS m/z: 489.3 (M+1), $t_R$: 2.030 min, Purity: 93.64% (UV).

HPLC: (Method 2a) $t_R$: 4.10 min, Purity: 95.37% (UV).

¹H-NMR (400 MHz, CD₃OD): δ 7.27 (s, 1H), 4.04-3.93 (m, 2H), 3.69-3.64 (m, 2H), 3.35-3.33 (m, 1H), 3.23-3.22 (m, 1H), 2.69-2.65 (m, 2H), 2.36-1.98 (m, 3H), 1.84-1.50 (m, 8H), 1.49-1.24 (m, 9H), 1.19-1.04 (m, 4H), 0.94-0.90 (m, 9H), 0.78 (m, 6H).

Synthetic Example 10

Synthesis of (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol (Compound Ia-10a) and (1R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol (Compound Ia-10b)

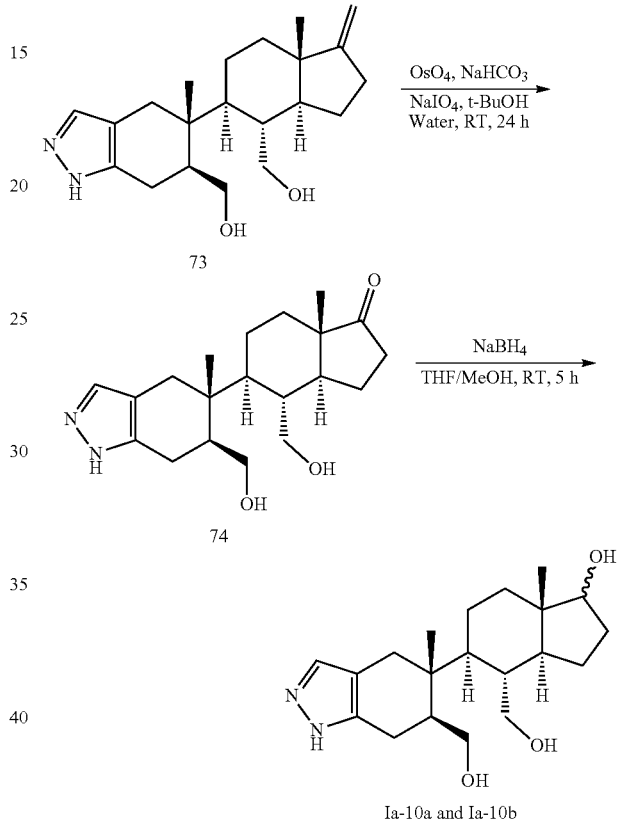

Ia-10a and Ia-10b

A. To a stirred solution of ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol (Compound 73, as prepared in U.S. Pat. No. 9,765,085, 0.25 g, 0.72 mmol) in water/t-BuOH (1:2, 10 mL) were added sodium bicarbonate (0.91 g, 10.88 mmol) and sodium metaperiodate (1.54 g, 7.26 mmol) at room temperature. The reaction mixture was cooled to 0° C. and added osmium tetroxide (2.5% in t-BuOH, 73.83 mL, 7.26 mmol) dropwise. The resultant solution was stirred at room temperature for 24 hours. The reaction was quenched with sodium thiosulphate solution (5 g dissolved in 10 mL water) and stirred for 20 minutes. The organic layer was extracted with ethyl acetate (2×20 mL) and washed consecutively with water (1×10 mL) and brine (1×10 mL). It was dried over sodium sulphate and concentrated to give the desired dialcohol (3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-one (Compound 74, 0.20 g, 80%) as an off white solid after purification by column chromatography (230-400 mesh silica gel, eluted with 0-5% dichloromethane/methanol).

B. Using General Procedure G with Compound 74 (0.25 g, 0.722 mmol, 1 eq), sodium borohydride (0.054 g, 1.44 mmol, 2 eq), THF (10 mL) and methanol (5 mL) and gave a mixture of the triols (1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol (Compound Ia-10a) and (1R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol (Compound Ia-10b) as a white solid (0.125 g, 49%) after purification by flash column chromatography (230-400 mesh silica gel, eluted with 0-20% dichloromethane/methanol).

LCMS: (Method 1b) MS m/z: 349.2 (M+1), $t_R$: 2.05 min, Purity: (25.41+73.71) % (ELSD), (30.68+64.61) % (220 nm), isomeric masses observed.

HPLC: (Method 2a) $t_R$: 1.94/2.04 min, Purity: (56.86+42.66) % (ELSD), (58.68+41.05) % (220 nm).

$^1$H-NMR (400 MHz, DMSO-d$_6$): δ 12.17 (s, 1H), 7.17-7.13 (m, 1H), 4.42-4.41 (m, 2H), 4.17-4.07 (m, 2H), 3.78-3.77 (m, 2H), 3.44-3.42 (m, 2H), 3.18-3.10 (m, 3H), 2.96-2.92 (m, 1H), 2.51-2.45 (m, 2H), 2.19-2.05 (m, 3H), 1.80-1.72 (m, 1H), 1.64-1.60 (m, 2H), 1.50-1.48 (m, 2H), 1.42-1.18 (m, 5H), 0.96-0.93 (s, 3H), 0.82-0.78 (m, 1H), 0.63 (s, 3H).

Synthetic Example 11

Synthesis of ((4aS,5R,6S,8aS)-6-((5R,6S)-6-(hydroxymethyl)-5-methyl-4,5,6,7-tetrahydro-1H-indazol-5-yl)-8a-methyl-1,4,4a, 5,6,7,8,8a-octahydroindeno[1,2-c]pyrazol-5-yl)methanol (Compound Ia-11)

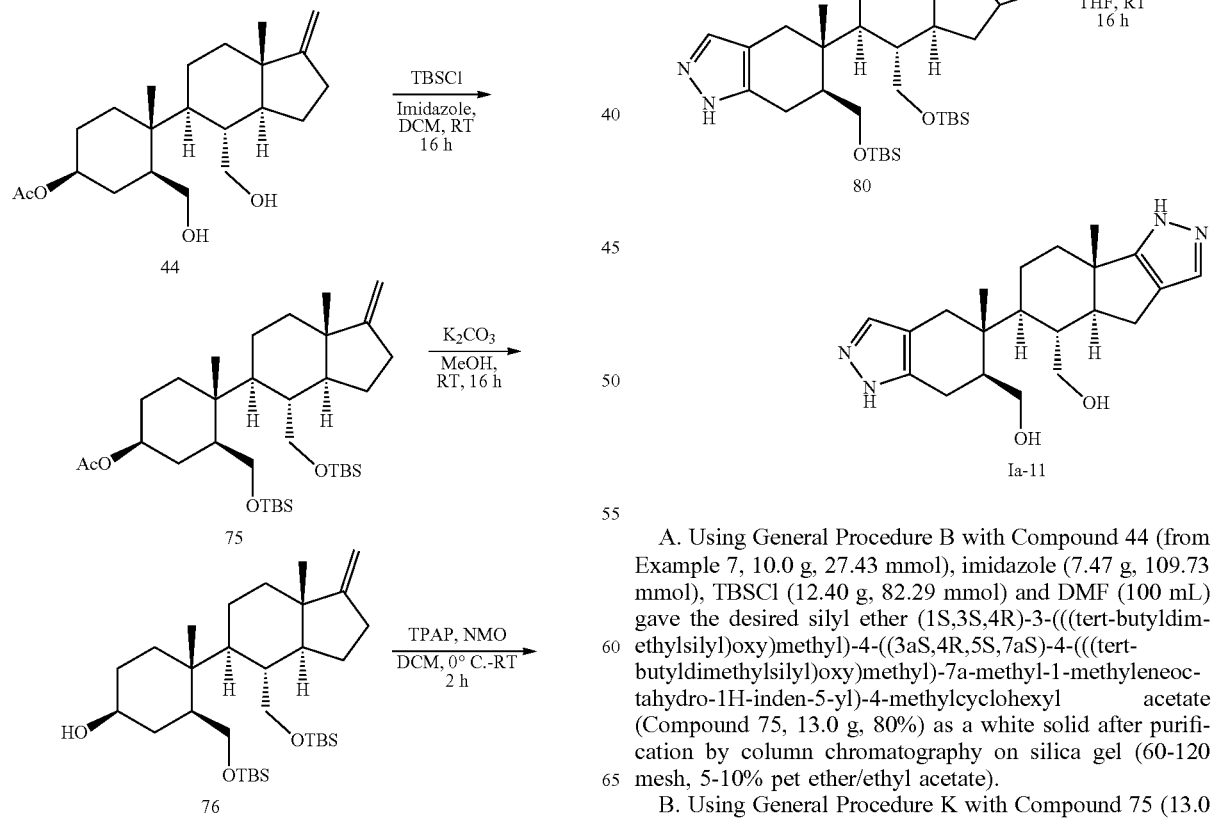

A. Using General Procedure B with Compound 44 (from Example 7, 10.0 g, 27.43 mmol), imidazole (7.47 g, 109.73 mmol), TBSCl (12.40 g, 82.29 mmol) and DMF (100 mL) gave the desired silyl ether (1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexyl acetate (Compound 75, 13.0 g, 80%) as a white solid after purification by column chromatography on silica gel (60-120 mesh, 5-10% pet ether/ethyl acetate).

B. Using General Procedure K with Compound 75 (13.0 g, 21.94 mmol), potassium carbonate (6.06 g, 43.84 mmol)

and MeOH (130 mL) gave the desired alcohol (1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexan-1-ol (Compound 76, 11.0 g, 91%) as a white solid after purification by column chromatography on silica gel (60-120 mesh, 10-20% pet ether/ethyl acetate).

C. Using General Procedure L with Compound 76 (11.0 g, 19.96 mmol), NMO hydrate (5.40 g, 39.93 mmol), 4 Å molecular sieves (11.0 g), TPAP (0.70 g, 1.97 mmol) and CH$_2$Cl$_2$ (100 mL) gave the desired ketone (3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexan-1-one (Compound 77, 9.0 g, 82%) as an off white solid after purification by column chromatography (230-400 mesh silica gel, eluted with 10-15% pet ether/ethyl acetate).

D. To a stirred solution of Compound 77 (8.0 g, 14.59 mmol) in methanol:dichloromethane (1:4, 80 mL) at −78° C. was bubbled ozone gas until the reaction solution turned blue in colour. The reaction mixture was quenched with dimethyl sulphide (1.81 g, 29.14 mmol) and stirred at room temperature for 4 hours. The resultant solution was concentrated under reduced pressure to give the desired ketone (3aS,4R,5S,7aS)-4-(((tert-butyldimethylsilyl)oxy)methyl)-5-((1R,2S)-2-(((tert-butyldimethylsilyl)oxy)methyl)-1-methyl-4-oxocyclohexyl)-7a-methyloctahydro-1H-inden-1-one (Compound 78, 3.0 g, 37%) as a yellow solid after purification by column chromatography (230-400 mesh silica gel, eluted with 10-15% pet ether/ethyl acetate).

E. Following the General Procedure N with Compound 78 (1.5 g, 2.72 mmol), (60% in paraffin oil, 1.09 g, 27.22 mmol), ethyl formate (3.30 mL, 40.83 mmol) and THF (15 mL) gave the desired ketone (3aS,4R,5S,7aS)-4-(((tert-butyldimethylsilyl)oxy)methyl)-5-((1R,2S)-2-(((tert-butydimethylsilyl)oxy)methyl)-5-(hydroxymethylene)-1-methyl-4-oxocyclohexyl)-2-(hydroxymethylene)-7a-methyloctahydro-1H-inden-1-one (Compound 79, 0.6 g, 36%) as a pale yellow solid after purification by column chromatography (230-400 mesh silica gel, eluted with 10-15% pet ether/ethyl acetate).

F. Following the General Procedure O with Compound 79 (0.6 g, 0.99 mmol), hydrazine hydrate (0.24 mL, 4.94 mmol) and THF (5 mL) gave the desired pyrazole (4aS,5R,6S,8aS)-5-(((tert-butydimethylsilyl)oxy)methyl)-6-((5R,6S)-6-(((tert-butyldimethylsilyl)oxy)methyl)-5-methyl-4,5,6,7-tetrahydro-1H-indazol-5-yl)-8a-methyl-1,4,4a,5,6,7,8,8a-octahydroindeno[1,2-c]pyrazole (Compound 80, 0.3 g, 51%) as an off white solid after purification by column chromatography (230-400 mesh silica gel, eluted with 30-40% pet ether/ethyl acetate).

G. Following the General Procedure P with Compound 80 (0.3 g, 0.50 mmol), TBAF (1M in THF, 1.0 mL, 1.0 mmol) and THF (5 mL), gave the desired alcohol ((4aS,5R,6S,8aS)-6-((5R,6S)-6-(hydroxymethyl)-5-methyl-4,5,6,7-tetrahydro-1H-indazol-5-yl)-8a-methyl-1,4,4a,5,6,7,8,8a-octahydroindeno[1,2-c]pyrazol-5-yl)methanol (Compound Ia-11, 28 mg, 15%) as an off white solid after purification by preparative HPLC (Method 3a).

LCMS: (Method 1d) MS m/z: 371.2 (M+1), t$_R$: 1.194 min, Purity: 99.58% (UV).
HPLC: (Method 2b) t$_R$: 6.097 min, Purity: 99.44% (UV).
$^1$H-NMR (400 MHz, CD$_3$OD): δ 7.29 (s, 1H), 7.21 (s, 1H), 4.13-4.10 (m, 1H), 3.99-3.96 (m, 1H), 3.80-3.77 (m, 1H), 3.40-3.37 (m, 1H), 3.23-3.14 (m, 2H), 2.81-2.67 (m, 3H), 2.36-2.10 (m, 4H), 1.98-1.84 (m, 3H), 1.71-1.51 (m, 2H), 1.15 (s, 3H), 1.03 (s, 3H).

Synthetic Example 12

Synthesis of ((5R,6S)-5-((3aS,4R,5S7aS)-4-(aminomethyl)-7a-methyl-1-methyleneoctahydro-1H-inden-5-yl)-1-(4-fluorophenyl)-5-methyl-4,5,6,7-tetrahydro-1H-indazol-6-yl)methanol (Compound Ia-12) and ((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol (Compound Ia-13)

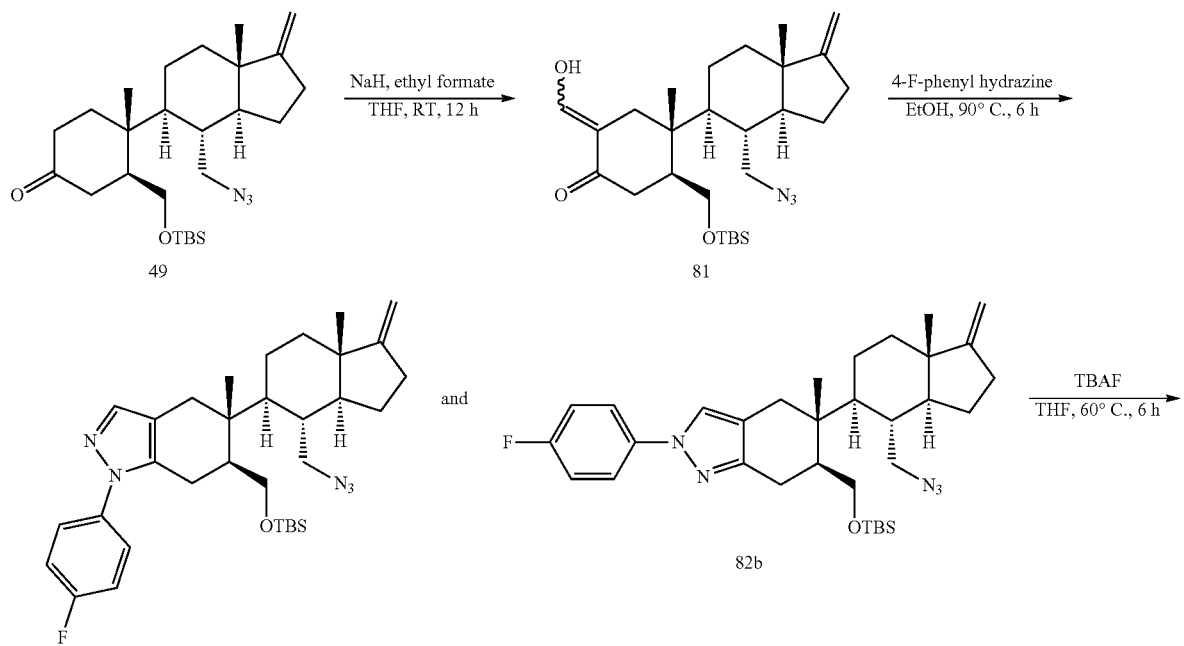

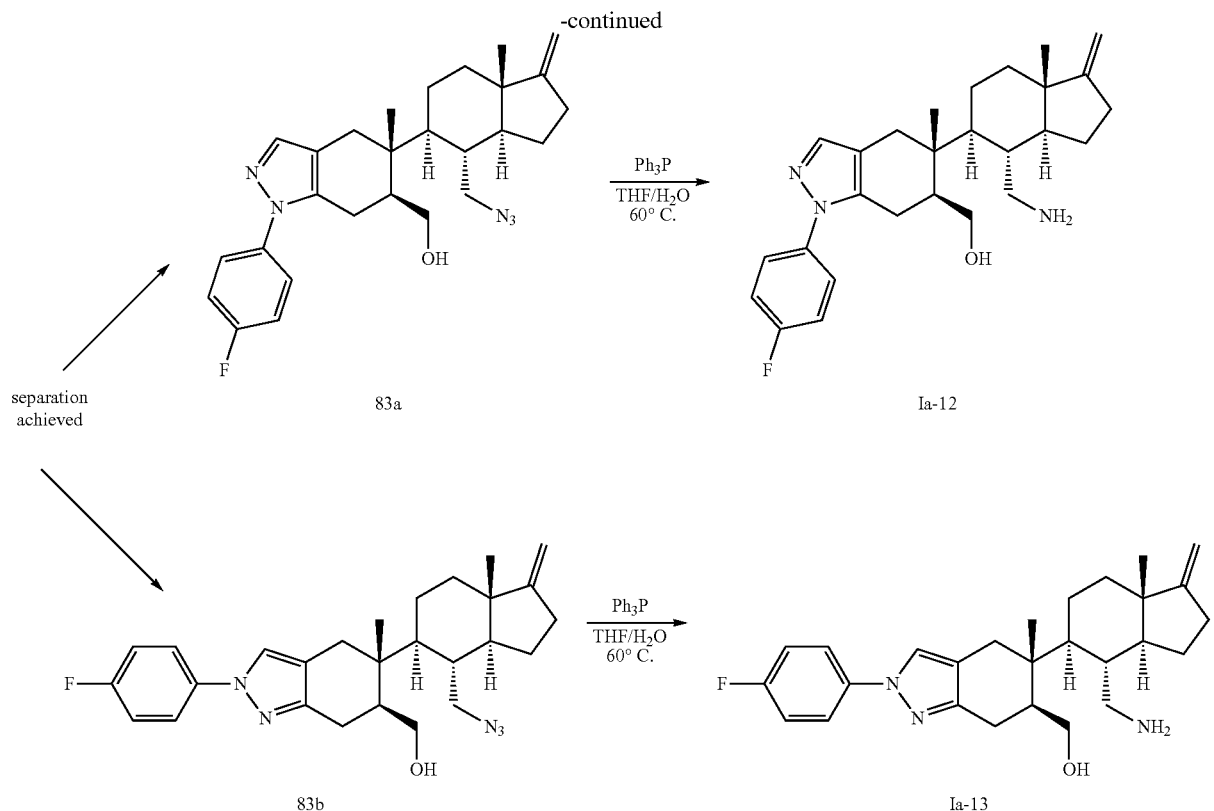

A. Using General Procedure N with Compound 49 (from Example 7, 1.5 g, 3.27 mmol), NaH (60% in paraffin oil, 0.52 g, 13.06 mmol), ethyl formate (1.6 mL, 19.59 mmol) and THF (15 mL) gave the desired ketone (4R,5S)-4-((3aS,4R,5S,7aS)-4-(azidomethyl)-7a-methyl-1-methyleneoctahydro-1H-inden-5-yl)-5-(((tert-butyldimethylsilyl)oxy)methyl)-2-(hydroxymethylene)-4-methylcyclohexan-1-one (Compound 81, 1.4 g, 88%) as a pale brown solid after purification by column chromatography (230-400 mesh silica gel, eluted with 0-5% pet ether/ethyl acetate).

B. Using General Procedure O with Compound 81 (1 g, 2.06 mmol, 1 eq), 4-fluorophenylhydrazine (0.5 g, 3.07 mmol, 1.5 eq) and ethanol (20 mL) gave a mixture of pyrazoles (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-1-(4-fluorophenyl)-5-methyl-4,5,6,7-tetrahydro-1H-indazole (Compound 82a, 0.5 g, 42%) and (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-2-(4-fluorophenyl)-5-methyl-4,5,6,7-tetrahydro-2H-indazole (Compound 82b) as a pale brown gum after purification by flash column chromatography (230-400 mesh silica gel, eluted with 0-30% pet ether/ethyl acetate).

C. Using General Procedure P with the mixture of Compound 82a and Compound 82b (0.5 g, 0.87 mmol, 1 eq), TBAF solution (1M in THF, 1.7 mL, 1.73 mmol, 2 eq) and THF (15 mL) gave the desired alcohols (((5R,6S)-5-((3aS,4R,5S,7aS)-4-(azidomethyl)-7a-methyl-1-methyleneoctahydro-1H-inden-5-yl)-1-(4-fluorophenyl)-5-methyl-4,5,6,7-tetrahydro-1H-indazol-6-yl)methanol (Compound 83a, 0.26 g, 65%) and ((5R,6S)-5-((3aS,4R,5S,7aS)-4-(azidomethyl)-7a-methyl-1-methyleneoctahydro-1H-inden-5-yl)-2-(4-fluorophenyl)-5-methyl-4,5,6,7-tetrahydro-2H-indazol-6-yl)methanol (Compound 83b) as a pale yellow solids after purification by flash column chromatography (230-400 mesh silica gel, eluted with 0-40% pet ether/ethyl acetate).

D. Using General Procedure Q with Compound 83a (0.260 g, 0.561 mmol, 1 eq), triphenylphosphine (0.294 g, 1.12 mmol, 2 eq) water (1 mL) and THF (15 mL) gave the desired amine ((R,6S)-5-((3aS,4R,5S,7aS)-4-(aminomethyl)-7a-methyl-1-methyleneoctahydro-1H-inden-5-yl)-1-(4-fluorophenyl)-5-methyl-4,5,6,7-tetrahydro-1H-indazol-6-yl)methanol (Compound Ia-12, 55 mg, 22%) as an off-white solid after purification by preparative HPLC (method 3b).

LCMS: (Method 1b) MS m/z: 438.3 (M+1), $t_R$: 3.923 min, Purity: 98.07% (ELSD), 93.9% (220 nm).

HPLC: (Method 2b) $t_R$: 3.914 min, 96.55% (ELSD), 91.9% (220 nm).

$^1$H-NMR (400 MHz, MeOD): δ 7.59-7.54 (m, 2H), 7.49-7.45 (m, 1H), 7.30-7.24 (m, 2H), 4.67-4.63 (m, 2H), 3.97-3.93 (m, 1H), 3.44-3.41 (m, 1H), 3.11-3.07 (m, 1H), 2.97-2.94 (m, 1H), 2.78-2.74 (m, 1H), 2.67-2.50 (m, 2H), 2.48-2.44 (m, 1H), 2.15-2.14 (m, 2H), 1.94-1.82 (m, 4H), 1.68-1.60 (m, 3H), 1.46-1.44 (m, 2H), 1.31-1.25 (m, 2H), 1.14-1.00 (s, 3H), 0.90-0.82 (s, 3H).

E. Using General Procedure Q with Compound 83b (0.260 g, 0.561 mmol, 1 eq), triphenylphosphine (0.294 g, 1.12 mmol, 2 eq) water (1 mL) and THF (15 mL) gave the desired amine ((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol (Compound Ia-13).

LCMS: (Method 1b) MS m/z: 438.2 (M+1), $t_R$: 2.502 min, Purity: 94.40% (UV).

Synthetic Example 12.1

Synthesis of ((5R,6S)-5-((3aS,4R,5S,7aS)-4-(aminomethyl)-7a-methyl-1-methyleneoctahydro-1H-inden-5-yl)-1-(4-methoxyphenyl)-5-methyl-4,5,6,7-tetrahydro-1H-indazol-6-yl)methanol (Compound Ia-14) and ((5R,6S)-5-((3aS,4R,5S,7aS)-4-(aminomethyl)-7a-methyl-1-methyleneoctahydro-1H-inden-5-yl)-2-(4-methoxyphenyl)-5-methyl-4,5,6,7-tetrahydro-2H-indazol-6-yl)methanol (Compound Ia-15)

Following the procedure as described in Synthetic Example 12 and making non-critical variations using 4-methoxyphenyl hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-H-inden-5-yl)-1-(4-methoxyphenyl)-5-methyl-4,5,6,7-tetrahydro-1H-indazol-6-yl)methanol (Compound Ia-14) and ((5R,6S)-5-((3aS,4R,5S,7aS)-4-(aminomethyl)-7a-methyl-1-methyleneoctahydro-1H-inden-5-yl)-2-(4-methoxyphenyl)-5-methyl-4,5,6,7-tetrahydro-2H-indazol-1-yl)methanol (Compound Ia-15) were obtained.

Compound Ia-14: LCMS: (Method 1c) MS m/z: 450.3 (M+1), $t_R$: 1.949 min, Purity: 94.29% (UV).
Compound Ia-15: LCMS: (Method 1d) MS m/z: 450.3 (M+1), $t_R$: 1.566 min, Purity: 99.49% (UV).

Synthetic Example 12.2

Synthesis of ((5R,6S)-5-((3aS,4R,5S,7aS)-4-(aminomethyl)-7a-methyl-1-methyleneoctahydro-1H-inden-5-yl)-1-(4-methoxybenzyl)-5-methyl-4,5,6,7-tetrahydro-1H-indazol-6-yl)methanol (Compound Ia-16) and ((5R,6S)-5-((3aS,4R,5S,7aS)-4-(aminomethyl)-7a-methyl-1-methyleneoctahydro-1H-inden-5-yl)-2-(4-methoxybenzyl)-5-methyl-4,5,6,7-tetrahydro-2H-indazol-1-yl)methanol (Compound Ia-17)

Following the procedure as described in Synthetic Example 12 and making non-critical variations using (4-methoxybenzyl)hydrazine to replace 4-fluorophenyl hydrazine in the conversion of Compound 81 to the mixture of Compounds 82a and 82b, the title compounds of ((5R,6S)-5-((3aS,4R,5S,7aS)-4-(aminomethyl)-7a-methyl-1-methyleneoctahydro-1H-inden-5-yl)-1-(4-methoxybenzyl)-5-methyl-4,5,6,7-tetrahydro-1H-indazol-1-yl)methanol (Compound Ia-16) and ((5R,6S)-5-((3aS,4R,5S,7aS)-4-(aminomethyl)-7a-methyl-1-methyleneoctahydro-H-inden-5-yl)-2-(4-methoxybenzyl)-5-methyl-4,5,6,7-tetrahydro-2H-indazol-6-yl)methanol (Compound Ia-17) were obtained.

Compound Ia-17: LCMS: (Method 1c) MS m/z: 464.3 (M+1), $t_R$: 2.322 min, Purity: 98.70% (UV).

Synthetic Example 12.3

Synthesis of ((5R,6S)-5-((3aS,4R,5S,7aS)-4-(aminomethyl)-7a-methyl-1-methyleneoctahydro-1H-inden-5-yl)-1-(4-fluorobenzyl)-5-methyl-4,5,6,7-tetrahydro-1H-indazol-6-yl)methanol (Compound Ia-18) and ((5R,6S)-5-((3aS,4R,5S,7aS)-4-(aminomethyl)-7a-methyl-1-methyleneoctahydro-1H-inden-5-yl)-2-(4-fluorobenzyl)-5-methyl-4,5,6,7-tetrahydro-2H-indazol-6-yl)methanol (Compound Ia-19)

Following the procedure as described in Synthetic Example 12 and making non-critical variations using (4-fluorobenzyl)hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(4-fluorobenzyl)-5-methyl-4,5,6,7-tetrahydro-1H-indazol-6-yl)methanol (Compound Ia-18) and ((5R,6S)-5-((3aS,4R,5S,7aS)-4-(aminomethyl)-7a-methyl-1-methyleneoctahydro-1H-inden-5-yl)-2-(4-fluorobenzyl)-5-methyl-4,5,6,7-tetrahydro-2H-indazol-6-yl)methanol (Compound Ia-19) were obtained.

Compound Ia-19: LCMS: (Method 1c) MS m/z: 452.3 (M+1), $t_R$: 2.386 min, Purity: 99.29% (UV).

Synthetic Example 12.4

Synthesis of 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(phenyl) methanone (Compound Ia-20) and (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(phenyl)methanone (Compound Ia-21)

Following the procedure as described in Synthetic Example 12 and making non-critical variations using (4-hydrazineylphenyl)(phenyl)methanone to replace 4-fluorophenyl hydrazine in the conversion of Compound 81 to the mixture of Compounds 82a and 82b, the title compounds 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(phenyl)methanone (Compound Ia-20) and (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl) (phenyl)methanone (Compound Ia-21) were obtained.

Compound Ia-20: LCMS: (Method 1d) MS m/z: 524.3 (M+1), $t_R$: 1.678 min, Purity: 98.70% (UV).

Synthetic Example 12.5

Synthesis of ((5R,6S)-5-((3aS,4R,5S,7aS)-4-(aminomethyl)-7a-methyl-1-methyleneoctahydro-1H-inden-5-yl)-1-(3,4-difluorophenyl)-5-methyl-4,5,6,7-tetrahydro-1H-indazol-6-yl)methanol (Compound Ia-22) and ((5R,6S)-5-((3aS,4R,5S,7aS)-4-(aminomethyl)-7a-methyl-1-methyleneoctahydro-1H-inden-5-yl)-2-(3,4-difluorophenyl)-5-methyl-4,5,6,7-tetrahydro-2H-indazol-6-yl)methanol (Compound Ia-23)

Following the procedure as described in Synthetic Example 12 and making non-critical variations using (3,4-difluorophenyl)hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-H-inden-5-yl)-1-(3,4-difluorophenyl)-5-methyl-4,5,6,7-tetrahydro-1H-indazol-6-yl)methanol (Compound Ia-22) and ((5R,6S)-5-((3aS,4R,5S,7aS)-4-(aminomethyl)-7a-methyl-1-methyleneoctahydro-1H-inden-5-yl)-2-(3,4-difluorophenyl)-5-methyl-4,5,6,7-tetrahydro-2H-indazol-6-yl)methanol (Compound Ia-23) were obtained.

Compound Ia-22: LCMS: (Method 1d) MS m/z: 456.2 (M+1), $t_R$: 2.014 min, Purity: 99.42% (UV).

Compound Ia-23: LCMS: (Method 1d) MS m/z: 456.3 (M+1), $t_R$: 1.547 min, Purity: 97.38% (UV).

Synthetic Example 12.6

Synthesis of ((5R,6S)-5-((3aS,4R,5S,7aS)-4-(aminomethyl)-7a-methyl-1-methyleneoctahydro-1H-inden-5-yl)-1-(4-(4-fluorophenoxy)phenyl)-5-methyl-4,5,6,7-tetrahydro-1H-indazol-6-yl)methanol (Compound Ia-24) and ((5R,6S)-5-((3aS,4R,5S,7aS)-4-(aminomethyl)-7a-methyl-1-methyleneoctahydro-1H-inden-5-yl)-2-(4-(4-fluorophenoxy)phenyl)-5-methyl-4,5,6,7-tetrahydro-2H-indazol-6-yl)methanol (Compound Ia-25)

Following the procedure as described in Synthetic Example 12 and making non-critical variations using (4-(4-fluorophenoxy)phenyl)hydrazine to replace 4-fluorophenyl hydrazine in the conversion of Compound 81 to the mixture of Compounds 82a and 82b, the title compounds ((R,6S)-5-((3aS,4R,5S,7aS)-4-(aminomethyl)-7a-methyl-1-methyleneoctahydro-1H-inden-5-yl)-1-(4-(4-fluorophenoxy)phenyl)-5-methyl-4,5,6,7-tetrahydro-1H-indazol-6-yl)methanol (Compound Ia-24) and ((5R,6S)-5-((3aS,4R,5S,7aS)-4-(aminomethyl)-7a-methyl-1-methyleneoctahydro-1H-inden-5-yl)-2-(4-(4-fluorophenoxy)phenyl)-5-methyl-4,5,6,7-tetrahydro-2H-indazol-6-yl)methanol (Compound Ia-25) were obtained.

Compound Ia-24: LCMS: (Method 1c) MS m/z: 530.2 (M+1), $t_R$: 0.995 min, Purity: 97.05% (UV).

Compound Ia-25: LCMS: (Method 1d) MS m/z: 530.3 (M+1), $t_R$: 1.801 min, Purity: 98.10% (UV).

Synthetic Example 12.7

Synthesis of ((5R,6S)-5-((3aS,4R,5S,7aS)-4-(aminomethyl)-7a-methyl-1-methyleneoctahydro-1H-inden-5-yl)-1-(5-fluoropyrimidin-2-yl)-5-methyl-4,5,6,7-tetrahydro-1H-indazol-6-yl)methanol (Compound Ia-26) and ((5R,6S)-5-((3aS,4R,5S,7aS)-4-(aminomethyl)-7a-methyl-1-methyleneoctahydro-1H-inden-5-yl)-2-(5-fluoropyrimidin-2-yl)-5-methyl-4,5,6,7-tetrahydro-2H-indazol-6-yl)methanol (Compound Ia-27)

Following the procedure as described in Synthetic Example 12 and making non-critical variations using 5-fluoro-2-hydrazineylpyrimidine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(5-fluoropyrimidin-2-yl)-5-methyl-4,5,6,7-tetrahydro-1H-indazol-6-yl)methanol (Compound Ia-26) and ((5R,6S)-5-((3aS,4R,5S,7aS)-4-(aminomethyl)-7a-methyl-1-methyleneoctahydro-1H-inden-5-yl)-2-(5-fluoropyrimidin-2-yl)-5-methyl-4,5,6,7-tetrahydro-2H-indazol-6-yl)methanol (Compound Ia-27) were obtained.

Compound Ia-26: LCMS: (Method 1c) MS m/z: 440.2 (M+1), $t_R$: 2.126 min, Purity: 96.50% (UV).

Compound Ia-27: LCMS: (Method 1c) MS m/z: 440.2 (M+1), $t_R$: 2.237 min, Purity: 95.86% (UV).

Synthetic Example 12.8

Synthesis of ((5R,6S)-5-((3aS,4R,5S,7aS)-4-(aminomethyl)-7a-methyl-1-methyleneoctahydro-1H-inden-5-yl)-5-methyl-1-(4-phenoxyphenyl)-4,5,6,7-tetrahydro-1H-indazol-6-yl)methanol (Compound Ia-28) and ((5R,6S)-5-((3aS,4R,5S,7aS)-4-(aminomethyl)-7a-methyl-1-methyleneoctahydro-1H-inden-5-yl)-5-methyl-2-(4-phenoxyphenyl)-4,5,6,7-tetrahydro-2H-indazol-6-yl)methanol (Compound Ia-29)

Following the procedure as described in Synthetic Example 12 and making non-critical variations using (4-phenoxyphenyl)hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-5-methyl-1-(4-phenoxyphenyl)-4,5,6,7-tetrahydro-1H-indazol-6-yl)methanol (Compound Ia-28) and ((5R,6S)-5-((3aS,4R,5S,7aS)-4-(aminomethyl)-7a-methyl-1-methyleneoctahydro-1H-inden-5-yl)-5-methyl-2-(4-phenoxyphenyl)-4,5,6,7-tetrahydro-2H-indazol-6-yl)methanol (Compound Ia-29) were obtained.

Compound Ia-28: LCMS: (Method 1c) MS m/z: 512.3 (M+1), $t_R$: 2.706 min, Purity: 91.51% (UV).

Compound Ia-29: LCMS: (Method 1d) MS m/z: 512.3 (M+1), $t_R$: 2.056 min, Purity: 94.40% (UV).

Synthetic Example 12.9

Synthesis of ((5R,6S)-5-((3aS,4R,5S,7aS)-4-(aminomethyl)-7a-methyl-1-methyleneoctahydro-1H-inden-5-yl)-1-(5-fluoropyridin-2-yl)-5-methyl-4,5,6,7-tetrahydro-1H-indazol-6-yl)methanol (Compound Ia-30) and ((5R,6S)-5-((3aS,4R,5S,7aS)-4-(aminomethyl)-7a-methyl-1-methyleneoctahydro-1H-inden-5-yl)-2-(5-fluoropyridin-2-yl)-5-methyl-4,5,6,7-tetrahydro-2H-indazol-6-yl)methanol (Compound Ia-31)

Following the procedure as described in Synthetic Example 12 and making non-critical variations using 5-fluoro-2-hydrazineylpyridine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(5-fluoropyridin-2-yl)-5-methyl-4,5,6,7-tetrahydro-1H-indazol-6-yl)methanol (Compound Ia-30) and ((5R,6S)-5-((3aS,4R,5S,7aS)-4-(aminomethyl)-7a-methyl-1-methyleneoctahydro-1H-inden-5-yl)-2-(5-fluoropyridin-2-yl)-5-methyl-4,5,6,7-tetrahydro-2H-indazol-6-yl)methanol (Compound Ia-31) were obtained.

Compound Ia-30: LCMS: (Method 1c) MS m/z: 439.2 (M+1), $t_R$: 2.494 min, Purity: 99.71% (UV).

Synthetic Example 12.10

Synthesis of ((5R,6S)-5-((3aS,4R,5S,7aS)-4-(aminomethyl)-7a-methyl-1-methyleneoctahydro-1H-inden-5-yl)-1-(2-fluorophenyl)-5-methyl-4,5,6,7-tetrahydro-1H-indazol-6-yl)methanol (Compound Ia-32) and ((5R,6S)-5-((3aS,4R,5S,7aS)-4-(aminomethyl)-7a-methyl-1-methyleneoctahydro-1H-inden-5-yl)-2-(2-fluorophenyl)-5-methyl-4,5,6,7-tetrahydro-2H-indazol-6-yl)methanol (Compound Ia-33)

Following the procedure as described in Synthetic Example 12 and making non-critical variations using 2-fluorophenyl hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(2-fluorophenyl)-5-methyl-4,5,6,7-tetrahydro-1H-indazol-6-yl)methanol (Compound Ia-32) and ((5R,6S)-5-((3aS,4R,5S,7aS)-4-(aminomethyl)-7a-methyl-1-methyleneoctahydro-1H-inden-5-yl)-2-(2-fluorophenyl)-5-methyl-4,5,6,7-tetrahydro-2H-indazol-6-yl)methanol (Compound Ia-33) were obtained.

Compound Ia-32: LCMS: (Method 1c) MS m/z: 438.3 (M+1), $t_R$: 1.503 min, Purity: 89.45% (UV).

Synthetic Example 12.11

Synthesis of ((5R,6S)-5-((3aS,4R,5S,7aS)-4-(aminomethyl)-7a-methyl-1-methyleneoctahydro-1H-inden-5-yl)-1-(2,4-difluorophenyl)-5-methyl-4,5,6,7-tetrahydro-1H-indazol-6-yl)methanol (Compound Ia-34) and ((5R,6S)-5-((3aS,4R,5S,7aS)-4-(aminomethyl)-7a-methyl-1-methyleneoctahydro-1H-inden-5-yl)-2-(2,4-difluorophenyl)-5-methyl-4,5,6,7-tetrahydro-2H-indazol-6-yl)methanol (Compound Ia-35)

Following the procedure as described in Synthetic Example 12 and making non-critical variations using 2,4-difluorophenyl hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(2,4-difluorophenyl)-5-methyl-4,5,6,7-tetrahydro-1H-indazol-6-yl)methanol (Compound Ia-34) and ((5R,6S)-5-((3aS,4R,5S,7aS)-4-(aminomethyl)-7a-methyl-1-methyleneoctahydro-1H-inden-5-yl)-2-(2,4-difluorophenyl)-5-methyl-4,5,6,7-tetrahydro-2H-indazol-6-yl)methanol (Compound Ia-35) were obtained.

Compound Ia-34: LCMS: (Method 1d) MS m/z: 456.2 (M+1), $t_R$: 1.443 min, Purity: 99.10% (ELSD).

Synthetic Example 12.12

Synthesis of 4-(4-((5R,6S)-5-((3aS,4R,5S,7aS)-4-(aminomethyl)-7a-methyl-1-methyleneoctahydro-H-inden-5-yl)-6-(hydroxymethyl)-5-methyl-4,5,6,7-tetrahydro-1H-indazol-1-yl)phenoxy)benzoic acid (Compound Ia-36) and 4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenoxy)benzoic acid (Compound Ia-37)

Following the procedure as described in Synthetic Example 12 and making non-critical variations using methyl 4-(4-hydrazineylphenoxy)benzoate to replace 4-fluorophenyl hydrazine in the conversion of Compound 81 to the mixture of Compounds 82a and 82b, the title compounds 4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenoxy)benzoic acid (Compound Ia-36) and 4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenoxy)benzoic acid (Compound Ia-37) were obtained after hydrolysis of the ester with LiH in THF:MeOH:water (7:2:1) at 65° C. for 2 hours.

Compound Ia-36: LCMS: (Method 1c) MS m/z: 556.3 (M+1), $t_R$: 2.552 min, Purity: 99.977% (ELSD).

Synthetic Example 12.13

Synthesis of ((5R,6S)-5-((3aS,4R,5S,7aS)-4-(aminomethyl)-7a-methyl-1-methyleneoctahydro-1H-inden-5-yl)-1-(4,4-difluorocyclohexyl)-5-methyl-4,5,6,7-tetrahydro-1H-indazol-6-yl)methanol (Compound Ia-38) and ((5R,6S)-5-((3aS,4R,5S,7aS)-4-(aminomethyl)-7a-methyl-1-methyleneoctahydro-1H-inden-5-yl)-2-(4,4-difluorocyclohexyl)-5-methyl-4,5,6,7-tetrahydro-2H-indazol-6-yl)methanol (Compound Ia-39)

Following the procedure as described in Synthetic Example 12 and making non-critical variations using (4,4-difluorocyclohexyl)hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(4,4-difluorocyclohexyl)-5-methyl-4,5,6,7-tetrahydro-1H-indazol-6-yl)methanol (Compound Ia-38) and ((5R,6S)-5-((3aS,4R,5S,7aS)-4-(aminomethyl)-7a-methyl-1-methyleneoctahydro-1H-inden-5-yl)-2-(4,4-difluorocyclohexyl)-5-methyl-4,5,6,7-tetrahydro-2H-indazol-6-yl)methanol (Compound Ia-39) were obtained.

Compound Ia-39: LCMS: (Method 1c) MS m/z: 462.3 (M+1), $t_R$: 2.295 min, Purity: 97.32% (UV).

Synthetic Example 12.14

Synthesis of ((5R,6S)-5-((3aS,4R,5S,7aS)-4-(aminomethyl)-7a-methyl-1-methyleneoctahydro-1H-inden-5-yl)-1-(3-fluorophenyl)-5-methyl-4,5,6,7-tetrahydro-1H-indazol-6-yl)methanol (Compound Ia-40) and ((5R,6S)-5-((3aS,4R,5S,7aS)-4-(aminomethyl)-7a-methyl-1-methyleneoctahydro-1H-inden-5-yl)-2-(3-fluorophenyl)-5-methyl-4,5,6,7-tetrahydro-2H-indazol-6-yl)methanol (Compound Ia-41)

Following the procedure as described in Synthetic Example 12 and making non-critical variations using 3-fluorophenyl hydrazine to replace 4-fluorophenyl hydrazine in the conversion of Compound 81 to the mixture of Compounds 82a and 82b, the title compounds ((5R,6S)-5-((3aS,4R,5S,7aS)-4-(aminomethyl)-7a-methyl-1-methyleneoctahydro-1H-inden-5-yl)-1-(3-fluorophenyl)-5-methyl-4,5,6,7-tetrahydro-1H-indazol-6-yl)methanol (Compound Ia-40) and ((5R,6S)-5-((3aS,4R,5S,7aS)-4-(aminomethyl)-7a-methyl-1-methyleneoctahydro-1H-inden-5-yl)-2-(3-fluorophenyl)-5-methyl-4,5,6,7-tetrahydro-2H-indazol-6-yl)methanol (Compound Ia-41) were obtained.

Compound Ia-40: LCMS: (Method 1d) MS m/z: 438.3 (M+1), $t_R$: 1.524 min, Purity: 93.14% (UV).

Synthetic Example 12.15

Synthesis of (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(4-(pent-4-yn-1-yloxy)phenyl)methanone (Compound Ia-62) and (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(4-(pent-4-yn-1-yloxy)phenyl)methanone (Compound Ia-63)

A. To a solution of 4-nitrobenzoyl chloride (4.25 g, 23.1 mmol) in DCM (50 mL) was added anisole (5.0 g, 46.3 mmol) and AlCl$_3$ (3.08 g, 23.1 mmol) at 0° C. The reaction mixture was stirred at 0° C. for 1h then at RT for 12h under N$_2$. Reaction completion was checked by TLC. The reaction mixture was quenched with ice, extracted with DCM (50 mL), and washed with brine (2×25 mL). The organic layer was separated and dried over Na$_2$SO$_4$ then concentrated to dryness. The crude product was purified by column chromatography (230-400 mesh silica gel, eluted with 40-50% pet ether/EtOAc) to give (4-methoxyphenyl)(4-nitrophenyl) methanone (6.50 g, 54%) as a colourless solid. LCMS: (Method 1d) MS m/z: 258 (M+1), t$_R$: 2.36 min, Purity: 75.3% (UV).

B. To a solution of (4-methoxyphenyl)(4-nitrophenyl) methanone (6.50 g, 26.8 mmol) in glacial AcOH (20 mL) was added HBr in AcOH (33%, 33.0 mL, 134 mmol). The reaction mixture was refluxed for 16 h under N$_2$. Reaction completion was checked by LCMS. The reaction mixture was cooled to RT, quenched with ice water (50 mL) and concentrated by rotary evaporator to remove AcOH. The residue obtained was diluted with EtOAc (50 mL), washed with brine (2×25 mL). The organic layer was dried over Na$_2$SO$_4$ and concentrated to dryness. The crude product was purified by column chromatography (230-400 mesh silica gel, eluted with 40-50% pet. ether/EtOAc) to give (4-hydroxyphenyl)(4-nitrophenyl)methanone (5.70 g, 93%) as a colorless solid. LCMS: (Method 1d) MS m/z: 243 (M+1), t$_R$: 1.93 min, Purity: 74.6% (UV).

C. To a solution of triphenylphosphine (9.26 g, 35.3 mmol) in THF (45 mL) was added DIAD (7.00 mL, 35.3 mmol) at 0° C. Stirring was continued for 30 min after which pent-4-yn-1-ol (3.20 mL, 35.3 mmol) was added at 0° C. Reaction was stirred for a further 30 min, after which (4-hydroxyphenyl)(4-nitrophenyl)methanone (5.70 g, 23.5 mmol) in THF (5 mL) was added dropwise. The reaction mixture was stirred for 3 h under N$_2$. Reaction completion was checked by TLC. The reaction mixture was diluted with EtOAc (50 mL), washed with brine (2×25 mL). The organic layer was dried over Na$_2$SO$_4$ and concentrated to dryness. The crude product purified by column chromatography (230-400 mesh silica gel, eluted with 30-40% pet. ether/EtOAc) to give (4-nitrophenyl)(4-(pent-4-yn-1-yloxy)phenyl)methanone (3.80 g, 53%) as an off white solid. LCMS: (Method 1f) MS m/z: 310 (M+1), t$_R$: 2.75 min, Purity: 89.1% (UV).

D. To a solution of (4-nitrophenyl)(4-(pent-4-yn-1-yloxy) phenyl)methanone (3.80 g, 12.3 mmol,) in EtOH (40 mL) and water (5 mL) was added NH$_4$Cl (3.20 g, 61.4 mmol). The reaction mixture was heated at 80° C. under N$_2$. At this temperature, Fe metal powder (3.43 g, 61.4 mmol) was added and stirring was continued for 4 h. The reaction mixture was cooled to RT, filtered through CELITE™ bed and concentrated to dryness. The crude product was purified by column chromatography (230-400 mesh silica gel, eluted with 40-50% pet. ether/EtOAc) to get the desired (4-aminophenyl)(4-(pent-4-yn-1-yloxy)phenyl)methanone (2.20 g, 64%) as a pale, yellow solid. LCMS: (Method 1k), MS m/z: 280 (M+1), t$_R$: 2.75 min, Purity: 83.5% (UV).

E. To a cold aqueous solution of HCl (12 N, 5.2 mL) was added (4-nitrophenyl)(4-(pent-4-yn-1-yloxy)phenyl)methanone (1.30 g, 4.6 mmol). An ice-cold solution of NaNO$_2$ (0.26 g, 3.8 mmol) in water (4.5 mL) was added dropwise to the reaction mass and stirred for 20 min at 0° C. SnCl$_2$ (2.3 g, 12.2 mmol) in HCl (12 N, 8.8 mL) was added dropwise to the reaction flask and stirring was continued for 4 h at RT. The precipitate formed was filtered, washed with HCl (1 N) to give (4-hydrazineylphenyl)(4-(pent-4-yn-1-yloxy)phenyl)methanone, hydrogen chloride salt (1.20 g, 86%) as a yellow solid, which was taken to next step without any further purification. LCMS: (Method 1) MS m/z: 295 (M+1), t$_R$: 1.76 min, Purity: 76.7% (UV).

F. Following the procedure as described in Synthetic Example 12 and making non-critical variations using (4-hydrazineylphenyl)(4-(pent-4-yn-1-yloxy)phenyl)methanone hydrochloride (prepared above) to replace phenyl hydrazine, the title compounds, (4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(4-(pent-4-yn-1-yloxy)phenyl) methanone (Compound Ia-62) and (4-((5R,6S)-5-((3aS,4R, 5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(4-(pent-4-yn-1-yloxy)phenyl)methanone (Compound Ia-63), were obtained after purification by preparative HPLC (Method 3c).

Compound Ia-62: LCMS: (Method 1k) MS m/z: 606 (M+1), t$_R$: 3.17 min, Purity: 99.21% (UV).

HPLC: (Method 2d) t$_R$: 11.65 min, Purity: 98.8% (UV).
1H-NMR (400 MHz, CD$_3$OD): δ 7.91-7.88 (m, 4H), 7.86-7.82 (m, 2H), 7.57 (s, 1H), 7.10-7.07 (m, 2H), 4.69 (s, 2H), 4.20 (t, J=6.0 Hz, 2H), 3.94 (dd, J=10.8, 2.4 Hz, 1H), 3.50-3.31 (m, 2H), 3.25-3.12 (m, 2H), 2.80-2.76 (m, 2H), 2.51-2.37 (m, 5H), 2.28-2.27 (m, 1H), 2.05-1.88 (m, 6H), 1.70-1.29 (m, 6H), 1.14 (s, 3H), 0.91 (s, 3H).

Synthetic Example 12.16

Synthesis of 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)benzoic acid (Compound Ia-64) and 4-((5R,6S)-5-((3aS,4R,5S, 7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)benzoic acid (Compound Ia-65)

Following the procedure as described in Synthetic Example 12 and making non-critical variations using 4-hydrazineylbenzoic acid hydrochloride to replace phenyl hydrazine, the title compounds, 4-((5R,6S)-5-((3aS,4R,5S, 7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)benzoic acid (Compound Ia-64) and 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)benzoic acid (Compound Ia-65), were obtained after purification by preparative HPLC (Method 3a).

Compound Ia-64: LCMS: (Method 1d) MS m/z: 464 (M+1), t$_R$: 1.65 min, Purity: 94.1% (UV).

HPLC: (Method 2b) t$_R$: 6.41 min, Purity: 93.5% (UV).
1H-NMR (400 MHz, CD$_3$OD): δ 8.10 (d, J=8.4 Hz, 2H), 7.57 (d, J=8.4 Hz, 2H), 7.51 (s, 1H), 4.70 (s, 2H), 3.91 (d, J=8.8 Hz, 1H), 3.54 (dd, J=2.0, 14.2 Hz, 1H), 3.44 (t, J=9.6 Hz, 1H), 3.39-3.20 (m, 1H), 3.21-3.14 (m, 2H), 2.80-2.71 (m, 2H), 2.64-2.55 (m, 1H), 2.47 (d, J=16.0 Hz, 1H), 2.41-2.32 (m, 1H), 2.22-2.01 (m, 2H), 1.99-1.85 (m, 2H), 1.75-1.59 (m, 2H), 1.53-1.41 (m, 1H), 1.39-1.25 (m, 2H), 1.13 (s, 3H), 0.87 (s, 3H).

Compound Ia-65: LCMS: (Method 1d) MS m/z: 464 (M+1), t$_R$: 1.58 min, Purity: 97.3.91% (UV).

HPLC: (Method 2b) t$_R$: 6.49 m, Purity: 98.4% (UV).
1H-NMR (400 MHz, CD$_3$OD): δ 8.04 (d, J=8.4 Hz, 2H), 7.94 (s, 1H), 7.66 (d, J=8.4 Hz, 2H), 4.70 (s, 2H), 3.96 (d, J=10.0 Hz, 1H), 3.47 (q, J=14.0 Hz, 2H), 3.32-3.19 (m, 3H), 2.78 (d, J=16.0 Hz, 1H), 2.65-2.50 (m, 2H), 2.38-2.33 (m, 1H), 2.22-2.20 (m, 1H), 2.14-1.99 (m, 2H), 1.95-1.85 (m, 2H), 1.80-1.65 (m, 2H), 1.58-1.25 (m, 3H), 1.11 (s, 3H), 0.91 (s, 3H).
Synthetic Example 13
Synthesis of ((5aS,6R,7S,9aS)-7-((5R,6S)-6-(hydroxymethyl)-5-methyl-4,5,6,7-tetrahydro-1H-indazol-5-yl)-9a-methyl-5a,6,7,8,9,9a-hexahydro-5H-indeno[1,2-b]pyridin-6-yl)methanol (Compound Ia-43) and ((5R,6S)-5-((5aS,6R,7S,9aS)-6-(aminomethyl)-9a-methyl-5a,6,7,8,9,9a-hexahydro-5H-indeno[1,2-b]pyridin-7-yl)-5-methyl-4,5,6,7-tetrahydro-1H-indazol-6-yl)methanol (Compound Ia-44)
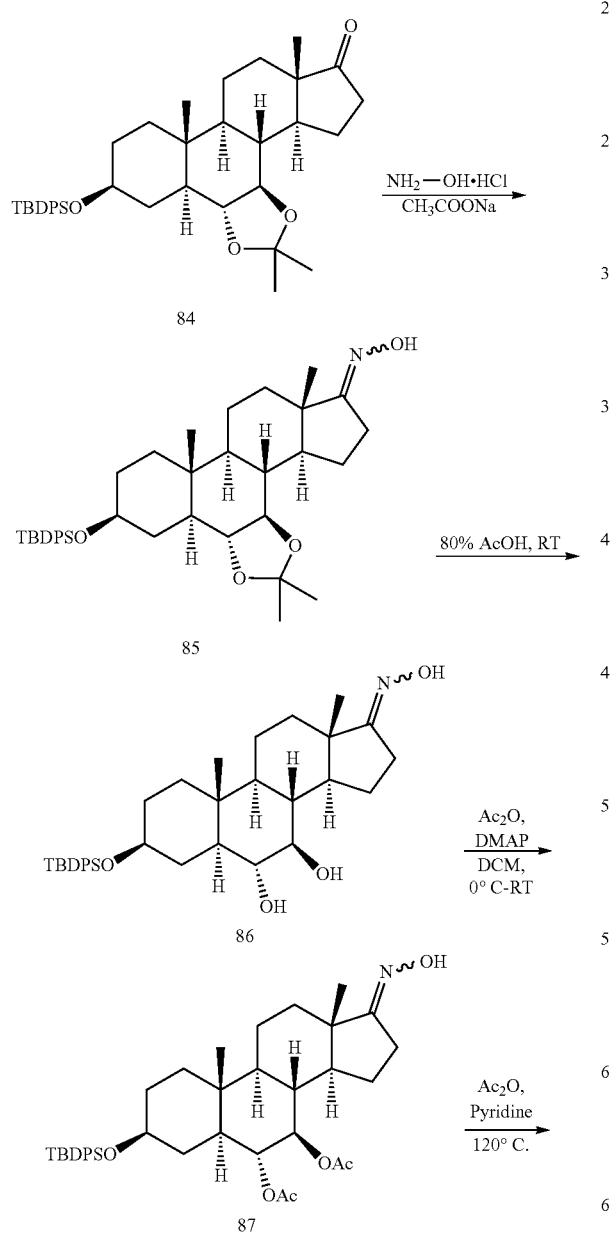
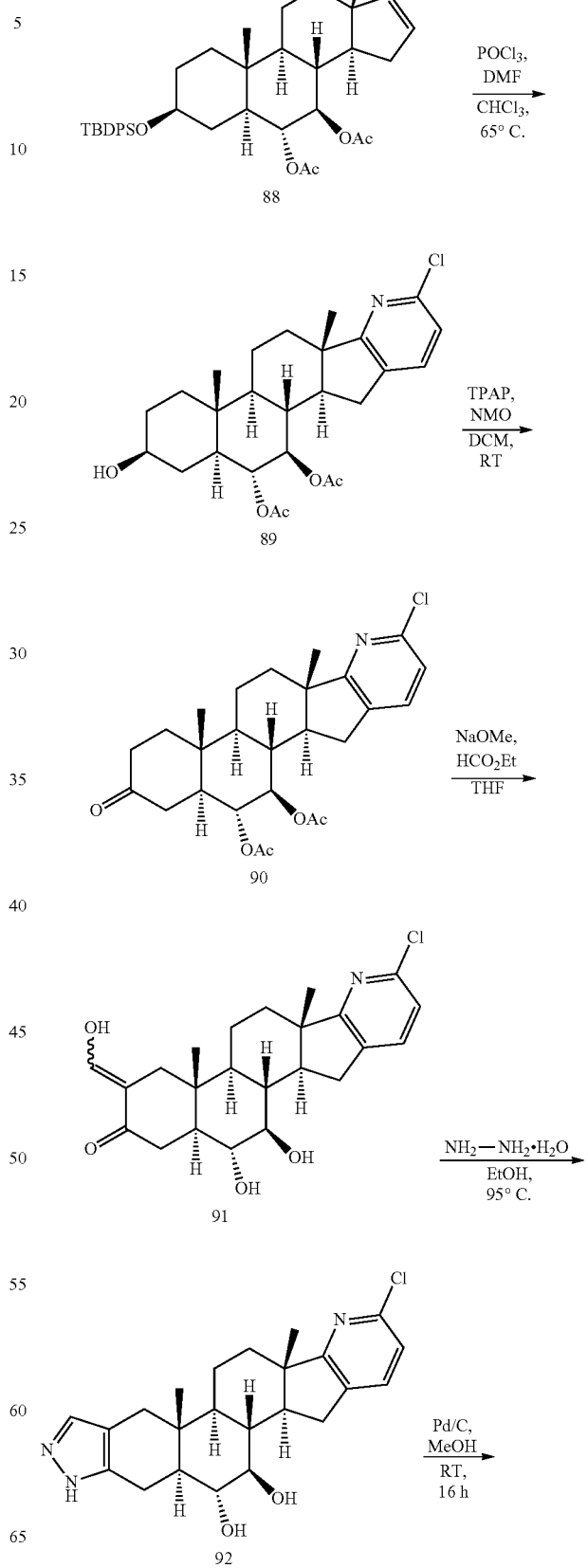

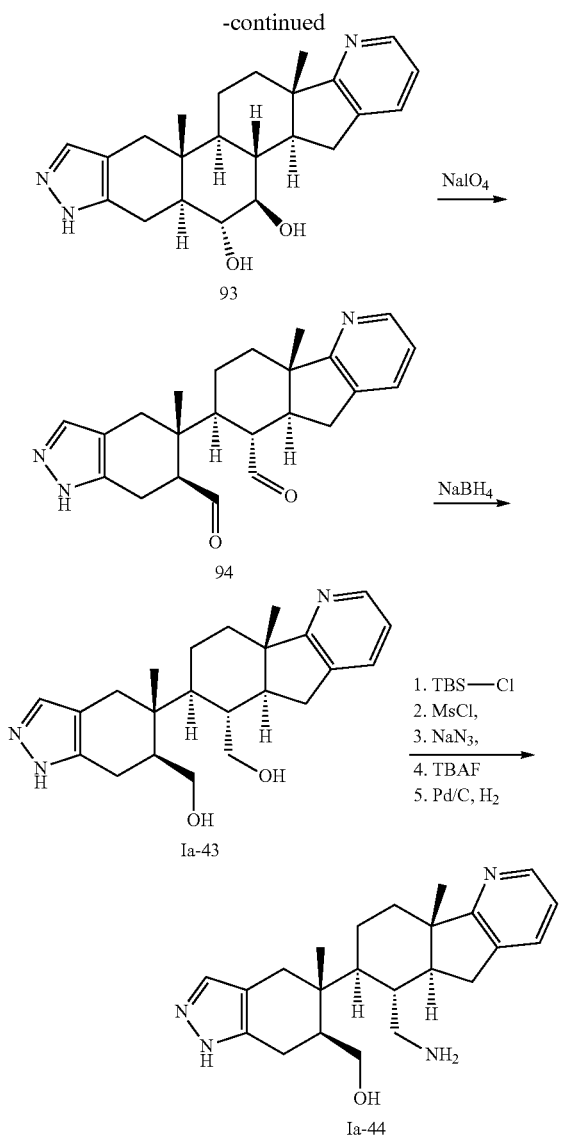

E. Compound 88 was treated with POCl₃ which cyclized to form a chloropyridine, while the TBDPS alcohol protecting group was simultaneously removed to form (1R,2R,2aS,4S,6aR,6bS,8aS,13aS,13bR)-10-chloro-4-hydroxy-6a,8a-dimethyl-2,2a,3,4,5,6,6a,6b,7,8,8a,13,13a,13b-tetradecahydro-1H-naphtho[2',1':4,5]indeno[1,2-b]pyridine-1,2-diyl diacetate (Compound 89).

F. Compound 89 was oxidized to form the ketone, (1R,2R,2aS,6aR,6bS,8aS,13aS,13bR)-10-chloro-6a,8a-dimethyl-4-oxo-2,2a,3,4,5,6,6a,6b,7,8,8a,13,13a,13b-tetradecahydro-1H-naphtho[2',1':4,5]indeno[1,2-b]pyridine-1,2-diyl diacetate (Compound 90).

G. Compound 90 underwent a Knoevenagel condensation to form (1R,2R,2aS,6aR,6bS,8aS,13aS,13bR)-10-chloro-1,2-dihydroxy-5-(hydroxymethylene)-6a,8a-dimethyl-1,2,2a,3,5,6,6a,6b,7,8,8a,13,13a,13b-tetradecahydro-4H-naphtho[2',1':4,5]indeno[1,2-b]pyridin-4-one Compound 91.

H. (5aS,5bR,6R,7R,7aS,12aR,12bS,14aS)-2-chloro-12a,14a-dimethyl-5,5a,5b,6,7,7a,8,9,12,12a,12b,13,14,14a-tetradecahydropyrido[2'',3'':3',4']cyclopenta[1',2':5,6]naphtho[1,2-f]indazole-6,7-diol (Compound 92) was obtained from the treatment fo Compound 91 with hydrazine.

LCMS: (Method 1e) MS m/z: 414.2 (M+1), $t_R$: 2.682 min, Purity: 76.30% (UV).

¹H-NMR (400 MHz, DMSO-d6): δ 12.20 (broad s, 1H), 7.66 (d, J=7.8 Hz, 1H), 7.19 (d, J=7.8 Hz, 2H), 4.68 (d, J=3.8 Hz, 1H), 4.60 (d, J=4.4 Hz, 1H), 3.40 (m, 1H), 3.17-2.92 (m, 4H), 2.08-2.01 (m, 3H), 1.92-1.59 (m, 3H), 1.40-1.35 (m, 2H), 1.10-0.87 (m, 5H), 0.61-0.57 (m, 1H), 0.39 (s, 3H).

I. (5aS,5bR,6R,7R,7aS,12aR,12bS,14aS)-12a,14a-dimethyl-5,5a,5b,6,7,7a,8,9,12,12a,12b,13,14,14a-tetradecahydropyrido[2'',3'':3',4']cyclopenta[1',2':5,6]naphtho[1,2-f]indazole-6,7-diol (Compound 93) was obtained from the reduction of Compound 92.

LCMS: (Method 1e) MS m/z: 380.2 (M+1), $t_R$: 2.140 min, Purity: 97.24% (UV).

HPLC: (Method 2e) $t_R$: 4.135 min, Purity: 99.95% (UV).

¹H-NMR (400 MHz, MeOH-d4): δ 8.29 (d, J=5.2 Hz, 1H), 7.65 (d, J=7.2 Hz, 1H), 7.28 (s, 1H), 7.16-7.19 (m, 1H), 3.47 (d, J=16.8 Hz, 1H), 3.23-3.35 (m, 3H), 3.11 (dd, J=5.2, 16.4 Hz, 1H), 2.60-2.66 (m, 2H), 2.13-2.28 (m, 3H), 1.74 (d, J=12.0 Hz, 1H), 1.75-1.59 (m, 2H), 1.11-1.20 (m, 5H), 0.82 (q, J=13.2 Hz, 1H), 0.52 (s, 3H).

J. Compound 93 was opened using periodate to generate (5aS,6R,7S,9aS)-7-((5R,6S)-6-formyl-5-methyl-4,5,6,7-tetrahydro-1H-indazol-5-yl)-9a-methyl-5a,6,7,8,9,9a-hexahydro-5H-indeno[1,2-b]pyridine-8-carbaldehyde (Compound 94).

K. Title compound ((5aS,6R,7S,9aS)-7-((5R,6S)-6-(hydroxymethyl)-5-methyl-4,5,6,7-tetrahydro-1H-indazol-5-yl)-9a-methyl-5a,6,7,8,9,9a-hexahydro-5H-indeno[1,2-b]pyridin-6-yl)methanol (Compound Ia-43) was obtained from the sodium borohydride reduction of Compound 94.

LCMS: (Method 1d) MS m/z: 382.2 (M+1), $t_R$: 0.327 min, Purity: 99.43% (ELSD).

L. Title compound ((5R,6S)-5-((5aS,6R,7S,9aS)-6-(aminomethyl)-9a-methyl-5a,6,7,8,9,9a-hexahydro-5H-indeno[1,2-b]pyridin-7-yl)-5-methyl-4,5,6,7-tetrahydro-1H-indazol-6-yl)methanol (Compound Ia-44) was obtained from the conversion of Compound Ia-43, as per the scheme above.

LCMS: (Method 1h) MS m/z: 381.3 (M+1), $t_R$: 1.673 min, Purity: 97.537% (UV).

A. Compound 84 (as prepared in U.S. Pat. No. 9,765,085) was converted to (2S,4aR,4bS,6aS,9aS,9bR,9cR,12aR,12bS)-2-((tert-butyldiphenylsilyl)oxy)-4a,6a,11,11-tetramethylhexadecahydro-7H-cyclopenta[1,2]phenanthro[9,10-d][1,3]dioxol-7-one oxime (Compound 85) through oxime formation.

B. Compound 85 was deprotected under acidic conditions to form (3S,5S,6R,7R,8R,9S,10R,13S,14S)-3-((tert-butyldiphenylsilyl)oxy)-6,7-dihydroxy-10,13-dimethylhexadecahydro-17H-cyclopenta[a]phenanthren-17-one oxime (Compound 86).

C. (3S,5S,6R,7R,8R,9S,10R,13S,14S)-3-((tert-butyldiphenylsilyl)oxy)-17-(hydroxyimino)-10,13-dimethylhexadecahydro-1H-cyclopenta[a]phenanthrene-6,7-diyl diacetate (Compound 87) was prepared by acetylating the diol, Compound 86.

D. Compound 87 was converted to (3S,5S,6R,7R,8R,9S,10R,13S,14S)-17-acetamido-3-((tert-butyldiphenylsilyl)oxy)-10,13-dimethyl-2,3,4,5,6,7,8,9,10,11,12,13,14,15-tetradecahydro-1H-cyclopenta[a]phenanthrene-6,7-diyl diacetate (Compound 88) using acetic anhydride under basic conditions.

Synthetic Example 14

Synthesis of (4-((5R,6S)-5-((1S,3aS,4S,5S7aR)-4-(aminomethyl)-1,7a-dimethyloctahydro-1H-inden-5-yl)-6-(hydroxymethyl)-5-methyl-4,5,6,7-tetrahydro-1H-indazol-1-yl)phenyl)(phenyl)methanone (Compound Ia-45) and (4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-2H-indazol-2-yl)phenyl)(phenyl)methanone (Compound Ia-46)

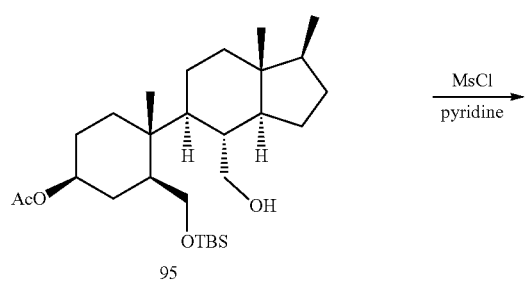

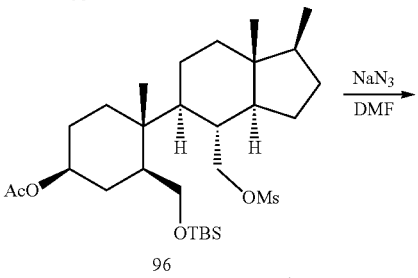

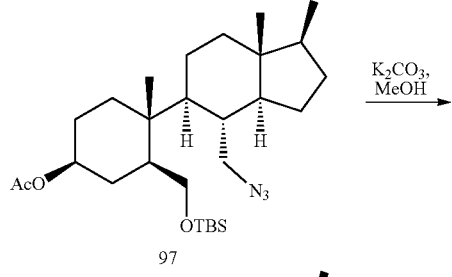

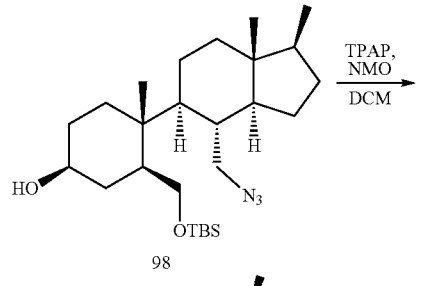

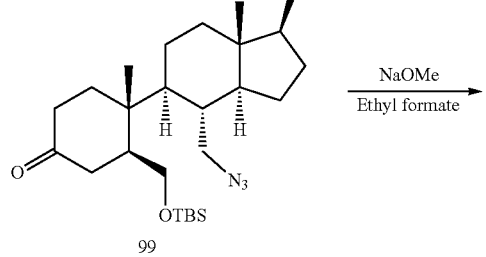

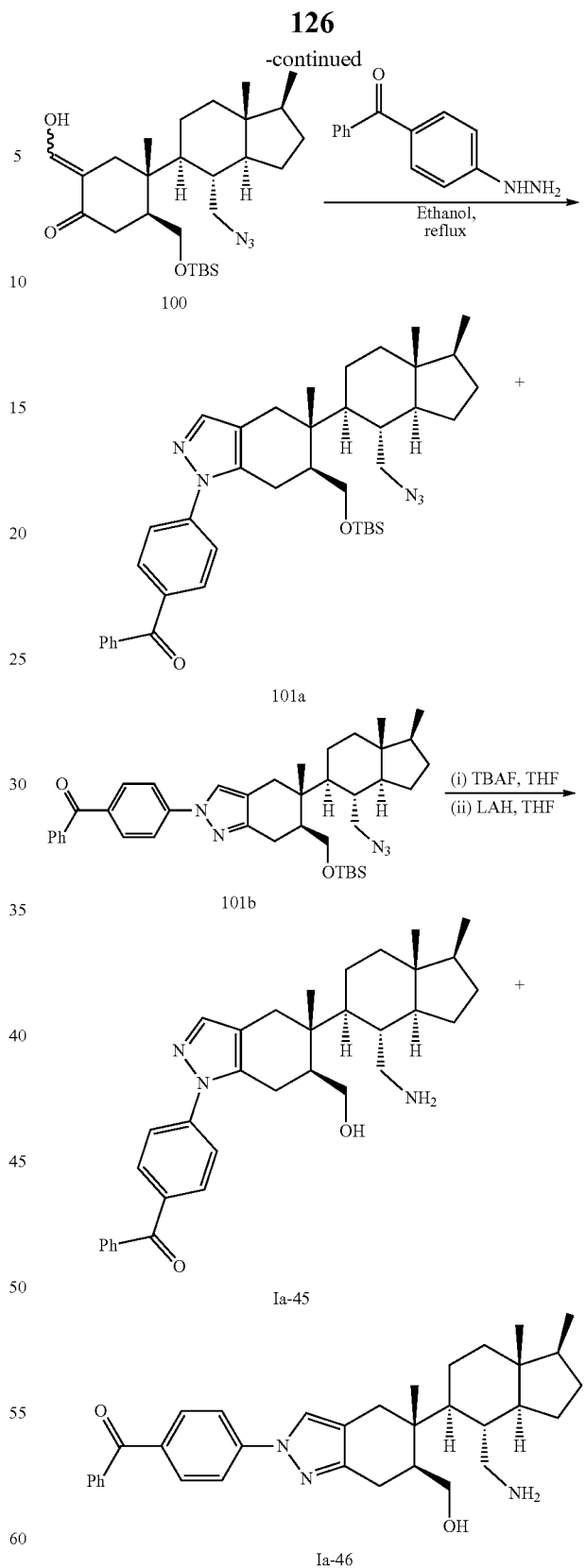

A. (1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl acetate (Compound 95, as prepared in U.S. Pat. No. 7,601,874) was converted to the mesylate (1S,3S,4R)-3-(((tert-butyldimethylsilyl)oxy) methyl)-4-((1S,3aS,4S,5S,7aR)-1,7a-dimethyl-4-(((methylsulfonyl)oxy)methyl)octahydro-1H-inden-5-yl)-4-methylcyclohexyl acetate (Compound 96) using mesyl chloride in pyridine.

B. Compound 96 was converted to the azide (1S,3S,4R)-4-((1S,3aS,4S,5S,7aR)-4-(azidomethyl)-1,7a-dimethyloctahydro-1H-inden-5-yl)-3-(((tert-butyldimethylsilyl)oxy) methyl)-4-methylcyclohexyl acetate (Compound 97) using sodium azide in DMF.

C. Compound 97 was deprotected under mild basic conditions to obtain (1S,3S,4R)-4-((1S,3aS,4S,5S,7aR)-4-(azidomethyl)-1,7a-dimethyloctahydro-1H-inden-5-yl)-3-(((tert-butyldimethylsilyl)oxy)methyl)-4-methylcyclohexan-1-ol (Compound 98).

D. Compound 98 was oxidized to the ketone (3S,4R)-4-((1S,3aS,4S,5S,7aR)-4-(azidomethyl)-1,7a-dimethyloctahydro-1H-inden-5-yl)-3-(((tert-butyldimethylsilyl)oxy) methyl)-4-methylcyclohexan-1-one (Compound 99) using TPAP and NMO.

E. Compound 99 underwent a Knoevenagel condensation with sodium methoxide and ethyl formate to obtain (4R,5S)-4-((1S,3aS,4S,5S,7aR)-4-(azidomethyl)-1,7a-dimethyloctahydro-1H-inden-5-yl)-5-(((tert-butyldimethylsilyl)oxy) methyl)-2-(hydroxymethylene)-4-methylcyclohexan-1-one (Compound 100).

F. Compound 100 was reacted with (4-hydrazineylphenyl)(phenyl)methanone to generate (4-((5R,6S)-5-((1S,3aS,4S,5S,7aR)-4-(azidomethyl)-1,7a-dimethyloctahydro-1H-inden-5-yl)-6-(((tert-butyldimethylsilyl)oxy)methyl)-5-methyl-4,5,6,7-tetrahydro-1H-indazol-1-yl)phenyl)(phenyl) methanone (Compound 101a) and (4-((5R,6S)-5-((1S,3aS,4S,5S,7aR)-4-(azidomethyl)-1,7a-dimethyloctahydro-1H-inden-5-yl)-6-(((tert-butyldimethylsilyl)oxy)methyl)-5-methyl-4,5,6,7-tetrahydro-2H-indazol-2-yl)phenyl)(phenyl) methanone (Compound 101b) as a mixture.

G. Title compound (4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-1H-indazol-1-yl)phenyl)(phenyl)methanone (Compound Ia-45) and title compound (4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-2H-indazol-2-yl)phenyl)(phenyl)methanone (Compound Ia-46) were obtained as pure compounds by deprotection and reduction of the mixture of Compounds 101a and 101b.

Compound Ia-45: LCMS: (Method 1c) MS m/z: 526.3 (M+1), $t_R$: 2.704 min, Purity: 91.11% (UV).

Compound Ia-46: LCMS: (Method 1c) MS m/z: 526.3 (M+1), $t_R$: 2.773 min, Purity: 92.41% (UV).

Synthetic Example 14.1

Synthesis of ((5R,6S)-5-((1S,3aS,4S,5S,7aR)-4-(aminomethyl)-1,7a-dimethyloctahydro-1H-inden-5-yl)-1-(4-fluorophenyl)-5-methyl-4,5,6,7-tetrahydro-1H-indazol-6-yl)methanol (Compound Ia-47) and ((5R,6S)-5-((1S,3aS,4S,5S,7aR)-4-(aminomethyl)-1,7a-dimethyloctahydro-1H-inden-5-yl)-2-(4-fluorophenyl)-5-methyl-4,5,6,7-tetrahydro-2H-indazol-6-yl)methanol (Compound Ia-48)

Following the procedure as described in Synthetic Example 14 and making non-critical variations using 4-fluorophenylhydrazine to replace (3-hydrazineylphenyl)(phenyl)methanone in the conversion of Compound 100 to the mixture of Compounds 101a and 101b, the title compounds ((5R,6S)-5-((1S,3aS,4S,5S,7aR)-4-(aminomethyl)-1,7a-dimethyloctahydro-1H-inden-5-yl)-1-(4-fluorophenyl)-5-methyl-4,5,6,7-tetrahydro-1H-indazol-6-yl)methanol (Compound Ia-47) and ((5R,6S)-5-((1S,3aS,4S,5S,7aR)-4-(aminomethyl)-1,7a-dimethyloctahydro-1H-inden-5-yl)-2-(4-fluorophenyl)-5-methyl-4,5,6,7-tetrahydro-2H-indazol-6-yl)methanol (Compound Ia-48) were obtained.

Compound Ia-47: LCMS: (Method 1c) MS m/z: 440.2 (M+1), $t_R$: 2.494 min, Purity: 97.38% (UV).

Synthetic Example 14.2

Synthesis of ((5R,6S)-5-((1S,3aS,4S,5S,7aR)-4-(aminomethyl)-1,7a-dimethyloctahydro-1H-inden-5-yl)-1-(4-methoxyphenyl)-5-methyl-4,5,6,7-tetrahydro-1H-indazol-6-yl)methanol (Compound Ia-49) and ((5R,6S)-5-((1S,3aS,4S,5S,7aR)-4-(aminomethyl)-1,7a-dimethyloctahydro-1H-inden-5-yl)-2-(4-methoxyphenyl)-5-methyl-4,5,6,7-tetrahydro-2H-indazol-6-yl)methanol (Compound Ia-50)

Following the procedure as described in Synthetic Example 14 and making non-critical variations using 4-methoxyphenylhydrazine to replace (3-hydrazineylphenyl)(phenyl)methanone in the conversion of Compound 100 to the mixture of Compounds 101a and 101b, the title compounds ((5R,6S)-5-((1S,3aS,4S,5S,7aR)-4-(aminomethyl)-1,7a-dimethyloctahydro-1H-inden-5-yl)-1-(4-methoxyphenyl)-5-methyl-4,5,6,7-tetrahydro-1H-indazol-6-yl)methanol (Compound Ia-49) and ((5R,6S)-5-((1S,3aS,4S,5S,7aR)-4-(aminomethyl)-1,7a-dimethyloctahydro-1H-inden-5-yl)-2-(4-methoxyphenyl)-5-methyl-4,5,6,7-tetrahydro-2H-indazol-6-yl)methanol (Compound Ia-50) were obtained.

Compound Ia-49: LCMS: (Method 1c) MS m/z: 452.2 (M+1), $t_R$: 2.428 min, Purity: 95.12% (UV).

Synthetic Example 14.3

Synthesis of ((5R,6S)-5-((1S,3aS,4S,5S,7aR)-4-(aminomethyl)-1,7a-dimethyloctahydro-1H-inden-5-yl)-1-(4-methoxybenzyl)-5-methyl-4,5,6,7-tetrahydro-1H-indazol-6-yl)methanol (Compound Ia-51) and ((5R,6S)-5-((1S,3aS,4S,5S,7aR)-4-(aminomethyl)-1,7a-dimethyloctahydro-1H-inden-5-yl)-2-(4-methoxybenzyl)-5-methyl-4,5,6,7-tetrahydro-2H-indazol-6-yl)methanol (Compound Ia-52)

Following the procedure as described in Synthetic Example 14 and making non-critical variations using 4-methoxybenzylhydrazine to replace (3-hydrazineylphenyl)(phenyl)methanone in the conversion of Compound 100 to the mixture of Compounds 101a and 101b, the title compounds ((5R,6S)-5-((1S,3aS,4S,5S,7aR)-4-(aminomethyl)-1,7a-dimethyloctahydro-1H-inden-5-yl)-1-(4-methoxybenzyl)-5-methyl-4,5,6,7-tetrahydro-1H-indazol-6-yl)methanol (Compound Ia-51) and ((5R,6S)-5-((1S,3aS,4S,5S,7aR)-4-(aminomethyl)-1,7a-dimethyloctahydro-1H-inden-5-yl)-2-(4-methoxybenzyl)-5-methyl-4,5,6,7-tetrahydro-2H-indazol-6-yl)methanol (Compound Ia-52) were obtained.

Compound Ia-52: LCMS: (Method 1c) MS m/z: 466.3 (M+1), $t_R$: 2.381 min, Purity: 99.94% (UV).

Synthetic Example 15

Synthesis of ((5R,6S)-5-((1S,3aS,4S,5S,7aR)-4-(aminomethyl)-1,7a-dimethyloctahydro-1H-inden-5-yl)-2-(4-(4-fluorophenoxy)phenyl)-5-methyl-4,5,6,7-tetrahydro-2H-indazol-6-yl)methanol (Compound Ia-54), ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol (Compound Ia-55) and ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol hydrochloride (Compound Ia-55 HCl)

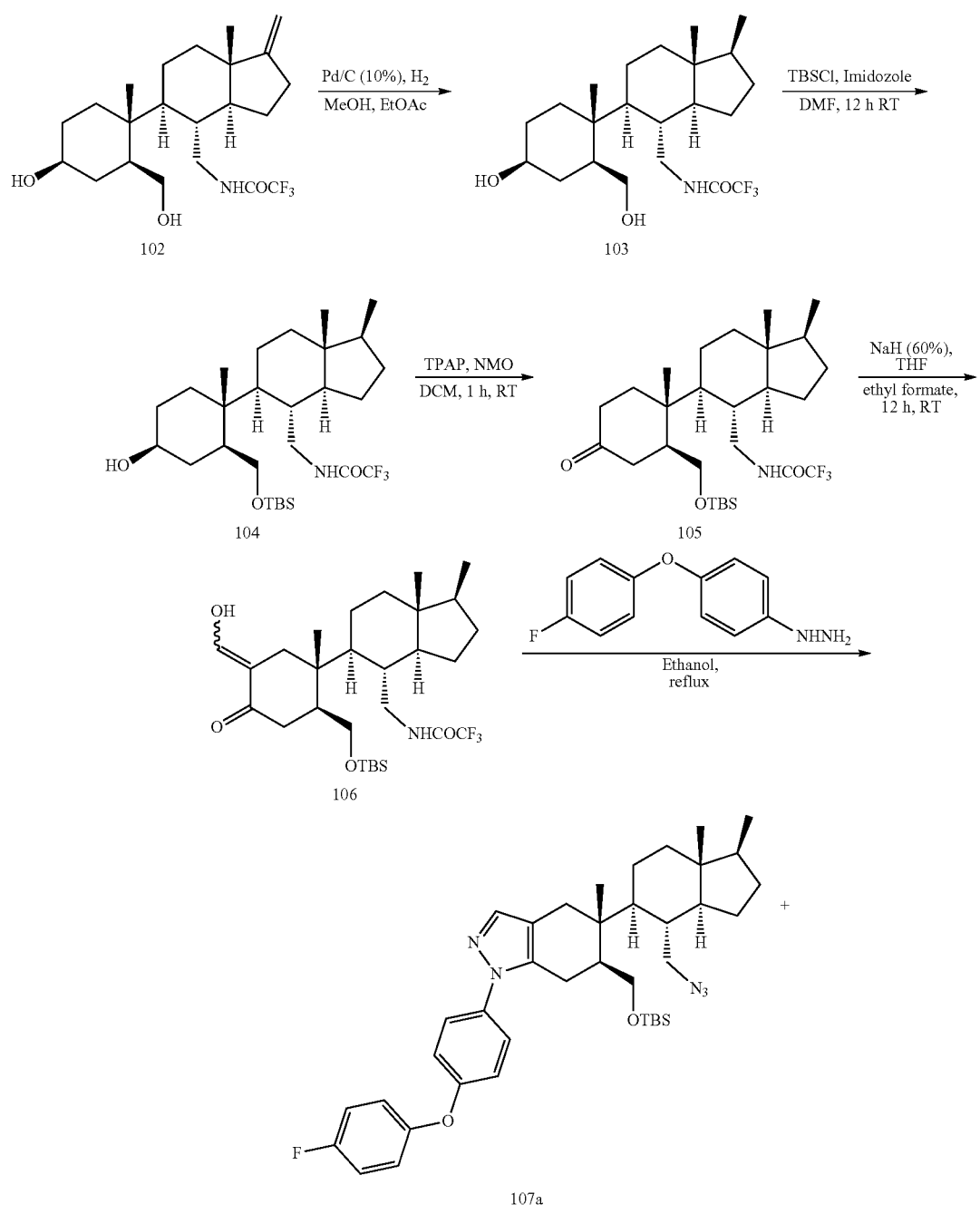

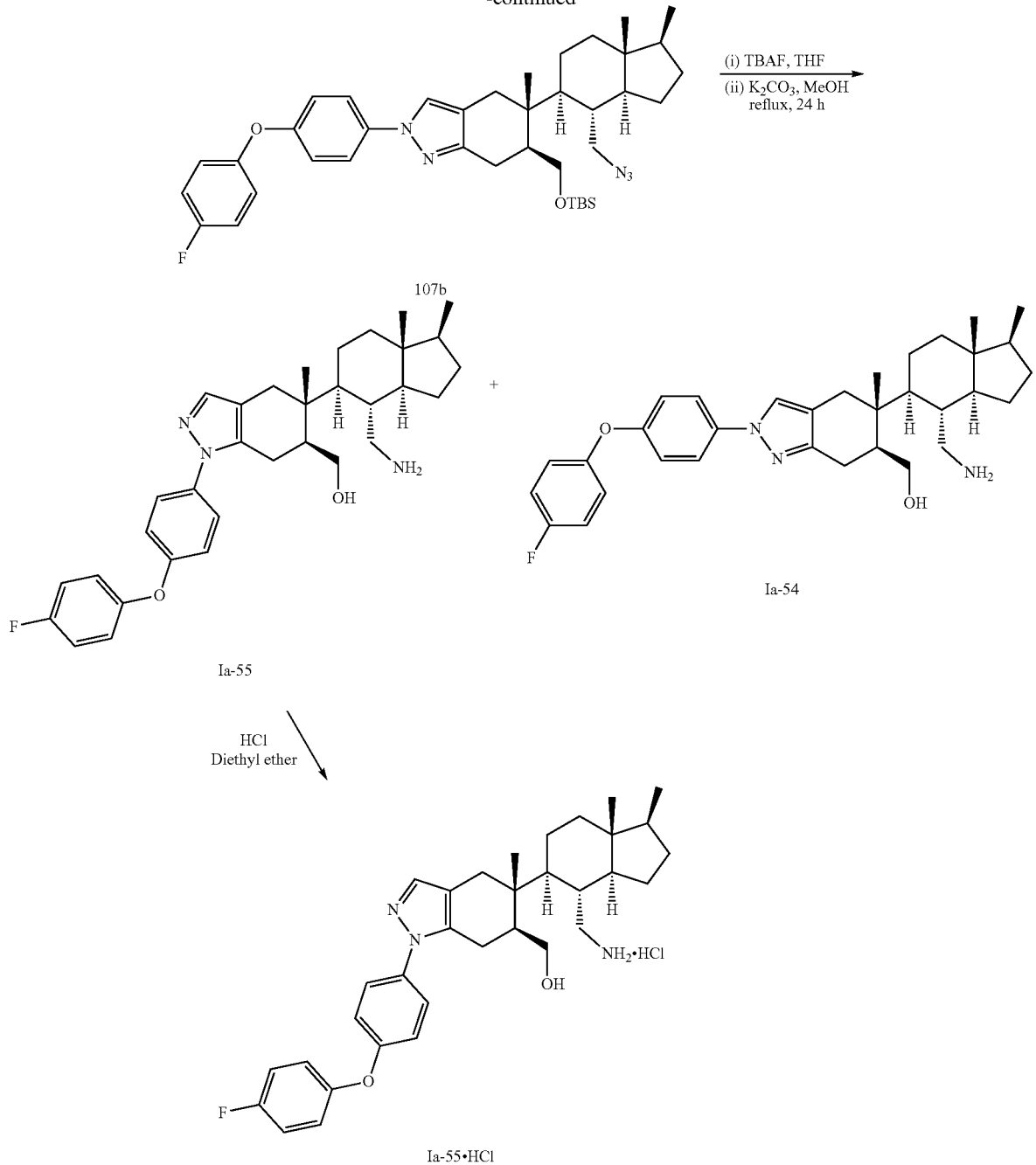

A. Using General Procedure S with 2,2,2-trifluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)acetamide (Compound 102 as prepared in U.S. Pat. No. 10,100,056, 20.0 g, 47.9 mmol), Pd/C (5-10%, 2.0 g (w/w)), and EtOAc:MeOH (1:9, 200 mL) gave 2,2,2-trifluoro-N-(((1S,3aS,4S,5S,7aR)-5-((1R,2S,4S)-4-hydroxy-2-(hydroxymethyl)-1-methylcyclohexyl)-1,7a-dimethyloctahydro-1H-inden-4-yl)methyl)acetamide (Compound 103, 17.4 g, 87%) as an off white solid after purification by column chromatography (230-400 mesh silica gel, eluted with 0-5% MeOH/DCM).

LCMS: (Method 1d) MS m/z: 418 (M-1), $t_R$: 2.24 min, Purity: 99.4% (UV).

B. Using General Procedure B with 2,2,2-trifluoro-N-(((1S,3aS,4S,5S,7aR)-5-((1R,2S,4S)-4-hydroxy-2-(hydroxymethyl)-1-methylcyclohexyl)-1,7a-dimethyloctahydro-1H-inden-4-yl)methyl)acetamide (Compound 103, 17.4 g, 41.5 mmol), imidazole (4.20 g, 62.3 mmol), TBSCl (7.47 g, 49.8 mmol) and DMF (170 mL) gave N-(((1S,3aS,4S,5S,7aR)-5-((1R,2S,4S)-2-(((tert-butydimethylsilyl)oxy)methyl)-4-hydroxy-1-methylcyclohexyl)-1,7a-dimethyloctahydro-1H-inden-4-yl)methyl)-2,2,2-trifluoroacetamide (Compound 104, 9.50 g, 43%) as a white solid after purification by column chromatography on silica gel (230-400 mesh, 20-30% pet. ether/EtOAc).

LCMS: (Method 1d) MS m/z: 520 (M+1), $t_R$: 3.86 min, Purity: 99.6% (ELSD).

C. Using General Procedure L with N-(((1S,3aS,4S,5S,7aR)-5-((1R,2S,4S)-2-(((tert-butyldimethylsilyl)oxy)methyl)-4-hydroxy-1-methylcyclohexyl)-1,7a-dimethyloctahydro-1H-inden-4-yl)methyl)-2,2,2-trifluoroacetamide (Compound 104, 9.50 g, 17.8 mmol), NMO (4.80 g, 35.6 mmol), 4 Å molecular sieves (9.00 g), TPAP (1.20 g, 3.5 mmol) and DCM (100 mL) gave N-(((1S,3aS,4S,5S,7aR)-5-((1R,2S)-2-(((tert-butyldimethylsilyl)oxy)methyl)-1-methyl-4-oxocyclohexyl)-1,7a-dimethyloctahydro-1H-inden-4-yl)methyl)-2,2,2-trifluoroacetamide (Compound 105, 8.00 g, 82%) as an off white solid after purification by column chromatography (230-400 mesh silica gel, eluted with 10-15% pet. ether/EtOAc).

LCMS: (Method 1c) MS m/z: 514 (M+1), $t_R$: 3.29 min, Purity: 97.5% (UV).

D. Following the General Procedure N with N-(((1S,3aS,4S,5S,7aR)-5-((1R,2S)-2-(((tert-butyldimethylsilyl)oxy)methyl)-1-methyl-4-oxocyclohexyl)-1,7a-dimethyloctahydro-1H-inden-4-yl)methyl)-2,2,2-trifluoroacetamide (Compound 105, 8.00 g, 15.1 mmol), NaH (60%, 2.90 g, 60.2 mmol), ethyl formate (7.3 mL, 90.4 mmol) and THF (80 mL) gave N-(((S,3aS,4S,5S,7aR)-5-((1R,2S)-2-(((tert-butyldimethylsilyl)oxy)methyl)-5-(hydroxymethylene)-1-methyl-4-oxocyclohexyl)-1,7a-dimethyloctahydro-1H-inden-4-yl)methyl)-2,2,2-trifluoroacetamide (Compound 106, 7.00 g, 83%) as a white solid after purification by column chromatography (230-400 mesh silica gel, eluted with 5-10% pet. ether/EtOAc).

LCMS: (Method 1c) MS m/z: 560 (M+1), $t_R$: 3.38 min, Purity: 84.3% (UV).

E. Following the General Procedure O with N-(((1S,3aS,4S,5S,7aR)-5-((1R,2S)-2-(((tert-butyldimethylsilyl)oxy)methyl)-5-(hydroxymethylene)-1-methyl-4-oxocyclohexyl)-1,7a-dimethyloctahydro-1H-inden-4-yl)methyl)-2,2,2-trifluoroacetamide (Compound 106, 4.00 g, 7.15 mmol) in EtOH (40 mL), TEA (2.00 mL, 14.3 mmol) and (4-(4-fluorophenoxy)phenyl)hydrazine hydrochloride (as prepared in U.S. Pat. No. 6,919,363 or 7,078,426, 1.80 g, 7.15 mmol) gave both N-(((1S,3aS,4S,5S,7aR)-5-((5R,6S)-6-(((tert-butyldimethylsilyl)oxy)methyl)-1-(4-(4-fluorophenoxy)phenyl)-5-methyl-4,5,6,7-tetrahydro-1H-indazol-5-yl)-1,7a-dimethyloctahydro-1H-inden-4-yl)methyl)-2,2,2-trifluoroacetamide (Compound 107a) and N-(((1S,3aS,4S,5S,7aR)-5-((5R,6S)-6-(((tert-butyldimethylsilyl)oxy)methyl)-2-(4-(4-fluorophenoxy)phenyl)-5-methyl-4,5,6,7-tetrahydro-2H-indazol-5-yl)-1,7a-dimethyloctahydro-1H-inden-4-yl)methyl)-2,2,2-trifluoroacetamide (Compound 107b, 3.00 g, 56%) as a brown solid after purification by column chromatography (230-400 mesh silica gel, eluted with 20-30% pet ether/EtOAc).

LCMS: (Method 1c) MS m/z: 742 (M+1), $t_R$: 2.90 min, Purity: 78.4% (UV).

F. Following the General Procedure P with both N-(((1S,3aS,4S,5S,7aR)-5-((5R,6S)-6-(((tert-butyldimethylsilyl)oxy)methyl)-1-(4-(4-fluorophenoxy)phenyl)-5-methyl-4,5,6,7-tetrahydro-1H-indazol-5-yl)-1,7a-dimethyloctahydro-1H-inden-4-yl)methyl)-2,2,2-trifluoroacetamide (Compound 107a) and N-(((1S,3aS,4S,5S,7aR)-5-((5R,6S)-6-(((tert-butyldimethylsilyl)oxy)methyl)-2-(4-(4-fluorophenoxy)phenyl)-5-methyl-4,5,6,7-tetrahydro-2H-indazol-5-yl)-1,7a-dimethyloctahydro-1H-inden-4-yl)methyl)-2,2,2-trifluoroacetamide (Compound 107b, 3.00 g, 4.04 mmol), TBAF (1 M in THF, 8.0 mL, 8.0 mmol) and THF (30 mL), gave both 2,2,2-trifluoro-N-(((1S,3aS,4S,5S,7aR)-5-((5R,6S)-1-(4-(4-fluorophenoxy)phenyl)-6-(hydroxymethyl)-5-methyl-4,5,6,7-tetrahydro-1H-indazol-5-yl)-1,7a-dimethyloctahydro-1H-inden-4-yl)methyl)acetamide and 2,2,2-trifluoro-N-(((1S,3aS,4S,5S,7aR)-5-((5R,6S)-2-(4-(4-fluorophenoxy)phenyl)-6-(hydroxymethyl)-5-methyl-4,5,6,7-tetrahydro-2H-indazol-5-yl)-1,7a-dimethyloctahydro-1H-inden-4-yl)methyl)acetamide, 1.50 g, 59%) as off white solids after purification by column chromatography (230-400 mesh silica gel, eluted with 30-50% pet ether/EtOAc).

LCMS: (Method 1c) MS m/z: 628 (M+1), $t_R$: 3.53 min, Purity: 99.9%.

G. Following the General Procedure K with both 2,2,2-trifluoro-N-(((1S,3aS,4S,5S,7aR)-5-((5R,6S)-1-(4-(4-fluorophenoxy)phenyl)-6-(hydroxymethyl)-5-methyl-4,5,6,7-tetrahydro-1H-indazol-5-yl)-1,7a-dimethyloctahydro-1H-inden-4-yl)methyl)acetamide and, 2,2-trifluoro-N-(((1S,3aS,4S,5S,7aR)-5-((5R,6S)-2-(4-(4-fluorophenoxy)phenyl)-6-(hydroxymethyl)-5-methyl-4,5,6,7-tetrahydro-1H-indazol-5-yl)-1,7a-dimethyloctahydro-2H-inden-4-yl)methyl)acetamide (from F above, 1.50 g, 2.39 mmol), $K_2CO_3$ (0.65 g, 4.78 mmol) and MeOH (15 mL), gave both ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol (Compound Ia-55, 0.8 g, 63%) and ((5R,6S)-5-((1S,3aS,4S,5S,7aR)-4-(aminomethyl)-1,7a-dimethyloctahydro-1H-inden-5-yl)-2-(4-(4-fluorophenoxy)phenyl)-5-methyl-4,5,6,7-tetrahydro-2H-indazol-6-yl)methanol (Compound Ia-54) as an off white solid after purification by column chromatography (230-400 mesh silica gel, eluted with 0-5% MeOH/DCM).

Compound Ia-55: LCMS: (Method 1I) MS m/z: 532 (M+1), $t_R$: 2.75 min, Purity: 98.3% (UV).

HPLC: (Method 2a) $t_R$: 4.66 min, Purity: 98.1% (UV).

$^1$H-NMR (400 MHz, CD$_3$OD): δ 7.51-7.44 (m, 3H), 7.16-7.06 (m, 6H), 3.93 (dd, J=2.4, 10.8 Hz, 1H), 3.38 (t, J=10.0 Hz, 1H), 3.17 (d, J=14.0 Hz, 1H), 3.08 (dd, J=5.6, 17.2 Hz, 1H), 2.78-2.58 (m, 3H), 2.41 (d, J=16.0 Hz, 1H), 2.15-2.07 (m, 1H), 1.86-1.62 (m, 6H), 1.51-1.44 (m, 3H), 1.29-1.24 (m, 2H), 1.11 (s, 3H), 1.02-0.98 (m, 1H), 0.88-0.86 (m, 3H), 0.65 (s, 3H).

H. Following the General Procedure T with ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol (Compound Ia-55, 0.100 g, 0.188 mmol), HCl in diethyl ether (2M, 0.5 mL) and MeOH (1 mL), gave the desired ((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol hydrochloride (Compound Ia-55-HCl, 0.030 mg, 28%) as an off white solid after drying.

LCMS: (Method 1c) MS m/z: 532 (M+1), $t_R$: 2.15 min, Purity: 99.4% (UV).

HPLC: (Method 2a) $t_R$: 4.70 min, Purity: 96.1% (UV).

$^1$H-NMR (400 MHz, DMSO-d6): δ 7.81 (s, 3H), 7.59 (d, J=8.8 Hz, 2H), 7.44 (s, 1H), 7.27 (t, J=8.7 Hz, 2H), 7.17-7.10 (m, 4H), 3.75-3.69 (m, 1H), 3.46-3.30 (m, 1H), 3.21 (t, J=9.9 Hz, 1H), 3.01-2.82 (m, 2H), 2.68-2.33 (m, 2H), 2.40-2.30 (m, 1H), 1.91-1.63 (m, 7H), 1.41-1.39 (m, 2H), 1.27-1.18 (m, 4H), 1.02 (s, 3H), 0.94-0.87 (m, 1H), 0.82 (d, J=6.4 Hz 3H), 0.57 (s, 3H).

Synthetic Example 15.1

Synthesis of ((5R,6S)-5-((1S,3aS,4S,5S,7aR)-4-(aminomethyl)-1,7a-dimethyloctahydro-1H-inden-5-yl)-5-methyl-2-(4-(pyridin-2-yloxy)phenyl)-4,5,6,7-tetrahydro-2H-indazol-6-yl)methanol (Compound Ia-56) and ((5R,6S)-5-((1S,3aS,4S,5S,7aR)-4-(aminomethyl)-1,7a-dimethyloctahydro-1H-inden-5-yl)-5-methyl-1-(4-(pyridin-2-yloxy)phenyl)-4,5,6,7-tetrahydro-1H-indazol-6-yl)methanol (Compound Ia-57)

Following the procedure as described in Synthetic Example 15 and making non-critical variations using 2-(4-hydrazineylphenoxy)pyridine hydrochloride (as prepared in PCT Published Patent Application No. WO 2009/117421) in place of (4-(4-fluorophenoxy)phenyl)hydrazine hydrochloride in Step E, the title compounds ((5R,6S)-5-((1S,3aS,4S,5S,7aR)-4-(aminomethyl)-1,7a-dimethyloctahydro-1H-inden-5-yl)-5-methyl-2-(4-(pyridin-2-yloxy)phenyl)-4,5,6,7-tetrahydro-2H-indazol-6-yl)methanol (Compound Ia-56) and ((5R,6S)-5-((1S,3aS,4S,5S,7aR)-4-(aminomethyl)-1,7a-dimethyloctahydro-1H-inden-5-yl)-2-(4-methoxybenzyl)-5-methyl-4,5,6,7-tetrahydro-2H-indazol-6-yl)methanol (Compound Ia-57) were obtained.

Compound Ia-57: LCMS: (Method 1c) MS m/z: 515 (M+1), $t_R$: 1.80 min, Purity: 98.1% (UV).

HPLC: (Method 2a) $t_R$: 3.90 min, Purity: 93.7% (UV).

$^1$H-NMR (400 MHz, CD$_3$OD): δ 8.14 (d, J=3.6 Hz, 1H), 7.87-7.28 (m, 1H), 7.57-7.55 (m, 2H), 7.46 (s, 1H), 7.25-7.22 (m, 2H), 7.14 (t, J=6.0 Hz, 1H), 7.01 (d, J=8.4 Hz, 1H), 3.92 (d, J=10.0 Hz, 1H), 3.39 (t, J=10.0 Hz, 1H), 3.29-3.09 (m, 1H), 2.93-2.89 (m, 1H), 2.74-2.62 (m, 2H), 2.43 (d, J=16.0 Hz, 1H), 2.11 (s, 1H), 1.88-1.71 (m, 4H), 1.66-1.48 (m, 3H), 1.39-1.27 (m, 4H), 1.10-1.03 (m, 4H), 0.89-0.86 (m, 4H), 0.66 (s, 3H).

Synthetic Example 15.2

Synthesis of ((5R,6S)-5-((1S,3aS,4S,5S,7aR)-4-(aminomethyl)-1,7a-dimethyloctahydro-1H-inden-5-yl)-5-methyl-2-(4-(pyridin-4-yloxy)phenyl)-4,5,6,7-tetrahydro-2H-indazol-6-yl)methanol (Compound Ia-58), and ((5R,6S)-5-((1S,3aS,4S,5S,7aR)-4-(aminomethyl)-1,7a-dimethyloctahydro-1H-inden-5-yl)-5-methyl-1-(4-(pyridin-4-yloxy)phenyl)-4,5,6,7-tetrahydro-1H-indazol-6-yl)methanol (Compound Ia-59)

Following the procedure as described in Synthetic Example 15 and making non-critical variations using 4-(4-hydrazineylphenoxy)pyridine hydrochloride (as prepared in U.S. Published Patent Application No. 2009/0253688) in place of (4-(4-fluorophenoxy)phenyl)hydrazine hydrochloride in Step E, the title compounds ((5R,6S)-5-((1S,3aS,4S,5S,7aR)-4-(aminomethyl)-1,7a-dimethyloctahydro-1H-inden-5-yl)-5-methyl-2-(4-(pyridin-4-yloxy)phenyl)-4,5,6,7-tetrahydro-2H-indazol-6-yl)methanol (Compound Ia-58), and ((5R,6S)-5-((1S,3aS,4S,5S,7aR)-4-(aminomethyl)-1,7a-dimethyloctahydro-1H-inden-5-yl)-5-methyl-1-(4-(pyridin-4-yloxy)phenyl)-4,5,6,7-tetrahydro-1H-indazol-6-yl)methanol (Compound Ia-59) were obtained.

Compound Ia-58: LCMS: (Method 1c) MS m/z: 515 (M+1), $t_R$: 1.59 min, Purity: 98.2% (UV).

HPLC: (Method 2a) $t_R$: 3.17 min, Purity: 98.2% (UV).

$^1$H-NMR (400 MHz, DMSO-d6): δ 8.50 (d, J=6.0 Hz, 2H), 7.71 (d, J=8.8 Hz, 2H), 7.48 (s, 1H), 7.33 (d, J=8.8 Hz, 2H), 7.00 (d, J=6.0 Hz, 2H), 4.53 (s, 1H), 3.74 (d, J=9.9 Hz, 1H), 3.21-3.09 (m, 4H), 2.76-2.60 (m, 4H), 2.34-2.29 (m, 1H), 2.05-1.99 (m, 1H), 1.77-1.61 (m, 6H), 1.41-1.36 (m, 3H), 1.24-1.13 (m, 2H), 1.04 (s, 3H), 1.01-0.87 (m, 1H), 0.87 (d, J=5.6 Hz, 3H), 0.57 (s, 3H).

Compound Ia-59: LCMS: (Method 1c) MS m/z: 515 (M+1), $t_R$: 1.58 min, Purity: 98.5% (UV).

HPLC: (Method 2a) $t_R$: 3.15 min, Purity: 97.5% (UV).

$^1$H-NMR (400 MHz, DMSO-d6): δ 8.48 (dd, J=1.4, 4.8 Hz, 2H), 8.15 (s, 1H), 7.85 (d, J=8.9 Hz, 2H), 7.28 (d, J=8.9 Hz, 2H), 6.95 (dd, J=1.4, 4.8 Hz, 2H), 4.52 (s, 1H), 3.76 (d, J=9.7 Hz, 1H), 3.24-3.11 (m, 3H), 3.10-3.06 (m, 1H), 2.83-2.80 (m, 1H), 2.68-2.56 (m, 2H), 2.38-2.34 (m, 1H), 2.09-1.97 (m, 1H), 1.78-1.63 (m, 6H), 1.49-1.13 (m, 6H), 1.00 (s, 3H), 0.94-0.90 (m, 1H), 0.83 (d, J=6.6 Hz, 3H), 0.58 (s, 3H).

Synthetic Example 15.3

Synthesis of ((5R,6S)-5-((1S,3aS,4S,5S,7aR)-4-(aminomethyl)-1,7a-dimethyloctahydro-1H-inden-5-yl)-5-methyl-1-(4-(pyrimidin-5-yloxy)phenyl)-4,5,6,7-tetrahydro-1H-indazol-6-yl)methanol (Compound Ia-60), and ((5R,6S)-5-((1S,3aS,4S,5S,7aR)-4-(aminomethyl)-1,7a-dimethyloctahydro-1H-inden-5-yl)-5-methyl-2-(4-(pyrimidin-5-yloxy)phenyl)-4,5,6,7-tetrahydro-2H-indazol-6-yl)methanol (Compound Ia-61)

Following a portion of the procedure as described in Synthetic Example 15 and making non-critical variations 5-(4-hydrazineylphenoxy)pyrimidine hydrochloride (prepared from known methods as in U.S. Published Patent Application No. 2009/0253688 or PCT Published Patent Application No. WO 2009/117421) in place of hydrazine hydrate in Step E, the respective title compounds, ((5R,6S)-5-((1S,3aS,4S,5S,7aR)-4-(aminomethyl)-1,7a-dimethyloctahydro-1H-inden-5-yl)-5-methyl-1-(4-(pyrimidin-5-yloxy)phenyl)-4,5,6,7-tetrahydro-1H-indazol-6-yl)methanol (Compound Ia-60) and ((5R,6S)-5-((1S,3aS,4S,5S,7aR)-4-(aminomethyl)-1,7a-dimethyloctahydro-1H-inden-5-yl)-5-methyl-2-(4-(pyrimidin-5-yloxy)phenyl)-4,5,6,7-tetrahydro-2H-indazol-6-yl)methanol (Compound Ia-61), were obtained.

Compound Ia-60: LCMS: (Method 1c) MS m/z: 516 (M+1), $t_R$: 1.78 min, Purity: 99.2% (UV).

HPLC: (Method 2a) $t_R$: 3.67 min, Purity: 95.1% (UV)

$^1$H-NMR (400 MHz, DMSO-d6): δ 9.04 (s, 1H), 8.71 (s, 2H), 7.66 (d, J=8.8 Hz, 2H), 7.46 (s, 1H), 7.30 (d, J=8.8 Hz, 2H), 4.50 (s, 1H), 3.73 (d, J=9.2 Hz, 1H), 3.22-3.17 (m, 1H), 3.09-3.06 (m, 2H), 2.69-2.59 (m, 4H), 2.33-2.26 (m, 1H), 2.05-1.91 (m, 1H), 1.77-1.51 (m, 7H), 1.42-1.39 (m, 3H), 1.19-1.15 (m, 2H), 1.04 (s, 3H), 0.92-0.86 (m, 3H), 0.82 (d, J=6.8 Hz, 3H), 0.56 (s, 3H).

Compound Ia-61: LCMS: (Method 1c) MS m/z: 516 (M+1), $t_R$: 1.84 min, Purity: 99.8% (UV).

HPLC: (Method 2a) $t_R$: 3.74 min, Purity: 92.6% (UV).

$^1$H-NMR (400 MHz, DMSO-d6): δ 9.02 (s, 1H), 8.65 (s, 2H), 8.13 (s, 1H), 7.81 (d, J=8.5 Hz, 2H), 7.27 (d, J=8.5 Hz, 2H), 4.52 (s, 1H), 3.77-3.75 (m, 1H), 3.24-3.17 (m, 2H), 3.10-3.04 (m, 1H), 2.83-2.80 (m, 1H), 2.68-2.60 (m, 2H), 2.51-2.33 (m, 2H), 2.11-2.03 (m, 1H), 1.78-1.63 (m, 6H), 1.49-1.17 (m, 6H), 1.00 (s, 3H), 0.98-0.84 (m, 1H), 0.83 (d, J=6.5 Hz, 3H), 0.57 (s, 3H).

Biological Example 1

Rat Dorsal Root Ganglion Excitability Response of Representative Compounds

Dorsal root ganglions (DRGs) were dissected from adult rats. The tissue was processed, and cells were seeded into cell culture plates (48 center wells of one quadrant in 384-well plates) and cultured for 2 days prior to Electrical field stimulation (EFS). To visualize the neuronal excitability response, intracellular $Ca^{+2}$ transients were monitored using the $Ca^{+2}$ indicator, Ca5. Ca5 was added to the cultures 1 h prior to EFS. Representative compounds of the invention (i.e., test compounds) and reference compound, tetracaine, were added in concentration-response format encompassing six concentrations, performed in duplicate. The highest concentration tested was typically 30 μM with 1 in 3 dilutions generating the subsequent concentrations.'

Effects on DRG excitability by the test compounds and standard were evaluated using four EFS protocols as disclosed in Table 2.

TABLE 2

EFS PROTOCOL PARAMETERS

| Protocol # | Voltage (V) | Frequency (Hz) | Pulse duration (ms) | # of pulses |
|---|---|---|---|---|
| 1 | 20 | 5 | 0.3 | 25 |
| 2 | 20 | 30 | 0.3 | 150 |
| 3 | 30 | 5 | 0.3 | 25 |
| 4 | 30 | 30 | 0.3 | 150 |

Experimental results were performed using two seperate sets of plates using separate test compound and standard dilutions, to provide n=2. In the first set of experiments, compounds were added 24 h prior to EFS to increase the possibility to also detect more long-term compound effects. In the second set of experiments the compounds were added directly prior to EFS. Excitability response to EFS was analyzed as the average fluorescence ratio (peak/baseline) change per well. All plates were evaluated using high content imaging equipment post-EFS, imaging the Ca5 background staining to detect any possible compound-related toxic effects.

According to the above assay, the representative compounds listed in Table 3 below were found to modulate rat DRG excitability at the concentrations indicated. Average response by the reference compound, tetracaine, was 4.05 μM. Scoring for the representative compounds was as follows: "A" represents an $EC_{50}$ below 2 μM, "B" represents an $EC_{50}$ between 2 and 6 μM, "C" represents an $EC_{50}$ between 6 and 15 μM and "D" represents an $EC_{50}$ above 15 μM.

TABLE 3

| Cpd. No. | Scoring |
|---|---|
| Ia-24 | A |
| Ia-22 | A |
| Ia-12 | A |
| Ia-20 | A |
| Ia-40 | B |
| Ia-34 | B |
| Ia-23 | B |
| Ia-30 | B |
| Ia-32 | B |
| Ia-25 | B |
| Ia-13 | B |
| Ia-38 | B |
| Ia-14 | B |
| Ia-6 | B |
| Ia-26 | C |
| Ia-15 | C |
| Ia-27 | C |
| Ia-2 | C |
| Ia-17 | B |
| Ia-18 | A |
| Ia-52 | A |
| Ia-28 | A |
| Ia-29 | A |
| Ia-49 | B |
| Ia-36 | D |
| Ia-47 | A |

Biological Example 2

T Cell Proliferation and Cytokine Release Activity of Representative Compounds Spleens were obtained from six male, CD-1 outbred mice, approximately 8 weeks old. Cells were harvested under sterile conditions by forcing each spleen though a cell filter (pore size 100 μm diameter). A homogenous cell suspension was obtained by washing the cells in fresh medium and passing cells through a smaller cell filter (pore size 70 μm).

Untouched T cells were isolated using the Pan T cell isolation kit (Miltenyi Biotech). Briefly, cells were counted and incubated with the required volume of antibody cocktail for 5 minutes at 4° C. before addition of microbeads and incubation for 10 minutes at 4° C. Labeled cells were retained in a magnetic column while unlabeled cells (T cells) passed through the column and were retained for use in the assay.

Cell viability was assessed by Trypan Blue exclusion and found to be >99% prior to transfer to plates. Isolated T cells were seeded out in 96 well plates at a density of 50,000 cells per well and allowed to incubate for 60 minutes in a humidified cell culture (37° C., 5% $CO_2$) incubator prior to compound treatment. The media used for this assay (TexMACS, Miltenyi Biotech) was previously optimized for proliferation of T cells in serum free conditions.

Representative compounds of the invention (i.e., test compounds) were prepared as 30 mM stocks in 100% DMSO. Test compounds were initially diluted in media to yield 3 mM stocks before an additional 1:10 dilution in media was performed to yield working stocks of 300 μM (1% DMSO). Subsequent dilutions were performed in media (supplemented with 1% DMSO). When added to the assay plates (1:10 dilution), these yielded final concentrations in the assay plates of in 0.1% DMSO. The reference compound, Cyclosporin A, was prepared in an identical manner as above.

Unstimulated and Stimulated Control wells received an identical volume of TexMACS media/1% DMSO at this time, resulting in a final concentration of 0.1% DMSO across the plate. Mouse anti-CD3/anti-CD28 dynabeads were prepared (following the manufacturers' instructions) in TexMACS media and added to appropriate wells to achieve a final concentration of 1 bead per cell. Unstimulated Control wells then received an identical volume of TexMACS. Plates were centrifuged 72 hours after addition of dynabeads, (300×g for 3 minutes) to pellet the cells and 60% of the supernatant was removed to a fresh plate for analysis by ELISA. After removal of 60% of the supernatant for subsequent ELISA, cell proliferation was assessed using the CCK-8 assay.

According to the above assay, the representative compounds of the invention listed in Table 4 below were found to modulate cell proliferation at the concentrations indicated. Average response by the standard compound, cyclosporin A, was 1 µM. Scoring for the representative compounds was as follows: "A" represents an $IC_{50}$ below 0.5 µM, "B" represents an $IC_{50}$ between 0.5 and 1.5 µM, "C" represents an $IC_{50}$ between 1.5 and 15 µM and "D" represents an $IC_{50}$ above 15 µM.

TABLE 4

| Cpd. No. | Scoring |
| --- | --- |
| Ia-1 | C |
| Ia-2 | C |
| Ia-9 | C |

Biological Example 3

Human Dorsal Root Ganglion (DRG) Excitability Response of Representative Compounds Human DRGs are transferred into a dissection vessel containing a cold (4° C.), fresh proprietary dissection solution. DRGs are maintained completely submerged in dissection solution followed by dissection by an appropriate method.

Cells are plated into a 96 well plate. Calcium dye (Fluo 8-AM) is loaded in each well for a period of 20 to 25 min, maintaining temperature at ambient. The baseline excitability profile (ability of firing action potentials) of the cells is assessed at both low and high threshold stimulations using optical EFS. Following baseline profiling, cells are subjected to test compounds.

Representative compounds of the invention (i.e., test compounds) are added to cells and the cells are stimulated (using EFS) to induce action potentials at regular intervals, according to the parameters outlined in TABLE 5. Four concentrations of each compound are utilized and directly injected into separate wells to allow for determination of a dose response ($IC_{50}$). At the end of the protocol, the nociceptor positive control compound (capsaicin) is perfused into the cells at 200 nM and signal recorded. TTX (300 nM) is also examined using this protocol in a separate well.

TABLE 5

| EFS PROTOCOL AND RECORDING SEQUENCE | |
| --- | --- |
| Action | Parameter/Detail |
| Baseline Low Voltage | 2 s recording with stimulation (5 Hz) |
| Rest | 3 min |
| Baseline High Voltage | 2 s recording with stimulation (5 Hz) |
| Preincubation of Test compounds | 5 min |
| Test Compound Low Votage Signal | 2 s recording with stimulation (5 Hz) |
| Rest | 3 min |
| Test Compound High Votage Signal | 2 s recording with stimulation (5 Hz) |
| Washout | 5 min |
| Capsaicin | 20s (recording 3 min) |

Recordings are performed in stream mode at 100 Hz for the EFS portion of the above protocol and in time lapse model at 0.2 Hz for the final step utilizing capsaicin. For each concentration tested, the number of cells blocked vs baseline will be counted at different thresholds.

Compounds of the invention may be tested in this assay to determine their ability to modulate human DRG excitability.

Biological Example 4

Pulmonary LPS Challenge Assay of Representative Compounds in Mice

Mice (male, C57Bl/16) are acclimatized for a period of about 7 days before initiation of the experiment and are randomized on the day prior to treatment. Mice receive vehicle or a representative compound of the invention (i.e., test compound) once daily for three days by oral gavage on Day −2, Day −1 and on Day 0 (the last dose being 1 h prior to LPS administration). One group of mice receive the reference standard, dexamethasone, once, IP on Day 0 at 1 h prior to LPS administration. Pulmonary inflammation is induced in all animals except the sham control animals by intratracheal instillation of 20 µg LPS per animal in 50 µl saline. Sham control animals receive 50 µl saline alone.

Twenty-four hours post LPS administration, animals are euthanized and the trachea is cannulated. Cold Hanks Balanced Salt Solution (SIGMA; Catalogue number: H1387), pH 7.2, is infused into the lungs and bronchoalveolar lavage fluid (BALF) is collected.

Total leukocyte counts are performed from the collected BALF using a mini flow-cytometer and differential counts are performed in cytospin smears stained with Leishman's staining manually. ELISA kits are used for quantification of cytokines in the BALF (TNFα, IL-1β, IL-6 and KC). Reagents, samples and standards are prepared as per kit manual. Total protein analysis in BALF samples is performed using the Biorad protein assay reagent.

Compounds of the invention may be tested in this assay to determine their ability to modulate inflammatory markers in BALF, indicating their efficacy against LPS-induced inflammation.

Biological Example 5

Formalin Pain Assay of Representative Compounds in Mice

Mice (male, C57BL/6) were placed singly in a Perspex chamber for approximately 30 min on three successive days to acclimate and thereby reduce stress-induced behaviors. On the fourth day, the experimental animals received a 25 µl injection of 2.5% formalin beneath the left plantar skin using a 29-gauge syringe. Animals were administered vehicle, reference standard Tramadol or a representative compound of the invention (i.e., test compound) prior to formalin injection. The total time spent on flinches/licking/biting of the hind paw was recorded by visual observation for every 5 min period/interval for total observation duration of 60 min in two phases, the early phase (0-5 min) and the late phase (15-40 min). Observers were blinded to the treatment group allocation.

According to the above assay, the test compounds listed in Table 6 below were active in the formalin pain assay in mice at the concentrations indicated. Average AUC % Inhibition by the standard compound, tramadol was 59%. For test compounds, % protection from 0-60 min was used to assess activity. Scoring for the test compounds was as follows: "A" represents a % protection of 81 to 100%, "B" represents a % protection of 61 to 80%, "C" represents a % protection of 31 to 60% and "D" represents a % protection of 0 to 30%.

TABLE 6

| Cpd. No. | Scoring |
|---|---|
| Ia-10a and Ia-10b | C |
| Ia-2 | D |

Biological Example 6

TNBS Colitis Assay of Representative Compounds in Rats

Rats (male, Sprague-Dawley) are anaesthetized and a solution of TNBS (48 mg/kg) in ethanol, is instilled intra-rectally to induce colitis, 1 h after oral dosing of representative compounds of the invention (i.e., test compounds). Test compounds are dosed PO (by mouth, per os), QD (once of day, quaque die) for 7 days, using prednisolone as a reference standard. Rats are observed for body weight loss and fecal output. On Day 7, rats are euthanized and the colon are evaluated for length, weight, wall thickness, ulcer number and length and for the presence of adhesions and strictures. A colonic score is calculated based on the severity of the colonic parameters.

Compounds of the invention may be tested in this assay to determine their ability to modulate colonic parameters, indicating their efficacy against colitis.

Biological Example 7

Cyclophosphamide-Induced Cystitis in Rats (Visceral Pain)

Representative compounds of the invention (i.e., test compounds) are administered to female Sprague-Dawley rats, for four days by oral gavage in 0.9% saline. Two hours after the fourth dose, the rats are challenged by intraperitoneal administration of cyclophosphamide (150 mg/kg). Referred mechanical sensitivity is measured four hours later by applying a series of eight von Frey filaments to the lower abdomen, three times each for 1-2 seconds with a 5 second interval between applications. Responses are scored (zero-no response; one-response, two-response and change of position, and three-response, change of position and licking the site or vocalization), totaled and the percent of maximal possible nociceptive score calculated. Ibuprofen is used as a reference standard.

Compounds of the invention may be tested in this assay to determine their ability to modulate nociceptive pain, indicating efficacy against cystitis.

Biological Example 8

Rat Ketamine Cystitis (Visceral Pain)

Rats (female, Sprague-Dawley) receive daily intraperitoneal injections of saline (sham control) or ketamine (50 mg/kg) for 14 days. Representative compounds of the invention (i.e., test compounds) are administered PO, QD starting on Day 0 at doses of 10, 3 or 1 mg/kg and Tramadol is used as a reference control compound at 10 mg/kg. Referred mechanical sensitivity is assessed on Day 7 and day 14 by application of a series of von Frey filaments to the lower abdomen and the nociceptive threshold was scored.

Compounds of the invention may be tested in this assay to determine their ability to modulate nociceptive pain and/or inflammation, indicating efficacy against cystitis.

Biological Example 9

Rat Chronic Prostatitis/Chronic Pelvic Pain (Pelvic Pain)

Representative compounds of the invention (i.e., test compounds) are administered for 11 days by oral gavage in 0.9% saline (3, 10 or 30 mg/kg QD; 5 mL/kg dose volume) to male Sprague-Dawley rats. Carrageenan-mediated chronic prostatitis/chronic pelvic pain (CP/CPPS) is established in rats (10 per group) by administration of an intraprostatic injection of carrageenan (~12.5 μL/lobe of a 30 mg/mL solution) into both ventral prostate lobes, on Day 0. Referred mechanical sensitivity is measured on Days 0, 1, 3 and 7, 2 hours after test compound or vehicle (saline) administration, by applying 6 von Frey filaments with increasing forces of 0.16-2 g to the scrotal skin area, 3 times each for 1-2 seconds, with a 5-second interval between applications. Responses are scored (zero-no response; one-reaction of the animal, two-jump, and three-licking the site) and expressed as the nociceptive threshold for each day of assessment. Ibuprofen is used as a reference standard.

Compounds of the invention may be tested in this assay to determine their ability to modulate nociceptive pain, indicating efficacy against chronic prostatitis/chronic pelvic pain.

Biological Example 10

Rat Monosodium Iodoacetate-Induced Osteoarthritis (Osteoarthritis/Inflammatory Pain)

Representative compounds of the invention (i.e., test compounds) are administered to rats (male, Wistar) PO, QD, at 3 or 30 mg/kg, starting on Day 0 through to Day 21 of the study. Osteoarthritis is modeled by intra-articular injection of 3 mg of monosodium iodoacetate (MIA) in the right knee. Knee swelling, paw withdrawal threshold (mechanical allodynia) and the difference in weight bearing are measured on Day 0 (pre-induction) and on Days 3, 7, 14 and 21 post-MIA injection. Tramadol is used as a reference standard.

Compounds of the invention may be tested in this assay to determine their ability to modulate knee swelling, paw withdrawal threshold and difference in weight bearing, indicating efficacy against osteoarthritis.

Biological Example 11

Complete Freund's Adjuvant (CFA) Model of Inflammatory Pain in Rats (Inflammatory Pain)

Representative compounds of the invention (i.e., test compounds) are tested in this model of inflammatory pain. The rats (male, Wistar) are acclimatized to the instruments (plantar test surface and dynamic plantar aesthesiometer) on two consecutive days prior to the initiation of the study. On Day 0, basal paw withdrawal latency and paw withdrawal threshold are taken and animals are randomized to different groups. Complete Freund's Adjuvant (CFA) at 1 mg/mL (0.1 mL) was injected into the plantar surface of right hind paw. Test compounds (3 or 30 mg/kg) are administered PO, twice (Day 0 and Day 1) or once, on Day 1 (24 h after CFA). Thermal hyperalgesia and mechanical allodynia are assessed at 0 (baseline), 1, 3 and 6 h after administration of the test compound on Day 1. Diclofenac is used as a reference compound, given once on Day 1.

Compounds of the invention may be tested in this assay to determine their ability to modulate inflammatory pain.

Biological Example 12

Rat Carrageenan-Induced Hyperalgesia and Paw Edema (Inflammatory Pain)

Representative compounds of the invention (i.e., test compounds) are administered PO, QD, for 3 days prior to carrageenan injection, once at 1 h prior to carrageen, or at 5 min or 1 h post-challenge to Rats (male, Sprague-Dawley). Rats receive either an intraplantar injection of saline (sham) or carrageen (0.1 mL of a 2% solution [w/v]) in the right hind paw. Mechanical hyperalgesia (using an analgesymeter) and paw volume (using a digital plethysmometer) are measured at baseline (0 hr), 2, 4 and 6 h post carrageenan injection for all the animals. Celecoxib, given 1 h prior to carrageen challenge, is used as a reference standard.

Compounds of the invention may be tested in this assay to determine their ability to modulate mechanical hyperalgesia and paw volume, indicating their efficacy against hyperalgesia.

Biological Example 13

Spinal Nerve Ligation (Neuropathic Pain)

Rats (male, Sprague-Dawley) are anaesthetized and placed in a prone position and the left paraspinal muscles are separated from the spinous processes at the L6-S2 levels. The L6 transverse process is carefully removed to visually identify the L4-L6 spinal nerves. The left L5 spinal nerves are isolated and tightly ligated with 6-0 silk thread. The skin is sutured to close the open tissue and animals are allowed to recover for 1 week before pain assessment. Basal readings for mechanical allodynia and thermal hyperalgesia are performed using a dynamic plantar aesthesiometer and plantar test surface, respectively, before surgery. On Day 7 following surgery, mechanical allodynia and thermal hyperalgesia are assessed and animals are randomized into treatment groups based on these baseline readings. From Day 7 to Day 14, the rats either receive vehicle, tramadol (reference standard) or representative compounds of the invention (i.e., test compounds). Thermal hyperalgesia and mechanical allodynia are tested at 0, 60 and 120 minutes post administration of compounds on Days 7 and 14.

Compounds of the invention may be tested in this assay to determine their ability to modulate neuropathic pain.

Biological Example 14

Bleomycin Lung Fibrosis

Mice (male, C57BL/6) are randomized into treatment groups and fibrosis is induced by intratracheal administration of bleomycin. Treatment with representative compounds of the invention (i.e., test compounds) or reference standard (pirfenidone) is initiated on Day −1 and administered daily unto Day 7 or Day 21. For groups undergoing bronchoalveolar lavage (BAL), the trachea is cannulated and infused with ice cold Hank's Balanced Salt Solution (HBSS, pH 7.2). The collected lavage fluid is analyzed for cell numbers (total and differential counts) and levels of soluble TGFβ and collagen. For other groups, the lungs are either snap-frozen or formalin-fixed for further analyses.

Compounds of the invention may be tested in this assay to determine their ability to modulate pulmonary inflammation and fibrosis.

Biological Example 15

Metabolism by Human Liver Microsomes

Representative compounds of the invention (i.e., test compounds) and the positive control, 7-ethoxycoumarin, were prepared as stock solutions at 10 mM in DMSO and eventually diluted to 10 μM in the test plate, with an appropriate amount of acetonitrile and tris HCl buffer. Final DMSO and acetonitrile concentrations were 0.01% and 0.5% respectively. NADPH was prepared in tris HCl buffer to a stock of 10 mM. A frozen aliquot of liver microsomes was retrieved from the freezer (−80° C.) and thawed by placing the tube on wet ice. After thawing, the tubes were gently mixed and the required amount, transferred to tris HCl buffer. Test compounds or positive control were pre-incubated, separately, for 10 minutes, with liver microsomes (1 mg/mL protein), at 37° C., in 100 mM Tris HCl at pH 7.5. After preincubation the reaction was started by adding 1 mM NADPH (pre-equilibrated to 30° C.) and the reaction allowed to proceed for 60 minutes. At 60 minutes, a 50 μL aliquot was removed and quenched with 200 uL of acetonitrile containing a mixture of internal standards (Tolbutamide (500 ng/mL) and Telmistartan (500 ng/mL)) and vortexed then centrifuged at 4000 rpm for 10 minutes (Eppendorf 5810R). The supernatant was transferred to a 96 well plate for LC-MS/MS analysis.

An LC-MS/MS method was devised for the test compounds and the control, using a AB Sciex API 4000 system coupled to a NEXAR™ UHPLC (Shimadzu) system. Analytes were separated on a Phenomenex Kinetex C18 column (50×2.1 mm, 5 μm) using a gradient that was appropriate for each compound, at a flow rate of 1 ml/minute, utilizing a mobile phase of 0.1% formic acid in MILLI-Q™ water (A) and 0.1% formic acid in acetonitrile (B). The MS instrument was operated in positive mode (ESI+)/negative (ESI−). The multiple reaction monitoring (MRM) transition for test and control compounds was used for the LC-MS/MS analysis. MRM transitions for control compound 7-ethoxycoumarinm were Quadropole 1: 191.0, Quadropole 3:163.0, dwell time: 75 msec, using curtain gas settings of 5 V, ion-spray voltage of 5500 V, temperature of 50° C. and gas settings for nebulizer and auxiliary set to 30 and 40 psi, respectively. The interface heater was kept on. Entrance potential and collision cell exit potential were varied to tune for a specific compound.

Using a suitable LC-MS/MS method, the percentage of drug remaining at 60 minutes (PCR60) was assessed by comparing the average analyte to internal standard area ratio at 60 minutes to the average analyte to internal standard area ratio at 0 time control, as a percentage, from a 5 to 10 μL sample injection.

According to the above assay, the test compounds listed in Table 7 below were active in the Human liver microsome assay at 10 μM and the % of drug remaining after 60 minutes (PDR60), in the presence of NADPH, was assessed by LC-MS/MS. Average PDR60 for the standard compound, 7-ethoxycoumarin was <=65% in the presence of NADPH. Scoring for the test compounds, in the presence of NADPH, was as follows: "A" represents a PDR60 of 81 to 100%, "B" represents a PDR60 of 61 to 80%, "C" represents a PDR60 of 31 to 60% and "D" represents a PDR60 of 0 to 30%.

TABLE 7

| Cpd. No. | Scoring |
|---|---|
| Ia-2 | A |
| Ia-6 | A |
| Ia-7 | B |
| Ia-10a and Ia-10b | C |
| Ia-12 | D |
| Ia-13 | A |
| Ia-14 | D |
| Ia-15 | B |
| Ia-17 | C |
| Ia-19 | B |
| Ia-20 | B |
| Ia-22 | D |
| Ia-23 | C |
| Ia-24 | B |
| Ia-25 | B |
| Ia-26 | D |
| Ia-27 | C |
| Ia-28 | B |
| Ia-29 | C |
| Ia-30 | D |
| Ia-32 | D |
| Ia-34 | D |
| Ia-36 | A |
| Ia-39 | A |
| Ia-40 | D |
| Ia-49 | D |
| Ia-52 | A |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

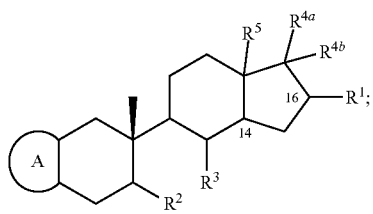

wherein:

is an optionally substituted fused 5- or 6-membered N-heteroaryl;

$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
or $R^{4a}$ is an optionally substituted aryl and $R^4$ is a bond to C16;
or $R^{4a}$ and $R^{4b}$ together form alkylidene, provided that

is a fused 5- or 6-membered N-heteroaryl substituted by substituted aryl, substituted aralkyl, substituted cycloalkyl or substituted heteroaryl;
or $R^{4a}$ is alkyl and $R^{4b}$ is hydrogen, provided that

is a fused 5- or 6-membered N-heteroaryl substituted by substituted aryl, substituted aralkyl, substituted cycloalkyl or substituted heteroaryl;
or $R^{4a}$ and $R^1$ together form an optionally substituted bicyclic heterocyclyl and $R^{4b}$ is hydrogen;
or $R^{4a}$, $R^{4b}$ and $R^1$ together form a fused optionally substituted heteroaryl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl; and
$R^9$ is a direct bond or a straight or branched alkylene chain;
or a stereoisomer, enantiomer or tautomer thereof or mixtures thereof, or a pharmaceutically acceptable salt or solvate thereof.

2. The compound of claim 1 wherein:

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl; and
$R^9$ is a direct bond or a straight or branched alkylene chain.

3. The compound of claim 2 wherein:

$\overset{A}{\bigcirc}$ is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is a direct bond.

4. The compound of claim 3 wherein:

$\overset{A}{\bigcirc}$ is a fused 5-membered N-heteroaryl optionally substituted by one or more substitutents selected from alkyl, haloalkyl, —$C(O)OR^7$, —$N(R^8)_2$, —$C(O)N(R^8)_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is a direct bond.

5. The compound of claim 4 selected from:
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol;
(1R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-ol;
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-1,7a-dimethyloctahydro-1H-inden-1-ol;
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol;
(1S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol;
(1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(thiazol-2-yl)octahydro-1H-inden-1-ol; and
(1S,3aS,4R,5S,7aS)-4-(aminomethyl)-5-((5R,6S)-6-(hydroxymethyl)-5-methyl-4,5,6,7-tetrahydro-1H-indazol-5-yl)-7a-methyl-1-(pyridin-2-yl)octahydro-1H-inden-1-ol.

6. The compound of claim 2 wherein:

$\overset{A}{\bigcirc}$ is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is straight or branched alkylene chain.

7. The compound of claim 6 wherein:

$\overset{A}{\bigcirc}$ is a fused 5-membered N-heteroaryl optionally substituted by one or more substitutents selected from alkyl, haloalkyl, —$C(O)OR^7$, —$N(R^8)_2$, —$C(O)N(R^8)_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ is —$R^9$—$OR^7$ and $R^{4b}$ is hydrogen, alkyl or optionally substituted heteroaryl;
$R^5$ is alkyl;
each $R^6$ is a straight or branched alkylene chain;
each $R^7$ is independently selected from hydrogen or alkyl;
each $R^8$ is independently selected from hydrogen or alkyl; and
$R^9$ is a straight or branched alkylene chain.

8. The compound of claim 7 selected from:
(2S,5R)-5-ethyl-2-((1R,3aS,4S,5S,7aS)-4-(hydroxymethyl)-5-((5R,6S)-6-(hydroxymethyl)-5-methyl-4,5,6,7-tetrahydro-1H-indazol-5-yl)-7a-methyloctahydro-1H-inden-1-yl)-6-methylheptan-3-ol.

9. The compound of claim 1 wherein:

$\overset{A}{\bigcirc}$ is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ and $R^1$ together form an optionally substituted bicyclic heterocyclyl and $R^{4b}$ is hydrogen;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen or alkyl.

10. The compound of claim 9 wherein:

(A)

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ and $R^1$ together form an optionally substituted bicyclic heterocyclyl and $R^{4b}$ is hydrogen;
$R^5$ is alkyl;
each $R^6$ is a straight or branched alkylene chain;
each $R^7$ is independently selected from hydrogen or alkyl; and
each $R^8$ is independently selected from hydrogen or alkyl.

11. The compound of claim 10 wherein:

(A)

is a fused 5-membered N-heteroaryl optionally substituted by one or more substitutents selected from alkyl, haloalkyl, —C(O)$OR^7$, —$N(R^8)_2$, —C(O)$N(R^8)_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
$R^{4a}$ and $R^1$ together form an optionally substituted bicyclic heterocyclyl and $R^{4b}$ is hydrogen;
$R^5$ is alkyl;
each $R^6$ is a straight or branched alkylene chain;
each $R^7$ is independently selected from hydrogen or alkyl; and
each $R^8$ is independently selected from hydrogen or alkyl.

12. The compound of claim 11 selected from:
((5R,6S)-5-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol; and
((5R,6S)-5-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-5-methyl-4,5,6,7-tetrahydro-1H-indazol-6-yl)methanol.

13. The compound of claim 1 wherein:

(A)

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
or $R^{4a}$, $R^{4b}$ and $R^1$ together form a fused optionally substituted heteroaryl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen or alkyl.

14. The compound of claim 13 wherein:

(A)

is an optionally substituted fused 5- or 6-membered N-heteroaryl;
$R^1$ is hydrogen;
$R^2$ is —$R^6$—$OR^7$;
$R^3$ is —$R^6$—$OR^7$ or —$R^6$—$N(R^8)_2$;
or $R^{4a}$, $R^{4b}$ and $R^1$ together form a fused optionally substituted heteroaryl;
$R^5$ is alkyl;
each $R^6$ is a straight or branched alkylene chain;
each $R^7$ is independently selected from hydrogen or alkyl; and
each $R^8$ is independently selected from hydrogen or alkyl.

15. The compound of claim 14 wherein:

(A)

is a fused 5-membered N-heteroaryl optionally substituted by one or more substitutents selected from alkyl, haloalkyl, —C(O)$OR^7$, —$N(R^8)_2$, —C(O)$N(R^8)_2$ or optionally substituted aryl;
$R^1$ is hydrogen;
$R^2$ is —$R^6$—$OR^7$;
$R^3$ is —$R^6$—$OR^7$ or —$R^6$—$N(R^8)_2$;
or $R^{4a}$, $R^{4b}$ and $R^1$ together form a fused optionally substituted heteroaryl;
$R^5$ is alkyl;
each $R^6$ is a straight or branched alkylene chain;
each $R^7$ is independently selected from hydrogen or alkyl; and
each $R^8$ is independently selected from hydrogen or alkyl.

16. The compound of claim 15 selected from:
((4aS,5R,6S,8aS)-6-((5R,6S)-6-(hydroxymethyl)-5-methyl-4,5,6,7-tetrahydro-1H-indazol-5-yl)-8a-methyl-1,4,4a,5,6,7,8,8a-octahydroindeno[1,2-c]pyrazol-5-yl)methanol;
((5R,6S)-5-((4aS,5R,6S,8aS)-5-(aminomethyl)-8a-methyl-1,4,4a,5,6,7,8,8a-octahydroindeno[1,2-c]pyrazol-6-yl)-5-methyl-4,5,6,7-tetrahydro-1H-indazol-6-yl)methanol;
((5R,6S)-5-((5aS,6R,7S,9aS)-6-(aminomethyl)-9a-methyl-5a,6,7,8,9,9a-hexahydro-5H-indeno[1,2-b]pyridin-7-yl)-5-methyl-4,5,6,7-tetrahydro-1H-indazol-6-yl)methanol; and
((5aS,6R,7S,9aS)-7-((5R,6S)-6-(hydroxymethyl)-5-methyl-4,5,6,7-tetrahydro-1H-indazol-5-yl)-9a-methyl-5a,6,7,8,9,9a-hexahydro-5H-indeno[1,2-b]pyridin-6-yl)methanol.

17. The compound of claim 1 wherein:

(A)

is an optionally substituted fused 5- or 6-membered N-heteroaryl;
R¹ is hydrogen;
R² is —R⁶—OR⁷;
R³ is —R⁶—OR⁷ or —R⁶—N(R⁸)₂;
R⁴ᵃ is an optionally substituted aryl and R⁴ᵇ is a bond to C16;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen or alkyl.

18. The compound of claim 17 wherein:

(A)

is an optionally substituted fused 5- or 6-membered N-heteroaryl;
R¹ is hydrogen;
R² is —R⁶—OR⁷;
R³ is —R⁶—OR⁷ or —R⁶—N(R⁸)₂;
R⁴ᵃ is an optionally substituted aryl and R⁴ is a bond to C16;
R⁵ is alkyl;
each R⁶ is a straight or branched alkylene chain;
each R⁷ is independently selected from hydrogen or alkyl; and
each R⁸ is independently selected from hydrogen or alkyl.

19. The compound of claim 18 wherein:

(A)

is a fused 5-membered N-heteroaryl optionally substituted by one or more substitutents selected from alkyl, haloalkyl, —C(O)OR⁷, —N(R⁸)₂, —C(O)N(R⁸)₂ or optionally substituted aryl;
R¹ is hydrogen;
R² is —R⁶—OR⁷;
R³ is —R⁶—OR⁷ or —R⁶—N(R⁸)₂;
R⁴ᵃ is an optionally substituted aryl and R⁴ᵇ is a bond to C16;
R⁵ is alkyl;
each R⁶ is a straight or branched alkylene chain;
each R⁷ is independently selected from hydrogen or alkyl; and
each R⁸ is independently selected from hydrogen or alkyl.

20. The compound of claim 19 selected from:
((5R,6S)-5-((3aS,6S,7R,7aS)-7-(aminomethyl)-3a-methyl-3-phenyl-3a,4,5,6,7,7a-hexahydro-1H-inden-6-yl)-5-methyl-4,5,6,7-tetrahydro-1H-indazol-6-yl)methanol; and
((5R,6S)-5-((3aS,6S,7R,7aS)-7-(hydroxymethyl)-3a-methyl-3-phenyl-3a,4,5,6,7,7a-hexahydro-1H-inden-6-yl)-5-methyl-4,5,6,7-tetrahydro-1H-indazol-6-yl)methanol.

21. The compound of claim 1 wherein:

(A)

is a fused 5- or 6-membered N-heteroaryl substituted by substituted aryl, substituted aralkyl, substituted cycloalkyl or substituted heteroaryl;
R¹ is hydrogen;
R² is —R⁶—OR⁷;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen or alkyl.

22. The compound of claim 21 wherein:

(A)

is a fused pyrazolyl substituted by substituted aryl, substituted aralkyl, substituted cycloalkyl or substituted heteroaryl;
R¹ is hydrogen;
R² is —R⁶—OR⁷;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen or alkyl.

23. The compound of claim 22 wherein:

(A)

is a fused pyrazolyl substituted by aryl substituted by one or more substituents selected from halo, —R¹⁰—OR¹¹, —R¹⁰—C(O)R¹¹ or —R¹⁰—C(O)OR¹¹;
R¹ is hydrogen;
R² is —R⁶—OR⁷;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl;
each R⁸ is independently selected from hydrogen or alkyl;
each R¹⁰ is independently a direct bond or a straight or branched alkylene chain; and
each R¹¹ is independently hydrogen, alkyl, cycloalkyl or optionally substituted aryl.

24. The compound of claim 23 selected from:
((5R,6S)-5-((3aS,4R,5S,7aS)-4-(aminomethyl)-7a-methyl-1-methyleneoctahydro-1H-inden-5-yl)-1-(4-fluorophenyl)-5-methyl-4,5,6,7-tetrahydro-1H-indazol-6-yl)methanol;

4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenoxy)benzoic acid;

((5R,6S)-5-((3aS,4R,5S,7aS)-4-(aminomethyl)-7a-methyl-1-methyleneoctahydro-1H-inden-5-yl)-2-(4-methoxyphenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(phenyl)methanone;

((5R,6S)-5-((3aS,4R,5S,7aS)-4-(aminomethyl)-7a-methyl-1-methyleneoctahydro-1H-inden-5-yl)-1-(2-fluorophenyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1-(2,4-difluorophenyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1-(3,4-difluorophenyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1-(3-fluorophenyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-2-(3,4-difluorophenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(4-fluorophenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(4-(4-fluorophenoxy)phenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-(4-phenoxyphenyl)-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1-(4-(4-fluorophenoxy)phenyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-(4-phenoxyphenyl)-4,5,6,7-tetrahydro-2H-indazol-6-yl)methanol;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(phenyl)methanone;

((5R,6S)-5-((3aS,4R,5S,7aS)-4-(aminomethyl)-7a-methyl-1-methyleneoctahydro-1H-inden-5-yl)-2-(2-fluorophenyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(2,4-difluorophenyl)-5-methyl-4,5,6,7-tetrahydro-2H-indazol-6-yl)methanol;

4-(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenoxy)benzoic acid;

((5R,6S)-5-((3aS,4R,5S,7aS)-4-(aminomethyl)-7a-methyl-1-methyleneoctahydro-1H-inden-5-yl)-2-(3-fluorophenyl)-5-methyl-4,5,6,7-tetrahydro-2H-indazol-6-yl)methanol;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)phenyl)(4-(pent-4-yn-1-yloxy)phenyl)methanone;

(4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)phenyl)(4-(pent-4-yn-1-yloxy)phenyl)methanone;

4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-1H-indazol-1-yl)benzoic acid; and 4-((5R,6S)-5-((3aS,4R,5S,7aS)-4-(aminomethyl)-7a-methyl-1-methyleneoctahydro-1H-inden-5-yl)-6-(hydroxymethyl)-5-methyl-4,5,6,7-tetrahydro-2H-indazol-2-yl)benzoic acid.

25. The compound of claim 22 wherein:

is a fused pyrazolyl substituted by aralkyl substituted by one or more substituents selected from halo, —$R^{10}$—$OR^{11}$ or —$R^{10}$—$C(O)R^{11}$;

$R^1$ is hydrogen;
$R^2$ is —$R^6$—$OR^7$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl;
each $R^{10}$ is independently a direct bond or a straight or branched alkylene chain; and
each $R^{11}$ is independently hydrogen, alkyl, cycloalkyl or optionally substituted aryl.

26. The compound of claim 25 selected from:
((5R,6S)-5-((3aS,4R,5S,7aS)-4-(aminomethyl)-7a-methyl-1-methyleneoctahydro-1H-inden-5-yl)-2-(4-methoxybenzyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-(4-fluorobenzyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-(4-methoxybenzyl)-5-methyl-4,5,6,7-tetrahydro-1H-indazol-6-yl)methanol; and ((5R,6S)-5-((3aS,4R,5S,7aS)-4-(aminomethyl)-7a-methyl-1-methyleneoctahydro-1H-inden-5-yl)-1-(4-fluorobenzyl)-5-methyl-4,5,6,7-tetrahydro-1H-indazol-6-yl)methanol.

27. The compound of claim 22 wherein:

is a fused pyrazolyl substituted by cycloalkyl substituted by one or more substituents selected from halo, $-R^{10}-OR^{11}$ or $-R^{10}-C(O)R^{11}$;
$R^1$ is hydrogen;
$R^2$ is $-R^6-OR^7$;
$R^3$ is $-R^6-OR^7$ or $-R^6-N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl;
each $R^{10}$ is independently a direct bond or a straight or branched alkylene chain; and
each $R^{11}$ is independently hydrogen, alkyl, cycloalkyl or optionally substituted aryl.

28. The compound of claim 27 selected from:
((5R,6S)-5-((3aS,4R,5S,7aS)-4-(aminomethyl)-7a-methyl-1-methyleneoctahydro-1H-inden-5-yl)-2-(4,4-difluorocyclohexyl)-5-methyl-4,5,6,7-tetrahydro-2H-indazol-6-yl)methanol; and
((5R,6S)-5-((3aS,4R,5S,7aS)-4-(aminomethyl)-7a-methyl-1-methyleneoctahydro-1H-inden-5-yl)-1-(4,4-difluorocyclohexyl)-5-methyl-4,5,6,7-tetrahydro-1H-indazol-6-yl)methanol.

29. The compound of claim 22 wherein:

is a fused pyrazolyl substituted by heteroaryl substituted by one or more substituents selected from halo, $-R^{10}-OR^{11}$ or $-R^{10}-C(O)R^{11}$;
$R^1$ is hydrogen;
$R^2$ is $-R^6-OR^7$;
$R^3$ is $-R^6-OR^7$ or $-R^6-N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;
each $R^8$ is independently selected from hydrogen or alkyl;
each $R^{10}$ is independently a direct bond or a straight or branched alkylene chain; and
each $R^{11}$ is independently hydrogen, alkyl, cycloalkyl or optionally substituted aryl.

30. The compound of claim 29 selected from:
((5R,6S)-5-((3aS,4R,5S,7aS)-4-(aminomethyl)-7a-methyl-1-methyleneoctahydro-1H-inden-5-yl)-1-(5-fluoropyridin-2-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-1-(5-fluoropyrimidin-2-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-2-(5-fluoropyrimidin-2-yl)-5-methyl-4,5,6,7-tetrahydro-2H-indazol-6-yl)methanol; and
((5R,6S)-5-((3aS,4R,5S,7aS)-4-(aminomethyl)-7a-methyl-1-methyleneoctahydro-1H-inden-5-yl)-2-(5-fluoropyridin-2-yl)-5-methyl-4,5,6,7-tetrahydro-2H-indazol-6-yl)methanol.

31. The compound of claim 1 wherein:

is a fused 5- or 6-membered N-heteroaryl substituted by substituted aryl, substituted aralkyl, substituted cycloalkyl or substituted heteroaryl;
$R^1$ is hydrogen;
$R^2$ is $-R^6-OR^7$;
$R^3$ is $-R^6-OR^7$ or $-R^6-N(R^8)_2$;
$R^{4a}$ is alkyl and $R^{4b}$ is hydrogen;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen or alkyl.

32. The compound of claim 31 wherein:

is a fused pyrazolyl substituted by substituted aryl, substituted aralkyl, substituted cycloalkyl or substituted heteroaryl;
$R^1$ is hydrogen;
$R^2$ is $-R^6-OR^7$;
$R^3$ is $-R^6-OR^7$ or $-R^6-N(R^8)_2$;
$R^{4a}$ is alkyl and $R^{4b}$ is hydrogen;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen or alkyl.

33. The compound of claim 32 wherein:

is a fused pyrazolyl substituted by aryl substituted by one or more substituents selected from halo, $-R^{10}-OR^{11}$ or $-R^{10}-C(O)R^{11}$;
$R^1$ is hydrogen;
$R^2$ is $-R^6-OR^7$;
$R^3$ is $-R^6-OR^7$ or $-R^6-N(R^8)_2$;
$R^{4a}$ is alkyl and $R^{4b}$ is hydrogen;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl;

each R⁸ is independently selected from hydrogen or alkyl;
each R¹⁰ independently is a direct bond or a straight or branched alkylene chain; and
each R¹¹ is independently hydrogen, alkyl, cycloalkyl, optionally substituted aryl, or optionally substituted heteroaryl.

34. The compound of claim 33 selected from:
(4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-1H-indazol-1-yl)phenyl)(phenyl)methanone;
(4-((5R,6S)-5-((1S,3aS,4S,5S,7aR)-4-(aminomethyl)-1,7a-dimethyloctahydro-1H-inden-5-yl)-6-(hydroxymethyl)-5-methyl-4,5,6,7-tetrahydro-2H-indazol-2-yl)phenyl)(phenyl)methanone;
((5R,6S)-5-((1S,3aS,4S,5S,7aR)-4-(aminomethyl)-1,7a-dimethyloctahydro-1H-inden-5-yl)-1-(4-fluorophenyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-1-(4-methoxyphenyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-2-(4-fluorophenyl)-5-methyl-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-2-(4-methoxyphenyl)-5-methyl-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-2-(4-(4-fluorophenoxy)phenyl)-5-methyl-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-1-(4-(4-fluorophenoxy)phenyl)-5-methyl-4,5,6,7-tetrahydro-1H-indazol-6-yl)methanol hydrochloride;
((5R,6S)-5-((1S,3aS,4S,5S,7aR)-4-(aminomethyl)-1,7a-dimethyloctahydro-1H-inden-5-yl)-5-methyl-2-(4-(pyridin-2-yloxy)phenyl)-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-(4-(pyridin-2-yloxy)phenyl)-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-2-(4-(pyridin-4-yloxy)phenyl)-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-(4-(pyridin-4-yloxy)phenyl)-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-(4-(pyrimidin-5-yloxy)phenyl)-4,5,6,7-tetrahydro-1H-indazol-6-yl)methanol; and
((5R,6S)-5-((1S,3aS,4S,5S,7aR)-4-(aminomethyl)-1,7a-dimethyloctahydro-1H-inden-5-yl)-5-methyl-2-(4-(pyrimidin-5-yloxy)phenyl)-4,5,6,7-tetrahydro-2H-indazol-6-yl)methanol.

35. The compound of claim 32 wherein:

is a fused pyrazolyl substituted by aralkyl substituted by one or more substituents selected from halo, —R¹⁰—OR¹¹ or —R¹⁰—C(O)R¹¹;
R¹ is hydrogen;
R² is —R⁶—OR⁷;
R³ is —R⁶—OR⁷ or —R⁶—N(R⁸)₂;
R⁴ᵃ is alkyl and R⁴ᵇ is hydrogen;
R⁵ is alkyl or R⁵ is a direct bond to the carbon at C14;
each R⁶ is independently selected from a direct bond or a straight or branched alkylene chain;
each R⁷ is independently selected from hydrogen or alkyl;
each R⁸ is independently selected from hydrogen or alkyl;
each R¹⁰ is independently a direct bond or a straight or branched alkylene chain; and
each R¹¹ is independently hydrogen, alkyl, cycloalkyl or optionally substituted aryl.

36. The compound of claim 35 selected from:
((5R,6S)-5-((1S,3aS,4S,5S,7aR)-4-(aminomethyl)-1,7a-dimethyloctahydro-1H-inden-5-yl)-2-(4-methoxybenzyl)-5-methyl-4,5,6,7-tetrahydro-2H-indazol-6-yl)methanol; and
((5R,6S)-5-((1S,3aS,4S,5S,7aR)-4-(aminomethyl)-1,7a-dimethyloctahydro-1H-inden-5-yl)-1-(4-methoxybenzyl)-5-methyl-4,5,6,7-tetrahydro-1H-indazol-6-yl)methanol.

37. A composition comprising a compound of claim 1, or a stereoisomer, enantiomer or tautomer thereof or mixtures thereof, or a pharmaceutically acceptable salt or solvate thereof, and a pharmaceutically acceptable excipient.

38. A method for treating inflammation and/or pain comprising administering an effective amount of a compound of claim 1, or a stereoisomer, enantiomer or tautomer thereof or mixtures thereof, or a pharmaceutically acceptable salt or solvate thereof, or a composition of claim 37 to a mammal in need thereof.

* * * * *